US011041013B2

(12) United States Patent
Zimmerman

(10) Patent No.: US 11,041,013 B2
(45) Date of Patent: Jun. 22, 2021

(54) METHODS OF PREPARATION AND COMPOSITION OF PEPTIDE CONSTRUCTS USEFUL FOR TREATMENT OF RHEUMATOID ARTHRITIS

(75) Inventor: Daniel H. Zimmerman, Bethesda, MD (US)

(73) Assignee: Cel-Sci Corporation, Vienna, VA (US)

( * ) Notice: Subject to any disclaimer, the term of this patent is extended or adjusted under 35 U.S.C. 154(b) by 659 days.

(21) Appl. No.: 12/922,687

(22) PCT Filed: Mar. 16, 2009

(86) PCT No.: PCT/US2009/037312
§ 371 (c)(1),
(2), (4) Date: Jan. 13, 2011

(87) PCT Pub. No.: WO2009/114869
PCT Pub. Date: Sep. 17, 2009

(65) Prior Publication Data
US 2011/0098444 A1 Apr. 28, 2011

Related U.S. Application Data

(60) Provisional application No. 61/036,566, filed on Mar. 14, 2008, provisional application No. 61/100,383, filed on Sep. 26, 2008.

(51) Int. Cl.
| *A61K 39/008* | (2006.01) |
| *C07K 14/705* | (2006.01) |
| *A61K 39/00* | (2006.01) |
| *A61K 38/00* | (2006.01) |
| *A61K 35/12* | (2015.01) |

(52) U.S. Cl.
CPC ........ *C07K 14/7055* (2013.01); *A61K 39/001* (2013.01); *A61K 39/008* (2013.01); *A61K 38/00* (2013.01); *A61K 2035/122* (2013.01)

(58) Field of Classification Search
None
See application file for complete search history.

(56) References Cited

U.S. PATENT DOCUMENTS

| 6,995,237 B1 * | 2/2006 | Zimmerman ................. 530/324 |
| 2006/0257420 A1 | 11/2006 | Zimmerman |

FOREIGN PATENT DOCUMENTS

| EP | 1598370 A2 | 11/2005 |
| WO | 1998/005684 A2 | 2/1998 |
| WO | 2001/12222 A1 | 2/2001 |
| WO | 2001/036448 A2 | 5/2001 |
| WO | 2001/043695 A2 | 6/2001 |
| WO | 2007/058587 A1 | 5/2007 |

OTHER PUBLICATIONS

Krco, C.J., et al. J. Immunol. 1996;156:2761-2768.*
Schenk et al. 1999 Immunization with amyloid-beta attenuates Alzheimerdisease-like pathology in the PDAPP mouse Nature 400: 173.
Sigurdsson et al. 2001 Immunization with a nontoxic/nonfibrillar amyloid-beta homologous peptide reduces Alzheimer's disease-associated pathology in transgenic mice Am J Pathol 159:439.
Krco et al., "Characterization of the antigenic structure of human type II collagen", J Immunol, Apr. 15, 1996;156(8):2761-8.
Kurte et al., "A Synthetic Peptide Homologous to Functional Domain of Human IL-10 Down-Regulates Expression of MHC Class I and Transporter Associated with Antigen Processing 1/2 in Human Melanoma Cells", J of Immunol 2004, 173:1731-1737.
Lie et al., Synthesis and biological activity of four kinds of reversed peptides 1996, Biol. Pharma. Bul. 19:1602.
Lowrie et al., Therapy of tuberculosis in mice by DNA vaccination 1999, Nature, 400:269.
Malissen, B. Dancing the immunological two-step. Science (New York, N.Y.) 285, 207â€"8 (1999).
Meda et al., Betaamyloid (25-35) peptide and IFN-gamma synergistically induce the production of the chemotactic cytokine MCP-1/JE in monocytes and microglial cells 1996, J. Immunol., 157:1213.
Muran-yiova et al. 1991 Immunoprecipitation of herpes simplex virus polypeptides with human sera is related to their ELISA titre. Acta Virol. 35:252-9.
Myers et al., "Characterization of a tolerogenic T cell epitope of type II collagen and its relevance to collagen-induced arthritis", J Immunol., Aug. 15, 1992;149(4):1439-43.
Oksenberg, et al., Limited heterogeneity of rearranged T-cell receptor V alpha transcripts in brains of multiple sclerosis patients. 1990, Nature, 345:344.
Ota et al., T-cell recognition of an immunodominant myelin basic protein epitope in multiple sclerosis 1990, Nature, 346;183.
Wucherpfennig et al., Shared human T cell receptor V beta usage to immunodominant regwns of myelin basic protein.1990, Science, 248:1016.
Yamamoto et al., (2003) Essential role of the cryptic epitope SLA YGLR within osteopontin in a murine model of rheumatoid arthritis. J. Clin. Invest. 112:181-188.
Zhang et al., "GABAergic signaling facilitate breast cancer metastasis by promoting ERK1/2-dependent phosphorylation", Cancer Letters, 2014, pp. 100-108.

(Continued)

*Primary Examiner* — G. R. Ewoldt
(74) *Attorney, Agent, or Firm* — Hahn & Associates PLLC; Roger Hahn

(57) ABSTRACT

The invention is related to peptide constructs, i.e., polypeptides obtained by linking together two or more peptides based on or derived from different molecules, which are useful in the treatment or prevention of autoimmune diseases, specifically rheumatoid arthritis (RA) and compositions containing same, methods for producing same and methods for using same; wherein the peptide constructs have the formula $P_1$-x-$P_2$ where $P_1$ is a peptide associated with autoimmune disease, allergy, asthma, host-versus-graft rejection, myocarditis, diabetes, and immune-mediated disease, which binds to an antigen receptor on a set or subset of T cells; $P_2$ is a peptide which will cause a $T_h2$ directed immune response by the set or subset of T cells to which the peptide $P_1$ is attached or which will bind to a T cell receptor which will cause the set or subset of T cells to which the peptide $P_1$ is attached to initiate, but not complete, an immune response causing the set or subset of T cells to undergo anergy and apoptosis; and x is a direct bond or linker for covalently bonding $P_1$ and $P_2$.

3 Claims, 4 Drawing Sheets

Specification includes a Sequence Listing.

(56) References Cited

OTHER PUBLICATIONS

Zimmerman et al. ("LEAPS peptide vaccination alters T cell phenotype and suppresses joint inflammation in a murine nidek if rheumatoid arthritis" Journal of Immunology, V 190 (1 supplement) 67.6 May 1, 2013, printed as total of 6 pages , year 2013).
Taylor et tal., Cellular Immunology 2010 vol. 262, pp. 1-5, online on Feb. 1, 2010"Maturation of dendritic cell precursors into IL12-producing DCs by J-LEAPS immunogens".
Ternynck, T. & Avrameas, S. Conjugation of p-benzoquinone treated enzymes with antibodies and Fab fragments. Immunochemistry 14, 767—74.
Tomita et al., Tetrapeptide DEVD-aldehyde or YVADchloromethylketone inhibits Pas/Apo-I(CD95)-mediated apoptosis in renal-cell-cancer cells 1996, Int. J. Can., 68: 132.
Uniport Accession #O 19507, Jan. 1, 1999 and Uniport Accession #O 00664, Jul. 1, 1997.
Wooley et al., Influence of a recombinant human soluble tumor necrosis factor receptor FC fusion protein on type II collagen-induced arthritis in mice 1993, J. Immunol., 151:6602.
Anderton, S.M. Immunology 2001, vol. 104, pp. 367-376.
Glant, T. & Oláh, I. Experimental arthritis produced by proteoglycan antigens in rabbits. Scandinavian journal of rheumatology 9, 271—9 (1980).
Glant, T. T., Cs-Szabó, G., Nagase, H., Jacobs, J. J. & Mikecz, K. Progressive polyarthritis induced in BALB/c mice by aggrecan from normal and osteoarthritic human cartilage. Arthritis and rheumatism 41, 1007—18 (1998).
Gogolak et al., Collaboration of TCR-, CD4- and CD28-mediated signaling in antigen-specific MHC class II-restricted T-cells 1996, Immunol. Let. 54:135.
Hafler, D. A., Ritz, J., Schlossman, S. F. & Weiner, H. L. Anti-CD4 and anti-CD2 monoclonal antibody infusions in subjects with multiple sclerosis. Immunosuppressive effects and human anti-mouse responses. Journal of immunology (Baltimore, Md.€: 1950) 141, 131—8 (1988).
Harley et al., nucleoprotein—influenza A virus (strain A/Shearwater/Aust/1/72[H6N5]). GenBank Direct Submission Asscession A60028, Feb. 26, 1999 [online] [Retrieved on Jun. 6, 1999]. Retrieved from the Internet: ,URL: http://www.ncbi.nlm.nih.gov/protein/A60028>, p. 1.
Herrmann et al. Leflunomide: an immunomodulatory drug for the treatment of rheumatoid arthritis and other autoimmune diseases, Immunopharmacology, May 2000; 47(2-3): 273-289.
Howard et al., Mechanisms of immunotherapeutic intervention by anti-CD40L (CD154) antibody in an animal model of multiple sclerosis 1999, J. Clin. Invest., 103:281.
Kis-Toth et al. ("Arthritogenic T cells drive the recover of autoantibody-producing B cell homeostasis and the adoptive transfer of arthritis in SCID mice" International Immunology v24(8) 2012 pp. 507-517 (Year: 2012).
Kleinau et al., Importance of CD23 for Collagen-Induced Arthritis: Delayed Onset and Reduced Severity in CD23-Deficient Mice 1999, J. Immunol. 162:4266.
Fosgerau et al. "Peptide therapeutics: current status and future directions", Drug Discovery Today, 2015, 20(1):122-128.
Fresca et al., In vivo restoration of T cell functions by human IL-I beta or its 163-171 nonapeptide in immunodepressed mice 1988, J. Immunol., 141:2651.
Gharavi et al., GDKV-Induced Antiphospholipid Antibodies Enhance Thrombosis and Activate Endothelial Cells In Vivo and In Vitro 1999, J.Immunol., 163:2922.
Glant TT et al., Critical role of glycosaminoglycan side chains of cartilage proteoglycan (aggrecan) in antigen recognition and presentation 1998 J. Immunol. 160: 3812.
Glant TT et al., Proteoglycan-induced arthritis and recombinant human proteoglycan aggrecan G1 domain-induced arthritis in BALB/c mice resembling two subtypes of rheumatoid arthritis 2011 Arthritis & Rheumatism 63: 1312-1321.
Preckel et al., Partial agonism and independent modulation of T cell receptor and CD5 in hapten-specific cytotoxic T cells 1998, Eur. J. Immunol., 28:3706.
Reineke et al., A synthetic mimic of a discontinuous binding site on interleukin-10 1999, Nature Biotechnology, 17:271.
Sambhara et al., Programmed cell death of T cells signaled by the T cell receptor and the alpha 3 domain of class I MHC 1991, Science, 252:1424.
De Lalla et al., Cutting Edge: Identification of Novel T Cell Epitopes in Lol p5a by Computational Prediction 1999, J. Immunol., 163:1725.
DeMattos et al. Peripheral anti-A beta antibody alters CNS and plasma A beta clearance and decreases brain A beta burden in a mouse model of Alzheimer's disease, Proc Natl Acad Sci U.S.A. Jul. 17, 2001;98(15):8850-5).
Antoni, et al., A short synthetic peptide fragment of human interleukin 1 with immunostimulatory but not inflammatory activity 1986, J. Immunol, 137:3201.
Bajpai et al., Immunomodulating activity of analogs of noninflammatory fragment 163-171 of human interleukin-Ibeta 1998 Immunopharmacology, 38:237.
Baldwin et al., "Structure of eDNA clones coding for human type II procollagen. The alpha 1 (II) chain is more similar to the alpha 1 (I) chain than two other alpha chains of fibrillar collagens", Biochem J. Sep. 1, 1989;262(2):521-8.
Bard et al., Epitope and isotype specificities of antibodies to beta-amyloid peptide for protection against Alzheimer's disease-like neuropathology, Proc Natl Acad Sci U.S.A. Feb. 18, 2003; 100(4):2023-8.
Bauer et al., "Maximizing Immune Responses: The Effect of Covalent Peptide Linkage to beta-2 Microglobulin," Oncology Research, 2008, pp. 205-216.
Beckers et al., Increasing the immunogenicity of protein antigens through the genetic insertion of VQGEESNDK sequence of human IL-I beta into their sequence 1993, J. Immunol., 151:1757.
Benham, Citrullinated peptide dentritic cell immunotherapy in LA risk genotype-positive rheumatoid arthritis patients, Rheumatoid Arthritis, vol. 7, issue 290, p. 1-12.
Bolon B et al., Rodent preclinical models for developing novel antiarthritic molecules: Comparative biology and preferred methods for evaluating efficacy 2011, J. Biomed. & Biotech.
Briand et al., Synthetic peptides as antigens: pitfalls of conjugation methods, 1985, J. Immunol. Meth., 78: 59.
Daniel H Zimmerman: "LEAPS Therapeutic Vaccines As antigen specific inflammation in infectious and autoimmune diseases" Journal of Vaccines & Vaccination, vol. 03, No. 05, Jan. 1, 2012, XP 055303198.

\* cited by examiner

Evaluation of L.E.A.P.S. vaccine for therapy of CIA. Treatment started on day 28

Evaluation of CEL-2000 therapeutic vaccine for therapy of CIA

Left rear foot pad thickness in mice immunized on day 0 and 14 after initiation of therapy with CEL-2000 or CEL-2003

Histopathology results for the sum scores of the 4 individual areas for Groups 1, 2 3 and 5 of first study (Fig. 1) and groups 4 and 7 of second study (Fig. 2)

```
                          SEQUENCE LISTING

<160> NUMBER OF SEQ ID NOS: 126

<210> SEQ ID NO 1
<211> LENGTH: 13
<212> TYPE: PRT
<213> ORGANISM: Homo sapiens
<220> FEATURE:
<221> NAME/KEY: MISC_FEATURE
<222> LOCATION: (260)..(272)
<223> OTHER INFORMATION: Type II Collagen

<400> SEQUENCE: 1

Ile Ala Gly Phe Lys Gly Glu Gln Gly Pro Lys Gly Glu
1               5                   10

<210> SEQ ID NO 2
<211> LENGTH: 8
<212> TYPE: PRT
<213> ORGANISM: Homo sapiens
<220> FEATURE:
<221> NAME/KEY: MISC_FEATURE
<222> LOCATION: (92)..(98)
<223> OTHER INFORMATION: Myelin Basic Protein

<400> SEQUENCE: 2

Lys Asn Ile Val Thr Pro Arg Thr
1               5

<210> SEQ ID NO 3
<211> LENGTH: 15
<212> TYPE: PRT
<213> ORGANISM: Homo sapiens
<220> FEATURE:
<221> NAME/KEY: MISC_FEATURE
<222> LOCATION: (274)..(288)
<223> OTHER INFORMATION: Beta-2 Glycoprotein 1

<400> SEQUENCE: 3

Gly Asp Lys Val Ser Phe Phe Cys Lys Asn Lys Glu Lys Lys Cys
1               5                   10                  15

<210> SEQ ID NO 4
<211> LENGTH: 17
<212> TYPE: PRT
<213> ORGANISM: Homo sapiens
<220> FEATURE:
<221> NAME/KEY: MISC_FEATURE
<222> LOCATION: (274)..(288)
<223> OTHER INFORMATION: LFA-3

<400> SEQUENCE: 4

Val Leu Trp Lys Lys Gln Lys Asp Lys Val Ala Glu Leu Glu Asn Ser
1               5                   10                  15
Glu

<210> SEQ ID NO 5
<211> LENGTH: 11
<212> TYPE: PRT
<213> ORGANISM: Homo sapiens
<220> FEATURE:
<221> NAME/KEY: MISC_FEATURE
<222> LOCATION: (70)..(80)
```

```
<223> OTHER INFORMATION: TNF alpha

<400> SEQUENCE: 5

Pro Ser Thr His Val Leu Ile Thr His Thr Ile
1               5                   10

<210> SEQ ID NO 6
<211> LENGTH: 15
<212> TYPE: PRT
<213> ORGANISM: Artificial
<220> FEATURE:
<223> OTHER INFORMATION: Peptide Construct

<400> SEQUENCE: 6

Asp Phe Leu Pro His Tyr Lys Asn Thr Ser Leu Gly His Arg Pro
1               5                   10                  15

<210> SEQ ID NO 7
<211> LENGTH: 4
<212> TYPE: PRT
<213> ORGANISM: Artificial Sequence
<220> FEATURE:
<223> OTHER INFORMATION: peptide construct

<400> SEQUENCE: 7

Gly Gly Gly Ser
1

<210> SEQ ID NO 8
<211> LENGTH: 5
<212> TYPE: PRT
<213> ORGANISM: Artificial Sequence
<220> FEATURE:
<223> OTHER INFORMATION: peptide construct

<400> SEQUENCE: 8

Gly Gly Gly Ser Ser
1               5

<210> SEQ ID NO 9
<211> LENGTH: 5
<212> TYPE: PRT
<213> ORGANISM: Artificial Sequence
<220> FEATURE:
<223> OTHER INFORMATION: peptide construct

<400> SEQUENCE: 9

Gly Gly Gly Gly Ser
1               5

<210> SEQ ID NO 10
<211> LENGTH: 6
<212> TYPE: PRT
<213> ORGANISM: Artificial Sequence
<220> FEATURE:
<223> OTHER INFORMATION: peptide construct

<400> SEQUENCE: 10

Gly Gly Gly Gly Ser Ser
1               5

<210> SEQ ID NO 11
<211> LENGTH: 8
<212> TYPE: PRT
<213> ORGANISM: Artificial Sequence
<220> FEATURE:
<223> OTHER INFORMATION: peptide construct
```

```
<400> SEQUENCE: 11

Gly Gly Gly Ser Gly Gly Gly Ser
1               5

<210> SEQ ID NO 12
<211> LENGTH: 8
<212> TYPE: PRT
<213> ORGANISM: Artificial Sequence
<220> FEATURE:
<223> OTHER INFORMATION: peptide construct

<400> SEQUENCE: 12

Leu Arg Gly Gly Gly Gly Ser Ser
1               5

<210> SEQ ID NO 13
<211> LENGTH: 9
<212> TYPE: PRT
<213> ORGANISM: Homo sapiens
<220> FEATURE:
<221> NAME/KEY: MISC_FEATURE
<222> LOCATION: (163)..(171)
<223> OTHER INFORMATION: IL-1 beta

<400> SEQUENCE: 13

Val Gln Gly Glu Glu Ser Asn Asp Lys
1               5

<210> SEQ ID NO 14
<211> LENGTH: 15
<212> TYPE: PRT
<213> ORGANISM: Homo sapiens
<220> FEATURE:
<221> NAME/KEY: MISC_FEATURE
<222> LOCATION: (135)..(149)
<223> OTHER INFORMATION: MHCII Beta-2

<400> SEQUENCE: 14

Asn Gly Gln Glu Glu Lys Ala Gly Val Val Ser Thr Gly Leu Ile
1               5                   10                  15

<210> SEQ ID NO 15
<211> LENGTH: 9
<212> TYPE: PRT
<213> ORGANISM: Homo sapiens
<220> FEATURE:
<221> NAME/KEY: MISC_FEATURE
<222> LOCATION: (152)..(160)
<223> OTHER INFORMATION: IL-10

<400> SEQUENCE: 15

Ala Tyr Met Thr Met Lys Ile Arg Asn
1               5

<210> SEQ ID NO 16
<211> LENGTH: 7
<212> TYPE: PRT
<213> ORGANISM: Homo sapiens
<220> FEATURE:
<221> NAME/KEY: MISC_FEATURE
<222> LOCATION: (223)..(229)
<223> OTHER INFORMATION: MHCI Alpha-3

<400> SEQUENCE: 16

Asp Gln Thr Gln Asp Thr Glu
1               5
```

<210> SEQ ID NO 17
<211> LENGTH: 29
<212> TYPE: PRT
<213> ORGANISM: Artificial Sequence
<220> FEATURE:
<223> OTHER INFORMATION: peptide construct

<400> SEQUENCE: 17

Asp Gln Thr Gln Asp Thr Glu Gly Gly Gly Gly Ser Glu Ile Ile Val
1               5                   10                  15

Thr His Phe Pro Phe Asp Glu Gln Asn Cys Ser Met Lys
            20                  25

<210> SEQ ID NO 18
<211> LENGTH: 15
<212> TYPE: PRT
<213> ORGANISM: Artificial
<220> FEATURE:
<223> OTHER INFORMATION: Peptide Construct

<400> SEQUENCE: 18

Asp Phe Leu Pro His Tyr Lys Asn Thr Ser Leu Gly His Arg Pro
1               5                   10                  15

<210> SEQ ID NO 19
<211> LENGTH: 31
<212> TYPE: PRT
<213> ORGANISM: Artificial
<220> FEATURE:
<223> OTHER INFORMATION: Peptide Construct

<400> SEQUENCE: 19

Asp Asn Gln Leu Leu Glu Thr Cys Lys Gln Asp Arg Leu Arg Asn Arg
1               5                   10                  15

Arg Gly Asn Gly Ser Ser Thr His Phe Glu Gly Asn Leu Pro Cys
            20                  25                  30

<210> SEQ ID NO 20
<211> LENGTH: 15
<212> TYPE: PRT
<213> ORGANISM: Homo sapiens
<220> FEATURE:
<221> NAME/KEY: MISC_FEATURE
<222> LOCATION: (135)..(149)
<223> OTHER INFORMATION: MHCII Beta-2

<400> SEQUENCE: 20

Asp Gly Gln Glu Glu Lys Ala Gly Val Val Ser Thr Gly Leu Ile
1               5                   10                  15

<210> SEQ ID NO 21
<211> LENGTH: 13
<212> TYPE: PRT
<213> ORGANISM: Homo sapiens
<220> FEATURE:
<221> NAME/KEY: MISC_FEATURE
<222> LOCATION: (38)..(50)
<223> OTHER INFORMATION: Beta-2 Microglobulin

<400> SEQUENCE: 21

Asp Leu Leu Lys Asn Gly Glu Arg Ile Glu Lys Val Glu
1               5                   10

<210> SEQ ID NO 22
<211> LENGTH: 12
<212> TYPE: PRT

```
<213> ORGANISM: Artificial Sequence
<220> FEATURE:
<223> OTHER INFORMATION: peptide construct

<400> SEQUENCE: 22

Gly Gly Gly Ser Gly Thr Gly Ser Gly Ser Gly Ser
1               5                   10

<210> SEQ ID NO 23
<211> LENGTH: 13
<212> TYPE: PRT
<213> ORGANISM: Artificial
<220> FEATURE:
<223> OTHER INFORMATION: peptide construct
<220> FEATURE:
<221> NAME/KEY: MISC_FEATURE
<222> LOCATION: (1)..(1)
<223> OTHER INFORMATION: X is I, L or V
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: X is A or G
<220> FEATURE:
<221> NAME/KEY: MISC_FEATURE
<222> LOCATION: (3)..(3)
<223> OTHER INFORMATION: X is A or G
<220> FEATURE:
<221> NAME/KEY: MISC_FEATURE
<222> LOCATION: (4)..(4)
<223> OTHER INFORMATION: X is F,  W or Y for aromatic amino acids
<220> FEATURE:
<221> NAME/KEY: MISC_FEATURE
<222> LOCATION: (5)..(5)
<223> OTHER INFORMATION: X is K, R or H for basic amino acids
<220> FEATURE:
<221> NAME/KEY: MISC_FEATURE
<222> LOCATION: (6)..(6)
<223> OTHER INFORMATION: X is A or G
<220> FEATURE:
<221> NAME/KEY: MISC_FEATURE
<222> LOCATION: (7)..(7)
<223> OTHER INFORMATION: X is D and E for acidic amino acids
<220> FEATURE:
<221> NAME/KEY: MISC_FEATURE
<222> LOCATION: (8)..(8)
<223> OTHER INFORMATION: X is N or Q for amidated amino acids
<220> FEATURE:
<221> NAME/KEY: MISC_FEATURE
<222> LOCATION: (9)..(9)
<223> OTHER INFORMATION: X is A or G
<220> FEATURE:
<221> NAME/KEY: MISC_FEATURE
<222> LOCATION: (10)..(10)
<223> OTHER INFORMATION: X is F or P
<220> FEATURE:
<221> NAME/KEY: MISC_FEATURE
<222> LOCATION: (11)..(11)
<223> OTHER INFORMATION: X is K, R or H for basic amino acids
<220> FEATURE:
<221> NAME/KEY: MISC_FEATURE
<222> LOCATION: (12)..(12)
<223> OTHER INFORMATION: X is A or G
<220> FEATURE:
<221> NAME/KEY: MISC_FEATURE
<222> LOCATION: (13)..(13)
<223> OTHER INFORMATION: X is D and E for acidic amino acids

<400> SEQUENCE: 23

Xaa Xaa Xaa Xaa Xaa Xaa Xaa Xaa Xaa Xaa Xaa Xaa Xaa
1               5                   10
```

```
<210> SEQ ID NO 24
<211> LENGTH: 18
<212> TYPE: PRT
<213> ORGANISM: Artificial
<220> FEATURE:
<223> OTHER INFORMATION: peptide construct
<220> FEATURE:
<221> NAME/KEY: MISC_FEATURE
<222> LOCATION: (1)..(1)
<223> OTHER INFORMATION: X is N or Q for amidated amino acids
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: X is A or G
<220> FEATURE:
<221> NAME/KEY: MISC_FEATURE
<222> LOCATION: (3)..(3)
<223> OTHER INFORMATION: X is N or Q for amidated amino acids
<220> FEATURE:
<221> NAME/KEY: MISC_FEATURE
<222> LOCATION: (4)..(4)
<223> OTHER INFORMATION: X is D and E for acidic amino acids
<220> FEATURE:
<221> NAME/KEY: MOD_RES
<222> LOCATION: (4)..(4)
<223> OTHER INFORMATION: 4Abu
<220> FEATURE:
<221> NAME/KEY: MISC_FEATURE
<222> LOCATION: (5)..(5)
<223> OTHER INFORMATION: X is D and E for acidic amino acids
<220> FEATURE:
<221> NAME/KEY: MISC_FEATURE
<222> LOCATION: (6)..(6)
<223> OTHER INFORMATION: X is K, R or H for basic amino acids
<220> FEATURE:
<221> NAME/KEY: MISC_FEATURE
<222> LOCATION: (7)..(7)
<223> OTHER INFORMATION: X is A or G
<220> FEATURE:
<221> NAME/KEY: MISC_FEATURE
<222> LOCATION: (8)..(8)
<223> OTHER INFORMATION: X is A or G
<220> FEATURE:
<221> NAME/KEY: MISC_FEATURE
<222> LOCATION: (9)..(9)
<223> OTHER INFORMATION: X is I, L or V
<220> FEATURE:
<221> NAME/KEY: MOD_RES
<222> LOCATION: (9)..(9)
<223> OTHER INFORMATION: 4Abu
<220> FEATURE:
<221> NAME/KEY: MISC_FEATURE
<222> LOCATION: (10)..(10)
<223> OTHER INFORMATION: X is I, L or V
<220> FEATURE:
<221> NAME/KEY: MISC_FEATURE
<222> LOCATION: (11)..(11)
<223> OTHER INFORMATION: X is  C or S
<220> FEATURE:
<221> NAME/KEY: MISC_FEATURE
<222> LOCATION: (12)..(12)
<223> OTHER INFORMATION: X is T or S
<220> FEATURE:
<221> NAME/KEY: MISC_FEATURE
<222> LOCATION: (13)..(13)
<223> OTHER INFORMATION: X is A or G
<220> FEATURE:
<221> NAME/KEY: MISC_FEATURE
<222> LOCATION: (14)..(14)
<223> OTHER INFORMATION: X is I, L or V
<220> FEATURE:
<221> NAME/KEY: MOD_RES
<222> LOCATION: (14)..(14)
<223> OTHER INFORMATION: 4Abu
<220> FEATURE:
```

```
<221> NAME/KEY: MISC_FEATURE
<222> LOCATION: (15)..(15)
<223> OTHER INFORMATION: X is I, L or V
<220> FEATURE:
<221> NAME/KEY: MISC_FEATURE
<222> LOCATION: (16)..(16)
<223> OTHER INFORMATION: X is A or G
<220> FEATURE:
<221> NAME/KEY: MISC_FEATURE
<222> LOCATION: (17)..(17)
<223> OTHER INFORMATION: X is A or G
<220> FEATURE:
<221> NAME/KEY: MISC_FEATURE
<222> LOCATION: (18)..(18)
<223> OTHER INFORMATION: X is A or G

<400> SEQUENCE: 24

Xaa Xaa Xaa Xaa Xaa Xaa Xaa Xaa Xaa Xaa Xaa Xaa Xaa Xaa Xaa Xaa
1               5                   10                  15

Xaa Xaa

<210> SEQ ID NO 25
<211> LENGTH: 18
<212> TYPE: PRT
<213> ORGANISM: Artificial
<220> FEATURE:
<223> OTHER INFORMATION: peptide construct
<220> FEATURE:
<221> NAME/KEY: MISC_FEATURE
<222> LOCATION: (1)..(1)
<223> OTHER INFORMATION: X is D and E for acidic amino acids
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: X is A or G
<220> FEATURE:
<221> NAME/KEY: MISC_FEATURE
<222> LOCATION: (3)..(3)
<223> OTHER INFORMATION: X is N or Q for amidated amino acids
<220> FEATURE:
<221> NAME/KEY: MISC_FEATURE
<222> LOCATION: (4)..(4)
<223> OTHER INFORMATION: X is D and E for acidic amino acids
<220> FEATURE:
<221> NAME/KEY: MOD_RES
<222> LOCATION: (4)..(4)
<223> OTHER INFORMATION: 4Abu
<220> FEATURE:
<221> NAME/KEY: MISC_FEATURE
<222> LOCATION: (5)..(5)
<223> OTHER INFORMATION: X is D and E for acidic amino acids
<220> FEATURE:
<221> NAME/KEY: MISC_FEATURE
<222> LOCATION: (6)..(6)
<223> OTHER INFORMATION: X is K, R or H for basic amino acids
<220> FEATURE:
<221> NAME/KEY: MISC_FEATURE
<222> LOCATION: (7)..(7)
<223> OTHER INFORMATION: X is A or G
<220> FEATURE:
<221> NAME/KEY: MISC_FEATURE
<222> LOCATION: (8)..(8)
<223> OTHER INFORMATION: X is A or G
<220> FEATURE:
<221> NAME/KEY: MISC_FEATURE
<222> LOCATION: (9)..(9)
<223> OTHER INFORMATION: X is I, L or V
<220> FEATURE:
<221> NAME/KEY: MOD_RES
<222> LOCATION: (9)..(9)
<223> OTHER INFORMATION: 4Abu
<220> FEATURE:
```

```
<221> NAME/KEY: MISC_FEATURE
<222> LOCATION: (10)..(10)
<223> OTHER INFORMATION: X is I, L or V
<220> FEATURE:
<221> NAME/KEY: MISC_FEATURE
<222> LOCATION: (11)..(11)
<223> OTHER INFORMATION: X is C or S
<220> FEATURE:
<221> NAME/KEY: MISC_FEATURE
<222> LOCATION: (12)..(12)
<223> OTHER INFORMATION: X is T or S
<220> FEATURE:
<221> NAME/KEY: MISC_FEATURE
<222> LOCATION: (13)..(13)
<223> OTHER INFORMATION: X is A or G
<220> FEATURE:
<221> NAME/KEY: MISC_FEATURE
<222> LOCATION: (14)..(14)
<223> OTHER INFORMATION: X is I, L or V
<220> FEATURE:
<221> NAME/KEY: MOD_RES
<222> LOCATION: (14)..(14)
<223> OTHER INFORMATION: 4Abu
<220> FEATURE:
<221> NAME/KEY: MISC_FEATURE
<222> LOCATION: (15)..(15)
<223> OTHER INFORMATION: X is I, L or V
<220> FEATURE:
<221> NAME/KEY: MISC_FEATURE
<222> LOCATION: (16)..(16)
<223> OTHER INFORMATION: X is A or G
<220> FEATURE:
<221> NAME/KEY: MISC_FEATURE
<222> LOCATION: (17)..(17)
<223> OTHER INFORMATION: X is A or G
<220> FEATURE:
<221> NAME/KEY: MISC_FEATURE
<222> LOCATION: (18)..(18)
<223> OTHER INFORMATION: X is A or G

<400> SEQUENCE: 25

Xaa Xaa Xaa Xaa Xaa Xaa Xaa Xaa Xaa Xaa Xaa Xaa Xaa Xaa Xaa Xaa
1               5                   10                  15

Xaa Xaa

<210> SEQ ID NO 26
<211> LENGTH: 17
<212> TYPE: PRT
<213> ORGANISM: Artificial
<220> FEATURE:
<223> OTHER INFORMATION: peptide construct
<220> FEATURE:
<221> NAME/KEY: MISC_FEATURE
<222> LOCATION: (1)..(1)
<223> OTHER INFORMATION: X is I, L or V
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: 4Abu
<220> FEATURE:
<221> NAME/KEY: MISC_FEATURE
<222> LOCATION: (2)..(2)
<223> OTHER INFORMATION: X is I, L or V
<220> FEATURE:
<221> NAME/KEY: MISC_FEATURE
<222> LOCATION: (3)..(3)
<223> OTHER INFORMATION: X is F, W or Y for aromatic amino acids
<220> FEATURE:
<221> NAME/KEY: MISC_FEATURE
<222> LOCATION: (4)..(4)
<223> OTHER INFORMATION: X is K, R or H for basic amino acids
<220> FEATURE:
```

```
<221> NAME/KEY: MISC_FEATURE
<222> LOCATION: (5)..(5)
<223> OTHER INFORMATION: X is K, R or H for basic amino acids
<220> FEATURE:
<221> NAME/KEY: MISC_FEATURE
<222> LOCATION: (6)..(6)
<223> OTHER INFORMATION: X is N or Q for amidated amino acids
<220> FEATURE:
<221> NAME/KEY: MISC_FEATURE
<222> LOCATION: (7)..(7)
<223> OTHER INFORMATION: X is K, R or H for basic amino acids
<220> FEATURE:
<221> NAME/KEY: MISC_FEATURE
<222> LOCATION: (8)..(8)
<223> OTHER INFORMATION: X is D and E for acidic amino acids
<220> FEATURE:
<221> NAME/KEY: MISC_FEATURE
<222> LOCATION: (9)..(9)
<223> OTHER INFORMATION: X is K,  R or H for basic amino acids
<220> FEATURE:
<221> NAME/KEY: MISC_FEATURE
<222> LOCATION: (10)..(10)
<223> OTHER INFORMATION: X is I, L or V
<220> FEATURE:
<221> NAME/KEY: MISC_FEATURE
<222> LOCATION: (11)..(11)
<223> OTHER INFORMATION: X is A or G
<220> FEATURE:
<221> NAME/KEY: MISC_FEATURE
<222> LOCATION: (12)..(12)
<223> OTHER INFORMATION: X is D and E for acidic amino acids
<220> FEATURE:
<221> NAME/KEY: MOD_RES
<222> LOCATION: (12)..(12)
<223> OTHER INFORMATION: GAMMA-CARBOXYGLUTAMIC ACID HYDROXYLATION
<220> FEATURE:
<221> NAME/KEY: MISC_FEATURE
<222> LOCATION: (13)..(13)
<223> OTHER INFORMATION: X is I, L or V
<220> FEATURE:
<221> NAME/KEY: MISC_FEATURE
<222> LOCATION: (14)..(14)
<223> OTHER INFORMATION: X is D and E for acidic amino acids
<220> FEATURE:
<221> NAME/KEY: MISC_FEATURE
<222> LOCATION: (15)..(15)
<223> OTHER INFORMATION: X is N or Q for amidated amino acids
<220> FEATURE:
<221> NAME/KEY: MISC_FEATURE
<222> LOCATION: (16)..(16)
<223> OTHER INFORMATION: X is C or S
<220> FEATURE:
<221> NAME/KEY: MISC_FEATURE
<222> LOCATION: (17)..(17)
<223> OTHER INFORMATION: X is D and E for acidic amino acids

<400> SEQUENCE: 26

Xaa Xaa Xaa Xaa Xaa Xaa Xaa Xaa Xaa Xaa Xaa Xaa Xaa Xaa Xaa Xaa
1               5                   10                  15

Xaa

<210> SEQ ID NO 27
<211> LENGTH: 13
<212> TYPE: PRT
<213> ORGANISM: Artificial
<220> FEATURE:
<223> OTHER INFORMATION: peptide construct
<220> FEATURE:
<221> NAME/KEY: MISC_FEATURE
<222> LOCATION: (1)..(1)
<223> OTHER INFORMATION: X is D and E for acidic amino acids
<220> FEATURE:
<221> NAME/KEY: MOD_RES
<222> LOCATION: (1)..(1)
<223> OTHER INFORMATION: ACETYLATION
<220> FEATURE:
```

```
<221> NAME/KEY: MOD_RES
<222> LOCATION: (1)..(1)
<223> OTHER INFORMATION: 4Abu
<220> FEATURE:
<221> NAME/KEY: MOD_RES
<222> LOCATION: (1)..(1)
<223> OTHER INFORMATION: GAMMA-CARBOXYGLUTAMIC ACID HYDROXYLATION
<220> FEATURE:
<221> NAME/KEY: MISC_FEATURE
<222> LOCATION: (2)..(2)
<223> OTHER INFORMATION: X is I, L or V
<220> FEATURE:
<221> NAME/KEY: MISC_FEATURE
<222> LOCATION: (3)..(3)
<223> OTHER INFORMATION: X is I, L or V
<220> FEATURE:
<221> NAME/KEY: MISC_FEATURE
<222> LOCATION: (4)..(4)
<223> OTHER INFORMATION: X is K, R or H for basic amino acids
<220> FEATURE:
<221> NAME/KEY: MISC_FEATURE
<222> LOCATION: (5)..(5)
<223> OTHER INFORMATION: X is N or Q for amidated amino acids
<220> FEATURE:
<221> NAME/KEY: MISC_FEATURE
<222> LOCATION: (6)..(6)
<223> OTHER INFORMATION: X is A or G
<220> FEATURE:
<221> NAME/KEY: MISC_FEATURE
<222> LOCATION: (7)..(7)
<223> OTHER INFORMATION: X is D and E for acidic amino acids
<220> FEATURE:
<221> NAME/KEY: MISC_FEATURE
<222> LOCATION: (8)..(8)
<223> OTHER INFORMATION: X is K, R or H for basic amino acids
<220> FEATURE:
<221> NAME/KEY: MISC_FEATURE
<222> LOCATION: (9)..(9)
<223> OTHER INFORMATION: X is I, L or V
<220> FEATURE:
<221> NAME/KEY: MOD_RES
<222> LOCATION: (9)..(9)
<223> OTHER INFORMATION: 4Abu
<220> FEATURE:
<221> NAME/KEY: MISC_FEATURE
<222> LOCATION: (10)..(10)
<223> OTHER INFORMATION: X is D and E for acidic amino acids
<220> FEATURE:
<221> NAME/KEY: MISC_FEATURE
<222> LOCATION: (11)..(11)
<223> OTHER INFORMATION: X is K, R or H for basic amino acids
<220> FEATURE:
<221> NAME/KEY: MISC_FEATURE
<222> LOCATION: (12)..(12)
<223> OTHER INFORMATION: X is I, L or V
<220> FEATURE:
<221> NAME/KEY: MOD_RES
<222> LOCATION: (12)..(12)
<223> OTHER INFORMATION: 4Abu
<220> FEATURE:
<221> NAME/KEY: MISC_FEATURE
<222> LOCATION: (13)..(13)
<223> OTHER INFORMATION: X is D and E for acidic amino acids

<400> SEQUENCE: 27

Xaa Xaa Xaa Xaa Xaa Xaa Xaa Xaa Xaa Xaa Xaa Xaa Xaa
1               5                   10

<210> SEQ ID NO 28
<211> LENGTH: 11
<212> TYPE: PRT
<213> ORGANISM: Artificial
<220> FEATURE:
<223> OTHER INFORMATION: peptide construct
<220> FEATURE:
<221> NAME/KEY: MISC_FEATURE
<222> LOCATION: (1)..(1)
```

```
<223> OTHER INFORMATION: X is F or P
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: X is C or S
<220> FEATURE:
<221> NAME/KEY: MISC_FEATURE
<222> LOCATION: (3)..(3)
<223> OTHER INFORMATION: X is T or S
<220> FEATURE:
<221> NAME/KEY: MISC_FEATURE
<222> LOCATION: (4)..(4)
<223> OTHER INFORMATION: X is K, R or H for basic amino acids
<220> FEATURE:
<221> NAME/KEY: MISC_FEATURE
<222> LOCATION: (5)..(5)
<223> OTHER INFORMATION: X is I, L or V
<220> FEATURE:
<221> NAME/KEY: MOD_RES
<222> LOCATION: (5)..(5)
<223> OTHER INFORMATION: 4Abu
<220> FEATURE:
<221> NAME/KEY: MOD_RES
<222> LOCATION: (5)..(5)
<223> OTHER INFORMATION: GAMMA-CARBOXYGLUTAMIC ACID HYDROXYLATION
<220> FEATURE:
<221> NAME/KEY: MISC_FEATURE
<222> LOCATION: (6)..(6)
<223> OTHER INFORMATION: X is I, L or V
<220> FEATURE:
<221> NAME/KEY: MISC_FEATURE
<222> LOCATION: (7)..(7)
<223> OTHER INFORMATION: X is I, L or V
<220> FEATURE:
<221> NAME/KEY: MISC_FEATURE
<222> LOCATION: (8)..(8)
<223> OTHER INFORMATION: X is T or S
<220> FEATURE:
<221> NAME/KEY: MISC_FEATURE
<222> LOCATION: (9)..(9)
<223> OTHER INFORMATION: X is K, R or H for basic amino acids
<220> FEATURE:
<221> NAME/KEY: MISC_FEATURE
<222> LOCATION: (10)..(10)
<223> OTHER INFORMATION: X is T or S
<220> FEATURE:
<221> NAME/KEY: MISC_FEATURE
<222> LOCATION: (11)..(11)
<223> OTHER INFORMATION: X is I, L or V

<400> SEQUENCE: 28

Xaa Xaa Xaa Xaa Xaa Xaa Xaa Xaa Xaa Xaa Xaa
1               5                   10

<210> SEQ ID NO 29
<211> LENGTH: 15
<212> TYPE: PRT
<213> ORGANISM: Artificial
<220> FEATURE:
<223> OTHER INFORMATION: Peptide Construct

<400> SEQUENCE: 29

Asp Phe Leu Pro His Tyr Lys Asn Thr Ser Leu Gly His Arg Pro
1               5                   10                  15

<210> SEQ ID NO 30
<211> LENGTH: 15
<212> TYPE: PRT
<213> ORGANISM: Artificial
<220> FEATURE:
<223> OTHER INFORMATION: peptide construct
```

```
<220> FEATURE:
<221> NAME/KEY: MISC_FEATURE
<222> LOCATION: (1)..(1)
<223> OTHER INFORMATION: X is D and E for acidic amino acids
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: X is F, W or Y for aromatic amino acids
<220> FEATURE:
<221> NAME/KEY: MISC_FEATURE
<222> LOCATION: (3)..(3)
<223> OTHER INFORMATION: X is I, L or V
<220> FEATURE:
<221> NAME/KEY: MISC_FEATURE
<222> LOCATION: (4)..(4)
<223> OTHER INFORMATION: X is F or P
<220> FEATURE:
<221> NAME/KEY: MISC_FEATURE
<222> LOCATION: (5)..(5)
<223> OTHER INFORMATION: X is K, R or H for basic amino acids
<220> FEATURE:
<221> NAME/KEY: MISC_FEATURE
<222> LOCATION: (6)..(6)
<223> OTHER INFORMATION: X is F, W or Y for aromatic amino acids
<220> FEATURE:
<221> NAME/KEY: MISC_FEATURE
<222> LOCATION: (7)..(7)
<223> OTHER INFORMATION: X is K, R or H for basic amino acids
<220> FEATURE:
<221> NAME/KEY: MISC_FEATURE
<222> LOCATION: (8)..(8)
<223> OTHER INFORMATION: X is N or Q for amidated amino acids
<220> FEATURE:
<221> NAME/KEY: MISC_FEATURE
<222> LOCATION: (9)..(9)
<223> OTHER INFORMATION: X is T or S
<220> FEATURE:
<221> NAME/KEY: MISC_FEATURE
<222> LOCATION: (10)..(10)
<223> OTHER INFORMATION: X is  C or S
<220> FEATURE:
<221> NAME/KEY: MISC_FEATURE
<222> LOCATION: (11)..(11)
<223> OTHER INFORMATION: X is I, L or V
<220> FEATURE:
<221> NAME/KEY: MISC_FEATURE
<222> LOCATION: (12)..(12)
<223> OTHER INFORMATION: X is A  or G
<220> FEATURE:
<221> NAME/KEY: MISC_FEATURE
<222> LOCATION: (13)..(13)
<223> OTHER INFORMATION: X is K, R or H for basic amino acids
<220> FEATURE:
<221> NAME/KEY: MISC_FEATURE
<222> LOCATION: (14)..(14)
<223> OTHER INFORMATION: X is K, R or H for basic amino acids
<220> FEATURE:
<221> NAME/KEY: MISC_FEATURE
<222> LOCATION: (15)..(15)
<223> OTHER INFORMATION: X is F or P

<400> SEQUENCE: 30

Xaa Xaa Xaa Xaa Xaa Xaa Xaa Xaa Xaa Xaa Xaa Xaa Xaa Xaa Xaa
1               5                   10                  15

<210> SEQ ID NO 31
<211> LENGTH: 9
<212> TYPE: PRT
<213> ORGANISM: Artificial
<220> FEATURE:
<223> OTHER INFORMATION: peptide construct
<220> FEATURE:
<221> NAME/KEY: MISC_FEATURE
```

```
<222> LOCATION: (1)..(1)
<223> OTHER INFORMATION: X is A or G
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: X is F, W or Y for aromatic amino acids
<220> FEATURE:
<221> NAME/KEY: MISC_FEATURE
<222> LOCATION: (3)..(3)
<223> OTHER INFORMATION: X is M or Nle
<220> FEATURE:
<221> NAME/KEY: MISC_FEATURE
<222> LOCATION: (4)..(4)
<223> OTHER INFORMATION: X is T or S
<220> FEATURE:
<221> NAME/KEY: MISC_FEATURE
<222> LOCATION: (5)..(5)
<223> OTHER INFORMATION: X is M or Nle
<220> FEATURE:
<221> NAME/KEY: MISC_FEATURE
<222> LOCATION: (6)..(6)
<223> OTHER INFORMATION: X is K, R or H for basic amino acids
<220> FEATURE:
<221> NAME/KEY: MISC_FEATURE
<222> LOCATION: (7)..(7)
<223> OTHER INFORMATION: X is I, L or V
<220> FEATURE:
<221> NAME/KEY: MISC_FEATURE
<222> LOCATION: (8)..(8)
<223> OTHER INFORMATION: X is K, R or H for basic amino acids
<220> FEATURE:
<221> NAME/KEY: MISC_FEATURE
<222> LOCATION: (9)..(9)
<223> OTHER INFORMATION: X is N or Q for amidated amino acids

<400> SEQUENCE: 31

Xaa Xaa Xaa Xaa Xaa Xaa Xaa Xaa Xaa
1               5

<210> SEQ ID NO 32
<211> LENGTH: 31
<212> TYPE: PRT
<213> ORGANISM: Homo sapiens

<400> SEQUENCE: 32

Asp Asn Gln Leu Leu Glu Thr Cys Lys Gln Asp Arg Leu Arg Asn Arg
1               5                   10                  15

Arg Gly Asn Gly Ser Ser Thr His Phe Glu Gly Asn Leu Pro Cys
            20                  25                  30

<210> SEQ ID NO 33
<211> LENGTH: 31
<212> TYPE: PRT
<213> ORGANISM: Artificial
<220> FEATURE:
<223> OTHER INFORMATION: peptide construct
<220> FEATURE:
<221> NAME/KEY: MISC_FEATURE
<222> LOCATION: (1)..(1)
<223> OTHER INFORMATION: X is D and E for acidic amino acids
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: X is N or Q for amidated amino acids
<220> FEATURE:
<221> NAME/KEY: MISC_FEATURE
```

```
<222> LOCATION: (3)..(3)
<223> OTHER INFORMATION: X is N or Q for amidated amino acids
<220> FEATURE:
<221> NAME/KEY: MISC_FEATURE
<222> LOCATION: (4)..(4)
<223> OTHER INFORMATION: X is I, L or V
<220> FEATURE:
<221> NAME/KEY: MOD_RES
<222> LOCATION: (4)..(4)
<223> OTHER INFORMATION: 4Abu
<220> FEATURE:
<221> NAME/KEY: MOD_RES
<222> LOCATION: (4)..(4)
<223> OTHER INFORMATION: GAMMA-CARBOXYGLUTAMIC ACID HYDROXYLATION
<220> FEATURE:
<221> NAME/KEY: MISC_FEATURE
<222> LOCATION: (5)..(5)
<223> OTHER INFORMATION: X is I, L or V
<220> FEATURE:
<221> NAME/KEY: MISC_FEATURE
<222> LOCATION: (6)..(6)
<223> OTHER INFORMATION: X is D and E for acidic amino acids
<220> FEATURE:
<221> NAME/KEY: MISC_FEATURE
<222> LOCATION: (7)..(7)
<223> OTHER INFORMATION: X is T or S
<220> FEATURE:
<221> NAME/KEY: MISC_FEATURE
<222> LOCATION: (8)..(8)
<223> OTHER INFORMATION: X is C or S
<220> FEATURE:
<221> NAME/KEY: MISC_FEATURE
<222> LOCATION: (9)..(9)
<223> OTHER INFORMATION: X is K, R or H for basic amino acids
<220> FEATURE:
<221> NAME/KEY: MISC_FEATURE
<222> LOCATION: (10)..(10)
<223> OTHER INFORMATION: X is N or Q for amidated amino acids
<220> FEATURE:
<221> NAME/KEY: MISC_FEATURE
<222> LOCATION: (11)..(11)
<223> OTHER INFORMATION: X is  D and E for acidic amino acids
<220> FEATURE:
<221> NAME/KEY: MISC_FEATURE
<222> LOCATION: (12)..(12)
<223> OTHER INFORMATION: X is K, R or H for basic amino acids
<220> FEATURE:
<221> NAME/KEY: MISC_FEATURE
<222> LOCATION: (13)..(13)
<223> OTHER INFORMATION: X is I, L or V
<220> FEATURE:
<221> NAME/KEY: MISC_FEATURE
<222> LOCATION: (14)..(14)
<223> OTHER INFORMATION: X is K, R or H for basic amino acids
<220> FEATURE:
<221> NAME/KEY: MISC_FEATURE
<222> LOCATION: (15)..(15)
<223> OTHER INFORMATION: X is N or Q for amidated amino acids
<220> FEATURE:
<221> NAME/KEY: MISC_FEATURE
<222> LOCATION: (16)..(16)
<223> OTHER INFORMATION: X is K, R or H for basic amino acids
<220> FEATURE:
<221> NAME/KEY: MISC_FEATURE
<222> LOCATION: (17)..(17)
<223> OTHER INFORMATION: X is K, R or H for basic amino acids
<220> FEATURE:
<221> NAME/KEY: MISC_FEATURE
<222> LOCATION: (18)..(18)
<223> OTHER INFORMATION: X is  A or G
<220> FEATURE:
<221> NAME/KEY: MISC_FEATURE
<222> LOCATION: (19)..(19)
<223> OTHER INFORMATION: X is N or Q for amidated amino acids
<220> FEATURE:
<221> NAME/KEY: MISC_FEATURE
<222> LOCATION: (20)..(20)
<223> OTHER INFORMATION: X is A or G
<220> FEATURE:
```

<221> NAME/KEY: MISC_FEATURE
<222> LOCATION: (21)..(21)
<223> OTHER INFORMATION: X is C or S
<220> FEATURE:
<221> NAME/KEY: MISC_FEATURE
<222> LOCATION: (22)..(22)
<223> OTHER INFORMATION: X is C or S
<220> FEATURE:
<221> NAME/KEY: MISC_FEATURE
<222> LOCATION: (23)..(23)
<223> OTHER INFORMATION: X is T or S
<220> FEATURE:
<221> NAME/KEY: MISC_FEATURE
<222> LOCATION: (24)..(24)
<223> OTHER INFORMATION: X is K, R or H for basic amino acids
<220> FEATURE:
<221> NAME/KEY: MISC_FEATURE
<222> LOCATION: (25)..(25)
<223> OTHER INFORMATION: X is F, W or Y for aromatic amino acids
<220> FEATURE:
<221> NAME/KEY: MISC_FEATURE
<222> LOCATION: (26)..(26)
<223> OTHER INFORMATION: X is D and E for acidic amino acids
<220> FEATURE:
<221> NAME/KEY: MISC_FEATURE
<222> LOCATION: (27)..(27)
<223> OTHER INFORMATION: X is A or G
<220> FEATURE:
<221> NAME/KEY: MISC_FEATURE
<222> LOCATION: (28)..(28)
<223> OTHER INFORMATION: X is N or Q for amidated amino acids
<220> FEATURE:
<221> NAME/KEY: MISC_FEATURE
<222> LOCATION: (29)..(29)
<223> OTHER INFORMATION: X is I,  L or V
<220> FEATURE:
<221> NAME/KEY: MISC_FEATURE
<222> LOCATION: (30)..(30)
<223> OTHER INFORMATION: X is F or P
<220> FEATURE:
<221> NAME/KEY: MISC_FEATURE
<222> LOCATION: (31)..(31)
<223> OTHER INFORMATION: X is C or S

<400> SEQUENCE: 33

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

<210> SEQ ID NO 34
<211> LENGTH: 10
<212> TYPE: PRT
<213> ORGANISM: Artificial
<220> FEATURE:
<223> OTHER INFORMATION: peptide construct
<220> FEATURE:
<221> NAME/KEY: MISC_FEATURE
<222> LOCATION: (1)..(1)
<223> OTHER INFORMATION: X is D and E for acidic amino acids
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: X is N or Q for amidated amino acids
<220> FEATURE:
<221> NAME/KEY: MISC_FEATURE
<222> LOCATION: (3)..(3)
<223> OTHER INFORMATION: X is T or S
<220> FEATURE:
<221> NAME/KEY: MISC_FEATURE
<222> LOCATION: (4)..(4)
<223> OTHER INFORMATION: X is N or Q for amidated amino acids

```
<220> FEATURE:
<221> NAME/KEY: MISC_FEATURE
<222> LOCATION: (5)..(5)
<223> OTHER INFORMATION: X is D and E for acidic amino acids
<220> FEATURE:
<221> NAME/KEY: MISC_FEATURE
<222> LOCATION: (6)..(6)
<223> OTHER INFORMATION: X is T or S
<220> FEATURE:
<221> NAME/KEY: MISC_FEATURE
<222> LOCATION: (7)..(7)
<223> OTHER INFORMATION: X is D and E for acidic amino acids
<220> FEATURE:
<221> NAME/KEY: MISC_FEATURE
<222> LOCATION: (8)..(8)
<223> OTHER INFORMATION: X is A or G
<220> FEATURE:
<221> NAME/KEY: MISC_FEATURE
<222> LOCATION: (9)..(9)
<223> OTHER INFORMATION: X is A or G
<220> FEATURE:
<221> NAME/KEY: MISC_FEATURE
<222> LOCATION: (10)..(10)
<223> OTHER INFORMATION: X is C or S

<400> SEQUENCE: 34

Xaa Xaa Xaa Xaa Xaa Xaa Xaa Xaa Xaa Xaa
 1               5                  10

<210> SEQ ID NO 35
<211> LENGTH: 9
<212> TYPE: PRT
<213> ORGANISM: Artificial
<220> FEATURE:
<223> OTHER INFORMATION: peptide construct
<220> FEATURE:
<221> NAME/KEY: MISC_FEATURE
<222> LOCATION: (1)..(1)
<223> OTHER INFORMATION: X is I, L or V
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: X is N or Q for amidated amino acids
<220> FEATURE:
<221> NAME/KEY: MISC_FEATURE
<222> LOCATION: (3)..(3)
<223> OTHER INFORMATION: X is A or G
<220> FEATURE:
<221> NAME/KEY: MISC_FEATURE
<222> LOCATION: (4)..(4)
<223> OTHER INFORMATION: X is D and E for acidic amino acids
<220> FEATURE:
<221> NAME/KEY: MOD_RES
<222> LOCATION: (4)..(4)
<223> OTHER INFORMATION: 4Abu
<220> FEATURE:
<221> NAME/KEY: MISC_FEATURE
<222> LOCATION: (5)..(5)
<223> OTHER INFORMATION: X is D and E for acidic amino acids
<220> FEATURE:
<221> NAME/KEY: MISC_FEATURE
<222> LOCATION: (6)..(6)
<223> OTHER INFORMATION: X is C or S
<220> FEATURE:
<221> NAME/KEY: MISC_FEATURE
<222> LOCATION: (7)..(7)
<223> OTHER INFORMATION: X is N or Q for amidated amino acids
<220> FEATURE:
<221> NAME/KEY: MISC_FEATURE
<222> LOCATION: (8)..(8)
<223> OTHER INFORMATION: X is D and E for acidic amino acids
<220> FEATURE:
<221> NAME/KEY: MISC_FEATURE
```

<222> LOCATION: (9)..(9)
<223> OTHER INFORMATION: X is K, R or H for basic amino acids

<400> SEQUENCE: 35

Xaa Xaa Xaa Xaa Xaa Xaa Xaa Xaa Xaa
1               5

<210> SEQ ID NO 36
<211> LENGTH: 16
<212> TYPE: PRT
<213> ORGANISM: Artificial
<220> FEATURE:
<223> OTHER INFORMATION: peptide construct
<220> FEATURE:
<221> NAME/KEY: MISC_FEATURE
<222> LOCATION: (1)..(1)
<223> OTHER INFORMATION: X is D and E for acidic amino acids
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: 4Abu
<220> FEATURE:
<221> NAME/KEY: MOD_RES
<222> LOCATION: (1)..(1)
<223> OTHER INFORMATION: GAMMA-CARBOXYGLUTAMIC ACID HYDROXYLATION
<220> FEATURE:
<221> NAME/KEY: MISC_FEATURE
<222> LOCATION: (2)..(2)
<223> OTHER INFORMATION: X is I, L or V
<220> FEATURE:
<221> NAME/KEY: MISC_FEATURE
<222> LOCATION: (3)..(3)
<223> OTHER INFORMATION: X is I, L or V
<220> FEATURE:
<221> NAME/KEY: MISC_FEATURE
<222> LOCATION: (4)..(4)
<223> OTHER INFORMATION: X is K, R or H for basic amino acids
<220> FEATURE:
<221> NAME/KEY: MISC_FEATURE
<222> LOCATION: (5)..(5)
<223> OTHER INFORMATION: X is N or Q for amidated amino acids
<220> FEATURE:
<221> NAME/KEY: MISC_FEATURE
<222> LOCATION: (6)..(6)
<223> OTHER INFORMATION: X is A or G
<220> FEATURE:
<221> NAME/KEY: MISC_FEATURE
<222> LOCATION: (7)..(7)
<223> OTHER INFORMATION: X is D and E for acidic amino acids
<220> FEATURE:
<221> NAME/KEY: MISC_FEATURE
<222> LOCATION: (8)..(8)
<223> OTHER INFORMATION: X is K, R or H for basic amino acids
<220> FEATURE:
<221> NAME/KEY: MISC_FEATURE
<222> LOCATION: (9)..(9)
<223> OTHER INFORMATION: X is I, L or V
<220> FEATURE:
<221> NAME/KEY: MOD_RES
<222> LOCATION: (9)..(9)
<223> OTHER INFORMATION: 4Abu
<220> FEATURE:
<221> NAME/KEY: MISC_FEATURE
<222> LOCATION: (10)..(10)
<223> OTHER INFORMATION: X is D and E for acidic amino acids
<220> FEATURE:
<221> NAME/KEY: MISC_FEATURE
<222> LOCATION: (11)..(11)
<223> OTHER INFORMATION: X is K, R or H for basic amino acids
<220> FEATURE:
<221> NAME/KEY: MISC_FEATURE
<222> LOCATION: (12)..(12)
<223> OTHER INFORMATION: X is I, L or V

```
<220> FEATURE:
<221> NAME/KEY: MOD_RES
<222> LOCATION: (12)..(12)
<223> OTHER INFORMATION: 4Abu
<220> FEATURE:
<221> NAME/KEY: MISC_FEATURE
<222> LOCATION: (13)..(13)
<223> OTHER INFORMATION: X is D and E for acidic amino acids
<220> FEATURE:
<221> NAME/KEY: MISC_FEATURE
<222> LOCATION: (14)..(14)
<223> OTHER INFORMATION: X is A or G
<220> FEATURE:
<221> NAME/KEY: MISC_FEATURE
<222> LOCATION: (15)..(15)
<223> OTHER INFORMATION: X is A or G
<220> FEATURE:
<221> NAME/KEY: MISC_FEATURE
<222> LOCATION: (16)..(16)
<223> OTHER INFORMATION: X is A or G

<400> SEQUENCE: 36

Xaa Xaa Xaa Xaa Xaa Xaa Xaa Xaa Xaa Xaa Xaa Xaa Xaa Xaa Xaa Xaa
1               5                   10                  15

<210> SEQ ID NO 37
<211> LENGTH: 4
<212> TYPE: PRT
<213> ORGANISM: Artificial
<220> FEATURE:
<223> OTHER INFORMATION: peptide construct
<220> FEATURE:
<221> NAME/KEY: MISC_FEATURE
<222> LOCATION: (1)..(1)
<223> OTHER INFORMATION: X is A or G
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: X is A or G
<220> FEATURE:
<221> NAME/KEY: MISC_FEATURE
<222> LOCATION: (3)..(3)
<223> OTHER INFORMATION: X is A or G
<220> FEATURE:
<221> NAME/KEY: MISC_FEATURE
<222> LOCATION: (4)..(4)
<223> OTHER INFORMATION: X is C or S

<400> SEQUENCE: 37

Xaa Xaa Xaa Xaa
1

<210> SEQ ID NO 38
<211> LENGTH: 5
<212> TYPE: PRT
<213> ORGANISM: Artificial
<220> FEATURE:
<223> OTHER INFORMATION: peptide construct
<220> FEATURE:
<221> NAME/KEY: MISC_FEATURE
<222> LOCATION: (1)..(1)
<223> OTHER INFORMATION: X is A or G
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: X is A or G
<220> FEATURE:
```

```
<221> NAME/KEY: MISC_FEATURE
<222> LOCATION: (3)..(3)
<223> OTHER INFORMATION: X is A or G
<220> FEATURE:
<221> NAME/KEY: MISC_FEATURE
<222> LOCATION: (4)..(4)
<223> OTHER INFORMATION: X is C or S
<220> FEATURE:
<221> NAME/KEY: MISC_FEATURE
<222> LOCATION: (5)..(5)
<223> OTHER INFORMATION: X is C or S

<400> SEQUENCE: 38

Xaa Xaa Xaa Xaa Xaa
1               5

<210> SEQ ID NO 39
<211> LENGTH: 5
<212> TYPE: PRT
<213> ORGANISM: Artificial
<220> FEATURE:
<223> OTHER INFORMATION: peptide construct
<220> FEATURE:
<221> NAME/KEY: MISC_FEATURE
<222> LOCATION: (1)..(1)
<223> OTHER INFORMATION: X is A or G
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: X is A or G
<220> FEATURE:
<221> NAME/KEY: MISC_FEATURE
<222> LOCATION: (3)..(3)
<223> OTHER INFORMATION: X is A or G
<220> FEATURE:
<221> NAME/KEY: MISC_FEATURE
<222> LOCATION: (4)..(4)
<223> OTHER INFORMATION: X is A or G
<220> FEATURE:
<221> NAME/KEY: MISC_FEATURE
<222> LOCATION: (5)..(5)
<223> OTHER INFORMATION: X is C or S

<400> SEQUENCE: 39

Xaa Xaa Xaa Xaa Xaa
1               5

<210> SEQ ID NO 40
<211> LENGTH: 5
<212> TYPE: PRT
<213> ORGANISM: Artificial
<220> FEATURE:
<223> OTHER INFORMATION: peptide construct
<220> FEATURE:
<221> NAME/KEY: MISC_FEATURE
<222> LOCATION: (1)..(1)
<223> OTHER INFORMATION: X is A or G
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: X is A or G
<220> FEATURE:
<221> NAME/KEY: MISC_FEATURE
<222> LOCATION: (3)..(3)
<223> OTHER INFORMATION: X is A or G
<220> FEATURE:
<221> NAME/KEY: MISC_FEATURE
```

```
<222> LOCATION: (4)..(4)
<223> OTHER INFORMATION: X is A or G
<220> FEATURE:
<221> NAME/KEY: MISC_FEATURE
<222> LOCATION: (5)..(5)
<223> OTHER INFORMATION: X is C or S

<400> SEQUENCE: 40

Xaa Xaa Xaa Xaa Xaa
1               5

<210> SEQ ID NO 41
<211> LENGTH: 8
<212> TYPE: PRT
<213> ORGANISM: Artificial
<220> FEATURE:
<223> OTHER INFORMATION: peptide construct
<220> FEATURE:
<221> NAME/KEY: MISC_FEATURE
<222> LOCATION: (1)..(1)
<223> OTHER INFORMATION: X is A or G
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: X is A or G
<220> FEATURE:
<221> NAME/KEY: MISC_FEATURE
<222> LOCATION: (3)..(3)
<223> OTHER INFORMATION: X is A or G
<220> FEATURE:
<221> NAME/KEY: MISC_FEATURE
<222> LOCATION: (4)..(4)
<223> OTHER INFORMATION: X is C or S
<220> FEATURE:
<221> NAME/KEY: MISC_FEATURE
<222> LOCATION: (5)..(5)
<223> OTHER INFORMATION: X is A or G
<220> FEATURE:
<221> NAME/KEY: MISC_FEATURE
<222> LOCATION: (6)..(6)
<223> OTHER INFORMATION: X is A or G
<220> FEATURE:
<221> NAME/KEY: MISC_FEATURE
<222> LOCATION: (7)..(7)
<223> OTHER INFORMATION: X is A or G
<220> FEATURE:
<221> NAME/KEY: MISC_FEATURE
<222> LOCATION: (8)..(8)
<223> OTHER INFORMATION: X is C or S

<400> SEQUENCE: 41

Xaa Xaa Xaa Xaa Xaa Xaa Xaa Xaa
1               5

<210> SEQ ID NO 42
<211> LENGTH: 8
<212> TYPE: PRT
<213> ORGANISM: Artificial
<220> FEATURE:
<223> OTHER INFORMATION: peptide construct
<220> FEATURE:
<221> NAME/KEY: MISC_FEATURE
<222> LOCATION: (1)..(1)
<223> OTHER INFORMATION: X is I, L or V
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
```

<223> OTHER INFORMATION: X is K, R or H for basic amino acids
<220> FEATURE:
<221> NAME/KEY: MISC_FEATURE
<222> LOCATION: (3)..(3)
<223> OTHER INFORMATION: X is A or G
<220> FEATURE:
<221> NAME/KEY: MISC_FEATURE
<222> LOCATION: (4)..(4)
<223> OTHER INFORMATION: X is A or G
<220> FEATURE:
<221> NAME/KEY: MISC_FEATURE
<222> LOCATION: (5)..(5)
<223> OTHER INFORMATION: X is A or G
<220> FEATURE:
<221> NAME/KEY: MISC_FEATURE
<222> LOCATION: (6)..(6)
<223> OTHER INFORMATION: X is A or G
<220> FEATURE:
<221> NAME/KEY: MISC_FEATURE
<222> LOCATION: (7)..(7)
<223> OTHER INFORMATION: X is C or S
<220> FEATURE:
<221> NAME/KEY: MISC_FEATURE
<222> LOCATION: (8)..(8)
<223> OTHER INFORMATION: X is C or S

<400> SEQUENCE: 42

Xaa Xaa Xaa Xaa Xaa Xaa Xaa Xaa
1               5

<210> SEQ ID NO 43
<211> LENGTH: 12
<212> TYPE: PRT
<213> ORGANISM: Artificial
<220> FEATURE:
<223> OTHER INFORMATION: peptide construct
<220> FEATURE:
<221> NAME/KEY: MISC_FEATURE
<222> LOCATION: (1)..(1)
<223> OTHER INFORMATION: X is A or G
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: X is A or G
<220> FEATURE:
<221> NAME/KEY: MISC_FEATURE
<222> LOCATION: (3)..(3)
<223> OTHER INFORMATION: X is A or G
<220> FEATURE:
<221> NAME/KEY: MISC_FEATURE
<222> LOCATION: (4)..(4)
<223> OTHER INFORMATION: X is C or S
<220> FEATURE:
<221> NAME/KEY: MISC_FEATURE
<222> LOCATION: (5)..(5)
<223> OTHER INFORMATION: X is A or G
<220> FEATURE:
<221> NAME/KEY: MISC_FEATURE
<222> LOCATION: (6)..(6)
<223> OTHER INFORMATION: X is T or S
<220> FEATURE:
<221> NAME/KEY: MISC_FEATURE
<222> LOCATION: (7)..(7)
<223> OTHER INFORMATION: X is A or G
<220> FEATURE:
<221> NAME/KEY: MISC_FEATURE
<222> LOCATION: (8)..(8)
<223> OTHER INFORMATION: X is C or S
<220> FEATURE:
<221> NAME/KEY: MISC_FEATURE
<222> LOCATION: (9)..(9)
<223> OTHER INFORMATION: X is A or G
<220> FEATURE:

```
<221> NAME/KEY: MISC_FEATURE
<222> LOCATION: (10)..(10)
<223> OTHER INFORMATION: X is C or S
<220> FEATURE:
<221> NAME/KEY: MISC_FEATURE
<222> LOCATION: (11)..(11)
<223> OTHER INFORMATION: X is A or G
<220> FEATURE:
<221> NAME/KEY: MISC_FEATURE
<222> LOCATION: (12)..(12)
<223> OTHER INFORMATION: X is C or S

<400> SEQUENCE: 43

Xaa Xaa Xaa Xaa Xaa Xaa Xaa Xaa Xaa Xaa Xaa Xaa
1               5                   10

<210> SEQ ID NO 44
<211> LENGTH: 31
<212> TYPE: PRT
<213> ORGANISM: Artificial
<220> FEATURE:
<223> OTHER INFORMATION: Completely synthesized peptide construct

<400> SEQUENCE: 44

Asp Gly Gln Glu Glu Lys Ala Gly Val Val Ser Thr Gly Leu Ile Gly
1               5                   10                  15

Gly Gly Ile Ala Gly Phe Lys Gly Glu Gln Gly Pro Lys Gly Glu
            20                  25                  30

<210> SEQ ID NO 45
<211> LENGTH: 31
<212> TYPE: PRT
<213> ORGANISM: Artificial
<220> FEATURE:
<223> OTHER INFORMATION: peptide construct
<220> FEATURE:
<221> NAME/KEY: MISC_FEATURE
<222> LOCATION: (1)..(1)
<223> OTHER INFORMATION: X is D and E for acidic amino acids
<220> FEATURE:
<221> NAME/KEY: MISC_FEATURE
<222> LOCATION: (2)..(2)
<223> OTHER INFORMATION: X is A or G
<220> FEATURE:
<221> NAME/KEY: MISC_FEATURE
<222> LOCATION: (3)..(3)
<223> OTHER INFORMATION: X is N or Q for amidated amino acids
<220> FEATURE:
<221> NAME/KEY: MISC_FEATURE
<222> LOCATION: (4)..(4)
<223> OTHER INFORMATION: X is D and E for acidic amino acids
<220> FEATURE:
<221> NAME/KEY: MISC_FEATURE
<222> LOCATION: (5)..(5)
<223> OTHER INFORMATION: X is D and E for acidic amino acids
<220> FEATURE:
<221> NAME/KEY: MISC_FEATURE
<222> LOCATION: (6)..(6)
<223> OTHER INFORMATION: X is K, R or H for basic amino acids
<220> FEATURE:
<221> NAME/KEY: MISC_FEATURE
<222> LOCATION: (7)..(7)
<223> OTHER INFORMATION: X is A or G
<220> FEATURE:
<221> NAME/KEY: MISC_FEATURE
<222> LOCATION: (8)..(8)
<223> OTHER INFORMATION: X is A or G
<220> FEATURE:
<221> NAME/KEY: MISC_FEATURE
<222> LOCATION: (9)..(9)
<223> OTHER INFORMATION: X is I, L or V
<220> FEATURE:
<221> NAME/KEY: MISC_FEATURE
<222> LOCATION: (10)..(10)
```

```
<223> OTHER INFORMATION: X is I, L or V
<220> FEATURE:
<221> NAME/KEY: MISC_FEATURE
<222> LOCATION: (11)..(11)
<223> OTHER INFORMATION: X is C or S
<220> FEATURE:
<221> NAME/KEY: MISC_FEATURE
<222> LOCATION: (12)..(12)
<223> OTHER INFORMATION: X is T or S
<220> FEATURE:
<221> NAME/KEY: MISC_FEATURE
<222> LOCATION: (13)..(13)
<223> OTHER INFORMATION: X is A or G
<220> FEATURE:
<221> NAME/KEY: MISC_FEATURE
<222> LOCATION: (14)..(14)
<223> OTHER INFORMATION: X is I, L or V
<220> FEATURE:
<221> NAME/KEY: MISC_FEATURE
<222> LOCATION: (15)..(15)
<223> OTHER INFORMATION: X is I, L or V
<220> FEATURE:
<221> NAME/KEY: MISC_FEATURE
<222> LOCATION: (16)..(16)
<223> OTHER INFORMATION: X is A or G
<220> FEATURE:
<221> NAME/KEY: MISC_FEATURE
<222> LOCATION: (17)..(17)
<223> OTHER INFORMATION: X is A or G
<220> FEATURE:
<221> NAME/KEY: MISC_FEATURE
<222> LOCATION: (18)..(18)
<223> OTHER INFORMATION: X is A or G
<220> FEATURE:
<221> NAME/KEY: MISC_FEATURE
<222> LOCATION: (19)..(19)
<223> OTHER INFORMATION: X is I, L or V
<220> FEATURE:
<221> NAME/KEY: MISC_FEATURE
<222> LOCATION: (20)..(20)
<223> OTHER INFORMATION: X is A or G
<220> FEATURE:
<221> NAME/KEY: MISC_FEATURE
<222> LOCATION: (21)..(21)
<223> OTHER INFORMATION: X is A or G
<220> FEATURE:
<221> NAME/KEY: MISC_FEATURE
<222> LOCATION: (22)..(22)
<223> OTHER INFORMATION: X is F, W or Y for aromatic amino acids
<220> FEATURE:
<221> NAME/KEY: MISC_FEATURE
<222> LOCATION: (23)..(23)
<223> OTHER INFORMATION: X is K, R or H for basic amino acids
<220> FEATURE:
<221> NAME/KEY: MISC_FEATURE
<222> LOCATION: (24)..(24)
<223> OTHER INFORMATION: X is A or G
<220> FEATURE:
<221> NAME/KEY: MISC_FEATURE
<222> LOCATION: (25)..(25)
<223> OTHER INFORMATION: X is D and E for acidic amino acids
<220> FEATURE:
<221> NAME/KEY: MISC_FEATURE
<222> LOCATION: (26)..(26)
<223> OTHER INFORMATION: X is N or Q for amidated amino acids
<220> FEATURE:
<221> NAME/KEY: MISC_FEATURE
<222> LOCATION: (27)..(27)
<223> OTHER INFORMATION: X is A or G
<220> FEATURE:
<221> NAME/KEY: MISC_FEATURE
<222> LOCATION: (28)..(28)
<223> OTHER INFORMATION: X is F or P
<220> FEATURE:
<221> NAME/KEY: MISC_FEATURE
<222> LOCATION: (29)..(29)
<223> OTHER INFORMATION: X is K, R or H for basic amino acids
<220> FEATURE:
<221> NAME/KEY: MISC_FEATURE
```

```
<222> LOCATION: (30)..(30)
<223> OTHER INFORMATION: X is A or G
<220> FEATURE:
<221> NAME/KEY: MISC_FEATURE
<222> LOCATION: (31)..(31)
<223> OTHER INFORMATION: X is D and E for acidic amino acids

<400> SEQUENCE: 45

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

<210> SEQ ID NO 46
<211> LENGTH: 31
<212> TYPE: PRT
<213> ORGANISM: Artificial
<220> FEATURE:
<223> OTHER INFORMATION: Completely synthesized peptide construct

<400> SEQUENCE: 46

Ile Ala Gly Phe Lys Gly Glu Gln Gly Pro Lys Gly Glu Gly Gly
1               5                   10                  15

Asp Gly Gln Glu Glu Lys Ala Gly Val Val Ser Thr Gly Leu Ile
            20                  25                  30

<210> SEQ ID NO 47
<211> LENGTH: 31
<212> TYPE: PRT
<213> ORGANISM: Artificial
<220> FEATURE:
<223> OTHER INFORMATION: peptide construct
<220> FEATURE:
<221> NAME/KEY: MISC_FEATURE
<222> LOCATION: (1)..(1)
<223> OTHER INFORMATION: X is I, L or V
<220> FEATURE:
<221> NAME/KEY: MISC_FEATURE
<222> LOCATION: (2)..(2)
<223> OTHER INFORMATION: X is A or G
<220> FEATURE:
<221> NAME/KEY: MISC_FEATURE
<222> LOCATION: (3)..(3)
<223> OTHER INFORMATION: X is A or G
<220> FEATURE:
<221> NAME/KEY: MISC_FEATURE
<222> LOCATION: (4)..(4)
<223> OTHER INFORMATION: X is F, W or Y for aromatic amino acids
<220> FEATURE:
<221> NAME/KEY: MISC_FEATURE
<222> LOCATION: (5)..(5)
<223> OTHER INFORMATION: X is K, R or H for basic amino acids
<220> FEATURE:
<221> NAME/KEY: MISC_FEATURE
<222> LOCATION: (6)..(6)
<223> OTHER INFORMATION: X is A or G
<220> FEATURE:
<221> NAME/KEY: MISC_FEATURE
<222> LOCATION: (7)..(7)
<223> OTHER INFORMATION: X is D and E for acidic amino acids
<220> FEATURE:
<221> NAME/KEY: MISC_FEATURE
<222> LOCATION: (8)..(8)
<223> OTHER INFORMATION: X is N or Q for amidated amino acids
<220> FEATURE:
<221> NAME/KEY: MISC_FEATURE
<222> LOCATION: (9)..(9)
<223> OTHER INFORMATION: X is A or G
<220> FEATURE:
<221> NAME/KEY: MISC_FEATURE
<222> LOCATION: (10)..(10)
<223> OTHER INFORMATION: X is F or P
<220> FEATURE:
```

```
<221> NAME/KEY: MISC_FEATURE
<222> LOCATION: (11)..(11)
<223> OTHER INFORMATION: X is K, R or H for basic amino acids
<220> FEATURE:
<221> NAME/KEY: MISC_FEATURE
<222> LOCATION: (12)..(12)
<223> OTHER INFORMATION: X is A or G
<220> FEATURE:
<221> NAME/KEY: MISC_FEATURE
<222> LOCATION: (13)..(13)
<223> OTHER INFORMATION: X is D and E for acidic amino acids
<220> FEATURE:
<221> NAME/KEY: MISC_FEATURE
<222> LOCATION: (14)..(14)
<223> OTHER INFORMATION: X is A and G
<220> FEATURE:
<221> NAME/KEY: MISC_FEATURE
<222> LOCATION: (15)..(15)
<223> OTHER INFORMATION: X is A for G
<220> FEATURE:
<221> NAME/KEY: MISC_FEATURE
<222> LOCATION: (16)..(16)
<223> OTHER INFORMATION: X is A and G
<220> FEATURE:
<221> NAME/KEY: MISC_FEATURE
<222> LOCATION: (17)..(17)
<223> OTHER INFORMATION: X is D and E for acidic amino acids
<220> FEATURE:
<221> NAME/KEY: MISC_FEATURE
<222> LOCATION: (18)..(18)
<223> OTHER INFORMATION: X is A and G
<220> FEATURE:
<221> NAME/KEY: MISC_FEATURE
<222> LOCATION: (19)..(19)
<223> OTHER INFORMATION: X is N or Q for amidated amino acids
<220> FEATURE:
<221> NAME/KEY: MISC_FEATURE
<222> LOCATION: (20)..(20)
<223> OTHER INFORMATION: X is D and E for acidic amino acids
<220> FEATURE:
<221> NAME/KEY: MISC_FEATURE
<222> LOCATION: (21)..(21)
<223> OTHER INFORMATION: X is D and E for acidic amino acids
<220> FEATURE:
<221> NAME/KEY: MISC_FEATURE
<222> LOCATION: (22)..(22)
<223> OTHER INFORMATION: X is K, R or H for basic amino acids
<220> FEATURE:
<221> NAME/KEY: MISC_FEATURE
<222> LOCATION: (23)..(23)
<223> OTHER INFORMATION: X is A and G
<220> FEATURE:
<221> NAME/KEY: MISC_FEATURE
<222> LOCATION: (24)..(24)
<223> OTHER INFORMATION: X is A and G
<220> FEATURE:
<221> NAME/KEY: MISC_FEATURE
<222> LOCATION: (25)..(25)
<223> OTHER INFORMATION: X is I, L or V
<220> FEATURE:
<221> NAME/KEY: MISC_FEATURE
<222> LOCATION: (26)..(26)
<223> OTHER INFORMATION: X is I, L or V
<220> FEATURE:
<221> NAME/KEY: MISC_FEATURE
<222> LOCATION: (27)..(27)
<223> OTHER INFORMATION: X is C or S
<220> FEATURE:
<221> NAME/KEY: MISC_FEATURE
<222> LOCATION: (28)..(28)
<223> OTHER INFORMATION: X is T or S
<220> FEATURE:
<221> NAME/KEY: MISC_FEATURE
<222> LOCATION: (29)..(29)
<223> OTHER INFORMATION: X is A and G
<220> FEATURE:
<221> NAME/KEY: MISC_FEATURE
<222> LOCATION: (30)..(30)
<223> OTHER INFORMATION: X is I, L or V
```

```
<220> FEATURE:
<221> NAME/KEY: MISC_FEATURE
<222> LOCATION: (31)..(31)
<223> OTHER INFORMATION: X is I, L or V

<400> SEQUENCE: 47

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa
            20                  25                  30

<210> SEQ ID NO 48
<211> LENGTH: 29
<212> TYPE: PRT
<213> ORGANISM: Artificial
<220> FEATURE:
<223> OTHER INFORMATION: Completely synthesized peptide construct

<400> SEQUENCE: 48

Asp Leu Leu Lys Asn Gly Glu Arg Ile Glu Lys Val Glu Gly Gly
1               5                   10                  15

Ile Ala Gly Phe Lys Gly Glu Gln Gly Pro Lys Gly Glu
            20                  25

<210> SEQ ID NO 49
<211> LENGTH: 29
<212> TYPE: PRT
<213> ORGANISM: Artificial
<220> FEATURE:
<223> OTHER INFORMATION: peptide construct
<220> FEATURE:
<221> NAME/KEY: MISC_FEATURE
<222> LOCATION: (1)..(1)
<223> OTHER INFORMATION: X is D and E for acidic amino acids
<220> FEATURE:
<221> NAME/KEY: MISC_FEATURE
<222> LOCATION: (2)..(2)
<223> OTHER INFORMATION: X is I, L or V
<220> FEATURE:
<221> NAME/KEY: MISC_FEATURE
<222> LOCATION: (3)..(3)
<223> OTHER INFORMATION: X is I, L or V
<220> FEATURE:
<221> NAME/KEY: MISC_FEATURE
<222> LOCATION: (4)..(4)
<223> OTHER INFORMATION: X is K, R or H for basic amino acids
<220> FEATURE:
<221> NAME/KEY: MISC_FEATURE
<222> LOCATION: (5)..(5)
<223> OTHER INFORMATION: X is N or Q for amidated amino acids
<220> FEATURE:
<221> NAME/KEY: MISC_FEATURE
<222> LOCATION: (6)..(6)
<223> OTHER INFORMATION: X is A or G
<220> FEATURE:
<221> NAME/KEY: MISC_FEATURE
<222> LOCATION: (7)..(7)
<223> OTHER INFORMATION: X is D and E for acidic amino acids
<220> FEATURE:
<221> NAME/KEY: MISC_FEATURE
<222> LOCATION: (8)..(8)
<223> OTHER INFORMATION: X is K, R or H for basic amino acids
<220> FEATURE:
<221> NAME/KEY: MISC_FEATURE
<222> LOCATION: (9)..(9)
<223> OTHER INFORMATION: X is I, L or V
<220> FEATURE:
<221> NAME/KEY: MISC_FEATURE
<222> LOCATION: (10)..(10)
<223> OTHER INFORMATION: X is D and E for acidic amino acids
<220> FEATURE:
<221> NAME/KEY: MISC_FEATURE
<222> LOCATION: (11)..(11)
```

-continued

```
<223> OTHER INFORMATION: X is K, R or H for basic amino acids
<220> FEATURE:
<221> NAME/KEY: MISC_FEATURE
<222> LOCATION: (12)..(12)
<223> OTHER INFORMATION: X is I, L or V
<220> FEATURE:
<221> NAME/KEY: MISC_FEATURE
<222> LOCATION: (13)..(13)
<223> OTHER INFORMATION: X is D and E for acidic amino acids
<220> FEATURE:
<221> NAME/KEY: MISC_FEATURE
<222> LOCATION: (14)..(14)
<223> OTHER INFORMATION: X is A or G
<220> FEATURE:
<221> NAME/KEY: MISC_FEATURE
<222> LOCATION: (15)..(15)
<223> OTHER INFORMATION: X is A or G
<220> FEATURE:
<221> NAME/KEY: MISC_FEATURE
<222> LOCATION: (16)..(16)
<223> OTHER INFORMATION: X is A or G
<220> FEATURE:
<221> NAME/KEY: MISC_FEATURE
<222> LOCATION: (17)..(17)
<223> OTHER INFORMATION: X is I, L or V
<220> FEATURE:
<221> NAME/KEY: MISC_FEATURE
<222> LOCATION: (18)..(18)
<223> OTHER INFORMATION: X is A or G
<220> FEATURE:
<221> NAME/KEY: MISC_FEATURE
<222> LOCATION: (19)..(19)
<223> OTHER INFORMATION: X is A or G
<220> FEATURE:
<221> NAME/KEY: MISC_FEATURE
<222> LOCATION: (20)..(20)
<223> OTHER INFORMATION: X is F, W or Y for aromatic amino acids
<220> FEATURE:
<221> NAME/KEY: MISC_FEATURE
<222> LOCATION: (21)..(21)
<223> OTHER INFORMATION: X is K, R or H for basic amino acids
<220> FEATURE:
<221> NAME/KEY: MISC_FEATURE
<222> LOCATION: (22)..(22)
<223> OTHER INFORMATION: X is A or G
<220> FEATURE:
<221> NAME/KEY: MISC_FEATURE
<222> LOCATION: (23)..(23)
<223> OTHER INFORMATION: X is D and E for acidic amino acids
<220> FEATURE:
<221> NAME/KEY: MISC_FEATURE
<222> LOCATION: (24)..(24)
<223> OTHER INFORMATION: X is N or Q for amidated amino acids
<220> FEATURE:
<221> NAME/KEY: MISC_FEATURE
<222> LOCATION: (25)..(25)
<223> OTHER INFORMATION: X is A or G
<220> FEATURE:
<221> NAME/KEY: MISC_FEATURE
<222> LOCATION: (26)..(26)
<223> OTHER INFORMATION: X is F or P
<220> FEATURE:
<221> NAME/KEY: MISC_FEATURE
<222> LOCATION: (27)..(27)
<223> OTHER INFORMATION: X is K, R or H for basic amino acids
<220> FEATURE:
<221> NAME/KEY: MISC_FEATURE
<222> LOCATION: (28)..(28)
<223> OTHER INFORMATION: X is A or G
<220> FEATURE:
<221> NAME/KEY: MISC_FEATURE
<222> LOCATION: (29)..(29)
<223> OTHER INFORMATION: X is D and E for acidic amino acids

<400> SEQUENCE: 49

Xaa Xaa Xaa Xaa Xaa Xaa Xaa Xaa Xaa Xaa Xaa Xaa Xaa Xaa Xaa Xaa
1               5                   10                  15
```

-continued

```
Xaa Xaa Xaa Xaa Xaa Xaa Xaa Xaa Xaa Xaa Xaa
            20                  25

<210> SEQ ID NO 50
<211> LENGTH: 29
<212> TYPE: PRT
<213> ORGANISM: Artificial
<220> FEATURE:
<223> OTHER INFORMATION: Completely synthesized peptide construct

<400> SEQUENCE: 50

Ile Ala Gly Phe Lys Gly Glu Gln Gly Pro Lys Gly Glu Gly Gly Gly
1               5                   10                  15

Asp Leu Leu Lys Asn Gly Glu Arg Ile Glu Lys Val Glu
            20                  25

<210> SEQ ID NO 51
<211> LENGTH: 29
<212> TYPE: PRT
<213> ORGANISM: Artificial
<220> FEATURE:
<223> OTHER INFORMATION: peptide construct
<220> FEATURE:
<221> NAME/KEY: MISC_FEATURE
<222> LOCATION: (1)..(1)
<223> OTHER INFORMATION: X is I, L or V
<220> FEATURE:
<221> NAME/KEY: MISC_FEATURE
<222> LOCATION: (2)..(2)
<223> OTHER INFORMATION: X is  A or G
<220> FEATURE:
<221> NAME/KEY: MISC_FEATURE
<222> LOCATION: (3)..(3)
<223> OTHER INFORMATION: X is  A or G
<220> FEATURE:
<221> NAME/KEY: MISC_FEATURE
<222> LOCATION: (4)..(4)
<223> OTHER INFORMATION: X is F, W or Y for aromatic amino acids
<220> FEATURE:
<221> NAME/KEY: MISC_FEATURE
<222> LOCATION: (5)..(5)
<223> OTHER INFORMATION: X is K, R or H for basic amino acids
<220> FEATURE:
<221> NAME/KEY: MISC_FEATURE
<222> LOCATION: (6)..(6)
<223> OTHER INFORMATION: X is A or G
<220> FEATURE:
<221> NAME/KEY: MISC_FEATURE
<222> LOCATION: (7)..(7)
<223> OTHER INFORMATION: X is D and E for acidic amino acids
<220> FEATURE:
<221> NAME/KEY: MISC_FEATURE
<222> LOCATION: (8)..(8)
<223> OTHER INFORMATION: X is N or Q for amidated amino acids
<220> FEATURE:
<221> NAME/KEY: MISC_FEATURE
<222> LOCATION: (9)..(9)
<223> OTHER INFORMATION: X is A or G
<220> FEATURE:
<221> NAME/KEY: MISC_FEATURE
<222> LOCATION: (10)..(10)
<223> OTHER INFORMATION: X is F or P
<220> FEATURE:
<221> NAME/KEY: MISC_FEATURE
<222> LOCATION: (11)..(11)
<223> OTHER INFORMATION: X is K, R or H for basic amino acids
<220> FEATURE:
<221> NAME/KEY: MISC_FEATURE
<222> LOCATION: (12)..(12)
<223> OTHER INFORMATION: X is A or G
<220> FEATURE:
<221> NAME/KEY: MISC_FEATURE
<222> LOCATION: (13)..(13)
<223> OTHER INFORMATION: X is D and E for acidic amino acids
<220> FEATURE:
```

```
<221> NAME/KEY: MISC_FEATURE
<222> LOCATION: (14)..(14)
<223> OTHER INFORMATION: X is A and G
<220> FEATURE:
<221> NAME/KEY: MISC_FEATURE
<222> LOCATION: (15)..(15)
<223> OTHER INFORMATION: X is A and G
<220> FEATURE:
<221> NAME/KEY: MISC_FEATURE
<222> LOCATION: (16)..(16)
<223> OTHER INFORMATION: X is A and G
<220> FEATURE:
<221> NAME/KEY: MISC_FEATURE
<222> LOCATION: (17)..(17)
<223> OTHER INFORMATION: X is D and E for acidic amino acids
<220> FEATURE:
<221> NAME/KEY: MISC_FEATURE
<222> LOCATION: (18)..(18)
<223> OTHER INFORMATION: X is I, L or V
<220> FEATURE:
<221> NAME/KEY: MISC_FEATURE
<222> LOCATION: (19)..(19)
<223> OTHER INFORMATION: X is I, L or V
<220> FEATURE:
<221> NAME/KEY: MISC_FEATURE
<222> LOCATION: (20)..(20)
<223> OTHER INFORMATION: X is K, R or H for basic amino acids
<220> FEATURE:
<221> NAME/KEY: MISC_FEATURE
<222> LOCATION: (21)..(21)
<223> OTHER INFORMATION: X is N or Q for amidated amino acids
<220> FEATURE:
<221> NAME/KEY: MISC_FEATURE
<222> LOCATION: (22)..(22)
<223> OTHER INFORMATION: X is A and G
<220> FEATURE:
<221> NAME/KEY: MISC_FEATURE
<222> LOCATION: (23)..(23)
<223> OTHER INFORMATION: X is D and E for acidic amino acids
<220> FEATURE:
<221> NAME/KEY: MISC_FEATURE
<222> LOCATION: (24)..(24)
<223> OTHER INFORMATION: X is K, R or H for basic amino acids
<220> FEATURE:
<221> NAME/KEY: MISC_FEATURE
<222> LOCATION: (25)..(25)
<223> OTHER INFORMATION: X is I, L or V
<220> FEATURE:
<221> NAME/KEY: MISC_FEATURE
<222> LOCATION: (26)..(26)
<223> OTHER INFORMATION: X is D and E for acidic amino acids
<220> FEATURE:
<221> NAME/KEY: MISC_FEATURE
<222> LOCATION: (27)..(27)
<223> OTHER INFORMATION: X is K, R or H for basic amino acids
<220> FEATURE:
<221> NAME/KEY: MISC_FEATURE
<222> LOCATION: (28)..(28)
<223> OTHER INFORMATION: X is I, L or V
<220> FEATURE:
<221> NAME/KEY: MISC_FEATURE
<222> LOCATION: (29)..(29)
<223> OTHER INFORMATION: X is D and E for acidic amino acids

<400> SEQUENCE: 51

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa
            20                  25

<210> SEQ ID NO 52
<211> LENGTH: 16
<212> TYPE: PRT
<213> ORGANISM: Artificial
<220> FEATURE:
<223> OTHER INFORMATION: completely synthesized peptide construct
```

<400> SEQUENCE: 52

Asp Leu Leu Lys Asn Gly Glu Arg Ile Glu Lys Val Glu Gly Gly Gly
1               5                   10                  15

<210> SEQ ID NO 53
<211> LENGTH: 22
<212> TYPE: PRT
<213> ORGANISM: Artificial
<220> FEATURE:
<223> OTHER INFORMATION: Completely synthesized peptide construct
<220> FEATURE:
<221> NAME/KEY: MISC_FEATURE
<222> LOCATION: (1)..(1)
<223> OTHER INFORMATION: X is acetyl or propionyl group, D glycine or D
      alanine, cyclohexylalanine at amino terminus
<220> FEATURE:
<221> NAME/KEY: MISC_FEATURE
<222> LOCATION: (2)..(2)
<223> OTHER INFORMATION: X is I, L or V
<220> FEATURE:
<221> NAME/KEY: MISC_FEATURE
<222> LOCATION: (3)..(3)
<223> OTHER INFORMATION: X is T or S
<220> FEATURE:
<221> NAME/KEY: MISC_FEATURE
<222> LOCATION: (4)..(4)
<223> OTHER INFORMATION: X is T or S
<220> FEATURE:
<221> NAME/KEY: MISC_FEATURE
<222> LOCATION: (5)..(5)
<223> OTHER INFORMATION: X is I, L or V
<220> FEATURE:
<221> NAME/KEY: MISC_FEATURE
<222> LOCATION: (6)..(6)
<223> OTHER INFORMATION: X is T or S
<220> FEATURE:
<221> NAME/KEY: MISC_FEATURE
<222> LOCATION: (7)..(7)
<223> OTHER INFORMATION: X is T or S
<220> FEATURE:
<221> NAME/KEY: MISC_FEATURE
<222> LOCATION: (8)..(8)
<223> OTHER INFORMATION: X is N or Q for amidated amino acids
<220> FEATURE:
<221> NAME/KEY: MISC_FEATURE
<222> LOCATION: (9)..(9)
<223> OTHER INFORMATION: X is F or P
<220> FEATURE:
<221> NAME/KEY: MISC_FEATURE
<222> LOCATION: (10)..(10)
<223> OTHER INFORMATION: X is T or S
<220> FEATURE:
<221> NAME/KEY: MISC_FEATURE
<222> LOCATION: (11)..(11)
<223> OTHER INFORMATION: X is D and E for acidic amino acids
<220> FEATURE:
<221> NAME/KEY: MISC_FEATURE
<222> LOCATION: (12)..(12)
<223> OTHER INFORMATION: X is A and G
<220> FEATURE:
<221> NAME/KEY: MISC_FEATURE
<222> LOCATION: (13)..(13)
<223> OTHER INFORMATION: X is A and G
<220> FEATURE:
<221> NAME/KEY: MISC_FEATURE
<222> LOCATION: (14)..(14)
<223> OTHER INFORMATION: X is T or S
<220> FEATURE:
<221> NAME/KEY: MISC_FEATURE
<222> LOCATION: (15)..(15)
<223> OTHER INFORMATION: X is A and G
<220> FEATURE:
<221> NAME/KEY: MISC_FEATURE
<222> LOCATION: (16)..(16)
<223> OTHER INFORMATION: X is T or S
<220> FEATURE:

```
<221> NAME/KEY: MISC_FEATURE
<222> LOCATION: (17)..(17)
<223> OTHER INFORMATION: X is F or P
<220> FEATURE:
<221> NAME/KEY: MISC_FEATURE
<222> LOCATION: (18)..(18)
<223> OTHER INFORMATION: X is T or S
<220> FEATURE:
<221> NAME/KEY: MISC_FEATURE
<222> LOCATION: (19)..(19)
<223> OTHER INFORMATION: X is T or S
<220> FEATURE:
<221> NAME/KEY: MISC_FEATURE
<222> LOCATION: (20)..(20)
<223> OTHER INFORMATION: X is K, R or H for basic amino acids
<220> FEATURE:
<221> NAME/KEY: MISC_FEATURE
<222> LOCATION: (21)..(21)
<223> OTHER INFORMATION: X is T or S
<220> FEATURE:
<221> NAME/KEY: MISC_FEATURE
<222> LOCATION: (22)..(22)
<223> OTHER INFORMATION: X is T or S

<400> SEQUENCE: 53

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa
            20

<210> SEQ ID NO 54
<211> LENGTH: 20
<212> TYPE: PRT
<213> ORGANISM: Homo sapiens
<220> FEATURE:
<221> NAME/KEY: MISC_FEATURE
<222> LOCATION: (54)..(73)
<223> OTHER INFORMATION: Type II Collagen

<400> SEQUENCE: 54

Asp Gly Glu Ala Gly Lys Pro Gly Lys Ala Gly Glu Arg Gly Pro Pro
1               5                   10                  15

Gly Pro Gln Gly
            20

<210> SEQ ID NO 55
<211> LENGTH: 20
<212> TYPE: PRT
<213> ORGANISM: Artificial
<220> FEATURE:
<223> OTHER INFORMATION: Completely synthesized peptide construct
<220> FEATURE:
<221> NAME/KEY: MISC_FEATURE
<222> LOCATION: (1)..(1)
<223> OTHER INFORMATION: X is D and E for acidic amino acids
<220> FEATURE:
<221> NAME/KEY: MISC_FEATURE
<222> LOCATION: (2)..(2)
<223> OTHER INFORMATION: X is A and G
<220> FEATURE:
<221> NAME/KEY: MISC_FEATURE
<222> LOCATION: (3)..(3)
<223> OTHER INFORMATION: X is D and E for acidic amino acids
<220> FEATURE:
<221> NAME/KEY: MISC_FEATURE
<222> LOCATION: (4)..(4)
<223> OTHER INFORMATION: X is A and G
<220> FEATURE:
<221> NAME/KEY: MISC_FEATURE
<222> LOCATION: (5)..(5)
<223> OTHER INFORMATION: X is A and G
<220> FEATURE:
<221> NAME/KEY: MISC_FEATURE
```

```
<222> LOCATION: (6)..(6)
<223> OTHER INFORMATION: X is K, R or H for basic amino acids
<220> FEATURE:
<221> NAME/KEY: MISC_FEATURE
<222> LOCATION: (7)..(7)
<223> OTHER INFORMATION: X is F or P
<220> FEATURE:
<221> NAME/KEY: MISC_FEATURE
<222> LOCATION: (8)..(8)
<223> OTHER INFORMATION: X is A and G
<220> FEATURE:
<221> NAME/KEY: MISC_FEATURE
<222> LOCATION: (9)..(9)
<223> OTHER INFORMATION: X is K, R or H for basic amino acids
<220> FEATURE:
<221> NAME/KEY: MISC_FEATURE
<222> LOCATION: (10)..(10)
<223> OTHER INFORMATION: X is A and G
<220> FEATURE:
<221> NAME/KEY: MISC_FEATURE
<222> LOCATION: (11)..(11)
<223> OTHER INFORMATION: X is A and G
<220> FEATURE:
<221> NAME/KEY: MISC_FEATURE
<222> LOCATION: (12)..(12)
<223> OTHER INFORMATION: X is D and E for acidic amino acids
<220> FEATURE:
<221> NAME/KEY: MISC_FEATURE
<222> LOCATION: (13)..(13)
<223> OTHER INFORMATION: X is K, R or H for basic amino acids
<220> FEATURE:
<221> NAME/KEY: MISC_FEATURE
<222> LOCATION: (14)..(14)
<223> OTHER INFORMATION: X is A and G
<220> FEATURE:
<221> NAME/KEY: MISC_FEATURE
<222> LOCATION: (15)..(15)
<223> OTHER INFORMATION: X is F or P
<220> FEATURE:
<221> NAME/KEY: MISC_FEATURE
<222> LOCATION: (16)..(16)
<223> OTHER INFORMATION: X is F or P
<220> FEATURE:
<221> NAME/KEY: MISC_FEATURE
<222> LOCATION: (17)..(17)
<223> OTHER INFORMATION: X is A and G
<220> FEATURE:
<221> NAME/KEY: MISC_FEATURE
<222> LOCATION: (18)..(18)
<223> OTHER INFORMATION: X is F or P
<220> FEATURE:
<221> NAME/KEY: MISC_FEATURE
<222> LOCATION: (19)..(19)
<223> OTHER INFORMATION: X is N or Q for amidated amino acids
<220> FEATURE:
<221> NAME/KEY: MISC_FEATURE
<222> LOCATION: (20)..(20)
<223> OTHER INFORMATION: X is A and G

<400> SEQUENCE: 55

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa
            20

<210> SEQ ID NO 56
<211> LENGTH: 21
<212> TYPE: PRT
<213> ORGANISM: Artificial
<220> FEATURE:
<223> OTHER INFORMATION: Completely synthesized peptide construct
<220> FEATURE:
<221> NAME/KEY: MISC_FEATURE
<222> LOCATION: (1)..(1)
<223> OTHER INFORMATION: X is acetyl or propionyl group, D glycine or D
      alanine, cyclohexylalanine at amino terminus
```

```
<220> FEATURE:
<221> NAME/KEY: MISC_FEATURE
<222> LOCATION: (2)..(2)
<223> OTHER INFORMATION: X is D and E for acidic amino acids
<220> FEATURE:
<221> NAME/KEY: MISC_FEATURE
<222> LOCATION: (3)..(3)
<223> OTHER INFORMATION: X is A and G
<220> FEATURE:
<221> NAME/KEY: MISC_FEATURE
<222> LOCATION: (4)..(4)
<223> OTHER INFORMATION: X is D and E for acidic amino acids
<220> FEATURE:
<221> NAME/KEY: MISC_FEATURE
<222> LOCATION: (5)..(5)
<223> OTHER INFORMATION: X is A and G
<220> FEATURE:
<221> NAME/KEY: MISC_FEATURE
<222> LOCATION: (6)..(6)
<223> OTHER INFORMATION: X is A and G
<220> FEATURE:
<221> NAME/KEY: MISC_FEATURE
<222> LOCATION: (7)..(7)
<223> OTHER INFORMATION: X is K, R or H for basic amino acids
<220> FEATURE:
<221> NAME/KEY: MISC_FEATURE
<222> LOCATION: (8)..(8)
<223> OTHER INFORMATION: X is A and G
<220> FEATURE:
<221> NAME/KEY: MISC_FEATURE
<222> LOCATION: (9)..(9)
<223> OTHER INFORMATION: X is K, R or H for basic amino acids
<220> FEATURE:
<221> NAME/KEY: MISC_FEATURE
<222> LOCATION: (10)..(10)
<223> OTHER INFORMATION: X is K, R or H for basic amino acids
<220> FEATURE:
<221> NAME/KEY: MISC_FEATURE
<222> LOCATION: (11)..(11)
<223> OTHER INFORMATION: X is A and G
<220> FEATURE:
<221> NAME/KEY: MISC_FEATURE
<222> LOCATION: (12)..(12)
<223> OTHER INFORMATION: X is A and G
<220> FEATURE:
<221> NAME/KEY: MISC_FEATURE
<222> LOCATION: (13)..(13)
<223> OTHER INFORMATION: X is D and E for acidic amino acids
<220> FEATURE:
<221> NAME/KEY: MISC_FEATURE
<222> LOCATION: (14)..(14)
<223> OTHER INFORMATION: X is K, R or H for basic amino acids
<220> FEATURE:
<221> NAME/KEY: MISC_FEATURE
<222> LOCATION: (15)..(15)
<223> OTHER INFORMATION: X is A and G
<220> FEATURE:
<221> NAME/KEY: MISC_FEATURE
<222> LOCATION: (16)..(16)
<223> OTHER INFORMATION: X is F or P
<220> FEATURE:
<221> NAME/KEY: MISC_FEATURE
<222> LOCATION: (17)..(17)
<223> OTHER INFORMATION: X is F or P
<220> FEATURE:
<221> NAME/KEY: MISC_FEATURE
<222> LOCATION: (18)..(18)
<223> OTHER INFORMATION: X is A and G
<220> FEATURE:
<221> NAME/KEY: MISC_FEATURE
<222> LOCATION: (19)..(19)
<223> OTHER INFORMATION: X is F or P
<220> FEATURE:
<221> NAME/KEY: MISC_FEATURE
<222> LOCATION: (20)..(20)
<223> OTHER INFORMATION: X is N or Q for amidated amino acids
<220> FEATURE:
<221> NAME/KEY: MISC_FEATURE
<222> LOCATION: (21)..(21)
```

```
<223> OTHER INFORMATION: X is A and G

<400> SEQUENCE: 56

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa
            20

<210> SEQ ID NO 57
<211> LENGTH: 20
<212> TYPE: PRT
<213> ORGANISM: Homo sapiens
<220> FEATURE:
<221> NAME/KEY: MISC_FEATURE
<222> LOCATION: (94)..(113)
<223> OTHER INFORMATION: Type II Collagen

<400> SEQUENCE: 57

Gly Leu Asp Gly Ala Lys Gly Glu Ala Gly Ala Pro Gly Val Lys Gly
1               5                   10                  15

Glu Ser Gly Ser
            20

<210> SEQ ID NO 58
<211> LENGTH: 21
<212> TYPE: PRT
<213> ORGANISM: Artificial
<220> FEATURE:
<223> OTHER INFORMATION: Completely synthesized peptide construct
<220> FEATURE:
<221> NAME/KEY: MISC_FEATURE
<222> LOCATION: (1)..(1)
<223> OTHER INFORMATION: X is A and G
<220> FEATURE:
<221> NAME/KEY: MISC_FEATURE
<222> LOCATION: (2)..(2)
<223> OTHER INFORMATION: X is I, L or V
<220> FEATURE:
<221> NAME/KEY: MISC_FEATURE
<222> LOCATION: (3)..(3)
<223> OTHER INFORMATION: X is D and E for acidic amino acids
<220> FEATURE:
<221> NAME/KEY: MISC_FEATURE
<222> LOCATION: (4)..(4)
<223> OTHER INFORMATION: X is A and G
<220> FEATURE:
<221> NAME/KEY: MISC_FEATURE
<222> LOCATION: (5)..(5)
<223> OTHER INFORMATION: X is A and G
<220> FEATURE:
<221> NAME/KEY: MISC_FEATURE
<222> LOCATION: (6)..(6)
<223> OTHER INFORMATION: X is K, R or H for basic amino acids
<220> FEATURE:
<221> NAME/KEY: MISC_FEATURE
<222> LOCATION: (7)..(7)
<223> OTHER INFORMATION: X is A and G
<220> FEATURE:
<221> NAME/KEY: MISC_FEATURE
<222> LOCATION: (8)..(8)
<223> OTHER INFORMATION: X is D and E for acidic amino acids
<220> FEATURE:
<221> NAME/KEY: MISC_FEATURE
<222> LOCATION: (9)..(9)
<223> OTHER INFORMATION: X is A and G
<220> FEATURE:
<221> NAME/KEY: MISC_FEATURE
<222> LOCATION: (10)..(10)
<223> OTHER INFORMATION: X is A and G
<220> FEATURE:
<221> NAME/KEY: MISC_FEATURE
<222> LOCATION: (11)..(11)
<223> OTHER INFORMATION: X is A and G
```

-continued

```
<220> FEATURE:
<221> NAME/KEY: MISC_FEATURE
<222> LOCATION: (12)..(12)
<223> OTHER INFORMATION: X is F or P
<220> FEATURE:
<221> NAME/KEY: MISC_FEATURE
<222> LOCATION: (13)..(13)
<223> OTHER INFORMATION: X is A and G
<220> FEATURE:
<221> NAME/KEY: MISC_FEATURE
<222> LOCATION: (14)..(14)
<223> OTHER INFORMATION: X is I, L or V
<220> FEATURE:
<221> NAME/KEY: MISC_FEATURE
<222> LOCATION: (15)..(15)
<223> OTHER INFORMATION: X is K, R or H for basic amino acids
<220> FEATURE:
<221> NAME/KEY: MISC_FEATURE
<222> LOCATION: (16)..(16)
<223> OTHER INFORMATION: X is A and G
<220> FEATURE:
<221> NAME/KEY: MISC_FEATURE
<222> LOCATION: (17)..(17)
<223> OTHER INFORMATION: X is D and E for acidic amino acids
<220> FEATURE:
<221> NAME/KEY: MISC_FEATURE
<222> LOCATION: (18)..(18)
<223> OTHER INFORMATION: X is T or S
<220> FEATURE:
<221> NAME/KEY: MISC_FEATURE
<222> LOCATION: (19)..(19)
<223> OTHER INFORMATION: X is A and G
<220> FEATURE:
<221> NAME/KEY: MISC_FEATURE
<222> LOCATION: (20)..(20)
<223> OTHER INFORMATION: X is A and G
<220> FEATURE:
<221> NAME/KEY: MISC_FEATURE
<222> LOCATION: (21)..(21)
<223> OTHER INFORMATION: X is T or S

<400> SEQUENCE: 58

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa
            20

<210> SEQ ID NO 59
<211> LENGTH: 21
<212> TYPE: PRT
<213> ORGANISM: Artificial
<220> FEATURE:
<223> OTHER INFORMATION: Completely synthesized peptide construct
<220> FEATURE:
<221> NAME/KEY: MISC_FEATURE
<222> LOCATION: (1)..(1)
<223> OTHER INFORMATION: X is acetyl or propionyl group, D glycine or D
      alanine, cyclohexylalanine at amino terminus
<220> FEATURE:
<221> NAME/KEY: MISC_FEATURE
<222> LOCATION: (2)..(2)
<223> OTHER INFORMATION: X is A and G
<220> FEATURE:
<221> NAME/KEY: MISC_FEATURE
<222> LOCATION: (3)..(3)
<223> OTHER INFORMATION: X is I, L or V
<220> FEATURE:
<221> NAME/KEY: MISC_FEATURE
<222> LOCATION: (4)..(4)
<223> OTHER INFORMATION: X is D and E for acidic amino acids
<220> FEATURE:
<221> NAME/KEY: MISC_FEATURE
<222> LOCATION: (5)..(5)
<223> OTHER INFORMATION: X is A and G
<220> FEATURE:
<221> NAME/KEY: MISC_FEATURE
```

```
<222> LOCATION: (6)..(6)
<223> OTHER INFORMATION: X is A and G
<220> FEATURE:
<221> NAME/KEY: MISC_FEATURE
<222> LOCATION: (7)..(7)
<223> OTHER INFORMATION: X is K, R or H for basic amino acids
<220> FEATURE:
<221> NAME/KEY: MISC_FEATURE
<222> LOCATION: (8)..(8)
<223> OTHER INFORMATION: X is A and G
<220> FEATURE:
<221> NAME/KEY: MISC_FEATURE
<222> LOCATION: (9)..(9)
<223> OTHER INFORMATION: X is D and E for acidic amino acids
<220> FEATURE:
<221> NAME/KEY: MISC_FEATURE
<222> LOCATION: (10)..(10)
<223> OTHER INFORMATION: X is A and G
<220> FEATURE:
<221> NAME/KEY: MISC_FEATURE
<222> LOCATION: (11)..(11)
<223> OTHER INFORMATION: X is A and G
<220> FEATURE:
<221> NAME/KEY: MISC_FEATURE
<222> LOCATION: (12)..(12)
<223> OTHER INFORMATION: X is A and G
<220> FEATURE:
<221> NAME/KEY: MISC_FEATURE
<222> LOCATION: (13)..(13)
<223> OTHER INFORMATION: X is F or P
<220> FEATURE:
<221> NAME/KEY: MISC_FEATURE
<222> LOCATION: (14)..(14)
<223> OTHER INFORMATION: X is A and G
<220> FEATURE:
<221> NAME/KEY: MISC_FEATURE
<222> LOCATION: (15)..(15)
<223> OTHER INFORMATION: X is I, L or V
<220> FEATURE:
<221> NAME/KEY: MISC_FEATURE
<222> LOCATION: (16)..(16)
<223> OTHER INFORMATION: X is K, R or H for basic amino acids
<220> FEATURE:
<221> NAME/KEY: MISC_FEATURE
<222> LOCATION: (17)..(17)
<223> OTHER INFORMATION: X is A and G
<220> FEATURE:
<221> NAME/KEY: MISC_FEATURE
<222> LOCATION: (18)..(18)
<223> OTHER INFORMATION: X is D and E for acidic amino acids
<220> FEATURE:
<221> NAME/KEY: MISC_FEATURE
<222> LOCATION: (19)..(19)
<223> OTHER INFORMATION: X is T or S
<220> FEATURE:
<221> NAME/KEY: MISC_FEATURE
<222> LOCATION: (20)..(20)
<223> OTHER INFORMATION: X is A and G
<220> FEATURE:
<221> NAME/KEY: MISC_FEATURE
<222> LOCATION: (21)..(21)
<223> OTHER INFORMATION: X is T or S

<400> SEQUENCE: 59

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa
            20

<210> SEQ ID NO 60
<211> LENGTH: 19
<212> TYPE: PRT
<213> ORGANISM: Artificial
<220> FEATURE:
<223> OTHER INFORMATION: Completely synthesized peptide construct
<220> FEATURE:
```

```
<221> NAME/KEY: MISC_FEATURE
<222> LOCATION: (1)..(1)
<223> OTHER INFORMATION: X is A and G
<220> FEATURE:
<221> NAME/KEY: MISC_FEATURE
<222> LOCATION: (2)..(2)
<223> OTHER INFORMATION: X is GabaX for X2X3 or X3X2 or X2X3 or X3X2 or
      X3X3 or X2X2
<220> FEATURE:
<221> NAME/KEY: MISC_FEATURE
<222> LOCATION: (3)..(3)
<223> OTHER INFORMATION: X is A and G
<220> FEATURE:
<221> NAME/KEY: MISC_FEATURE
<222> LOCATION: (4)..(4)
<223> OTHER INFORMATION: X is A and G
<220> FEATURE:
<221> NAME/KEY: MISC_FEATURE
<222> LOCATION: (5)..(5)
<223> OTHER INFORMATION: X is K, R or H for basic amino acids
<220> FEATURE:
<221> NAME/KEY: MISC_FEATURE
<222> LOCATION: (6)..(6)
<223> OTHER INFORMATION: X is A and G
<220> FEATURE:
<221> NAME/KEY: MISC_FEATURE
<222> LOCATION: (7)..(7)
<223> OTHER INFORMATION: X is D and E for acidic amino acids
<220> FEATURE:
<221> NAME/KEY: MISC_FEATURE
<222> LOCATION: (8)..(8)
<223> OTHER INFORMATION: X is A and G
<220> FEATURE:
<221> NAME/KEY: MISC_FEATURE
<222> LOCATION: (9)..(9)
<223> OTHER INFORMATION: X is A and G
<220> FEATURE:
<221> NAME/KEY: MISC_FEATURE
<222> LOCATION: (10)..(10)
<223> OTHER INFORMATION: X is A and G
<220> FEATURE:
<221> NAME/KEY: MISC_FEATURE
<222> LOCATION: (11)..(11)
<223> OTHER INFORMATION: X is F or P
<220> FEATURE:
<221> NAME/KEY: MISC_FEATURE
<222> LOCATION: (12)..(12)
<223> OTHER INFORMATION: X is A and G
<220> FEATURE:
<221> NAME/KEY: MISC_FEATURE
<222> LOCATION: (13)..(13)
<223> OTHER INFORMATION: X is I, L or V
<220> FEATURE:
<221> NAME/KEY: MISC_FEATURE
<222> LOCATION: (14)..(14)
<223> OTHER INFORMATION: X is K, R or H for basic amino acids
<220> FEATURE:
<221> NAME/KEY: MISC_FEATURE
<222> LOCATION: (15)..(15)
<223> OTHER INFORMATION: X is A and G
<220> FEATURE:
<221> NAME/KEY: MISC_FEATURE
<222> LOCATION: (16)..(16)
<223> OTHER INFORMATION: X is D and E for acidic amino acids
<220> FEATURE:
<221> NAME/KEY: MISC_FEATURE
<222> LOCATION: (17)..(17)
<223> OTHER INFORMATION: X is T or S
<220> FEATURE:
<221> NAME/KEY: MISC_FEATURE
<222> LOCATION: (18)..(18)
<223> OTHER INFORMATION: X is A and G
<220> FEATURE:
<221> NAME/KEY: MISC_FEATURE
<222> LOCATION: (19)..(19)
<223> OTHER INFORMATION: X is T or S

<400> SEQUENCE: 60
```

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa

<210> SEQ ID NO 61
<211> LENGTH: 20
<212> TYPE: PRT
<213> ORGANISM: Artificial
<220> FEATURE:
<223> OTHER INFORMATION: Completely synthesized peptide construct
<220> FEATURE:
<221> NAME/KEY: MISC_FEATURE
<222> LOCATION: (1)..(1)
<223> OTHER INFORMATION: X is acetyl or propionyl group, D glycine or D
      alanine, cyclohexylalanine at amino terminus
<220> FEATURE:
<221> NAME/KEY: MISC_FEATURE
<222> LOCATION: (2)..(2)
<223> OTHER INFORMATION: X is A and G
<220> FEATURE:
<221> NAME/KEY: MISC_FEATURE
<222> LOCATION: (3)..(3)
<223> OTHER INFORMATION: X is GabaX for X2X3 or X3X2 or X2X3 or X3X2 or
      X3X3 or X2X2
<220> FEATURE:
<221> NAME/KEY: MISC_FEATURE
<222> LOCATION: (4)..(4)
<223> OTHER INFORMATION: X is A and G
<220> FEATURE:
<221> NAME/KEY: MISC_FEATURE
<222> LOCATION: (5)..(5)
<223> OTHER INFORMATION: X is A and G
<220> FEATURE:
<221> NAME/KEY: MISC_FEATURE
<222> LOCATION: (6)..(6)
<223> OTHER INFORMATION: X is K, R or H for basic amino acids
<220> FEATURE:
<221> NAME/KEY: MISC_FEATURE
<222> LOCATION: (7)..(7)
<223> OTHER INFORMATION: X is A and G
<220> FEATURE:
<221> NAME/KEY: MISC_FEATURE
<222> LOCATION: (8)..(8)
<223> OTHER INFORMATION: X is D and E for acidic amino acids
<220> FEATURE:
<221> NAME/KEY: MISC_FEATURE
<222> LOCATION: (9)..(9)
<223> OTHER INFORMATION: X is A and G
<220> FEATURE:
<221> NAME/KEY: MISC_FEATURE
<222> LOCATION: (10)..(10)
<223> OTHER INFORMATION: X is A and G
<220> FEATURE:
<221> NAME/KEY: MISC_FEATURE
<222> LOCATION: (11)..(11)
<223> OTHER INFORMATION: X is A and G
<220> FEATURE:
<221> NAME/KEY: MISC_FEATURE
<222> LOCATION: (12)..(12)
<223> OTHER INFORMATION: X is F or P
<220> FEATURE:
<221> NAME/KEY: MISC_FEATURE
<222> LOCATION: (13)..(13)
<223> OTHER INFORMATION: X is A and G
<220> FEATURE:
<221> NAME/KEY: MISC_FEATURE
<222> LOCATION: (14)..(14)
<223> OTHER INFORMATION: X is I, L or V
<220> FEATURE:
<221> NAME/KEY: MISC_FEATURE
<222> LOCATION: (15)..(15)
<223> OTHER INFORMATION: X is K, R or H for basic amino acids
<220> FEATURE:
<221> NAME/KEY: MISC_FEATURE
<222> LOCATION: (16)..(16)
<223> OTHER INFORMATION: X is A and G
<220> FEATURE:
```

```
<221> NAME/KEY: MISC_FEATURE
<222> LOCATION: (17)..(17)
<223> OTHER INFORMATION: X is D and E for acidic amino acids
<220> FEATURE:
<221> NAME/KEY: MISC_FEATURE
<222> LOCATION: (18)..(18)
<223> OTHER INFORMATION: X is T or S
<220> FEATURE:
<221> NAME/KEY: MISC_FEATURE
<222> LOCATION: (19)..(19)
<223> OTHER INFORMATION: X is A and G
<220> FEATURE:
<221> NAME/KEY: MISC_FEATURE
<222> LOCATION: (20)..(20)
<223> OTHER INFORMATION: X is T or S

<400> SEQUENCE: 61

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa
            20

<210> SEQ ID NO 62
<211> LENGTH: 20
<212> TYPE: PRT
<213> ORGANISM: Homo sapiens
<220> FEATURE:
<221> NAME/KEY: MISC_FEATURE
<222> LOCATION: (544)..(573)
<223> OTHER INFORMATION: Type II Collagen

<400> SEQUENCE: 62

Glu Arg Gly Ala Ala Gly Ile Ala Gly Asp Lys Gly Asp Arg Gly Asp
1               5                   10                  15

Val Gly Glu Lys
            20

<210> SEQ ID NO 63
<211> LENGTH: 20
<212> TYPE: PRT
<213> ORGANISM: Artificial
<220> FEATURE:
<223> OTHER INFORMATION: Completely synthesized peptide construct
<220> FEATURE:
<221> NAME/KEY: MISC_FEATURE
<222> LOCATION: (1)..(1)
<223> OTHER INFORMATION: X is D and E for acidic amino acids
<220> FEATURE:
<221> NAME/KEY: MISC_FEATURE
<222> LOCATION: (2)..(2)
<223> OTHER INFORMATION: X is K, R or H for basic amino acids
<220> FEATURE:
<221> NAME/KEY: MISC_FEATURE
<222> LOCATION: (3)..(3)
<223> OTHER INFORMATION: X is A and G
<220> FEATURE:
<221> NAME/KEY: MISC_FEATURE
<222> LOCATION: (4)..(4)
<223> OTHER INFORMATION: X is A and G
<220> FEATURE:
<221> NAME/KEY: MISC_FEATURE
<222> LOCATION: (5)..(5)
<223> OTHER INFORMATION: X is A and G
<220> FEATURE:
<221> NAME/KEY: MISC_FEATURE
<222> LOCATION: (6)..(6)
<223> OTHER INFORMATION: X is A and G
<220> FEATURE:
<221> NAME/KEY: MISC_FEATURE
<222> LOCATION: (7)..(7)
<223> OTHER INFORMATION: X is I, L or V
<220> FEATURE:
<221> NAME/KEY: MISC_FEATURE
```

```
<222> LOCATION: (8)..(8)
<223> OTHER INFORMATION: X is A and G
<220> FEATURE:
<221> NAME/KEY: MISC_FEATURE
<222> LOCATION: (9)..(9)
<223> OTHER INFORMATION: X is A and G
<220> FEATURE:
<221> NAME/KEY: MISC_FEATURE
<222> LOCATION: (10)..(10)
<223> OTHER INFORMATION: X is D and E for acidic amino acids
<220> FEATURE:
<221> NAME/KEY: MISC_FEATURE
<222> LOCATION: (11)..(11)
<223> OTHER INFORMATION: X is K, R or H for basic amino acids
<220> FEATURE:
<221> NAME/KEY: MISC_FEATURE
<222> LOCATION: (12)..(12)
<223> OTHER INFORMATION: X is A and G
<220> FEATURE:
<221> NAME/KEY: MISC_FEATURE
<222> LOCATION: (13)..(13)
<223> OTHER INFORMATION: X is D and E for acidic amino acids
<220> FEATURE:
<221> NAME/KEY: MISC_FEATURE
<222> LOCATION: (14)..(14)
<223> OTHER INFORMATION: A is K, R or H for basic amino acids
<220> FEATURE:
<221> NAME/KEY: MISC_FEATURE
<222> LOCATION: (15)..(15)
<223> OTHER INFORMATION: X is A and G
<220> FEATURE:
<221> NAME/KEY: MISC_FEATURE
<222> LOCATION: (16)..(16)
<223> OTHER INFORMATION: X is D and E for acidic amino acids
<220> FEATURE:
<221> NAME/KEY: MISC_FEATURE
<222> LOCATION: (17)..(17)
<223> OTHER INFORMATION: X is I, L or V
<220> FEATURE:
<221> NAME/KEY: MISC_FEATURE
<222> LOCATION: (18)..(18)
<223> OTHER INFORMATION: X is A and G
<220> FEATURE:
<221> NAME/KEY: MISC_FEATURE
<222> LOCATION: (19)..(19)
<223> OTHER INFORMATION: X is D and E for acidic amino acids
<220> FEATURE:
<221> NAME/KEY: MISC_FEATURE
<222> LOCATION: (20)..(20)
<223> OTHER INFORMATION: X is K, R or H for basic amino acids

<400> SEQUENCE: 63

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa
            20

<210> SEQ ID NO 64
<211> LENGTH: 21
<212> TYPE: PRT
<213> ORGANISM: Artificial
<220> FEATURE:
<223> OTHER INFORMATION: Completely synthesized peptide construct
<220> FEATURE:
<221> NAME/KEY: MISC_FEATURE
<222> LOCATION: (1)..(1)
<223> OTHER INFORMATION: X is acetyl or propionyl group, D glycine or D
      alanine, cyclohexylalanine at amino terminus
<220> FEATURE:
<221> NAME/KEY: MISC_FEATURE
<222> LOCATION: (2)..(2)
<223> OTHER INFORMATION: X is D and E for acidic amino acids
<220> FEATURE:
<221> NAME/KEY: MISC_FEATURE
<222> LOCATION: (3)..(3)
<223> OTHER INFORMATION: X is K, R or H for basic amino acids
```

```
<220> FEATURE:
<221> NAME/KEY: MISC_FEATURE
<222> LOCATION: (4)..(4)
<223> OTHER INFORMATION: X is A and G
<220> FEATURE:
<221> NAME/KEY: MISC_FEATURE
<222> LOCATION: (5)..(5)
<223> OTHER INFORMATION: X is A and G
<220> FEATURE:
<221> NAME/KEY: MISC_FEATURE
<222> LOCATION: (6)..(6)
<223> OTHER INFORMATION: X is A and G
<220> FEATURE:
<221> NAME/KEY: MISC_FEATURE
<222> LOCATION: (7)..(7)
<223> OTHER INFORMATION: X is A and G
<220> FEATURE:
<221> NAME/KEY: MISC_FEATURE
<222> LOCATION: (8)..(8)
<223> OTHER INFORMATION: X is I, L or V
<220> FEATURE:
<221> NAME/KEY: MISC_FEATURE
<222> LOCATION: (9)..(9)
<223> OTHER INFORMATION: X is A and G
<220> FEATURE:
<221> NAME/KEY: MISC_FEATURE
<222> LOCATION: (10)..(10)
<223> OTHER INFORMATION: X is A and G
<220> FEATURE:
<221> NAME/KEY: MISC_FEATURE
<222> LOCATION: (11)..(11)
<223> OTHER INFORMATION: X is D and E for acidic amino acids
<220> FEATURE:
<221> NAME/KEY: MISC_FEATURE
<222> LOCATION: (12)..(12)
<223> OTHER INFORMATION: X is K, R or H for basic amino acids
<220> FEATURE:
<221> NAME/KEY: MISC_FEATURE
<222> LOCATION: (13)..(13)
<223> OTHER INFORMATION: X is D and E for acidic amino acids
<220> FEATURE:
<221> NAME/KEY: MISC_FEATURE
<222> LOCATION: (14)..(14)
<223> OTHER INFORMATION: X is K, R or H for basic amino acids
<220> FEATURE:
<221> NAME/KEY: MISC_FEATURE
<222> LOCATION: (15)..(15)
<223> OTHER INFORMATION: X is A and G
<220> FEATURE:
<221> NAME/KEY: MISC_FEATURE
<222> LOCATION: (16)..(16)
<223> OTHER INFORMATION: X is D and E for acidic amino acids
<220> FEATURE:
<221> NAME/KEY: MISC_FEATURE
<222> LOCATION: (17)..(17)
<223> OTHER INFORMATION: X is I, L or V
<220> FEATURE:
<221> NAME/KEY: MISC_FEATURE
<222> LOCATION: (18)..(18)
<223> OTHER INFORMATION: X is A and G
<220> FEATURE:
<221> NAME/KEY: MISC_FEATURE
<222> LOCATION: (19)..(19)
<223> OTHER INFORMATION: X is A and G
<220> FEATURE:
<221> NAME/KEY: MISC_FEATURE
<222> LOCATION: (20)..(20)
<223> OTHER INFORMATION: X is D and E for acidic amino acids
<220> FEATURE:
<221> NAME/KEY: MISC_FEATURE
<222> LOCATION: (21)..(21)
<223> OTHER INFORMATION: X is K, R or H for basic amino acids

<400> SEQUENCE: 64

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa
```

```
<210> SEQ ID NO 65
<211> LENGTH: 19
<212> TYPE: PRT
<213> ORGANISM: Artificial
<220> FEATURE:
<223> OTHER INFORMATION: Completely synthesized peptide construct
<220> FEATURE:
<221> NAME/KEY: MISC_FEATURE
<222> LOCATION: (1)..(1)
<223> OTHER INFORMATION: X is D and E for acidic amino acids
<220> FEATURE:
<221> NAME/KEY: MISC_FEATURE
<222> LOCATION: (2)..(2)
<223> OTHER INFORMATION: X is K, R or H for basic amino acids
<220> FEATURE:
<221> NAME/KEY: MISC_FEATURE
<222> LOCATION: (3)..(3)
<223> OTHER INFORMATION: X is A and G
<220> FEATURE:
<221> NAME/KEY: MISC_FEATURE
<222> LOCATION: (4)..(4)
<223> OTHER INFORMATION: X is A and G
<220> FEATURE:
<221> NAME/KEY: MISC_FEATURE
<222> LOCATION: (5)..(5)
<223> OTHER INFORMATION: X is A and G
<220> FEATURE:
<221> NAME/KEY: MISC_FEATURE
<222> LOCATION: (6)..(6)
<223> OTHER INFORMATION: X is A and G
<220> FEATURE:
<221> NAME/KEY: MISC_FEATURE
<222> LOCATION: (7)..(7)
<223> OTHER INFORMATION: X is I, L or V
<220> FEATURE:
<221> NAME/KEY: MISC_FEATURE
<222> LOCATION: (8)..(8)
<223> OTHER INFORMATION: X is A and G
<220> FEATURE:
<221> NAME/KEY: MISC_FEATURE
<222> LOCATION: (9)..(9)
<223> OTHER INFORMATION: X is A and G
<220> FEATURE:
<221> NAME/KEY: MISC_FEATURE
<222> LOCATION: (10)..(10)
<223> OTHER INFORMATION: X is D and E for acidic amino acids
<220> FEATURE:
<221> NAME/KEY: MISC_FEATURE
<222> LOCATION: (11)..(11)
<223> OTHER INFORMATION: X is K, R or H for basic amino acids
<220> FEATURE:
<221> NAME/KEY: MISC_FEATURE
<222> LOCATION: (12)..(12)
<223> OTHER INFORMATION: X is A and G
<220> FEATURE:
<221> NAME/KEY: MISC_FEATURE
<222> LOCATION: (13)..(13)
<223> OTHER INFORMATION: X is D and E for acidic amino acids
<220> FEATURE:
<221> NAME/KEY: MISC_FEATURE
<222> LOCATION: (14)..(14)
<223> OTHER INFORMATION: X is K. R or H for basic amino acids
<220> FEATURE:
<221> NAME/KEY: MISC_FEATURE
<222> LOCATION: (15)..(15)
<223> OTHER INFORMATION: X is A and G
<220> FEATURE:
<221> NAME/KEY: MISC_FEATURE
<222> LOCATION: (16)..(16)
<223> OTHER INFORMATION: X is GabaX for X2X3 or X3X2 or X2X3 or X3X2 or
      X3X3 or X2X2
<220> FEATURE:
<221> NAME/KEY: MISC_FEATURE
<222> LOCATION: (17)..(17)
<223> OTHER INFORMATION: X is A and G
<220> FEATURE:
```

```
<221> NAME/KEY: MISC_FEATURE
<222> LOCATION: (18)..(18)
<223> OTHER INFORMATION: X is D and E for acidic amino acids
<220> FEATURE:
<221> NAME/KEY: MISC_FEATURE
<222> LOCATION: (19)..(19)
<223> OTHER INFORMATION: X is K, R or H for basic amino acids

<400> SEQUENCE: 65

Xaa Xaa Xaa Xaa Xaa Xaa Xaa Xaa Xaa Xaa Xaa Xaa Xaa Xaa Xaa Xaa
1               5                   10                  15

Xaa Xaa Xaa

<210> SEQ ID NO 66
<211> LENGTH: 20
<212> TYPE: PRT
<213> ORGANISM: Artificial
<220> FEATURE:
<223> OTHER INFORMATION: Completely synthesized peptide construct
<220> FEATURE:
<221> NAME/KEY: MISC_FEATURE
<222> LOCATION: (1)..(1)
<223> OTHER INFORMATION: X is acetyl or propionyl group, D glycine or D
    alanine, cyclohexylalanine at amino terminus
<220> FEATURE:
<221> NAME/KEY: MISC_FEATURE
<222> LOCATION: (2)..(2)
<223> OTHER INFORMATION: X is D and E for acidic amino acids
<220> FEATURE:
<221> NAME/KEY: MISC_FEATURE
<222> LOCATION: (3)..(3)
<223> OTHER INFORMATION: X is K, R or H for basic amino acids
<220> FEATURE:
<221> NAME/KEY: MISC_FEATURE
<222> LOCATION: (4)..(4)
<223> OTHER INFORMATION: X is A and G
<220> FEATURE:
<221> NAME/KEY: MISC_FEATURE
<222> LOCATION: (5)..(5)
<223> OTHER INFORMATION: X is A and G
<220> FEATURE:
<221> NAME/KEY: MISC_FEATURE
<222> LOCATION: (6)..(6)
<223> OTHER INFORMATION: X is A and G
<220> FEATURE:
<221> NAME/KEY: MISC_FEATURE
<222> LOCATION: (7)..(7)
<223> OTHER INFORMATION: X is A and G
<220> FEATURE:
<221> NAME/KEY: MISC_FEATURE
<222> LOCATION: (8)..(8)
<223> OTHER INFORMATION: X is I, L or V
<220> FEATURE:
<221> NAME/KEY: MISC_FEATURE
<222> LOCATION: (9)..(9)
<223> OTHER INFORMATION: X is A and G
<220> FEATURE:
<221> NAME/KEY: MISC_FEATURE
<222> LOCATION: (10)..(10)
<223> OTHER INFORMATION: X is A and G
<220> FEATURE:
<221> NAME/KEY: MISC_FEATURE
<222> LOCATION: (11)..(11)
<223> OTHER INFORMATION: X is D and E for acidic amino acids
<220> FEATURE:
<221> NAME/KEY: MISC_FEATURE
<222> LOCATION: (12)..(12)
<223> OTHER INFORMATION: X is K, R or H for basic amino acids
<220> FEATURE:
<221> NAME/KEY: MISC_FEATURE
<222> LOCATION: (13)..(13)
<223> OTHER INFORMATION: X is A and G
<220> FEATURE:
<221> NAME/KEY: MISC_FEATURE
<222> LOCATION: (14)..(14)
<223> OTHER INFORMATION: X is D and E for acidic amino acids
```

```
<220> FEATURE:
<221> NAME/KEY: MISC_FEATURE
<222> LOCATION: (15)..(15)
<223> OTHER INFORMATION: X is K, R or H for basic amino acids
<220> FEATURE:
<221> NAME/KEY: MISC_FEATURE
<222> LOCATION: (16)..(16)
<223> OTHER INFORMATION: X is A and G
<220> FEATURE:
<221> NAME/KEY: MISC_FEATURE
<222> LOCATION: (17)..(17)
<223> OTHER INFORMATION: X is GabaX for X2X3 or X3X2 or X2X3 or
     X3X2 or X3X3 or X2X2
<220> FEATURE:
<221> NAME/KEY: MISC_FEATURE
<222> LOCATION: (18)..(18)
<223> OTHER INFORMATION: X is A and G
<220> FEATURE:
<221> NAME/KEY: MISC_FEATURE
<222> LOCATION: (19)..(19)
<223> OTHER INFORMATION: X is D and E for acidic amino acids
<220> FEATURE:
<221> NAME/KEY: MISC_FEATURE
<222> LOCATION: (20)..(20)
<223> OTHER INFORMATION: X is K, R or H for basic amino acids

<400> SEQUENCE: 66

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa
            20

<210> SEQ ID NO 67
<211> LENGTH: 7
<212> TYPE: PRT
<213> ORGANISM: Homo sapiens
<220> FEATURE:
<221> NAME/KEY: MISC_FEATURE
<222> LOCATION: (148)..(154)
<223> OTHER INFORMATION: Osteopontin

<400> SEQUENCE: 67

Ser Leu Ala Tyr Gly Leu Arg
1               5

<210> SEQ ID NO 68
<211> LENGTH: 7
<212> TYPE: PRT
<213> ORGANISM: Artificial
<220> FEATURE:
<223> OTHER INFORMATION: Completely synthesized peptide construct
<220> FEATURE:
<221> NAME/KEY: MISC_FEATURE
<222> LOCATION: (1)..(1)
<223> OTHER INFORMATION: X is T or S
<220> FEATURE:
<221> NAME/KEY: MISC_FEATURE
<222> LOCATION: (2)..(2)
<223> OTHER INFORMATION: X is I, L or V
<220> FEATURE:
<221> NAME/KEY: MISC_FEATURE
<222> LOCATION: (3)..(3)
<223> OTHER INFORMATION: X is A and G
<220> FEATURE:
<221> NAME/KEY: MISC_FEATURE
<222> LOCATION: (4)..(4)
<223> OTHER INFORMATION: X is F, W or Y for aromatic amino acids
<220> FEATURE:
<221> NAME/KEY: MISC_FEATURE
<222> LOCATION: (5)..(5)
<223> OTHER INFORMATION: X is A and G
<220> FEATURE:
<221> NAME/KEY: MISC_FEATURE
<222> LOCATION: (6)..(6)
```

```
<223> OTHER INFORMATION: X is I, L or V
<220> FEATURE:
<221> NAME/KEY: MISC_FEATURE
<222> LOCATION: (7)..(7)
<223> OTHER INFORMATION: X is K, R or H for basic amino acids

<400> SEQUENCE: 68

Xaa Xaa Xaa Xaa Xaa Xaa Xaa
1               5

<210> SEQ ID NO 69
<211> LENGTH: 8
<212> TYPE: PRT
<213> ORGANISM: Artificial
<220> FEATURE:
<223> OTHER INFORMATION: Completely synthesized peptide construct
<220> FEATURE:
<221> NAME/KEY: MISC_FEATURE
<222> LOCATION: (1)..(1)
<223> OTHER INFORMATION: X is acetyl or propionyl group, D glycine or D
      alanine, cyclohexylalanine at amino terminus
<220> FEATURE:
<221> NAME/KEY: MISC_FEATURE
<222> LOCATION: (2)..(2)
<223> OTHER INFORMATION: X is T or S
<220> FEATURE:
<221> NAME/KEY: MISC_FEATURE
<222> LOCATION: (3)..(3)
<223> OTHER INFORMATION: X is I, L or V
<220> FEATURE:
<221> NAME/KEY: MISC_FEATURE
<222> LOCATION: (4)..(4)
<223> OTHER INFORMATION: X is A and G
<220> FEATURE:
<221> NAME/KEY: MISC_FEATURE
<222> LOCATION: (5)..(5)
<223> OTHER INFORMATION: X is F, W or Y for aromatic amino acids
<220> FEATURE:
<221> NAME/KEY: MISC_FEATURE
<222> LOCATION: (6)..(6)
<223> OTHER INFORMATION: X is A and G
<220> FEATURE:
<221> NAME/KEY: MISC_FEATURE
<222> LOCATION: (7)..(7)
<223> OTHER INFORMATION: X is I, L or V
<220> FEATURE:
<221> NAME/KEY: MISC_FEATURE
<222> LOCATION: (8)..(8)
<223> OTHER INFORMATION: X is K, R or H for basic amino acids

<400> SEQUENCE: 69

Xaa Xaa Xaa Xaa Xaa Xaa Xaa Xaa
1               5

<210> SEQ ID NO 70
<211> LENGTH: 15
<212> TYPE: PRT
<213> ORGANISM: Homo sapiens
<220> FEATURE:
<221> NAME/KEY: MISC_FEATURE
<223> OTHER INFORMATION: DNA JI

<400> SEQUENCE: 70

Gln Lys Arg Ala Ala Tyr Lys Gln Tyr Gly His Ala Ala Phe Glu
1               5                   10                  15

<210> SEQ ID NO 71
<211> LENGTH: 15
<212> TYPE: PRT
<213> ORGANISM: Artificial
<220> FEATURE:
<223> OTHER INFORMATION: Completely synthesized peptide construct
<220> FEATURE:
```

<221> NAME/KEY: MISC_FEATURE
<222> LOCATION: (1)..(1)
<223> OTHER INFORMATION: X is N or Q for amidated amino acids
<220> FEATURE:
<221> NAME/KEY: MISC_FEATURE
<222> LOCATION: (2)..(2)
<223> OTHER INFORMATION: X is K, R or H for basic amino acids
<220> FEATURE:
<221> NAME/KEY: MISC_FEATURE
<222> LOCATION: (3)..(3)
<223> OTHER INFORMATION: X is K, R or H for basic amino acids
<220> FEATURE:
<221> NAME/KEY: MISC_FEATURE
<222> LOCATION: (4)..(4)
<223> OTHER INFORMATION: X is A and G
<220> FEATURE:
<221> NAME/KEY: MISC_FEATURE
<222> LOCATION: (5)..(5)
<223> OTHER INFORMATION: X is A and G
<220> FEATURE:
<221> NAME/KEY: MISC_FEATURE
<222> LOCATION: (6)..(6)
<223> OTHER INFORMATION: X is F, W or Y for aromatic amino acids
<220> FEATURE:
<221> NAME/KEY: MISC_FEATURE
<222> LOCATION: (7)..(7)
<223> OTHER INFORMATION: X is K, R or H for basic amino acids
<220> FEATURE:
<221> NAME/KEY: MISC_FEATURE
<222> LOCATION: (8)..(8)
<223> OTHER INFORMATION: X is N or Q for amidated amino acids
<220> FEATURE:
<221> NAME/KEY: MISC_FEATURE
<222> LOCATION: (9)..(9)
<223> OTHER INFORMATION: X is F, W or Y for aromatic amino acids
<220> FEATURE:
<221> NAME/KEY: MISC_FEATURE
<222> LOCATION: (10)..(10)
<223> OTHER INFORMATION: X is A and G
<220> FEATURE:
<221> NAME/KEY: MISC_FEATURE
<222> LOCATION: (11)..(11)
<223> OTHER INFORMATION: X is K, R or H for basic amino acids
<220> FEATURE:
<221> NAME/KEY: MISC_FEATURE
<222> LOCATION: (12)..(12)
<223> OTHER INFORMATION: X is A and G
<220> FEATURE:
<221> NAME/KEY: MISC_FEATURE
<222> LOCATION: (13)..(13)
<223> OTHER INFORMATION: X is A and G
<220> FEATURE:
<221> NAME/KEY: MISC_FEATURE
<222> LOCATION: (14)..(14)
<223> OTHER INFORMATION: X is F or P
<220> FEATURE:
<221> NAME/KEY: MISC_FEATURE
<222> LOCATION: (15)..(15)
<223> OTHER INFORMATION: X is D and E for acidic amino acids

<400> SEQUENCE: 71

Xaa Xaa Xaa Xaa Xaa Xaa Xaa Xaa Xaa Xaa Xaa Xaa Xaa Xaa Xaa
1               5                   10                  15

<210> SEQ ID NO 72
<211> LENGTH: 16
<212> TYPE: PRT
<213> ORGANISM: Artificial
<220> FEATURE:
<223> OTHER INFORMATION: Completely synthesized peptide construct
<220> FEATURE:
<221> NAME/KEY: MISC_FEATURE
<222> LOCATION: (1)..(1)
<223> OTHER INFORMATION: X is aceytl or propionyl group, D glycine or D
      alanine, cyclohexylalanine at amino terminus
<220> FEATURE:
<221> NAME/KEY: MISC_FEATURE

```
<222> LOCATION: (2)..(2)
<223> OTHER INFORMATION: X is N or Q for amidated amino acids
<220> FEATURE:
<221> NAME/KEY: MISC_FEATURE
<222> LOCATION: (3)..(3)
<223> OTHER INFORMATION: X is K, R or H for basic amino acids
<220> FEATURE:
<221> NAME/KEY: MISC_FEATURE
<222> LOCATION: (4)..(4)
<223> OTHER INFORMATION: X is K, R or H for basic amino acids
<220> FEATURE:
<221> NAME/KEY: MISC_FEATURE
<222> LOCATION: (5)..(5)
<223> OTHER INFORMATION: X A and G
<220> FEATURE:
<221> NAME/KEY: MISC_FEATURE
<222> LOCATION: (6)..(6)
<223> OTHER INFORMATION: X A and G
<220> FEATURE:
<221> NAME/KEY: MISC_FEATURE
<222> LOCATION: (7)..(7)
<223> OTHER INFORMATION: X is F, W or Y for aromatic amino acids
<220> FEATURE:
<221> NAME/KEY: MISC_FEATURE
<222> LOCATION: (8)..(8)
<223> OTHER INFORMATION: X is K, R or H for basic amino acids
<220> FEATURE:
<221> NAME/KEY: MISC_FEATURE
<222> LOCATION: (9)..(9)
<223> OTHER INFORMATION: X is N or Q for amidated amino acids
<220> FEATURE:
<221> NAME/KEY: MISC_FEATURE
<222> LOCATION: (10)..(10)
<223> OTHER INFORMATION: X is F, W or Y for aromatic amino acids
<220> FEATURE:
<221> NAME/KEY: MISC_FEATURE
<222> LOCATION: (11)..(11)
<223> OTHER INFORMATION: X is A and G
<220> FEATURE:
<221> NAME/KEY: MISC_FEATURE
<222> LOCATION: (12)..(12)
<223> OTHER INFORMATION: X is K, R or H for basic amino acids
<220> FEATURE:
<221> NAME/KEY: MISC_FEATURE
<222> LOCATION: (13)..(13)
<223> OTHER INFORMATION: X is A and G
<220> FEATURE:
<221> NAME/KEY: MISC_FEATURE
<222> LOCATION: (14)..(14)
<223> OTHER INFORMATION: X is A and G
<220> FEATURE:
<221> NAME/KEY: MISC_FEATURE
<222> LOCATION: (15)..(15)
<223> OTHER INFORMATION: X is F or P
<220> FEATURE:
<221> NAME/KEY: MISC_FEATURE
<222> LOCATION: (16)..(16)
<223> OTHER INFORMATION: X is D and E for acidic amino acids

<400> SEQUENCE: 72

Xaa Xaa Xaa Xaa Xaa Xaa Xaa Xaa Xaa Xaa Xaa Xaa Xaa Xaa Xaa Xaa
1               5                   10                  15

<210> SEQ ID NO 73
<211> LENGTH: 14
<212> TYPE: PRT
<213> ORGANISM: Homo sapiens
<220> FEATURE:
<221> NAME/KEY: MISC_FEATURE
<222> LOCATION: (461)..(474)
<223> OTHER INFORMATION: DNA JV

<400> SEQUENCE: 73

Glu Arg Ala Ala Tyr Asp Gln Tyr Gly His Ala Ala Phe Glu
1               5                   10
```

```
<210> SEQ ID NO 74
<211> LENGTH: 14
<212> TYPE: PRT
<213> ORGANISM: Artificial
<220> FEATURE:
<223> OTHER INFORMATION: Completely synthesized peptide construct
<220> FEATURE:
<221> NAME/KEY: MISC_FEATURE
<222> LOCATION: (1)..(1)
<223> OTHER INFORMATION: X is D and E for acidic amino acids
<220> FEATURE:
<221> NAME/KEY: MISC_FEATURE
<222> LOCATION: (2)..(2)
<223> OTHER INFORMATION: X is K, R or H for basic amino acids
<220> FEATURE:
<221> NAME/KEY: MISC_FEATURE
<222> LOCATION: (3)..(3)
<223> OTHER INFORMATION: X is A and G
<220> FEATURE:
<221> NAME/KEY: MISC_FEATURE
<222> LOCATION: (4)..(4)
<223> OTHER INFORMATION: X is A and G
<220> FEATURE:
<221> NAME/KEY: MISC_FEATURE
<222> LOCATION: (5)..(5)
<223> OTHER INFORMATION: X is F, W or Y for aromatic amino acids
<220> FEATURE:
<221> NAME/KEY: MISC_FEATURE
<222> LOCATION: (6)..(6)
<223> OTHER INFORMATION: X is D and E for acidic amino acids
<220> FEATURE:
<221> NAME/KEY: MISC_FEATURE
<222> LOCATION: (7)..(7)
<223> OTHER INFORMATION: X is N or Q for amidated amino acids
<220> FEATURE:
<221> NAME/KEY: MISC_FEATURE
<222> LOCATION: (8)..(8)
<223> OTHER INFORMATION: X is F, W or Y for aromatic amino acids
<220> FEATURE:
<221> NAME/KEY: MISC_FEATURE
<222> LOCATION: (9)..(9)
<223> OTHER INFORMATION: X is A and G
<220> FEATURE:
<221> NAME/KEY: MISC_FEATURE
<222> LOCATION: (10)..(10)
<223> OTHER INFORMATION: X is K, R or H for basic amino acids
<220> FEATURE:
<221> NAME/KEY: MISC_FEATURE
<222> LOCATION: (11)..(11)
<223> OTHER INFORMATION: X is A and G
<220> FEATURE:
<221> NAME/KEY: MISC_FEATURE
<222> LOCATION: (12)..(12)
<223> OTHER INFORMATION: X is A and G
<220> FEATURE:
<221> NAME/KEY: MISC_FEATURE
<222> LOCATION: (13)..(13)
<223> OTHER INFORMATION: X is F or P
<220> FEATURE:
<221> NAME/KEY: MISC_FEATURE
<222> LOCATION: (14)..(14)
<223> OTHER INFORMATION: X is D and E for acidic amino acids

<400> SEQUENCE: 74

Xaa Xaa Xaa Xaa Xaa Xaa Xaa Xaa Xaa Xaa Xaa Xaa Xaa Xaa
1               5                   10

<210> SEQ ID NO 75
<211> LENGTH: 15
<212> TYPE: PRT
<213> ORGANISM: Artificial
<220> FEATURE:
<223> OTHER INFORMATION: Completely synthesized peptide construct
<220> FEATURE:
<221> NAME/KEY: MISC_FEATURE
<222> LOCATION: (1)..(1)
```

```
<223> OTHER INFORMATION: X is acetyl or propionyl group, D glycine or D
      alanine, cyclohexylalanine at amino terminus
<220> FEATURE:
<221> NAME/KEY: MISC_FEATURE
<222> LOCATION: (2)..(2)
<223> OTHER INFORMATION: X is D and E for acidic amino acids
<220> FEATURE:
<221> NAME/KEY: MISC_FEATURE
<222> LOCATION: (3)..(3)
<223> OTHER INFORMATION: X is K, R or H for basic amino acids
<220> FEATURE:
<221> NAME/KEY: MISC_FEATURE
<222> LOCATION: (4)..(4)
<223> OTHER INFORMATION: X is A and G
<220> FEATURE:
<221> NAME/KEY: MISC_FEATURE
<222> LOCATION: (5)..(5)
<223> OTHER INFORMATION: X is A and G
<220> FEATURE:
<221> NAME/KEY: MISC_FEATURE
<222> LOCATION: (6)..(6)
<223> OTHER INFORMATION: X is F, W or Y for aromatic amino acids
<220> FEATURE:
<221> NAME/KEY: MISC_FEATURE
<222> LOCATION: (7)..(7)
<223> OTHER INFORMATION: X is D and E for acidic amino acids
<220> FEATURE:
<221> NAME/KEY: MISC_FEATURE
<222> LOCATION: (8)..(8)
<223> OTHER INFORMATION: X is N or Q for amidated amino acids
<220> FEATURE:
<221> NAME/KEY: MISC_FEATURE
<222> LOCATION: (9)..(9)
<223> OTHER INFORMATION: X is F, W or Y for aromatic amino acids
<220> FEATURE:
<221> NAME/KEY: MISC_FEATURE
<222> LOCATION: (10)..(10)
<223> OTHER INFORMATION: X is A and G
<220> FEATURE:
<221> NAME/KEY: MISC_FEATURE
<222> LOCATION: (11)..(11)
<223> OTHER INFORMATION: X is K, R or H for basic amino acids
<220> FEATURE:
<221> NAME/KEY: MISC_FEATURE
<222> LOCATION: (12)..(12)
<223> OTHER INFORMATION: X is A and G
<220> FEATURE:
<221> NAME/KEY: MISC_FEATURE
<222> LOCATION: (13)..(13)
<223> OTHER INFORMATION: X is A and G
<220> FEATURE:
<221> NAME/KEY: MISC_FEATURE
<222> LOCATION: (14)..(14)
<223> OTHER INFORMATION: X is F or P
<220> FEATURE:
<221> NAME/KEY: MISC_FEATURE
<222> LOCATION: (15)..(15)
<223> OTHER INFORMATION: X is A and G

<400> SEQUENCE: 75

Xaa Xaa Xaa Xaa Xaa Xaa Xaa Xaa Xaa Xaa Xaa Xaa Xaa Xaa Xaa
1               5                   10                  15

<210> SEQ ID NO 76
<211> LENGTH: 9
<212> TYPE: PRT
<213> ORGANISM: Artificial
<220> FEATURE:
<223> OTHER INFORMATION: Completely synthesized peptide construct
<220> FEATURE:
<221> NAME/KEY: MISC_FEATURE
<222> LOCATION: (1)..(1)
<223> OTHER INFORMATION: X is A and G
<220> FEATURE:
<221> NAME/KEY: MISC_FEATURE
<222> LOCATION: (2)..(2)
<223> OTHER INFORMATION: X is F, W or Y for aromatic amino acids
```

```
<220> FEATURE:
<221> NAME/KEY: MISC_FEATURE
<222> LOCATION: (3)..(3)
<223> OTHER INFORMATION: X is M or Nle (Norleucine)
<220> FEATURE:
<221> NAME/KEY: MISC_FEATURE
<222> LOCATION: (4)..(4)
<223> OTHER INFORMATION: X is T or S
<220> FEATURE:
<221> NAME/KEY: MISC_FEATURE
<222> LOCATION: (5)..(5)
<223> OTHER INFORMATION: X is M or Nle (Norleucine)
<220> FEATURE:
<221> NAME/KEY: MISC_FEATURE
<222> LOCATION: (6)..(6)
<223> OTHER INFORMATION: X is K, R or H for basic amino acids
<220> FEATURE:
<221> NAME/KEY: MISC_FEATURE
<222> LOCATION: (7)..(7)
<223> OTHER INFORMATION: X is I, L or V
<220> FEATURE:
<221> NAME/KEY: MISC_FEATURE
<222> LOCATION: (8)..(8)
<223> OTHER INFORMATION: X is K, R or H for basic amino acids
<220> FEATURE:
<221> NAME/KEY: MISC_FEATURE
<222> LOCATION: (9)..(9)
<223> OTHER INFORMATION: X is N or Q for amidated amino acids

<400> SEQUENCE: 76

Xaa Xaa Xaa Xaa Xaa Xaa Xaa Xaa Xaa
1               5

<210> SEQ ID NO 77
<211> LENGTH: 10
<212> TYPE: PRT
<213> ORGANISM: Artificial
<220> FEATURE:
<223> OTHER INFORMATION: Completely synthesized peptide construct
<220> FEATURE:
<221> NAME/KEY: MISC_FEATURE
<222> LOCATION: (1)..(1)
<223> OTHER INFORMATION: X is acetyl or propionyl group, D glycine or D
      alanine, cyclohexylalanine at amino terminus
<220> FEATURE:
<221> NAME/KEY: MISC_FEATURE
<222> LOCATION: (2)..(2)
<223> OTHER INFORMATION: X is A and G
<220> FEATURE:
<221> NAME/KEY: MISC_FEATURE
<222> LOCATION: (3)..(3)
<223> OTHER INFORMATION: X is F, W or Y for aromatic amino acids
<220> FEATURE:
<221> NAME/KEY: MISC_FEATURE
<222> LOCATION: (4)..(4)
<223> OTHER INFORMATION: X is M or Nle (Norleucine)
<220> FEATURE:
<221> NAME/KEY: MISC_FEATURE
<222> LOCATION: (5)..(5)
<223> OTHER INFORMATION: X is T or S
<220> FEATURE:
<221> NAME/KEY: MISC_FEATURE
<222> LOCATION: (6)..(6)
<223> OTHER INFORMATION: X is M or Nle (Norleucine)
<220> FEATURE:
<221> NAME/KEY: MISC_FEATURE
<222> LOCATION: (7)..(7)
<223> OTHER INFORMATION: X is K, R or H for basic amino acids
<220> FEATURE:
<221> NAME/KEY: MISC_FEATURE
<222> LOCATION: (8)..(8)
<223> OTHER INFORMATION: X is I, L or V
<220> FEATURE:
<221> NAME/KEY: MISC_FEATURE
<222> LOCATION: (9)..(9)
<223> OTHER INFORMATION: X is K, R or H for basic amino acids
<220> FEATURE:
```

```
<221> NAME/KEY: MISC_FEATURE
<222> LOCATION: (10)..(10)
<223> OTHER INFORMATION: X is N or Q for amidated amino acids

<400> SEQUENCE: 77

Xaa Xaa Xaa Xaa Xaa Xaa Xaa Xaa Xaa Xaa
1               5                   10

<210> SEQ ID NO 78
<211> LENGTH: 18
<212> TYPE: PRT
<213> ORGANISM: Artificial
<220> FEATURE:
<223> OTHER INFORMATION: Completely synthesized peptide construct
<220> FEATURE:
<221> NAME/KEY: MISC_FEATURE
<222> LOCATION: (1)..(1)
<223> OTHER INFORMATION: X is D and E for acidic amino acids
<220> FEATURE:
<221> NAME/KEY: MISC_FEATURE
<222> LOCATION: (2)..(2)
<223> OTHER INFORMATION: X is A and G
<220> FEATURE:
<221> NAME/KEY: MISC_FEATURE
<222> LOCATION: (3)..(3)
<223> OTHER INFORMATION: X is N or Q for amidated amino acids
<220> FEATURE:
<221> NAME/KEY: MISC_FEATURE
<222> LOCATION: (4)..(4)
<223> OTHER INFORMATION: X is D and E for acidic amino acids
<220> FEATURE:
<221> NAME/KEY: MISC_FEATURE
<222> LOCATION: (5)..(5)
<223> OTHER INFORMATION: X is D and E for acidic amino acids
<220> FEATURE:
<221> NAME/KEY: MISC_FEATURE
<222> LOCATION: (6)..(6)
<223> OTHER INFORMATION: X is K, R or H for basic amino acids
<220> FEATURE:
<221> NAME/KEY: MISC_FEATURE
<222> LOCATION: (7)..(7)
<223> OTHER INFORMATION: X is A and G
<220> FEATURE:
<221> NAME/KEY: MISC_FEATURE
<222> LOCATION: (8)..(8)
<223> OTHER INFORMATION: X is A and G
<220> FEATURE:
<221> NAME/KEY: MISC_FEATURE
<222> LOCATION: (9)..(9)
<223> OTHER INFORMATION: X is I, L or V
<220> FEATURE:
<221> NAME/KEY: MISC_FEATURE
<222> LOCATION: (10)..(10)
<223> OTHER INFORMATION: X is I, L or V
<220> FEATURE:
<221> NAME/KEY: MISC_FEATURE
<222> LOCATION: (11)..(11)
<223> OTHER INFORMATION: X is C or S
<220> FEATURE:
<221> NAME/KEY: MISC_FEATURE
<222> LOCATION: (12)..(12)
<223> OTHER INFORMATION: X is T or S
<220> FEATURE:
<221> NAME/KEY: MISC_FEATURE
<222> LOCATION: (13)..(13)
<223> OTHER INFORMATION: X is A and G
<220> FEATURE:
<221> NAME/KEY: MISC_FEATURE
<222> LOCATION: (14)..(14)
<223> OTHER INFORMATION: X is I, L or V
<220> FEATURE:
<221> NAME/KEY: MISC_FEATURE
<222> LOCATION: (15)..(15)
<223> OTHER INFORMATION: X is I, L or V
<220> FEATURE:
<221> NAME/KEY: MISC_FEATURE
<222> LOCATION: (16)..(16)
```

<223> OTHER INFORMATION: X is A and G
<220> FEATURE:
<221> NAME/KEY: MISC_FEATURE
<222> LOCATION: (17)..(17)
<223> OTHER INFORMATION: X is A and G
<220> FEATURE:
<221> NAME/KEY: MISC_FEATURE
<222> LOCATION: (18)..(18)
<223> OTHER INFORMATION: X is A and G

<400> SEQUENCE: 78

Xaa Xaa Xaa Xaa Xaa Xaa Xaa Xaa Xaa Xaa Xaa Xaa Xaa Xaa Xaa
1               5                   10                  15

Xaa Xaa

<210> SEQ ID NO 79
<211> LENGTH: 19
<212> TYPE: PRT
<213> ORGANISM: Artificial
<220> FEATURE:
<223> OTHER INFORMATION: Completely synthesized peptide construct
<220> FEATURE:
<221> NAME/KEY: MISC_FEATURE
<222> LOCATION: (1)..(1)
<223> OTHER INFORMATION: X is acetyl or propionyl group, D glycine or D
    alanine, cyclohexylalanine at amino terminus
<220> FEATURE:
<221> NAME/KEY: MISC_FEATURE
<222> LOCATION: (2)..(2)
<223> OTHER INFORMATION: X is D and E for acidic amino acids
<220> FEATURE:
<221> NAME/KEY: MISC_FEATURE
<222> LOCATION: (3)..(3)
<223> OTHER INFORMATION: X is A and G
<220> FEATURE:
<221> NAME/KEY: MISC_FEATURE
<222> LOCATION: (4)..(4)
<223> OTHER INFORMATION: X is N or Q for amidated amino acids
<220> FEATURE:
<221> NAME/KEY: MISC_FEATURE
<222> LOCATION: (5)..(5)
<223> OTHER INFORMATION: X is D and E for acidic amino acids
<220> FEATURE:
<221> NAME/KEY: MISC_FEATURE
<222> LOCATION: (6)..(6)
<223> OTHER INFORMATION: X is D and E for acidic amino acids
<220> FEATURE:
<221> NAME/KEY: MISC_FEATURE
<222> LOCATION: (7)..(7)
<223> OTHER INFORMATION: X is K, R or H for basic amino acids
<220> FEATURE:
<221> NAME/KEY: MISC_FEATURE
<222> LOCATION: (8)..(8)
<223> OTHER INFORMATION: X is A and G
<220> FEATURE:
<221> NAME/KEY: MISC_FEATURE
<222> LOCATION: (9)..(9)
<223> OTHER INFORMATION: X is A and G
<220> FEATURE:
<221> NAME/KEY: MISC_FEATURE
<222> LOCATION: (10)..(10)
<223> OTHER INFORMATION: X is I, L or V
<220> FEATURE:
<221> NAME/KEY: MISC_FEATURE
<222> LOCATION: (11)..(11)
<223> OTHER INFORMATION: X is I, L or V
<220> FEATURE:
<221> NAME/KEY: MISC_FEATURE
<222> LOCATION: (12)..(12)
<223> OTHER INFORMATION: X is C or S
<220> FEATURE:
<221> NAME/KEY: MISC_FEATURE
<222> LOCATION: (13)..(13)
<223> OTHER INFORMATION: X is T or S
<220> FEATURE:
<221> NAME/KEY: MISC_FEATURE

```
<222> LOCATION: (14)..(14)
<223> OTHER INFORMATION: X is A and G
<220> FEATURE:
<221> NAME/KEY: MISC_FEATURE
<222> LOCATION: (15)..(15)
<223> OTHER INFORMATION: X is I, L or V
<220> FEATURE:
<221> NAME/KEY: MISC_FEATURE
<222> LOCATION: (16)..(16)
<223> OTHER INFORMATION: X is I, L or V
<220> FEATURE:
<221> NAME/KEY: MISC_FEATURE
<222> LOCATION: (17)..(17)
<223> OTHER INFORMATION: X is A and G
<220> FEATURE:
<221> NAME/KEY: MISC_FEATURE
<222> LOCATION: (18)..(18)
<223> OTHER INFORMATION: X is A and G
<220> FEATURE:
<221> NAME/KEY: MISC_FEATURE
<222> LOCATION: (19)..(19)
<223> OTHER INFORMATION: X is A and G

<400> SEQUENCE: 79

Xaa Xaa Xaa Xaa Xaa Xaa Xaa Xaa Xaa Xaa Xaa Xaa Xaa Xaa Xaa
1               5                   10                  15

Xaa Xaa Xaa

<210> SEQ ID NO 80
<211> LENGTH: 16
<212> TYPE: PRT
<213> ORGANISM: Artificial
<220> FEATURE:
<223> OTHER INFORMATION: Completely synthesized peptide construct
<220> FEATURE:
<221> NAME/KEY: MISC_FEATURE
<222> LOCATION: (1)..(1)
<223> OTHER INFORMATION: X is acetyl or propionyl group, D glycine or D
      alanine, cyclohexylalanine at amino terminus
<220> FEATURE:
<221> NAME/KEY: MISC_FEATURE
<222> LOCATION: (2)..(2)
<223> OTHER INFORMATION: X is D and E for acidic amino acids
<220> FEATURE:
<221> NAME/KEY: MISC_FEATURE
<222> LOCATION: (3)..(3)
<223> OTHER INFORMATION: X is A and G
<220> FEATURE:
<221> NAME/KEY: MISC_FEATURE
<222> LOCATION: (4)..(4)
<223> OTHER INFORMATION: X is N or Q for amidated amino acids
<220> FEATURE:
<221> NAME/KEY: MISC_FEATURE
<222> LOCATION: (5)..(5)
<223> OTHER INFORMATION: X is GabaX for X2X3 or X3X2 or X2X3 or X3X2 or
      X3X3 or X2X2
<220> FEATURE:
<221> NAME/KEY: MISC_FEATURE
<222> LOCATION: (6)..(6)
<223> OTHER INFORMATION: X is K, R or H for basic amino acids
<220> FEATURE:
<221> NAME/KEY: MISC_FEATURE
<222> LOCATION: (7)..(7)
<223> OTHER INFORMATION: X is A and G
<220> FEATURE:
<221> NAME/KEY: MISC_FEATURE
<222> LOCATION: (8)..(8)
<223> OTHER INFORMATION: X is A and G
<220> FEATURE:
<221> NAME/KEY: MISC_FEATURE
<222> LOCATION: (9)..(9)
<223> OTHER INFORMATION: X is GabaX for X2X3 or X3X2 or X2X3 or X3X2 or
      X3X3 or X2X2
<220> FEATURE:
<221> NAME/KEY: MISC_FEATURE
<222> LOCATION: (10)..(10)
```

```
<223> OTHER INFORMATION: X is C or S
<220> FEATURE:
<221> NAME/KEY: MISC_FEATURE
<222> LOCATION: (11)..(11)
<223> OTHER INFORMATION: X is T or S
<220> FEATURE:
<221> NAME/KEY: MISC_FEATURE
<222> LOCATION: (12)..(12)
<223> OTHER INFORMATION: X is A and G
<220> FEATURE:
<221> NAME/KEY: MISC_FEATURE
<222> LOCATION: (13)..(13)
<223> OTHER INFORMATION: X is GabaX for X2X3 or X3X2 or X2X3 or X3X2 or
      X3X3 or X2X2
<220> FEATURE:
<221> NAME/KEY: MISC_FEATURE
<222> LOCATION: (14)..(14)
<223> OTHER INFORMATION: X is A and G
<220> FEATURE:
<221> NAME/KEY: MISC_FEATURE
<222> LOCATION: (15)..(15)
<223> OTHER INFORMATION: X is A and G
<220> FEATURE:
<221> NAME/KEY: MISC_FEATURE
<222> LOCATION: (16)..(16)
<223> OTHER INFORMATION: X is A and G

<400> SEQUENCE: 80

Xaa Xaa Xaa Xaa Xaa Xaa Xaa Xaa Xaa Xaa Xaa Xaa Xaa Xaa Xaa
1               5                   10                  15

<210> SEQ ID NO 81
<211> LENGTH: 38
<212> TYPE: PRT
<213> ORGANISM: Artificial
<220> FEATURE:
<223> OTHER INFORMATION: Completely synthesized peptide construct

<400> SEQUENCE: 81

Asp Gly Gln Glu Glu Lys Ala Gly Val Val Ser Thr Gly Leu Ile Gly
1               5                   10                  15

Gly Gly Asp Gly Glu Ala Gly Lys Pro Gly Lys Ala Gly Glu Arg Gly
            20                  25                  30

Pro Pro Gly Pro Gln Gly
        35

<210> SEQ ID NO 82
<211> LENGTH: 37
<212> TYPE: PRT
<213> ORGANISM: Artificial
<220> FEATURE:
<223> OTHER INFORMATION: Completely synthesized peptide construct
<220> FEATURE:
<221> NAME/KEY: MISC_FEATURE
<222> LOCATION: (1)..(1)
<223> OTHER INFORMATION: X is acetyl or propionyl group, D glycine or D
      alanine, cyclohexylalanine at amino terminus
<220> FEATURE:
<221> NAME/KEY: MISC_FEATURE
<222> LOCATION: (2)..(2)
<223> OTHER INFORMATION: X is D and E for acidic amino acids
<220> FEATURE:
<221> NAME/KEY: MISC_FEATURE
<222> LOCATION: (3)..(3)
<223> OTHER INFORMATION: X is A and G
<220> FEATURE:
<221> NAME/KEY: MISC_FEATURE
<222> LOCATION: (4)..(4)
<223> OTHER INFORMATION: X is N or Q for amidated amino acids
<220> FEATURE:
<221> NAME/KEY: MISC_FEATURE
<222> LOCATION: (5)..(5)
<223> OTHER INFORMATION: X is GabaX for X2X3 or X3X2 or X2X3 or X3X2 or
```

```
              X3X3 or X2X2
<220> FEATURE:
<221> NAME/KEY: MISC_FEATURE
<222> LOCATION: (6)..(6)
<223> OTHER INFORMATION: X is K, R or H for basic amino acids
<220> FEATURE:
<221> NAME/KEY: MISC_FEATURE
<222> LOCATION: (7)..(7)
<223> OTHER INFORMATION: X is A and G
<220> FEATURE:
<221> NAME/KEY: MISC_FEATURE
<222> LOCATION: (8)..(8)
<223> OTHER INFORMATION: X is A and G
<220> FEATURE:
<221> NAME/KEY: MISC_FEATURE
<222> LOCATION: (9)..(9)
<223> OTHER INFORMATION: X is GabaX for X2X3 or X3X2 or X2X3 or X3X2 or
              X3X3 or X2X2
<220> FEATURE:
<221> NAME/KEY: MISC_FEATURE
<222> LOCATION: (10)..(10)
<223> OTHER INFORMATION: X is C or S
<220> FEATURE:
<221> NAME/KEY: MISC_FEATURE
<222> LOCATION: (11)..(11)
<223> OTHER INFORMATION: X is T or S
<220> FEATURE:
<221> NAME/KEY: MISC_FEATURE
<222> LOCATION: (12)..(12)
<223> OTHER INFORMATION: X is A and G
<220> FEATURE:
<221> NAME/KEY: MISC_FEATURE
<222> LOCATION: (13)..(13)
<223> OTHER INFORMATION: X is GabaX for X2X3 or X3X2 or X2X3 or X3X2 or
              X3X3 or X2X2
<220> FEATURE:
<221> NAME/KEY: MISC_FEATURE
<222> LOCATION: (14)..(14)
<223> OTHER INFORMATION: X is A and G
<220> FEATURE:
<221> NAME/KEY: MISC_FEATURE
<222> LOCATION: (15)..(15)
<223> OTHER INFORMATION: X is A and G
<220> FEATURE:
<221> NAME/KEY: MISC_FEATURE
<222> LOCATION: (16)..(16)
<223> OTHER INFORMATION: X is A and G
<220> FEATURE:
<221> NAME/KEY: MISC_FEATURE
<222> LOCATION: (17)..(17)
<223> OTHER INFORMATION: X is A and G
<220> FEATURE:
<221> NAME/KEY: MISC_FEATURE
<222> LOCATION: (18)..(18)
<223> OTHER INFORMATION: X is D and E for acidic amino acids
<220> FEATURE:
<221> NAME/KEY: MISC_FEATURE
<222> LOCATION: (19)..(19)
<223> OTHER INFORMATION: X is A and G
<220> FEATURE:
<221> NAME/KEY: MISC_FEATURE
<222> LOCATION: (20)..(20)
<223> OTHER INFORMATION: X is D and E for acidic amino acids
<220> FEATURE:
<221> NAME/KEY: MISC_FEATURE
<222> LOCATION: (21)..(21)
<223> OTHER INFORMATION: X is A and G
<220> FEATURE:
<221> NAME/KEY: MISC_FEATURE
<222> LOCATION: (22)..(22)
<223> OTHER INFORMATION: X is A and G
<220> FEATURE:
<221> NAME/KEY: MISC_FEATURE
<222> LOCATION: (23)..(23)
<223> OTHER INFORMATION: X is K, R or H for basic amino acids
<220> FEATURE:
<221> NAME/KEY: MISC_FEATURE
<222> LOCATION: (24)..(24)
<223> OTHER INFORMATION: X is F or P
```

```
<220> FEATURE:
<221> NAME/KEY: MISC_FEATURE
<222> LOCATION: (25)..(25)
<223> OTHER INFORMATION: X is A and G
<220> FEATURE:
<221> NAME/KEY: MISC_FEATURE
<222> LOCATION: (26)..(26)
<223> OTHER INFORMATION: X is K, R or H for basic amino acids
<220> FEATURE:
<221> NAME/KEY: MISC_FEATURE
<222> LOCATION: (27)..(27)
<223> OTHER INFORMATION: X is A and G
<220> FEATURE:
<221> NAME/KEY: MISC_FEATURE
<222> LOCATION: (28)..(28)
<223> OTHER INFORMATION: X is A and G
<220> FEATURE:
<221> NAME/KEY: MISC_FEATURE
<222> LOCATION: (29)..(29)
<223> OTHER INFORMATION: X is D and E for acidic amino acids
<220> FEATURE:
<221> NAME/KEY: MISC_FEATURE
<222> LOCATION: (30)..(30)
<223> OTHER INFORMATION: X is K, R or H for basic amino acids
<220> FEATURE:
<221> NAME/KEY: MISC_FEATURE
<222> LOCATION: (31)..(31)
<223> OTHER INFORMATION: X is A and G
<220> FEATURE:
<221> NAME/KEY: MISC_FEATURE
<222> LOCATION: (32)..(32)
<223> OTHER INFORMATION: X is F or P
<220> FEATURE:
<221> NAME/KEY: MISC_FEATURE
<222> LOCATION: (33)..(33)
<223> OTHER INFORMATION: X is F or P
<220> FEATURE:
<221> NAME/KEY: MISC_FEATURE
<222> LOCATION: (34)..(34)
<223> OTHER INFORMATION: X is A and G
<220> FEATURE:
<221> NAME/KEY: MISC_FEATURE
<222> LOCATION: (35)..(35)
<223> OTHER INFORMATION: X is F or P
<220> FEATURE:
<221> NAME/KEY: MISC_FEATURE
<222> LOCATION: (36)..(36)
<223> OTHER INFORMATION: X is N or Q for amidated amino acids
<220> FEATURE:
<221> NAME/KEY: MISC_FEATURE
<222> LOCATION: (37)..(37)
<223> OTHER INFORMATION: X is A and G

<400> SEQUENCE: 82

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa
        35

<210> SEQ ID NO 83
<211> LENGTH: 20
<212> TYPE: PRT
<213> ORGANISM: Homo sapiens
<220> FEATURE:
<221> NAME/KEY: MISC_FEATURE
<222> LOCATION: (254)..(273)
<223> OTHER INFORMATION: Type II Collagen

<400> SEQUENCE: 83

Thr Gly Gly Lys Pro Gly Ile Ala Gly Phe Lys Gly Glu Gln Gly Pro
1               5                   10                  15
```

Lys Gly Glu Pro
            20

<210> SEQ ID NO 84
<211> LENGTH: 20
<212> TYPE: PRT
<213> ORGANISM: artificial
<220> FEATURE:
<223> OTHER INFORMATION: Completely synthesized peptide construct
<220> FEATURE:
<221> NAME/KEY: MISC_FEATURE
<222> LOCATION: (1)..(1)
<223> OTHER INFORMATION: X is T or S
<220> FEATURE:
<221> NAME/KEY: MISC_FEATURE
<222> LOCATION: (2)..(2)
<223> OTHER INFORMATION: X is A and G
<220> FEATURE:
<221> NAME/KEY: MISC_FEATURE
<222> LOCATION: (3)..(3)
<223> OTHER INFORMATION: X is A and G
<220> FEATURE:
<221> NAME/KEY: MISC_FEATURE
<222> LOCATION: (4)..(4)
<223> OTHER INFORMATION: X is K, R or H for basic amino acids
<220> FEATURE:
<221> NAME/KEY: MISC_FEATURE
<222> LOCATION: (5)..(5)
<223> OTHER INFORMATION: X is F or P
<220> FEATURE:
<221> NAME/KEY: MISC_FEATURE
<222> LOCATION: (6)..(6)
<223> OTHER INFORMATION: X is A and G
<220> FEATURE:
<221> NAME/KEY: MISC_FEATURE
<222> LOCATION: (7)..(7)
<223> OTHER INFORMATION: X is I, L or V
<220> FEATURE:
<221> NAME/KEY: MISC_FEATURE
<222> LOCATION: (8)..(8)
<223> OTHER INFORMATION: X is A and G
<220> FEATURE:
<221> NAME/KEY: MISC_FEATURE
<222> LOCATION: (9)..(9)
<223> OTHER INFORMATION: X is A and G
<220> FEATURE:
<221> NAME/KEY: MISC_FEATURE
<222> LOCATION: (10)..(10)
<223> OTHER INFORMATION: X is F, W or Y for aromatic amino acids
<220> FEATURE:
<221> NAME/KEY: MISC_FEATURE
<222> LOCATION: (11)..(11)
<223> OTHER INFORMATION: X is K, R or H for basic amino acids
<220> FEATURE:
<221> NAME/KEY: MISC_FEATURE
<222> LOCATION: (12)..(12)
<223> OTHER INFORMATION: X is A and G
<220> FEATURE:
<221> NAME/KEY: MISC_FEATURE
<222> LOCATION: (13)..(13)
<223> OTHER INFORMATION: X is D and E for acidic amino acids
<220> FEATURE:
<221> NAME/KEY: MISC_FEATURE
<222> LOCATION: (14)..(14)
<223> OTHER INFORMATION: X is N or Q for amidated amino acids
<220> FEATURE:
<221> NAME/KEY: MISC_FEATURE
<222> LOCATION: (15)..(15)
<223> OTHER INFORMATION: X is A and G
<220> FEATURE:
<221> NAME/KEY: MISC_FEATURE
<222> LOCATION: (16)..(16)
<223> OTHER INFORMATION: X is F or P
<220> FEATURE:
<221> NAME/KEY: MISC_FEATURE
<222> LOCATION: (17)..(17)
<223> OTHER INFORMATION: X is K, R or H for basic amino acids
<220> FEATURE:

```
<221> NAME/KEY: MISC_FEATURE
<222> LOCATION: (18)..(18)
<223> OTHER INFORMATION: X is A and G
<220> FEATURE:
<221> NAME/KEY: MISC_FEATURE
<222> LOCATION: (19)..(19)
<223> OTHER INFORMATION: X is D and E for acidic amino acids
<220> FEATURE:
<221> NAME/KEY: MISC_FEATURE
<222> LOCATION: (20)..(20)
<223> OTHER INFORMATION: X is F or P

<400> SEQUENCE: 84

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa
            20

<210> SEQ ID NO 85
<211> LENGTH: 15
<212> TYPE: PRT
<213> ORGANISM: artificial
<220> FEATURE:
<223> OTHER INFORMATION: Completely synthesized peptide construct
<220> FEATURE:
<221> NAME/KEY: MISC_FEATURE
<222> LOCATION: (1)..(1)
<223> OTHER INFORMATION: X is T or S
<220> FEATURE:
<221> NAME/KEY: MISC_FEATURE
<222> LOCATION: (2)..(2)
<223> OTHER INFORMATION: X is X1X1 or X1X3 or X3X1 or X1X2 or X2X1
<220> FEATURE:
<221> NAME/KEY: MISC_FEATURE
<222> LOCATION: (3)..(3)
<223> OTHER INFORMATION: X is K, R or H for basic amino acids
<220> FEATURE:
<221> NAME/KEY: MISC_FEATURE
<222> LOCATION: (4)..(4)
<223> OTHER INFORMATION: X is F or P
<220> FEATURE:
<221> NAME/KEY: MISC_FEATURE
<222> LOCATION: (5)..(5)
<223> OTHER INFORMATION: X is GabaX for X2X3 or X3X2 or X2X3 or X3X2 or
      X3X3 or X2X2
<220> FEATURE:
<221> NAME/KEY: MISC_FEATURE
<222> LOCATION: (5)..(5)
<223> OTHER INFORMATION: X is Gaba for X2X3 or X3X2 or X2X3 or X3X2 or
      X3X3 or X2X2
<220> FEATURE:
<221> NAME/KEY: MISC_FEATURE
<222> LOCATION: (6)..(6)
<223> OTHER INFORMATION: X is X1X1 or X1X3 or X3X1 or X1X2 or X2X1
<220> FEATURE:
<221> NAME/KEY: MISC_FEATURE
<222> LOCATION: (7)..(7)
<223> OTHER INFORMATION: X is F, W or Y for aromatic amino acids
<220> FEATURE:
<221> NAME/KEY: MISC_FEATURE
<222> LOCATION: (8)..(8)
<223> OTHER INFORMATION: X is K, R or H for basic amino acids
<220> FEATURE:
<221> NAME/KEY: MISC_FEATURE
<222> LOCATION: (9)..(9)
<223> OTHER INFORMATION: X is X1X1 or X1X3 or X3X1 or X1X2 or X2X1
<220> FEATURE:
<221> NAME/KEY: MISC_FEATURE
<222> LOCATION: (10)..(10)
<223> OTHER INFORMATION: X is N or Q for amidated amino acids
<220> FEATURE:
<221> NAME/KEY: MISC_FEATURE
<222> LOCATION: (11)..(11)
<223> OTHER INFORMATION: X is A and G
<220> FEATURE:
<221> NAME/KEY: MISC_FEATURE
```

```
<222> LOCATION: (12)..(12)
<223> OTHER INFORMATION: X is F or P
<220> FEATURE:
<221> NAME/KEY: MISC_FEATURE
<222> LOCATION: (13)..(13)
<223> OTHER INFORMATION: X is K, R or H for basic amino acids
<220> FEATURE:
<221> NAME/KEY: MISC_FEATURE
<222> LOCATION: (14)..(14)
<223> OTHER INFORMATION: X is X1X1 or X1X3 or X3X1 or X1X2 or X2X1
<220> FEATURE:
<221> NAME/KEY: MISC_FEATURE
<222> LOCATION: (15)..(15)
<223> OTHER INFORMATION: X is F or P

<400> SEQUENCE: 85

Xaa Xaa Xaa Xaa Xaa Xaa Xaa Xaa Xaa Xaa Xaa Xaa Xaa Xaa Xaa
1               5                   10                  15

<210> SEQ ID NO 86
<211> LENGTH: 34
<212> TYPE: PRT
<213> ORGANISM: artificial
<220> FEATURE:
<223> OTHER INFORMATION: Completely synthesized peptide construct

<400> SEQUENCE: 86

Pro Ser Thr His Val Leu Ile Thr His Thr Ile Gly Gly Gly Thr Gly
1               5                   10                  15

Gly Lys Pro Gly Ile Ala Gly Phe Lys Gly Glu Gln Gly Pro Lys Gly
            20                  25                  30

Glu Pro

<210> SEQ ID NO 87
<211> LENGTH: 38
<212> TYPE: PRT
<213> ORGANISM: artificial
<220> FEATURE:
<223> OTHER INFORMATION: Completely synthesized peptide construct

<400> SEQUENCE: 87

Asp Phe Leu Pro His Tyr Lys Asn Thr Ser Leu Gly His Arg Pro Gly
1               5                   10                  15

Gly Gly Thr Gly Gly Lys Pro Gly Ile Ala Gly Phe Lys Gly Glu Gln
            20                  25                  30

Gly Pro Lys Gly Glu Pro
        35

<210> SEQ ID NO 88
<211> LENGTH: 40
<212> TYPE: PRT
<213> ORGANISM: artificial
<220> FEATURE:
<223> OTHER INFORMATION: Completely synthesized peptide construct

<400> SEQUENCE: 88

Asn Gly Gln Glu Glu Lys Ala Gly Val Val Ser Thr Gly Leu Ile Gly
1               5                   10                  15

Gly Gly Gly Ser Thr Gly Gly Lys Pro Gly Ile Ala Gly Phe Lys Gly
            20                  25                  30

Glu Gln Gly Pro Lys Gly Glu Pro
        35                  40

<210> SEQ ID NO 89
<211> LENGTH: 40
```

```
<212> TYPE: PRT
<213> ORGANISM: artificial
<220> FEATURE:
<223> OTHER INFORMATION: Completely synthesized peptide construct

<400> SEQUENCE: 89

Asp Gly Gln Glu Glu Lys Ala Gly Val Val Ser Thr Gly Leu Ile Gly
1               5                   10                  15

Gly Gly Gly Ser Thr Gly Gly Lys Pro Gly Ile Ala Gly Phe Lys Gly
            20                  25                  30

Glu Gln Gly Pro Lys Gly Glu Pro
        35                  40

<210> SEQ ID NO 90
<211> LENGTH: 38
<212> TYPE: PRT
<213> ORGANISM: artificial
<220> FEATURE:
<223> OTHER INFORMATION: Completely synthesized peptide construct

<400> SEQUENCE: 90

Asp Gly Gln Glu Glu Lys Ala Gly Val Val Ser Thr Gly Leu Ile Gly
1               5                   10                  15

Gly Gly Thr Gly Gly Lys Pro Gly Ile Ala Gly Phe Lys Gly Glu Gln
            20                  25                  30

Gly Pro Lys Gly Glu Pro
        35

<210> SEQ ID NO 91
<211> LENGTH: 38
<212> TYPE: PRT
<213> ORGANISM: artificial
<220> FEATURE:
<223> OTHER INFORMATION: Completely synthesized peptide construct
<220> FEATURE:
<221> NAME/KEY: MISC_FEATURE
<222> LOCATION: (1)..(1)
<223> OTHER INFORMATION: X is D and E for acidic amino acids
<220> FEATURE:
<221> NAME/KEY: MISC_FEATURE
<222> LOCATION: (2)..(2)
<223> OTHER INFORMATION: X is A and G
<220> FEATURE:
<221> NAME/KEY: MISC_FEATURE
<222> LOCATION: (3)..(3)
<223> OTHER INFORMATION: X is N or Q for amidated amino acids
<220> FEATURE:
<221> NAME/KEY: MISC_FEATURE
<222> LOCATION: (4)..(4)
<223> OTHER INFORMATION: X is D and E for acidic amino acids
<220> FEATURE:
<221> NAME/KEY: MISC_FEATURE
<222> LOCATION: (5)..(5)
<223> OTHER INFORMATION: X is D and E for acidic amino acids
<220> FEATURE:
<221> NAME/KEY: MISC_FEATURE
<222> LOCATION: (6)..(6)
<223> OTHER INFORMATION: X is K, R or H for basic amino acids
<220> FEATURE:
<221> NAME/KEY: MISC_FEATURE
<222> LOCATION: (7)..(7)
<223> OTHER INFORMATION: X is A and G
<220> FEATURE:
<221> NAME/KEY: MISC_FEATURE
<222> LOCATION: (8)..(8)
<223> OTHER INFORMATION: X is A and G
<220> FEATURE:
<221> NAME/KEY: MISC_FEATURE
<222> LOCATION: (9)..(9)
<223> OTHER INFORMATION: X is I, L or V
<220> FEATURE:
```

```
<221> NAME/KEY: MISC_FEATURE
<222> LOCATION: (10)..(10)
<223> OTHER INFORMATION: X is I, L or V
<220> FEATURE:
<221> NAME/KEY: MISC_FEATURE
<222> LOCATION: (11)..(11)
<223> OTHER INFORMATION: X is C or S
<220> FEATURE:
<221> NAME/KEY: MISC_FEATURE
<222> LOCATION: (12)..(12)
<223> OTHER INFORMATION: X is T or S
<220> FEATURE:
<221> NAME/KEY: MISC_FEATURE
<222> LOCATION: (13)..(13)
<223> OTHER INFORMATION: X is A and G
<220> FEATURE:
<221> NAME/KEY: MISC_FEATURE
<222> LOCATION: (14)..(14)
<223> OTHER INFORMATION: X is I, L or V
<220> FEATURE:
<221> NAME/KEY: MISC_FEATURE
<222> LOCATION: (15)..(15)
<223> OTHER INFORMATION: X is I, L or V
<220> FEATURE:
<221> NAME/KEY: MISC_FEATURE
<222> LOCATION: (16)..(16)
<223> OTHER INFORMATION: X is A and G
<220> FEATURE:
<221> NAME/KEY: MISC_FEATURE
<222> LOCATION: (17)..(17)
<223> OTHER INFORMATION: X is A and G
<220> FEATURE:
<221> NAME/KEY: MISC_FEATURE
<222> LOCATION: (18)..(18)
<223> OTHER INFORMATION: X is A and G
<220> FEATURE:
<221> NAME/KEY: MISC_FEATURE
<222> LOCATION: (19)..(19)
<223> OTHER INFORMATION: X is T or S
<220> FEATURE:
<221> NAME/KEY: MISC_FEATURE
<222> LOCATION: (20)..(20)
<223> OTHER INFORMATION: X is A and G
<220> FEATURE:
<221> NAME/KEY: MISC_FEATURE
<222> LOCATION: (21)..(21)
<223> OTHER INFORMATION: X is A and G
<220> FEATURE:
<221> NAME/KEY: MISC_FEATURE
<222> LOCATION: (22)..(22)
<223> OTHER INFORMATION: X is K, R or H for basic amino acids
<220> FEATURE:
<221> NAME/KEY: MISC_FEATURE
<222> LOCATION: (23)..(23)
<223> OTHER INFORMATION: X is F or P
<220> FEATURE:
<221> NAME/KEY: MISC_FEATURE
<222> LOCATION: (24)..(24)
<223> OTHER INFORMATION: X is A and G
<220> FEATURE:
<221> NAME/KEY: MISC_FEATURE
<222> LOCATION: (25)..(25)
<223> OTHER INFORMATION: X is I, L or V
<220> FEATURE:
<221> NAME/KEY: MISC_FEATURE
<222> LOCATION: (26)..(26)
<223> OTHER INFORMATION: X is A and G
<220> FEATURE:
<221> NAME/KEY: MISC_FEATURE
<222> LOCATION: (27)..(27)
<223> OTHER INFORMATION: X is A and G
<220> FEATURE:
<221> NAME/KEY: MISC_FEATURE
<222> LOCATION: (28)..(28)
<223> OTHER INFORMATION: X is F, W or Y for aromatic amino acids
<220> FEATURE:
<221> NAME/KEY: MISC_FEATURE
<222> LOCATION: (29)..(29)
<223> OTHER INFORMATION: X is K, R or H for basic amino acids
```

```
<220> FEATURE:
<221> NAME/KEY: MISC_FEATURE
<222> LOCATION: (30)..(30)
<223> OTHER INFORMATION: X is A and G
<220> FEATURE:
<221> NAME/KEY: MISC_FEATURE
<222> LOCATION: (31)..(31)
<223> OTHER INFORMATION: X is D and E for acidic amino acids
<220> FEATURE:
<221> NAME/KEY: MISC_FEATURE
<222> LOCATION: (32)..(32)
<223> OTHER INFORMATION: X is N or Q for amidated amino acids
<220> FEATURE:
<221> NAME/KEY: MISC_FEATURE
<222> LOCATION: (33)..(33)
<223> OTHER INFORMATION: X is A and G
<220> FEATURE:
<221> NAME/KEY: MISC_FEATURE
<222> LOCATION: (34)..(34)
<223> OTHER INFORMATION: X is F or P
<220> FEATURE:
<221> NAME/KEY: MISC_FEATURE
<222> LOCATION: (35)..(35)
<223> OTHER INFORMATION: X is K, R or H for basic amino acids
<220> FEATURE:
<221> NAME/KEY: MISC_FEATURE
<222> LOCATION: (36)..(36)
<223> OTHER INFORMATION: X is A and G
<220> FEATURE:
<221> NAME/KEY: MISC_FEATURE
<222> LOCATION: (37)..(37)
<223> OTHER INFORMATION: X is D and E for acidic amino acids
<220> FEATURE:
<221> NAME/KEY: MISC_FEATURE
<222> LOCATION: (38)..(38)
<223> OTHER INFORMATION: X is F or P

<400> SEQUENCE: 91

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa
        35

<210> SEQ ID NO 92
<211> LENGTH: 39
<212> TYPE: PRT
<213> ORGANISM: artificial
<220> FEATURE:
<223> OTHER INFORMATION: Completely synthesized peptide construct
<220> FEATURE:
<221> NAME/KEY: MISC_FEATURE
<222> LOCATION: (1)..(1)
<223> OTHER INFORMATION: X is Acetyl or propionyl group, D glycine or D
      alanine, Cyclohexylalanine at amino terminus
<220> FEATURE:
<221> NAME/KEY: MISC_FEATURE
<222> LOCATION: (2)..(2)
<223> OTHER INFORMATION: X is D and E for acidic amino acids
<220> FEATURE:
<221> NAME/KEY: MISC_FEATURE
<222> LOCATION: (3)..(3)
<223> OTHER INFORMATION: X is A and G
<220> FEATURE:
<221> NAME/KEY: MISC_FEATURE
<222> LOCATION: (4)..(4)
<223> OTHER INFORMATION: X is N or Q for amidated amino acids
<220> FEATURE:
<221> NAME/KEY: MISC_FEATURE
<222> LOCATION: (5)..(5)
<223> OTHER INFORMATION: X is D and E for acidic amino acids
<220> FEATURE:
<221> NAME/KEY: MISC_FEATURE
<222> LOCATION: (6)..(6)
```

```
<223> OTHER INFORMATION: X is D and E for acidic amino acids
<220> FEATURE:
<221> NAME/KEY: MISC_FEATURE
<222> LOCATION: (7)..(7)
<223> OTHER INFORMATION: X is K, R or H for basic amino acids
<220> FEATURE:
<221> NAME/KEY: MISC_FEATURE
<222> LOCATION: (8)..(8)
<223> OTHER INFORMATION: X is A and G
<220> FEATURE:
<221> NAME/KEY: MISC_FEATURE
<222> LOCATION: (9)..(9)
<223> OTHER INFORMATION: X is A and G
<220> FEATURE:
<221> NAME/KEY: MISC_FEATURE
<222> LOCATION: (10)..(10)
<223> OTHER INFORMATION: X is I, L or V
<220> FEATURE:
<221> NAME/KEY: MISC_FEATURE
<222> LOCATION: (11)..(11)
<223> OTHER INFORMATION: X is I, L or V
<220> FEATURE:
<221> NAME/KEY: MISC_FEATURE
<222> LOCATION: (12)..(12)
<223> OTHER INFORMATION: X is C or S
<220> FEATURE:
<221> NAME/KEY: MISC_FEATURE
<222> LOCATION: (13)..(13)
<223> OTHER INFORMATION: X is T or S
<220> FEATURE:
<221> NAME/KEY: MISC_FEATURE
<222> LOCATION: (14)..(14)
<223> OTHER INFORMATION: X is A and G
<220> FEATURE:
<221> NAME/KEY: MISC_FEATURE
<222> LOCATION: (15)..(15)
<223> OTHER INFORMATION: X is I, L or V
<220> FEATURE:
<221> NAME/KEY: MISC_FEATURE
<222> LOCATION: (16)..(16)
<223> OTHER INFORMATION: X is I, L or V
<220> FEATURE:
<221> NAME/KEY: MISC_FEATURE
<222> LOCATION: (17)..(17)
<223> OTHER INFORMATION: X is A and G
<220> FEATURE:
<221> NAME/KEY: MISC_FEATURE
<222> LOCATION: (18)..(18)
<223> OTHER INFORMATION: X is A and G
<220> FEATURE:
<221> NAME/KEY: MISC_FEATURE
<222> LOCATION: (19)..(19)
<223> OTHER INFORMATION: X is A and G
<220> FEATURE:
<221> NAME/KEY: MISC_FEATURE
<222> LOCATION: (20)..(20)
<223> OTHER INFORMATION: X is T or S
<220> FEATURE:
<221> NAME/KEY: MISC_FEATURE
<222> LOCATION: (21)..(21)
<223> OTHER INFORMATION: X is A and G
<220> FEATURE:
<221> NAME/KEY: MISC_FEATURE
<222> LOCATION: (22)..(22)
<223> OTHER INFORMATION: X is A and G
<220> FEATURE:
<221> NAME/KEY: MISC_FEATURE
<222> LOCATION: (23)..(23)
<223> OTHER INFORMATION: X is K, R or H for basic amino acids
<220> FEATURE:
<221> NAME/KEY: MISC_FEATURE
<222> LOCATION: (24)..(24)
<223> OTHER INFORMATION: X is F or P
<220> FEATURE:
<221> NAME/KEY: MISC_FEATURE
<222> LOCATION: (25)..(25)
<223> OTHER INFORMATION: X is A and G
<220> FEATURE:
<221> NAME/KEY: MISC_FEATURE
```

```
<222> LOCATION: (26)..(26)
<223> OTHER INFORMATION: X is I, L or V
<220> FEATURE:
<221> NAME/KEY: MISC_FEATURE
<222> LOCATION: (27)..(27)
<223> OTHER INFORMATION: X is A and G
<220> FEATURE:
<221> NAME/KEY: MISC_FEATURE
<222> LOCATION: (28)..(28)
<223> OTHER INFORMATION: X is A and G
<220> FEATURE:
<221> NAME/KEY: MISC_FEATURE
<222> LOCATION: (29)..(29)
<223> OTHER INFORMATION: X is F, W or Y for aromatic amino acids
<220> FEATURE:
<221> NAME/KEY: MISC_FEATURE
<222> LOCATION: (30)..(30)
<223> OTHER INFORMATION: X is K, R or H for basic amino acids
<220> FEATURE:
<221> NAME/KEY: MISC_FEATURE
<222> LOCATION: (31)..(31)
<223> OTHER INFORMATION: X is A and G
<220> FEATURE:
<221> NAME/KEY: MISC_FEATURE
<222> LOCATION: (32)..(32)
<223> OTHER INFORMATION: X is D and E for acidic amino acids
<220> FEATURE:
<221> NAME/KEY: MISC_FEATURE
<222> LOCATION: (33)..(33)
<223> OTHER INFORMATION: X is N or Q for amidated amino acids
<220> FEATURE:
<221> NAME/KEY: MISC_FEATURE
<222> LOCATION: (34)..(34)
<223> OTHER INFORMATION: X is A and G
<220> FEATURE:
<221> NAME/KEY: MISC_FEATURE
<222> LOCATION: (35)..(35)
<223> OTHER INFORMATION: X is F or P
<220> FEATURE:
<221> NAME/KEY: MISC_FEATURE
<222> LOCATION: (36)..(36)
<223> OTHER INFORMATION: X is K, R or H for basic amino acids
<220> FEATURE:
<221> NAME/KEY: MISC_FEATURE
<222> LOCATION: (37)..(37)
<223> OTHER INFORMATION: X is A and G
<220> FEATURE:
<221> NAME/KEY: MISC_FEATURE
<222> LOCATION: (38)..(38)
<223> OTHER INFORMATION: X is D and E for acidic amino acids
<220> FEATURE:
<221> NAME/KEY: MISC_FEATURE
<222> LOCATION: (39)..(39)
<223> OTHER INFORMATION: X is F or P

<400> SEQUENCE: 92

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa
        35

<210> SEQ ID NO 93
<211> LENGTH: 39
<212> TYPE: PRT
<213> ORGANISM: artificial
<220> FEATURE:
<223> OTHER INFORMATION: Completely synthesized peptide construct
<220> FEATURE:
<221> NAME/KEY: MISC_FEATURE
<222> LOCATION: (1)..(1)
<223> OTHER INFORMATION: X is 5-aminopentanoic acid for replacement of 3
      or 4 amino acids of X2 and  X3
<220> FEATURE:
```

```
<221> NAME/KEY: MISC_FEATURE
<222> LOCATION: (2)..(2)
<223> OTHER INFORMATION: X is D and E for acidic amino acids
<220> FEATURE:
<221> NAME/KEY: MISC_FEATURE
<222> LOCATION: (3)..(3)
<223> OTHER INFORMATION: X is A and G
<220> FEATURE:
<221> NAME/KEY: MISC_FEATURE
<222> LOCATION: (4)..(4)
<223> OTHER INFORMATION: X is N or Q for amidated amino acids
<220> FEATURE:
<221> NAME/KEY: MISC_FEATURE
<222> LOCATION: (5)..(5)
<223> OTHER INFORMATION: X is D and E for acidic amino acids
<220> FEATURE:
<221> NAME/KEY: MISC_FEATURE
<222> LOCATION: (6)..(6)
<223> OTHER INFORMATION: X is D and E for acidic amino acids
<220> FEATURE:
<221> NAME/KEY: MISC_FEATURE
<222> LOCATION: (7)..(7)
<223> OTHER INFORMATION: X is K, R or H for basic amino acids
<220> FEATURE:
<221> NAME/KEY: MISC_FEATURE
<222> LOCATION: (8)..(8)
<223> OTHER INFORMATION: X is A and G
<220> FEATURE:
<221> NAME/KEY: MISC_FEATURE
<222> LOCATION: (9)..(9)
<223> OTHER INFORMATION: X is A and G
<220> FEATURE:
<221> NAME/KEY: MISC_FEATURE
<222> LOCATION: (10)..(10)
<223> OTHER INFORMATION: X is I, L or V
<220> FEATURE:
<221> NAME/KEY: MISC_FEATURE
<222> LOCATION: (11)..(11)
<223> OTHER INFORMATION: X is I, L or V
<220> FEATURE:
<221> NAME/KEY: MISC_FEATURE
<222> LOCATION: (12)..(12)
<223> OTHER INFORMATION: X is C or S
<220> FEATURE:
<221> NAME/KEY: MISC_FEATURE
<222> LOCATION: (13)..(13)
<223> OTHER INFORMATION: X is T or S
<220> FEATURE:
<221> NAME/KEY: MISC_FEATURE
<222> LOCATION: (14)..(14)
<223> OTHER INFORMATION: X is A and G
<220> FEATURE:
<221> NAME/KEY: MISC_FEATURE
<222> LOCATION: (15)..(15)
<223> OTHER INFORMATION: X is I, L or V
<220> FEATURE:
<221> NAME/KEY: MISC_FEATURE
<222> LOCATION: (16)..(16)
<223> OTHER INFORMATION: X is I, L or V
<220> FEATURE:
<221> NAME/KEY: MISC_FEATURE
<222> LOCATION: (17)..(17)
<223> OTHER INFORMATION: X is A and G
<220> FEATURE:
<221> NAME/KEY: MISC_FEATURE
<222> LOCATION: (18)..(18)
<223> OTHER INFORMATION: X is A and G
<220> FEATURE:
<221> NAME/KEY: MISC_FEATURE
<222> LOCATION: (19)..(19)
<223> OTHER INFORMATION: X is A and G
<220> FEATURE:
<221> NAME/KEY: MISC_FEATURE
<222> LOCATION: (20)..(20)
<223> OTHER INFORMATION: X is T or S
<220> FEATURE:
<221> NAME/KEY: MISC_FEATURE
<222> LOCATION: (21)..(21)
<223> OTHER INFORMATION: X is A and G
```

```
<220> FEATURE:
<221> NAME/KEY: MISC_FEATURE
<222> LOCATION: (22)..(22)
<223> OTHER INFORMATION: X is A and G
<220> FEATURE:
<221> NAME/KEY: MISC_FEATURE
<222> LOCATION: (23)..(23)
<223> OTHER INFORMATION: X is K, R or H for basic amino acids
<220> FEATURE:
<221> NAME/KEY: MISC_FEATURE
<222> LOCATION: (24)..(24)
<223> OTHER INFORMATION: X is F or P
<220> FEATURE:
<221> NAME/KEY: MISC_FEATURE
<222> LOCATION: (25)..(25)
<223> OTHER INFORMATION: X is A and G
<220> FEATURE:
<221> NAME/KEY: MISC_FEATURE
<222> LOCATION: (26)..(26)
<223> OTHER INFORMATION: X is I, L or V
<220> FEATURE:
<221> NAME/KEY: MISC_FEATURE
<222> LOCATION: (27)..(27)
<223> OTHER INFORMATION: X is A and G
<220> FEATURE:
<221> NAME/KEY: MISC_FEATURE
<222> LOCATION: (28)..(28)
<223> OTHER INFORMATION: X is A and G
<220> FEATURE:
<221> NAME/KEY: MISC_FEATURE
<222> LOCATION: (29)..(29)
<223> OTHER INFORMATION: X is F, W or Y for aromatic amino acids
<220> FEATURE:
<221> NAME/KEY: MISC_FEATURE
<222> LOCATION: (30)..(30)
<223> OTHER INFORMATION: X is K, R or H for basic amino acids
<220> FEATURE:
<221> NAME/KEY: MISC_FEATURE
<222> LOCATION: (31)..(31)
<223> OTHER INFORMATION: X is A and G
<220> FEATURE:
<221> NAME/KEY: MISC_FEATURE
<222> LOCATION: (32)..(32)
<223> OTHER INFORMATION: X is D and E for acidic amino acids
<220> FEATURE:
<221> NAME/KEY: MISC_FEATURE
<222> LOCATION: (33)..(33)
<223> OTHER INFORMATION: X is N or Q for amidated amino acids
<220> FEATURE:
<221> NAME/KEY: MISC_FEATURE
<222> LOCATION: (34)..(34)
<223> OTHER INFORMATION: X is A and G
<220> FEATURE:
<221> NAME/KEY: MISC_FEATURE
<222> LOCATION: (35)..(35)
<223> OTHER INFORMATION: X is F or P
<220> FEATURE:
<221> NAME/KEY: MISC_FEATURE
<222> LOCATION: (36)..(36)
<223> OTHER INFORMATION: X is K, R or H for basic amino acids
<220> FEATURE:
<221> NAME/KEY: MISC_FEATURE
<222> LOCATION: (37)..(37)
<223> OTHER INFORMATION: X is A and G
<220> FEATURE:
<221> NAME/KEY: MISC_FEATURE
<222> LOCATION: (38)..(38)
<223> OTHER INFORMATION: X is D and E for acidic amino acids
<220> FEATURE:
<221> NAME/KEY: MISC_FEATURE
<222> LOCATION: (39)..(39)
<223> OTHER INFORMATION: X is F or P

<400> SEQUENCE: 93

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
```

```
            20                  25                  30

Xaa Xaa Xaa Xaa Xaa Xaa Xaa
        35

<210> SEQ ID NO 94
<211> LENGTH: 36
<212> TYPE: PRT
<213> ORGANISM: artificial
<220> FEATURE:
<223> OTHER INFORMATION: Completely synthesized peptide construct
<220> FEATURE:
<221> NAME/KEY: MISC_FEATURE
<222> LOCATION: (1)..(1)
<223> OTHER INFORMATION: X is Acetyl or propionyl group, D glycine or D
      alanine, Cyclohexylalanine at amino terminus
<220> FEATURE:
<221> NAME/KEY: MISC_FEATURE
<222> LOCATION: (2)..(2)
<223> OTHER INFORMATION: X is D and E for acidic amino acids
<220> FEATURE:
<221> NAME/KEY: MISC_FEATURE
<222> LOCATION: (3)..(3)
<223> OTHER INFORMATION: X is A and G
<220> FEATURE:
<221> NAME/KEY: MISC_FEATURE
<222> LOCATION: (4)..(4)
<223> OTHER INFORMATION: X is N or Q for amidated amino acids
<220> FEATURE:
<221> NAME/KEY: MISC_FEATURE
<222> LOCATION: (5)..(5)
<223> OTHER INFORMATION: X is Gaba for X2X3 or X3X2 or X2X3 or X3X2 or
      X3X3 or X2X2
<220> FEATURE:
<221> NAME/KEY: MISC_FEATURE
<222> LOCATION: (6)..(6)
<223> OTHER INFORMATION: X is K, R or H for basic amino acids
<220> FEATURE:
<221> NAME/KEY: MISC_FEATURE
<222> LOCATION: (7)..(7)
<223> OTHER INFORMATION: X is A and G
<220> FEATURE:
<221> NAME/KEY: MISC_FEATURE
<222> LOCATION: (8)..(8)
<223> OTHER INFORMATION: X is A and G
<220> FEATURE:
<221> NAME/KEY: MISC_FEATURE
<222> LOCATION: (9)..(9)
<223> OTHER INFORMATION: X is Gaba for X2X3 or X3X2 or X2X3 or X3X2 or
      X3X3 or X2X2
<220> FEATURE:
<221> NAME/KEY: MISC_FEATURE
<222> LOCATION: (10)..(10)
<223> OTHER INFORMATION: X is C or S
<220> FEATURE:
<221> NAME/KEY: MISC_FEATURE
<222> LOCATION: (11)..(11)
<223> OTHER INFORMATION: X is T or S
<220> FEATURE:
<221> NAME/KEY: MISC_FEATURE
<222> LOCATION: (12)..(12)
<223> OTHER INFORMATION: X is A and G
<220> FEATURE:
<221> NAME/KEY: MISC_FEATURE
<222> LOCATION: (13)..(13)
<223> OTHER INFORMATION: X is Gaba for X2X3 or X3X2 or X2X3 or X3X2 or
      X3X3 or X2X2
<220> FEATURE:
<221> NAME/KEY: MISC_FEATURE
<222> LOCATION: (14)..(14)
<223> OTHER INFORMATION: X is A and G
<220> FEATURE:
<221> NAME/KEY: MISC_FEATURE
<222> LOCATION: (15)..(15)
<223> OTHER INFORMATION: X is A and G
<220> FEATURE:
<221> NAME/KEY: MISC_FEATURE
<222> LOCATION: (16)..(16)
```

```
<223> OTHER INFORMATION: X is A and G
<220> FEATURE:
<221> NAME/KEY: MISC_FEATURE
<222> LOCATION: (17)..(17)
<223> OTHER INFORMATION: X is T or S
<220> FEATURE:
<221> NAME/KEY: MISC_FEATURE
<222> LOCATION: (18)..(18)
<223> OTHER INFORMATION: X is A and G
<220> FEATURE:
<221> NAME/KEY: MISC_FEATURE
<222> LOCATION: (19)..(19)
<223> OTHER INFORMATION: X is A and G
<220> FEATURE:
<221> NAME/KEY: MISC_FEATURE
<222> LOCATION: (20)..(20)
<223> OTHER INFORMATION: X is K, R or H for basic amino acids
<220> FEATURE:
<221> NAME/KEY: MISC_FEATURE
<222> LOCATION: (21)..(21)
<223> OTHER INFORMATION: X is F or P
<220> FEATURE:
<221> NAME/KEY: MISC_FEATURE
<222> LOCATION: (22)..(22)
<223> OTHER INFORMATION: X is A and G
<220> FEATURE:
<221> NAME/KEY: MISC_FEATURE
<222> LOCATION: (23)..(23)
<223> OTHER INFORMATION: X is I, L or V
<220> FEATURE:
<221> NAME/KEY: MISC_FEATURE
<222> LOCATION: (24)..(24)
<223> OTHER INFORMATION: X is A and G
<220> FEATURE:
<221> NAME/KEY: MISC_FEATURE
<222> LOCATION: (25)..(25)
<223> OTHER INFORMATION: X is A and G
<220> FEATURE:
<221> NAME/KEY: MISC_FEATURE
<222> LOCATION: (26)..(26)
<223> OTHER INFORMATION: X is F, W or Y for aromatic amino acids
<220> FEATURE:
<221> NAME/KEY: MISC_FEATURE
<222> LOCATION: (27)..(27)
<223> OTHER INFORMATION: X is K, R or H for basic amino acids
<220> FEATURE:
<221> NAME/KEY: MISC_FEATURE
<222> LOCATION: (28)..(28)
<223> OTHER INFORMATION: X is A and G
<220> FEATURE:
<221> NAME/KEY: MISC_FEATURE
<222> LOCATION: (29)..(29)
<223> OTHER INFORMATION: X is D and E for acidic amino acids
<220> FEATURE:
<221> NAME/KEY: MISC_FEATURE
<222> LOCATION: (30)..(30)
<223> OTHER INFORMATION: X is N or Q for amidated amino acids
<220> FEATURE:
<221> NAME/KEY: MISC_FEATURE
<222> LOCATION: (31)..(31)
<223> OTHER INFORMATION: X is A and G
<220> FEATURE:
<221> NAME/KEY: MISC_FEATURE
<222> LOCATION: (32)..(32)
<223> OTHER INFORMATION: X is F or P
<220> FEATURE:
<221> NAME/KEY: MISC_FEATURE
<222> LOCATION: (33)..(33)
<223> OTHER INFORMATION: X is K, R or H for basic amino acids
<220> FEATURE:
<221> NAME/KEY: MISC_FEATURE
<222> LOCATION: (34)..(34)
<223> OTHER INFORMATION: X is A and G
<220> FEATURE:
<221> NAME/KEY: MISC_FEATURE
<222> LOCATION: (35)..(35)
<223> OTHER INFORMATION: X is D and E for acidic amino acids
<220> FEATURE:
<221> NAME/KEY: MISC_FEATURE
```

<222> LOCATION: (36)..(36)
<223> OTHER INFORMATION: X is F or P

<400> SEQUENCE: 94

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa
        35

<210> SEQ ID NO 95
<211> LENGTH: 33
<212> TYPE: PRT
<213> ORGANISM: artificial
<220> FEATURE:
<223> OTHER INFORMATION: Completely synthesized peptide construct
<220> FEATURE:
<221> NAME/KEY: MISC_FEATURE
<222> LOCATION: (1)..(1)
<223> OTHER INFORMATION: X is D and E for acidic amino acids
<220> FEATURE:
<221> NAME/KEY: MISC_FEATURE
<222> LOCATION: (2)..(2)
<223> OTHER INFORMATION: X is A and G
<220> FEATURE:
<221> NAME/KEY: MISC_FEATURE
<222> LOCATION: (3)..(3)
<223> OTHER INFORMATION: X is N or Q for amidated amino acids
<220> FEATURE:
<221> NAME/KEY: MISC_FEATURE
<222> LOCATION: (4)..(4)
<223> OTHER INFORMATION: X is D and E for acidic amino acids
<220> FEATURE:
<221> NAME/KEY: MISC_FEATURE
<222> LOCATION: (5)..(5)
<223> OTHER INFORMATION: X is D and E for acidic amino acids
<220> FEATURE:
<221> NAME/KEY: MISC_FEATURE
<222> LOCATION: (6)..(6)
<223> OTHER INFORMATION: X is K, R or H for basic amino acids
<220> FEATURE:
<221> NAME/KEY: MISC_FEATURE
<222> LOCATION: (7)..(7)
<223> OTHER INFORMATION: X is A and G
<220> FEATURE:
<221> NAME/KEY: MISC_FEATURE
<222> LOCATION: (8)..(8)
<223> OTHER INFORMATION: X is A and G
<220> FEATURE:
<221> NAME/KEY: MISC_FEATURE
<222> LOCATION: (9)..(9)
<223> OTHER INFORMATION: X is I, L or V
<220> FEATURE:
<221> NAME/KEY: MISC_FEATURE
<222> LOCATION: (10)..(10)
<223> OTHER INFORMATION: X is I, L or V
<220> FEATURE:
<221> NAME/KEY: MISC_FEATURE
<222> LOCATION: (11)..(11)
<223> OTHER INFORMATION: X is C or S
<220> FEATURE:
<221> NAME/KEY: MISC_FEATURE
<222> LOCATION: (12)..(12)
<223> OTHER INFORMATION: X is T or S
<220> FEATURE:
<221> NAME/KEY: MISC_FEATURE
<222> LOCATION: (13)..(13)
<223> OTHER INFORMATION: X is A and G
<220> FEATURE:
<221> NAME/KEY: MISC_FEATURE
<222> LOCATION: (14)..(14)
<223> OTHER INFORMATION: X is I, L or V
<220> FEATURE:
<221> NAME/KEY: MISC_FEATURE

```
<222> LOCATION: (15)..(15)
<223> OTHER INFORMATION: X is I, L or V
<220> FEATURE:
<221> NAME/KEY: MISC_FEATURE
<222> LOCATION: (16)..(16)
<223> OTHER INFORMATION: X is A and G
<220> FEATURE:
<221> NAME/KEY: MISC_FEATURE
<222> LOCATION: (17)..(17)
<223> OTHER INFORMATION: X is A and G
<220> FEATURE:
<221> NAME/KEY: MISC_FEATURE
<222> LOCATION: (18)..(18)
<223> OTHER INFORMATION: X is A and G
<220> FEATURE:
<221> NAME/KEY: MISC_FEATURE
<222> LOCATION: (19)..(19)
<223> OTHER INFORMATION: X is T or S
<220> FEATURE:
<221> NAME/KEY: MISC_FEATURE
<222> LOCATION: (20)..(20)
<223> OTHER INFORMATION: X is X1X1 or X1X3 or X3X1 or X1X2 or X2X1
<220> FEATURE:
<221> NAME/KEY: MISC_FEATURE
<222> LOCATION: (21)..(21)
<223> OTHER INFORMATION: X is K, R or H for basic amino acids
<220> FEATURE:
<221> NAME/KEY: MISC_FEATURE
<222> LOCATION: (22)..(22)
<223> OTHER INFORMATION: X is F or P
<220> FEATURE:
<221> NAME/KEY: MISC_FEATURE
<222> LOCATION: (23)..(23)
<223> OTHER INFORMATION: X is Gaba for X2 X3 or X3 X2 or X2X3 or X3X2 or
    X3X3 or X2X2
<220> FEATURE:
<221> NAME/KEY: MISC_FEATURE
<222> LOCATION: (24)..(24)
<223> OTHER INFORMATION: X is X1X1 or X1X3 or X3X1 or X1X2 or X2X1
<220> FEATURE:
<221> NAME/KEY: MISC_FEATURE
<222> LOCATION: (25)..(25)
<223> OTHER INFORMATION: X is F, W or Y for aromatic amino acids
<220> FEATURE:
<221> NAME/KEY: MISC_FEATURE
<222> LOCATION: (26)..(26)
<223> OTHER INFORMATION: X is K, R or H for basic amino acids
<220> FEATURE:
<221> NAME/KEY: MISC_FEATURE
<222> LOCATION: (27)..(27)
<223> OTHER INFORMATION: X is X1X1 or X1X3 or X3X1 or X1X2 or X2X1
<220> FEATURE:
<221> NAME/KEY: MISC_FEATURE
<222> LOCATION: (28)..(28)
<223> OTHER INFORMATION: X is N or Q for amidated amino acids
<220> FEATURE:
<221> NAME/KEY: MISC_FEATURE
<222> LOCATION: (29)..(29)
<223> OTHER INFORMATION: X is A and G
<220> FEATURE:
<221> NAME/KEY: MISC_FEATURE
<222> LOCATION: (30)..(30)
<223> OTHER INFORMATION: X is F or P
<220> FEATURE:
<221> NAME/KEY: MISC_FEATURE
<222> LOCATION: (31)..(31)
<223> OTHER INFORMATION: X is K, R or H for basic amino acids
<220> FEATURE:
<221> NAME/KEY: MISC_FEATURE
<222> LOCATION: (32)..(32)
<223> OTHER INFORMATION: X is X1X1 or X1X3 or X3X1 or X1X2 or X2X1
<220> FEATURE:
<221> NAME/KEY: MISC_FEATURE
<222> LOCATION: (33)..(33)
<223> OTHER INFORMATION: X is F or P

<400> SEQUENCE: 95

Xaa Xaa Xaa Xaa Xaa Xaa Xaa Xaa Xaa Xaa Xaa Xaa Xaa Xaa Xaa Xaa
```

```
1               5                   10                  15
Xaa Xaa Xaa Xaa Xaa Xaa Xaa Xaa Xaa Xaa Xaa Xaa Xaa Xaa Xaa
            20                  25                  30
Xaa

<210> SEQ ID NO 96
<211> LENGTH: 34
<212> TYPE: PRT
<213> ORGANISM: artificial
<220> FEATURE:
<223> OTHER INFORMATION: Completely synthesized peptide construct
<220> FEATURE:
<221> NAME/KEY: MISC_FEATURE
<222> LOCATION: (1)..(1)
<223> OTHER INFORMATION: X is Acetyl or propionyl group, D glycine or D
      alanine, Cyclohexylalanine at amino terminus
<220> FEATURE:
<221> NAME/KEY: MISC_FEATURE
<222> LOCATION: (2)..(2)
<223> OTHER INFORMATION: X is D and E for acidic amino acids
<220> FEATURE:
<221> NAME/KEY: MISC_FEATURE
<222> LOCATION: (3)..(3)
<223> OTHER INFORMATION: X is A and G
<220> FEATURE:
<221> NAME/KEY: MISC_FEATURE
<222> LOCATION: (4)..(4)
<223> OTHER INFORMATION: X is N or Q for amidated amino acids
<220> FEATURE:
<221> NAME/KEY: MISC_FEATURE
<222> LOCATION: (5)..(5)
<223> OTHER INFORMATION: X is D and E for acidic amino acids
<220> FEATURE:
<221> NAME/KEY: MISC_FEATURE
<222> LOCATION: (6)..(6)
<223> OTHER INFORMATION: X is D and E for acidic amino acids
<220> FEATURE:
<221> NAME/KEY: MISC_FEATURE
<222> LOCATION: (7)..(7)
<223> OTHER INFORMATION: X is K, R or H for basic amino acids
<220> FEATURE:
<221> NAME/KEY: MISC_FEATURE
<222> LOCATION: (8)..(8)
<223> OTHER INFORMATION: X is A and G
<220> FEATURE:
<221> NAME/KEY: MISC_FEATURE
<222> LOCATION: (9)..(9)
<223> OTHER INFORMATION: X is A and G
<220> FEATURE:
<221> NAME/KEY: MISC_FEATURE
<222> LOCATION: (10)..(10)
<223> OTHER INFORMATION: X is I, L or V
<220> FEATURE:
<221> NAME/KEY: MISC_FEATURE
<222> LOCATION: (11)..(11)
<223> OTHER INFORMATION: X is I, L or V
<220> FEATURE:
<221> NAME/KEY: MISC_FEATURE
<222> LOCATION: (12)..(12)
<223> OTHER INFORMATION: X is C or S
<220> FEATURE:
<221> NAME/KEY: MISC_FEATURE
<222> LOCATION: (13)..(13)
<223> OTHER INFORMATION: X is T or S
<220> FEATURE:
<221> NAME/KEY: MISC_FEATURE
<222> LOCATION: (14)..(14)
<223> OTHER INFORMATION: X is A and G
<220> FEATURE:
<221> NAME/KEY: MISC_FEATURE
<222> LOCATION: (15)..(15)
<223> OTHER INFORMATION: X is I, L or V
<220> FEATURE:
<221> NAME/KEY: MISC_FEATURE
<222> LOCATION: (16)..(16)
<223> OTHER INFORMATION: X is I, L or V
```

```
<220> FEATURE:
<221> NAME/KEY: MISC_FEATURE
<222> LOCATION: (17)..(17)
<223> OTHER INFORMATION: X is A and G
<220> FEATURE:
<221> NAME/KEY: MISC_FEATURE
<222> LOCATION: (18)..(18)
<223> OTHER INFORMATION: X is A and G
<220> FEATURE:
<221> NAME/KEY: MISC_FEATURE
<222> LOCATION: (19)..(19)
<223> OTHER INFORMATION: X is A and G
<220> FEATURE:
<221> NAME/KEY: MISC_FEATURE
<222> LOCATION: (20)..(20)
<223> OTHER INFORMATION: X is T or S
<220> FEATURE:
<221> NAME/KEY: MISC_FEATURE
<222> LOCATION: (21)..(21)
<223> OTHER INFORMATION: X is X1X1 or X1X3 or X3X1 or X1X2 or X2X1
<220> FEATURE:
<221> NAME/KEY: MISC_FEATURE
<222> LOCATION: (22)..(22)
<223> OTHER INFORMATION: X is K, R or H for basic amino acids
<220> FEATURE:
<221> NAME/KEY: MISC_FEATURE
<222> LOCATION: (23)..(23)
<223> OTHER INFORMATION: X is F or P
<220> FEATURE:
<221> NAME/KEY: MISC_FEATURE
<222> LOCATION: (24)..(24)
<223> OTHER INFORMATION: X is Gaba for X2X3 or X3X2 or X2X3 or X3X2 or
     X3X3 or X2X2
<220> FEATURE:
<221> NAME/KEY: MISC_FEATURE
<222> LOCATION: (25)..(25)
<223> OTHER INFORMATION: X is X1X1 or X1X3 or X3X1 or X1X2 or X2X1
<220> FEATURE:
<221> NAME/KEY: MISC_FEATURE
<222> LOCATION: (26)..(26)
<223> OTHER INFORMATION: X is F, W or Y for aromatic amino acids
<220> FEATURE:
<221> NAME/KEY: MISC_FEATURE
<222> LOCATION: (27)..(27)
<223> OTHER INFORMATION: X is K, R or H for basic amino acids
<220> FEATURE:
<221> NAME/KEY: MISC_FEATURE
<222> LOCATION: (28)..(28)
<223> OTHER INFORMATION: X is X1X1 or X1X3 or X3X1 or X1X2 or X2X1
<220> FEATURE:
<221> NAME/KEY: MISC_FEATURE
<222> LOCATION: (29)..(29)
<223> OTHER INFORMATION: X is N or Q for amidated amino acids
<220> FEATURE:
<221> NAME/KEY: MISC_FEATURE
<222> LOCATION: (30)..(30)
<223> OTHER INFORMATION: X is A and G
<220> FEATURE:
<221> NAME/KEY: MISC_FEATURE
<222> LOCATION: (31)..(31)
<223> OTHER INFORMATION: X is F or P
<220> FEATURE:
<221> NAME/KEY: MISC_FEATURE
<222> LOCATION: (32)..(32)
<223> OTHER INFORMATION: X is K, R or H for basic amino acids
<220> FEATURE:
<221> NAME/KEY: MISC_FEATURE
<222> LOCATION: (33)..(33)
<223> OTHER INFORMATION: X is X1X1 or X1X3 or X3X1 or X1X2 or X2X1
<220> FEATURE:
<221> NAME/KEY: MISC_FEATURE
<222> LOCATION: (34)..(34)
<223> OTHER INFORMATION: X is F or P

<400> SEQUENCE: 96

Xaa Xaa Xaa Xaa Xaa Xaa Xaa Xaa Xaa Xaa Xaa Xaa Xaa Xaa Xaa Xaa
1               5                   10                  15
```

```
Xaa Xaa Xaa Xaa Xaa Xaa Xaa Xaa Xaa Xaa Xaa Xaa Xaa Xaa
            20                  25                  30

Xaa Xaa

<210> SEQ ID NO 97
<211> LENGTH: 34
<212> TYPE: PRT
<213> ORGANISM: artificial
<220> FEATURE:
<223> OTHER INFORMATION: Completely synthesized peptide construct
<220> FEATURE:
<221> NAME/KEY: MISC_FEATURE
<222> LOCATION: (1)..(1)
<223> OTHER INFORMATION: X is 5-aminopentanoic acid for replacement of 3
      or 4 amino acids of X2 and  X3
<220> FEATURE:
<221> NAME/KEY: MISC_FEATURE
<222> LOCATION: (2)..(2)
<223> OTHER INFORMATION: X is D and E for acidic amino acids
<220> FEATURE:
<221> NAME/KEY: MISC_FEATURE
<222> LOCATION: (3)..(3)
<223> OTHER INFORMATION: X is A and G
<220> FEATURE:
<221> NAME/KEY: MISC_FEATURE
<222> LOCATION: (4)..(4)
<223> OTHER INFORMATION: X is N or Q for amidated amino acids
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: X is D and E for acidic amino acids
<220> FEATURE:
<221> NAME/KEY: MISC_FEATURE
<222> LOCATION: (7)..(7)
<223> OTHER INFORMATION: X is K, R or H for basic amino acids
<220> FEATURE:
<221> NAME/KEY: MISC_FEATURE
<222> LOCATION: (8)..(8)
<223> OTHER INFORMATION: X is A and G
<220> FEATURE:
<221> NAME/KEY: MISC_FEATURE
<222> LOCATION: (9)..(9)
<223> OTHER INFORMATION: X is A and G
<220> FEATURE:
<221> NAME/KEY: MISC_FEATURE
<222> LOCATION: (10)..(10)
<223> OTHER INFORMATION: X is A and G
<220> FEATURE:
<221> NAME/KEY: MISC_FEATURE
<222> LOCATION: (11)..(11)
<223> OTHER INFORMATION: X is I, L or V
<220> FEATURE:
<221> NAME/KEY: MISC_FEATURE
<222> LOCATION: (12)..(12)
<223> OTHER INFORMATION: X is C or S
<220> FEATURE:
<221> NAME/KEY: MISC_FEATURE
<222> LOCATION: (13)..(13)
<223> OTHER INFORMATION: X is T or S
<220> FEATURE:
<221> NAME/KEY: MISC_FEATURE
<222> LOCATION: (14)..(14)
<223> OTHER INFORMATION: X is A and G
<220> FEATURE:
<221> NAME/KEY: MISC_FEATURE
<222> LOCATION: (15)..(15)
<223> OTHER INFORMATION: X is I, L or V
<220> FEATURE:
<221> NAME/KEY: MISC_FEATURE
<222> LOCATION: (16)..(16)
<223> OTHER INFORMATION: X is I, L or V
<220> FEATURE:
<221> NAME/KEY: misc_feature
```

```
<222> LOCATION: (17)..(17)
<223> OTHER INFORMATION: Xaa can be any naturally occurring amino acid
<220> FEATURE:
<221> NAME/KEY: M Xaa Xaa
<210> SEQ ID NO 98
<211> LENGTH: 31
<212> TYPE: PRT
<213> ORGANISM: artificial
<220> FEATURE:
<223> OTHER INFORMATION: Completely synthesized peptide construct
<220> FEATURE:
<221> NAME/KEY: MISC_FEATURE
<222> LOCATION: (1)..(1)
<223> OTHER INFORMATION: X is Acetyl or propionyl group, D glycine or D
      alanine, Cyclohexylalanine at amino terminus
<220> FEATURE:
<221> NAME/KEY: MISC_FEATURE
<222> LOCATION: (2)..(2)
<223> OTHER INFORMATION: X is D and E for acidic amino acids
<220> FEATURE:
<221> NAME/KEY: MISC_FEATURE
<222> LOCATION: (3)..(3)
<223> OTHER INFORMATION: X is A and G
<220> FEATURE:
<221> NAME/KEY: MISC_FEATURE
<222> LOCATION: (4)..(4)
<223> OTHER INFORMATION: X is N or Q for amidated amino acids
<220> FEATURE:
<221> NAME/KEY: MISC_FEATURE
<222> LOCATION: (5)..(5)
<223> OTHER INFORMATION: X is Gaba for X2X3 or X3X3 or X2X3 or X3X2 or
      X3X3 or X2X2
<220> FEATURE:
<221> NAME/KEY: MISC_FEATURE
<222> LOCATION: (6)..(6)
<223> OTHER INFORMATION: X is K, R or H for basic amino acids
<220> FEATURE:
<221> NAME/KEY: MISC_FEATURE
<222> LOCATION: (7)..(7)
<223> OTHER INFORMATION: X is A and G
<220> FEATURE:
<221> NAME/KEY: MISC_FEATURE
<222> LOCATION: (8)..(8)
<223> OTHER INFORMATION: X is A and G
<220> FEATURE:
<221> NAME/KEY: MISC_FEATURE
<222> LOCATION: (9)..(9)
<223> OTHER INFORMATION: X is Gaba for X2X3 or X3X3 or X2X3 or X3X2 or
      X3X3 or X2X2
<220> FEATURE:
<221> NAME/KEY: MISC_FEATURE
<222> LOCATION: (10)..(10)
<223> OTHER INFORMATION: X is C or S
<220> FEATURE:
<221> NAME/KEY: MISC_FEATURE
<222> LOCATION: (11)..(11)
<223> OTHER INFORMATION: X is T or S
<220> FEATURE:
<221> NAME/KEY: MISC_FEATURE
<222> LOCATION: (12)..(12)
<223> OTHER INFORMATION: X is A and G
<220> FEATURE:
<221> NAME/KEY: MISC_FEATURE
<222> LOCATION: (13)..(13)
<223> OTHER INFORMATION: X is Gaba for X2X3 or X3X3 or X2X3 or X3X2 or
      X3X3 or X2X2
<220> FEATURE:
<221> NAME/KEY: MISC_FEATURE
<222> LOCATION: (14)..(14)
<223> OTHER INFORMATION: X is A and G
<220> FEATURE:
<221> NAME/KEY: MISC_FEATURE
<222> LOCATION: (15)..(15)
<223> OTHER INFORMATION: X is A and G
<220> FEATURE:
<221> NAME/KEY: MISC_FEATURE
<222> LOCATION: (16)..(16)
<223> OTHER INFORMATION: X is A and G
<220> FEATURE:

```
<221> NAME/KEY: MISC_FEATURE
<222> LOCATION: (17)..(17)
<223> OTHER INFORMATION: X is T or S
<220> FEATURE:
<221> NAME/KEY: MISC_FEATURE
<222> LOCATION: (18)..(18)
<223> OTHER INFORMATION: X is X1X1 or X1X3 or X3X1 or X1X2 or X2X1
<220> FEATURE:
<221> NAME/KEY: MISC_FEATURE
<222> LOCATION: (19)..(19)
<223> OTHER INFORMATION: X is K, R or H for basic amino acids
<220> FEATURE:
<221> NAME/KEY: MISC_FEATURE
<222> LOCATION: (20)..(20)
<223> OTHER INFORMATION: X is F or P
<220> FEATURE:
<221> NAME/KEY: MISC_FEATURE
<222> LOCATION: (21)..(21)
<223> OTHER INFORMATION: X is Gaba for X2X3 or X3X3 or X2X3 or
      X3X3 or X2X2
<220> FEATURE:
<221> NAME/KEY: MISC_FEATURE
<222> LOCATION: (22)..(22)
<223> OTHER INFORMATION: X is X is X1X1 or X1X3 or X3X1 or X1X2 or X2X1
<220> FEATURE:
<221> NAME/KEY: MISC_FEATURE
<222> LOCATION: (23)..(23)
<223> OTHER INFORMATION: X is F, W or Y for aromatic amino acids
<220> FEATURE:
<221> NAME/KEY: MISC_FEATURE
<222> LOCATION: (24)..(24)
<223> OTHER INFORMATION: X is K, R or H for basic amino acids
<220> FEATURE:
<221> NAME/KEY: MISC_FEATURE
<222> LOCATION: (25)..(25)
<223> OTHER INFORMATION: X is X is X1X1 or X1X3 or X3X1 or X1X2 or X2X1
<220> FEATURE:
<221> NAME/KEY: MISC_FEATURE
<222> LOCATION: (26)..(26)
<223> OTHER INFORMATION: X is N or Q for amidated amino acids
<220> FEATURE:
<221> NAME/KEY: MISC_FEATURE
<222> LOCATION: (27)..(27)
<223> OTHER INFORMATION: X is A and G
<220> FEATURE:
<221> NAME/KEY: MISC_FEATURE
<222> LOCATION: (28)..(28)
<223> OTHER INFORMATION: X is F or P
<220> FEATURE:
<221> NAME/KEY: MISC_FEATURE
<222> LOCATION: (29)..(29)
<223> OTHER INFORMATION: X is K, R or H for basic amino acids
<220> FEATURE:
<221> NAME/KEY: MISC_FEATURE
<222> LOCATION: (30)..(30)
<223> OTHER INFORMATION: X is X is X1X1 or X1X3 or X3X1 or X1X2 or X2X1
<220> FEATURE:
<221> NAME/KEY: MISC_FEATURE
<222> LOCATION: (31)..(31)
<223> OTHER INFORMATION: X is F or P

<400> SEQUENCE: 98

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

<210> SEQ ID NO 99
<211> LENGTH: 36
<212> TYPE: PRT
<213> ORGANISM: artificial
<220> FEATURE:
<223> OTHER INFORMATION: Completely synthesized peptide construct

<400> SEQUENCE: 99
```

```
Asp Leu Leu Lys Asn Gly Glu Arg Ile Glu Lys Val Glu Gly Gly Gly
1               5                   10                  15

Thr Gly Gly Lys Pro Gly Ile Ala Gly Phe Lys Gly Glu Gln Gly Pro
            20                  25                  30

Lys Gly Glu Pro
        35

<210> SEQ ID NO 100
<211> LENGTH: 36
<212> TYPE: PRT
<213> ORGANISM: artificial
<220> FEATURE:
<223> OTHER INFORMATION: Completely synthesized peptide construct
<220> FEATURE:
<221> NAME/KEY: MISC_FEATURE
<222> LOCATION: (1)..(1)
<223> OTHER INFORMATION: X is D and E for acidic amino acids
<220> FEATURE:
<221> NAME/KEY: MISC_FEATURE
<222> LOCATION: (2)..(2)
<223> OTHER INFORMATION: X is I, L or V
<220> FEATURE:
<221> NAME/KEY: MISC_FEATURE
<222> LOCATION: (3)..(3)
<223> OTHER INFORMATION: X is I, L or V
<220> FEATURE:
<221> NAME/KEY: MISC_FEATURE
<222> LOCATION: (4)..(4)
<223> OTHER INFORMATION: X is K, R or H for basic amino acids
<220> FEATURE:
<221> NAME/KEY: MISC_FEATURE
<222> LOCATION: (5)..(5)
<223> OTHER INFORMATION: X is N or Q for amidated amino acids
<220> FEATURE:
<221> NAME/KEY: MISC_FEATURE
<222> LOCATION: (6)..(6)
<223> OTHER INFORMATION: X is A and G
<220> FEATURE:
<221> NAME/KEY: MISC_FEATURE
<222> LOCATION: (7)..(7)
<223> OTHER INFORMATION: X is D and E for acidic amino acids
<220> FEATURE:
<221> NAME/KEY: MISC_FEATURE
<222> LOCATION: (8)..(8)
<223> OTHER INFORMATION: X is K, R or H for basic amino acids
<220> FEATURE:
<221> NAME/KEY: MISC_FEATURE
<222> LOCATION: (9)..(9)
<223> OTHER INFORMATION: X is I, L or V
<220> FEATURE:
<221> NAME/KEY: MISC_FEATURE
<222> LOCATION: (10)..(10)
<223> OTHER INFORMATION: X is D and E for acidic amino acids
<220> FEATURE:
<221> NAME/KEY: MISC_FEATURE
<222> LOCATION: (11)..(11)
<223> OTHER INFORMATION: X is K, R or H for basic amino acids
<220> FEATURE:
<221> NAME/KEY: MISC_FEATURE
<222> LOCATION: (12)..(12)
<223> OTHER INFORMATION: X is I, L or V
<220> FEATURE:
<221> NAME/KEY: MISC_FEATURE
<222> LOCATION: (13)..(13)
<223> OTHER INFORMATION: X is D and E for acidic amino acids
<220> FEATURE:
<221> NAME/KEY: MISC_FEATURE
<222> LOCATION: (14)..(14)
<223> OTHER INFORMATION: X is A and G
<220> FEATURE:
<221> NAME/KEY: MISC_FEATURE
<222> LOCATION: (15)..(15)
<223> OTHER INFORMATION: X is A and G
<220> FEATURE:
<221> NAME/KEY: MISC_FEATURE
<222> LOCATION: (16)..(16)
```

```
<223> OTHER INFORMATION: X is A and G
<220> FEATURE:
<221> NAME/KEY: MISC_FEATURE
<222> LOCATION: (17)..(17)
<223> OTHER INFORMATION: X is T or S
<220> FEATURE:
<221> NAME/KEY: MISC_FEATURE
<222> LOCATION: (18)..(18)
<223> OTHER INFORMATION: X is A and G
<220> FEATURE:
<221> NAME/KEY: MISC_FEATURE
<222> LOCATION: (19)..(19)
<223> OTHER INFORMATION: X is A and G
<220> FEATURE:
<221> NAME/KEY: MISC_FEATURE
<222> LOCATION: (20)..(20)
<223> OTHER INFORMATION: X is K, R or H for basic amino acids
<220> FEATURE:
<221> NAME/KEY: MISC_FEATURE
<222> LOCATION: (21)..(21)
<223> OTHER INFORMATION: X is F or P
<220> FEATURE:
<221> NAME/KEY: MISC_FEATURE
<222> LOCATION: (22)..(22)
<223> OTHER INFORMATION: X is A and G
<220> FEATURE:
<221> NAME/KEY: MISC_FEATURE
<222> LOCATION: (23)..(23)
<223> OTHER INFORMATION: X is I, L or V
<220> FEATURE:
<221> NAME/KEY: MISC_FEATURE
<222> LOCATION: (24)..(24)
<223> OTHER INFORMATION: X is A and G
<220> FEATURE:
<221> NAME/KEY: MISC_FEATURE
<222> LOCATION: (25)..(25)
<223> OTHER INFORMATION: X is A and G
<220> FEATURE:
<221> NAME/KEY: MISC_FEATURE
<222> LOCATION: (26)..(26)
<223> OTHER INFORMATION: X is F, W or Y for aromatic amino acids
<220> FEATURE:
<221> NAME/KEY: MISC_FEATURE
<222> LOCATION: (27)..(27)
<223> OTHER INFORMATION: X is K, R or H for basic amino acids
<220> FEATURE:
<221> NAME/KEY: MISC_FEATURE
<222> LOCATION: (28)..(28)
<223> OTHER INFORMATION: X is A and G
<220> FEATURE:
<221> NAME/KEY: MISC_FEATURE
<222> LOCATION: (29)..(29)
<223> OTHER INFORMATION: X is D and E for acidic amino acids
<220> FEATURE:
<221> NAME/KEY: MISC_FEATURE
<222> LOCATION: (30)..(30)
<223> OTHER INFORMATION: X is N or Q for amidated amino acids
<220> FEATURE:
<221> NAME/KEY: MISC_FEATURE
<222> LOCATION: (31)..(31)
<223> OTHER INFORMATION: X is A and G
<220> FEATURE:
<221> NAME/KEY: MISC_FEATURE
<222> LOCATION: (32)..(32)
<223> OTHER INFORMATION: X is F or P
<220> FEATURE:
<221> NAME/KEY: MISC_FEATURE
<222> LOCATION: (33)..(33)
<223> OTHER INFORMATION: X is K, R or H for basic amino acids
<220> FEATURE:
<221> NAME/KEY: MISC_FEATURE
<222> LOCATION: (34)..(34)
<223> OTHER INFORMATION: X is A and G
<220> FEATURE:
<221> NAME/KEY: MISC_FEATURE
<222> LOCATION: (35)..(35)
<223> OTHER INFORMATION: X is D and E for acidic amino acids
<220> FEATURE:
<221> NAME/KEY: MISC_FEATURE
```

<222> LOCATION: (36)..(36)
<223> OTHER INFORMATION: X is F or P

<400> SEQUENCE: 100

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
                20                  25                  30

Xaa Xaa Xaa Xaa
        35

<210> SEQ ID NO 101
<211> LENGTH: 37
<212> TYPE: PRT
<213> ORGANISM: artificial
<220> FEATURE:
<223> OTHER INFORMATION: Completely synthesized peptide construct
<220> FEATURE:
<221> NAME/KEY: MISC_FEATURE
<222> LOCATION: (1)..(1)
<223> OTHER INFORMATION: X is Acetyl or propionyl group, D glycine or D
      alanine, Cyclohexylalanine at amino terminus
<220> FEATURE:
<221> NAME/KEY: MISC_FEATURE
<222> LOCATION: (2)..(2)
<223> OTHER INFORMATION: X is D and E for acidic amino acids
<220> FEATURE:
<221> NAME/KEY: MISC_FEATURE
<222> LOCATION: (3)..(3)
<223> OTHER INFORMATION: X is I, L or V
<220> FEATURE:
<221> NAME/KEY: MISC_FEATURE
<222> LOCATION: (4)..(4)
<223> OTHER INFORMATION: X is I, L or V
<220> FEATURE:
<221> NAME/KEY: MISC_FEATURE
<222> LOCATION: (5)..(5)
<223> OTHER INFORMATION: X is K, R or H for basic amino acids
<220> FEATURE:
<221> NAME/KEY: MISC_FEATURE
<222> LOCATION: (6)..(6)
<223> OTHER INFORMATION: X is N or Q for amidated amino acids
<220> FEATURE:
<221> NAME/KEY: MISC_FEATURE
<222> LOCATION: (7)..(7)
<223> OTHER INFORMATION: X is A and G
<220> FEATURE:
<221> NAME/KEY: MISC_FEATURE
<222> LOCATION: (8)..(8)
<223> OTHER INFORMATION: X is D and E for acidic amino acids
<220> FEATURE:
<221> NAME/KEY: MISC_FEATURE
<222> LOCATION: (9)..(9)
<223> OTHER INFORMATION: X is K, R or H for basic amino acids
<220> FEATURE:
<221> NAME/KEY: MISC_FEATURE
<222> LOCATION: (10)..(10)
<223> OTHER INFORMATION: X is I, L or V
<220> FEATURE:
<221> NAME/KEY: MISC_FEATURE
<222> LOCATION: (11)..(11)
<223> OTHER INFORMATION: X is D and E for acidic amino acids
<220> FEATURE:
<221> NAME/KEY: MISC_FEATURE
<222> LOCATION: (12)..(12)
<223> OTHER INFORMATION: X is K, R or H for basic amino acids
<220> FEATURE:
<221> NAME/KEY: MISC_FEATURE
<222> LOCATION: (13)..(13)
<223> OTHER INFORMATION: X is I, L or V
<220> FEATURE:
<221> NAME/KEY: MISC_FEATURE
<222> LOCATION: (14)..(14)
<223> OTHER INFORMATION: X is D and E for acidic amino acids
<220> FEATURE:

```
<221> NAME/KEY: MISC_FEATURE
<222> LOCATION: (15)..(15)
<223> OTHER INFORMATION: X is A and G
<220> FEATURE:
<221> NAME/KEY: MISC_FEATURE
<222> LOCATION: (16)..(16)
<223> OTHER INFORMATION: X is A and G
<220> FEATURE:
<221> NAME/KEY: MISC_FEATURE
<222> LOCATION: (17)..(17)
<223> OTHER INFORMATION: X is A and G
<220> FEATURE:
<221> NAME/KEY: MISC_FEATURE
<222> LOCATION: (18)..(18)
<223> OTHER INFORMATION: X is T or S
<220> FEATURE:
<221> NAME/KEY: MISC_FEATURE
<222> LOCATION: (19)..(19)
<223> OTHER INFORMATION: X is A and G
<220> FEATURE:
<221> NAME/KEY: MISC_FEATURE
<222> LOCATION: (20)..(20)
<223> OTHER INFORMATION: X is A and G
<220> FEATURE:
<221> NAME/KEY: MISC_FEATURE
<222> LOCATION: (21)..(21)
<223> OTHER INFORMATION: X is K, R or H for basic amino acids
<220> FEATURE:
<221> NAME/KEY: MISC_FEATURE
<222> LOCATION: (22)..(22)
<223> OTHER INFORMATION: X is F or P
<220> FEATURE:
<221> NAME/KEY: MISC_FEATURE
<222> LOCATION: (23)..(23)
<223> OTHER INFORMATION: X is A and G
<220> FEATURE:
<221> NAME/KEY: MISC_FEATURE
<222> LOCATION: (24)..(24)
<223> OTHER INFORMATION: X is I, L or V
<220> FEATURE:
<221> NAME/KEY: MISC_FEATURE
<222> LOCATION: (25)..(25)
<223> OTHER INFORMATION: X is A and G
<220> FEATURE:
<221> NAME/KEY: MISC_FEATURE
<222> LOCATION: (26)..(26)
<223> OTHER INFORMATION: X is A and G
<220> FEATURE:
<221> NAME/KEY: MISC_FEATURE
<222> LOCATION: (27)..(27)
<223> OTHER INFORMATION: X is F, W or Y for aromatic amino acids
<220> FEATURE:
<221> NAME/KEY: MISC_FEATURE
<222> LOCATION: (28)..(28)
<223> OTHER INFORMATION: X is K, R or H for basic amino acids
<220> FEATURE:
<221> NAME/KEY: MISC_FEATURE
<222> LOCATION: (29)..(29)
<223> OTHER INFORMATION: X is A and G
<220> FEATURE:
<221> NAME/KEY: MISC_FEATURE
<222> LOCATION: (30)..(30)
<223> OTHER INFORMATION: X is D and E for acidic amino acids
<220> FEATURE:
<221> NAME/KEY: MISC_FEATURE
<222> LOCATION: (31)..(31)
<223> OTHER INFORMATION: X is N or Q for amidated amino acids
<220> FEATURE:
<221> NAME/KEY: MISC_FEATURE
<222> LOCATION: (32)..(32)
<223> OTHER INFORMATION: X is A and G
<220> FEATURE:
<221> NAME/KEY: MISC_FEATURE
<222> LOCATION: (33)..(33)
<223> OTHER INFORMATION: X is F or P
<220> FEATURE:
<221> NAME/KEY: MISC_FEATURE
<222> LOCATION: (34)..(34)
<223> OTHER INFORMATION: X is K, R or H for basic amino acids
```

```
<220> FEATURE:
<221> NAME/KEY: MISC_FEATURE
<222> LOCATION: (35)..(35)
<223> OTHER INFORMATION: X is A and G
<220> FEATURE:
<221> NAME/KEY: MISC_FEATURE
<222> LOCATION: (36)..(36)
<223> OTHER INFORMATION: X is D and E for acidic amino acids
<220> FEATURE:
<221> NAME/KEY: MISC_FEATURE
<222> LOCATION: (37)..(37)
<223> OTHER INFORMATION: X is F or P

<400> SEQUENCE: 101

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa
        35

<210> SEQ ID NO 102
<211> LENGTH: 33
<212> TYPE: PRT
<213> ORGANISM: artificial
<220> FEATURE:
<223> OTHER INFORMATION: Completely synthesized peptide construct
<220> FEATURE:
<221> NAME/KEY: MISC_FEATURE
<222> LOCATION: (1)..(1)
<223> OTHER INFORMATION: X is Acetyl or propionyl group, D glycine or D
      alanine, Cyclohexylalanine at amino terminus
<220> FEATURE:
<221> NAME/KEY: MISC_FEATURE
<222> LOCATION: (2)..(2)
<223> OTHER INFORMATION: X is Gaba for X2X3 or X3X2 or X2X3 or X3X2 or
      X3X3 or X2X2
<220> FEATURE:
<221> NAME/KEY: MISC_FEATURE
<222> LOCATION: (3)..(3)
<223> OTHER INFORMATION: X is K, R or H for basic amino acids
<220> FEATURE:
<221> NAME/KEY: MISC_FEATURE
<222> LOCATION: (4)..(4)
<223> OTHER INFORMATION: X is N or Q for amidated amino acids
<220> FEATURE:
<221> NAME/KEY: MISC_FEATURE
<222> LOCATION: (5)..(5)
<223> OTHER INFORMATION: X is A and G
<220> FEATURE:
<221> NAME/KEY: MISC_FEATURE
<222> LOCATION: (6)..(6)
<223> OTHER INFORMATION: X is D and E for acidic amino acids
<220> FEATURE:
<221> NAME/KEY: MISC_FEATURE
<222> LOCATION: (7)..(7)
<223> OTHER INFORMATION: X is K, R or H for basic amino acids
<220> FEATURE:
<221> NAME/KEY: MISC_FEATURE
<222> LOCATION: (8)..(8)
<223> OTHER INFORMATION: X is Gaba for X2X3 or X3X2 or X2X3 or X3X2 or
      X3X3 or X2X2
<220> FEATURE:
<221> NAME/KEY: MISC_FEATURE
<222> LOCATION: (9)..(9)
<223> OTHER INFORMATION: X is K, R or H for basic amino acids
<220> FEATURE:
<221> NAME/KEY: MISC_FEATURE
<222> LOCATION: (10)..(10)
<223> OTHER INFORMATION: X is Gaba for X2X3 or X3X2 or X2X3 or X3X2 or
      X3X3 or X2X2
<220> FEATURE:
<221> NAME/KEY: MISC_FEATURE
<222> LOCATION: (11)..(11)
<223> OTHER INFORMATION: X is A and G
```

-continued

```
<220> FEATURE:
<221> NAME/KEY: MISC_FEATURE
<222> LOCATION: (12)..(12)
<223> OTHER INFORMATION: X is A and G
<220> FEATURE:
<221> NAME/KEY: MISC_FEATURE
<222> LOCATION: (13)..(13)
<223> OTHER INFORMATION: X is A and G
<220> FEATURE:
<221> NAME/KEY: MISC_FEATURE
<222> LOCATION: (14)..(14)
<223> OTHER INFORMATION: X is T or S
<220> FEATURE:
<221> NAME/KEY: MISC_FEATURE
<222> LOCATION: (15)..(15)
<223> OTHER INFORMATION: X is A and G
<220> FEATURE:
<221> NAME/KEY: MISC_FEATURE
<222> LOCATION: (16)..(16)
<223> OTHER INFORMATION: X is A and G
<220> FEATURE:
<221> NAME/KEY: MISC_FEATURE
<222> LOCATION: (17)..(17)
<223> OTHER INFORMATION: X is K, R or H for basic amino acids
<220> FEATURE:
<221> NAME/KEY: MISC_FEATURE
<222> LOCATION: (18)..(18)
<223> OTHER INFORMATION: X is F or P
<220> FEATURE:
<221> NAME/KEY: MISC_FEATURE
<222> LOCATION: (19)..(19)
<223> OTHER INFORMATION: X is A and G
<220> FEATURE:
<221> NAME/KEY: MISC_FEATURE
<222> LOCATION: (20)..(20)
<223> OTHER INFORMATION: X is I, L or V
<220> FEATURE:
<221> NAME/KEY: MISC_FEATURE
<222> LOCATION: (21)..(21)
<223> OTHER INFORMATION: X is A and G
<220> FEATURE:
<221> NAME/KEY: MISC_FEATURE
<222> LOCATION: (22)..(22)
<223> OTHER INFORMATION: X is A and G
<220> FEATURE:
<221> NAME/KEY: MISC_FEATURE
<222> LOCATION: (23)..(23)
<223> OTHER INFORMATION: X is F, W or Y for aromatic amino acids
<220> FEATURE:
<221> NAME/KEY: MISC_FEATURE
<222> LOCATION: (24)..(24)
<223> OTHER INFORMATION: X is K, R or H for basic amino acids
<220> FEATURE:
<221> NAME/KEY: MISC_FEATURE
<222> LOCATION: (25)..(25)
<223> OTHER INFORMATION: X is A and G
<220> FEATURE:
<221> NAME/KEY: MISC_FEATURE
<222> LOCATION: (26)..(26)
<223> OTHER INFORMATION: X is D and E for acidic amino acids
<220> FEATURE:
<221> NAME/KEY: MISC_FEATURE
<222> LOCATION: (27)..(27)
<223> OTHER INFORMATION: X is N or Q for amidated amino acids
<220> FEATURE:
<221> NAME/KEY: MISC_FEATURE
<222> LOCATION: (28)..(28)
<223> OTHER INFORMATION: X is A and G
<220> FEATURE:
<221> NAME/KEY: MISC_FEATURE
<222> LOCATION: (29)..(29)
<223> OTHER INFORMATION: X is F or P
<220> FEATURE:
<221> NAME/KEY: MISC_FEATURE
<222> LOCATION: (30)..(30)
<223> OTHER INFORMATION: X is K, R or H for basic amino acids
<220> FEATURE:
<221> NAME/KEY: MISC_FEATURE
<222> LOCATION: (31)..(31)
```

```
<223> OTHER INFORMATION: X is A and G
<220> FEATURE:
<221> NAME/KEY: MISC_FEATURE
<222> LOCATION: (32)..(32)
<223> OTHER INFORMATION: X is D and E for acidic amino acids
<220> FEATURE:
<221> NAME/KEY: MISC_FEATURE
<222> LOCATION: (33)..(33)
<223> OTHER INFORMATION: X is F or P

<400> SEQUENCE: 102

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa

<210> SEQ ID NO 103
<211> LENGTH: 33
<212> TYPE: PRT
<213> ORGANISM: artificial
<220> FEATURE:
<223> OTHER INFORMATION: Completely synthesized peptide construct
<220> FEATURE:
<221> NAME/KEY: MISC_FEATURE
<222> LOCATION: (1)..(1)
<223> OTHER INFORMATION: X is Acetyl or propionyl group, D glycine or D
      alanine, Cyclohexylalanine at amino terminus
<220> FEATURE:
<221> NAME/KEY: MISC_FEATURE
<222> LOCATION: (2)..(2)
<223> OTHER INFORMATION: X is 5-aminopentanoic acid for replacement of 3
      or 4 amino acids of X2 and X3
<220> FEATURE:
<221> NAME/KEY: MISC_FEATURE
<222> LOCATION: (3)..(3)
<223> OTHER INFORMATION: X is K, R or H for basic amino acids
<220> FEATURE:
<221> NAME/KEY: MISC_FEATURE
<222> LOCATION: (4)..(4)
<223> OTHER INFORMATION: X is N or Q for amidated amino acids
<220> FEATURE:
<221> NAME/KEY: MISC_FEATURE
<222> LOCATION: (5)..(5)
<223> OTHER INFORMATION: X is A and G
<220> FEATURE:
<221> NAME/KEY: MISC_FEATURE
<222> LOCATION: (6)..(6)
<223> OTHER INFORMATION: X is D and E for acidic amino acids
<220> FEATURE:
<221> NAME/KEY: MISC_FEATURE
<222> LOCATION: (7)..(7)
<223> OTHER INFORMATION: X is K, R or H for basic amino acids
<220> FEATURE:
<221> NAME/KEY: MISC_FEATURE
<222> LOCATION: (8)..(8)
<223> OTHER INFORMATION: X is Gaba for X2X3 or X3X2 or X2X3 or X3X2 or
      X3X3 or X2X2
<220> FEATURE:
<221> NAME/KEY: MISC_FEATURE
<222> LOCATION: (9)..(9)
<223> OTHER INFORMATION: X is K, R or H for basic amino acids
<220> FEATURE:
<221> NAME/KEY: MISC_FEATURE
<222> LOCATION: (10)..(10)
<223> OTHER INFORMATION: X is Gaba for X2X3 or X3X2 or X2X3 or X3X2 or
      X3X3 or X2X2
<220> FEATURE:
<221> NAME/KEY: MISC_FEATURE
<222> LOCATION: (11)..(11)
<223> OTHER INFORMATION: X is A and G
<220> FEATURE:
<221> NAME/KEY: MISC_FEATURE
<222> LOCATION: (12)..(12)
<223> OTHER INFORMATION: X is A and G
```

```
<220> FEATURE:
<221> NAME/KEY: MISC_FEATURE
<222> LOCATION: (13)..(13)
<223> OTHER INFORMATION: X is A and G
<220> FEATURE:
<221> NAME/KEY: MISC_FEATURE
<222> LOCATION: (14)..(14)
<223> OTHER INFORMATION: X is T or S
<220> FEATURE:
<221> NAME/KEY: MISC_FEATURE
<222> LOCATION: (15)..(15)
<223> OTHER INFORMATION: X is A and G
<220> FEATURE:
<221> NAME/KEY: MISC_FEATURE
<222> LOCATION: (16)..(16)
<223> OTHER INFORMATION: X is A and G
<220> FEATURE:
<221> NAME/KEY: MISC_FEATURE
<222> LOCATION: (17)..(17)
<223> OTHER INFORMATION: X is K, R or H for basic amino acids
<220> FEATURE:
<221> NAME/KEY: MISC_FEATURE
<222> LOCATION: (18)..(18)
<223> OTHER INFORMATION: X is F or P
<220> FEATURE:
<221> NAME/KEY: MISC_FEATURE
<222> LOCATION: (19)..(19)
<223> OTHER INFORMATION: X is A and G
<220> FEATURE:
<221> NAME/KEY: MISC_FEATURE
<222> LOCATION: (20)..(20)
<223> OTHER INFORMATION: X is I, L or V
<220> FEATURE:
<221> NAME/KEY: MISC_FEATURE
<222> LOCATION: (21)..(21)
<223> OTHER INFORMATION: X is A and G
<220> FEATURE:
<221> NAME/KEY: MISC_FEATURE
<222> LOCATION: (22)..(22)
<223> OTHER INFORMATION: X is A and G
<220> FEATURE:
<221> NAME/KEY: MISC_FEATURE
<222> LOCATION: (23)..(23)
<223> OTHER INFORMATION: X is F, W or Y for aromatic amino acids
<220> FEATURE:
<221> NAME/KEY: MISC_FEATURE
<222> LOCATION: (24)..(24)
<223> OTHER INFORMATION: X is K, R or H for basic amino acids
<220> FEATURE:
<221> NAME/KEY: MISC_FEATURE
<222> LOCATION: (25)..(25)
<223> OTHER INFORMATION: X is A and G
<220> FEATURE:
<221> NAME/KEY: MISC_FEATURE
<222> LOCATION: (26)..(26)
<223> OTHER INFORMATION: X is D and E for acidic amino acids
<220> FEATURE:
<221> NAME/KEY: MISC_FEATURE
<222> LOCATION: (27)..(27)
<223> OTHER INFORMATION: X is N or Q for amidated amino acids
<220> FEATURE:
<221> NAME/KEY: MISC_FEATURE
<222> LOCATION: (28)..(28)
<223> OTHER INFORMATION: X is A and G
<220> FEATURE:
<221> NAME/KEY: MISC_FEATURE
<222> LOCATION: (29)..(29)
<223> OTHER INFORMATION: X is F or P
<220> FEATURE:
<221> NAME/KEY: MISC_FEATURE
<222> LOCATION: (30)..(30)
<223> OTHER INFORMATION: X is K, R or H for basic amino acids
<220> FEATURE:
<221> NAME/KEY: MISC_FEATURE
<222> LOCATION: (31)..(31)
<223> OTHER INFORMATION: X is A and G
<220> FEATURE:
<221> NAME/KEY: MISC_FEATURE
<222> LOCATION: (32)..(32)
```

```
<223> OTHER INFORMATION: X is D and E for acidic amino acids
<220> FEATURE:
<221> NAME/KEY: MISC_FEATURE
<222> LOCATION: (33)..(33)
<223> OTHER INFORMATION: X is F or P

<400> SEQUENCE: 103

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa

<210> SEQ ID NO 104
<211> LENGTH: 31
<212> TYPE: PRT
<213> ORGANISM: artificial
<220> FEATURE:
<223> OTHER INFORMATION: Completely synthesized peptide construct
<220> FEATURE:
<221> NAME/KEY: MISC_FEATURE
<222> LOCATION: (1)..(1)
<223> OTHER INFORMATION: X is D and E for acidic amino acids
<220> FEATURE:
<221> NAME/KEY: MISC_FEATURE
<222> LOCATION: (2)..(2)
<223> OTHER INFORMATION: X is I, L or V
<220> FEATURE:
<221> NAME/KEY: MISC_FEATURE
<222> LOCATION: (3)..(3)
<223> OTHER INFORMATION: X is I, L or V
<220> FEATURE:
<221> NAME/KEY: MISC_FEATURE
<222> LOCATION: (4)..(4)
<223> OTHER INFORMATION: X is K, R or H for basic amino acids
<220> FEATURE:
<221> NAME/KEY: MISC_FEATURE
<222> LOCATION: (5)..(5)
<223> OTHER INFORMATION: X is N or Q for amidated amino acids
<220> FEATURE:
<221> NAME/KEY: MISC_FEATURE
<222> LOCATION: (6)..(6)
<223> OTHER INFORMATION: X is A and G
<220> FEATURE:
<221> NAME/KEY: MISC_FEATURE
<222> LOCATION: (7)..(7)
<223> OTHER INFORMATION: X is D and E for acidic amino acids
<220> FEATURE:
<221> NAME/KEY: MISC_FEATURE
<222> LOCATION: (8)..(8)
<223> OTHER INFORMATION: X is K, R or H for basic amino acids
<220> FEATURE:
<221> NAME/KEY: MISC_FEATURE
<222> LOCATION: (9)..(9)
<223> OTHER INFORMATION: X is I, L or V
<220> FEATURE:
<221> NAME/KEY: MISC_FEATURE
<222> LOCATION: (10)..(10)
<223> OTHER INFORMATION: X is D and E for acidic amino acids
<220> FEATURE:
<221> NAME/KEY: MISC_FEATURE
<222> LOCATION: (11)..(11)
<223> OTHER INFORMATION: X is K, R or H for basic amino acids
<220> FEATURE:
<221> NAME/KEY: MISC_FEATURE
<222> LOCATION: (12)..(12)
<223> OTHER INFORMATION: X is I, L or V
<220> FEATURE:
<221> NAME/KEY: MISC_FEATURE
<222> LOCATION: (13)..(13)
<223> OTHER INFORMATION: X is D and E for acidic amino acids
<220> FEATURE:
<221> NAME/KEY: MISC_FEATURE
<222> LOCATION: (14)..(14)
<223> OTHER INFORMATION: X is A and G
```

```
<220> FEATURE:
<221> NAME/KEY: MISC_FEATURE
<222> LOCATION: (15)..(15)
<223> OTHER INFORMATION: X is A and G
<220> FEATURE:
<221> NAME/KEY: MISC_FEATURE
<222> LOCATION: (16)..(16)
<223> OTHER INFORMATION: X is A and G
<220> FEATURE:
<221> NAME/KEY: MISC_FEATURE
<222> LOCATION: (17)..(17)
<223> OTHER INFORMATION: X is T or S
<220> FEATURE:
<221> NAME/KEY: MISC_FEATURE
<222> LOCATION: (18)..(18)
<223> OTHER INFORMATION: X is X1X1 or X1X3 or X3X1 or X1X2 or X2X1
<220> FEATURE:
<221> NAME/KEY: MISC_FEATURE
<222> LOCATION: (19)..(19)
<223> OTHER INFORMATION: X is K, R or H for basic amino acids
<220> FEATURE:
<221> NAME/KEY: MISC_FEATURE
<222> LOCATION: (20)..(20)
<223> OTHER INFORMATION: X is F or P
<220> FEATURE:
<221> NAME/KEY: MISC_FEATURE
<222> LOCATION: (21)..(21)
<223> OTHER INFORMATION: X is Gaba for X2X3 or X3X2 or X2X3 or X3X2 or
      X3X3 or X2X2
<220> FEATURE:
<221> NAME/KEY: MISC_FEATURE
<222> LOCATION: (22)..(22)
<223> OTHER INFORMATION: X is X1X1 or X1X3 or X3X1 or X1X2 or X2X1
<220> FEATURE:
<221> NAME/KEY: MISC_FEATURE
<222> LOCATION: (23)..(23)
<223> OTHER INFORMATION: X is F, W or Y for aromatic amino acids
<220> FEATURE:
<221> NAME/KEY: MISC_FEATURE
<222> LOCATION: (24)..(24)
<223> OTHER INFORMATION: X is K, R or H for basic amino acids
<220> FEATURE:
<221> NAME/KEY: MISC_FEATURE
<222> LOCATION: (25)..(25)
<223> OTHER INFORMATION: X is X1X1 or X1X3 or X3X1 or X1X2 or X2X1
<220> FEATURE:
<221> NAME/KEY: MISC_FEATURE
<222> LOCATION: (26)..(26)
<223> OTHER INFORMATION: X is N or Q for amidated amino acids
<220> FEATURE:
<221> NAME/KEY: MISC_FEATURE
<222> LOCATION: (27)..(27)
<223> OTHER INFORMATION: X is A and G
<220> FEATURE:
<221> NAME/KEY: MISC_FEATURE
<222> LOCATION: (28)..(28)
<223> OTHER INFORMATION: X is F or P
<220> FEATURE:
<221> NAME/KEY: MISC_FEATURE
<222> LOCATION: (29)..(29)
<223> OTHER INFORMATION: X is K, R or H for basic amino acids
<220> FEATURE:
<221> NAME/KEY: MISC_FEATURE
<222> LOCATION: (30)..(30)
<223> OTHER INFORMATION: X is X1X1 or X1X3 or X3X1 or X1X2 or X2X1
<220> FEATURE:
<221> NAME/KEY: MISC_FEATURE
<222> LOCATION: (31)..(31)
<223> OTHER INFORMATION: X is F or P

<400> SEQUENCE: 104

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30
```

```
<210> SEQ ID NO 105
<211> LENGTH: 32
<212> TYPE: PRT
<213> ORGANISM: artificial
<220> FEATURE:
<223> OTHER INFORMATION: Completely synthesized peptide construct
<220> FEATURE:
<221> NAME/KEY: MISC_FEATURE
<222> LOCATION: (1)..(1)
<223> OTHER INFORMATION: X is Acetyl or propionyl group, D glycine or D
      alanine, Cyclohexylalanine at amino terminus
<220> FEATURE:
<221> NAME/KEY: MISC_FEATURE
<222> LOCATION: (2)..(2)
<223> OTHER INFORMATION: X is D and E for acidic amino acids
<220> FEATURE:
<221> NAME/KEY: MISC_FEATURE
<222> LOCATION: (3)..(3)
<223> OTHER INFORMATION: X is I, L or V
<220> FEATURE:
<221> NAME/KEY: MISC_FEATURE
<222> LOCATION: (4)..(4)
<223> OTHER INFORMATION: X is I, L or V
<220> FEATURE:
<221> NAME/KEY: MISC_FEATURE
<222> LOCATION: (5)..(5)
<223> OTHER INFORMATION: X is K, R or H for basic amino acids
<220> FEATURE:
<221> NAME/KEY: MISC_FEATURE
<222> LOCATION: (6)..(6)
<223> OTHER INFORMATION: X is N or Q for amidated amino acids
<220> FEATURE:
<221> NAME/KEY: MISC_FEATURE
<222> LOCATION: (7)..(7)
<223> OTHER INFORMATION: X is A and G
<220> FEATURE:
<221> NAME/KEY: MISC_FEATURE
<222> LOCATION: (8)..(8)
<223> OTHER INFORMATION: X is D and E for acidic amino acids
<220> FEATURE:
<221> NAME/KEY: MISC_FEATURE
<222> LOCATION: (9)..(9)
<223> OTHER INFORMATION: X is K, R or H for basic amino acids
<220> FEATURE:
<221> NAME/KEY: MISC_FEATURE
<222> LOCATION: (10)..(10)
<223> OTHER INFORMATION: X is I, L or V
<220> FEATURE:
<221> NAME/KEY: MISC_FEATURE
<222> LOCATION: (11)..(11)
<223> OTHER INFORMATION: X is D and E for acidic amino acids
<220> FEATURE:
<221> NAME/KEY: MISC_FEATURE
<222> LOCATION: (12)..(12)
<223> OTHER INFORMATION: X is K, R or H for basic amino acids
<220> FEATURE:
<221> NAME/KEY: MISC_FEATURE
<222> LOCATION: (13)..(13)
<223> OTHER INFORMATION: X is I, L or V
<220> FEATURE:
<221> NAME/KEY: MISC_FEATURE
<222> LOCATION: (14)..(14)
<223> OTHER INFORMATION: X is D and E for acidic amino acids
<220> FEATURE:
<221> NAME/KEY: MISC_FEATURE
<222> LOCATION: (15)..(15)
<223> OTHER INFORMATION: X is A and G
<220> FEATURE:
<221> NAME/KEY: MISC_FEATURE
<222> LOCATION: (16)..(16)
<223> OTHER INFORMATION: X is A and G
<220> FEATURE:
<221> NAME/KEY: MISC_FEATURE
<222> LOCATION: (17)..(17)
<223> OTHER INFORMATION: X is A and G
<220> FEATURE:
<221> NAME/KEY: MISC_FEATURE
<222> LOCATION: (18)..(18)
<223> OTHER INFORMATION: X is T or S
```

-continued

```
<220> FEATURE:
<221> NAME/KEY: MISC_FEATURE
<222> LOCATION: (19)..(19)
<223> OTHER INFORMATION: X is X1X1 or X1X3 or X3X1 or X1X2 or X2X1
<220> FEATURE:
<221> NAME/KEY: MISC_FEATURE
<222> LOCATION: (20)..(20)
<223> OTHER INFORMATION: X is K, R or H for basic amino acids
<220> FEATURE:
<221> NAME/KEY: MISC_FEATURE
<222> LOCATION: (21)..(21)
<223> OTHER INFORMATION: X is F or P
<220> FEATURE:
<221> NAME/KEY: MISC_FEATURE
<222> LOCATION: (22)..(22)
<223> OTHER INFORMATION: X is Gaba for X2X3 or X3X2 or X2X3 or X3X2 or
     X3X3 or X2X2
<220> FEATURE:
<221> NAME/KEY: MISC_FEATURE
<222> LOCATION: (23)..(23)
<223> OTHER INFORMATION: X is X1X1 or X1X3 or X3X1 or X1X2 or X2X1
<220> FEATURE:
<221> NAME/KEY: MISC_FEATURE
<222> LOCATION: (24)..(24)
<223> OTHER INFORMATION: X is F, W or Y for aromatic amino acids
<220> FEATURE:
<221> NAME/KEY: MISC_FEATURE
<222> LOCATION: (25)..(25)
<223> OTHER INFORMATION: X is K, R or H for basic amino acids
<220> FEATURE:
<221> NAME/KEY: MISC_FEATURE
<222> LOCATION: (26)..(26)
<223> OTHER INFORMATION: X is X1X1 or X1X3 or X3X1 or X1X2 or X2X1
<220> FEATURE:
<221> NAME/KEY: MISC_FEATURE
<222> LOCATION: (27)..(27)
<223> OTHER INFORMATION: X is N or Q for amidated amino acids
<220> FEATURE:
<221> NAME/KEY: MISC_FEATURE
<222> LOCATION: (28)..(28)
<223> OTHER INFORMATION: X is A and G
<220> FEATURE:
<221> NAME/KEY: MISC_FEATURE
<222> LOCATION: (29)..(29)
<223> OTHER INFORMATION: X is F or P
<220> FEATURE:
<221> NAME/KEY: MISC_FEATURE
<222> LOCATION: (30)..(30)
<223> OTHER INFORMATION: X is K, R or H for basic amino acids
<220> FEATURE:
<221> NAME/KEY: MISC_FEATURE
<222> LOCATION: (31)..(31)
<223> OTHER INFORMATION: X is X1X1 or X1X3 or X3X1 or X1X2 or X2X1
<220> FEATURE:
<221> NAME/KEY: MISC_FEATURE
<222> LOCATION: (32)..(32)
<223> OTHER INFORMATION: X is F or P

<400> SEQUENCE: 105

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

<210> SEQ ID NO 106
<211> LENGTH: 27
<212> TYPE: PRT
<213> ORGANISM: artificial
<220> FEATURE:
<223> OTHER INFORMATION: Completely synthesized peptide construct
<220> FEATURE:
<221> NAME/KEY: MISC_FEATURE
<222> LOCATION: (1)..(1)
<223> OTHER INFORMATION: X is Acetyl or propionyl group, D glycine or D
     alanine, Cyclohexylalanine at amino terminus
<220> FEATURE:
```

-continued

```
<221> NAME/KEY: MISC_FEATURE
<222> LOCATION: (2)..(2)
<223> OTHER INFORMATION: X is Gaba for X2X3 or X3X2 or X2X3 or X3X2 or
      X3X3 or X2X2
<220> FEATURE:
<221> NAME/KEY: MISC_FEATURE
<222> LOCATION: (3)..(3)
<223> OTHER INFORMATION: X is K, R or H for basic amino acids
<220> FEATURE:
<221> NAME/KEY: MISC_FEATURE
<222> LOCATION: (4)..(4)
<223> OTHER INFORMATION: X is N or Q for amidated amino acids
<220> FEATURE:
<221> NAME/KEY: MISC_FEATURE
<222> LOCATION: (5)..(5)
<223> OTHER INFORMATION: X is A and G
<220> FEATURE:
<221> NAME/KEY: MISC_FEATURE
<222> LOCATION: (6)..(6)
<223> OTHER INFORMATION: X is D and E for acidic amino acids
<220> FEATURE:
<221> NAME/KEY: MISC_FEATURE
<222> LOCATION: (7)..(7)
<223> OTHER INFORMATION: X is K, R or H for basic amino acids
<220> FEATURE:
<221> NAME/KEY: MISC_FEATURE
<222> LOCATION: (8)..(8)
<223> OTHER INFORMATION: X is Gaba for X2X3 or X3X2 or X2X3 or X3X2 or
      X3X3 or X2X2
<220> FEATURE:
<221> NAME/KEY: MISC_FEATURE
<222> LOCATION: (9)..(9)
<223> OTHER INFORMATION: X is K, R or H for basic amino acids
<220> FEATURE:
<221> NAME/KEY: MISC_FEATURE
<222> LOCATION: (10)..(10)
<223> OTHER INFORMATION: X is Gaba for X2X3 or X3X2 or X2X3 or X3X2 or
      X3X3 or X2X2
<220> FEATURE:
<221> NAME/KEY: MISC_FEATURE
<222> LOCATION: (11)..(11)
<223> OTHER INFORMATION: X is A and G
<220> FEATURE:
<221> NAME/KEY: MISC_FEATURE
<222> LOCATION: (12)..(12)
<223> OTHER INFORMATION: X is A and G
<220> FEATURE:
<221> NAME/KEY: MISC_FEATURE
<222> LOCATION: (13)..(13)
<223> OTHER INFORMATION: X is A and G
<220> FEATURE:
<221> NAME/KEY: MISC_FEATURE
<222> LOCATION: (14)..(14)
<223> OTHER INFORMATION: X is T or S
<220> FEATURE:
<221> NAME/KEY: MISC_FEATURE
<222> LOCATION: (15)..(15)
<223> OTHER INFORMATION: X is X1X1 or X1X3 or X3X1 or X1X2 or X2X1
<220> FEATURE:
<221> NAME/KEY: MISC_FEATURE
<222> LOCATION: (16)..(16)
<223> OTHER INFORMATION: X is K, R or H for basic amino acids
<220> FEATURE:
<221> NAME/KEY: MISC_FEATURE
<222> LOCATION: (17)..(17)
<223> OTHER INFORMATION: X is F or P
<220> FEATURE:
<221> NAME/KEY: MISC_FEATURE
<222> LOCATION: (18)..(18)
<223> OTHER INFORMATION: X is Gaba for X2X3 or X3X2 or X2X3 or X3X2 or
      X3X3 or X2X2
<220> FEATURE:
<221> NAME/KEY: MISC_FEATURE
<222> LOCATION: (19)..(19)
<223> OTHER INFORMATION: X is X1X1 or X1X3 or X3X1 or X1X2 or X2X1
<220> FEATURE:
<221> NAME/KEY: MISC_FEATURE
<222> LOCATION: (20)..(20)
<223> OTHER INFORMATION: X is F, W or Y for aromatic amino acids
```

-continued

```
<220> FEATURE:
<221> NAME/KEY: MISC_FEATURE
<222> LOCATION: (21)..(21)
<223> OTHER INFORMATION: X is K, R or H for basic amino acids
<220> FEATURE:
<221> NAME/KEY: MISC_FEATURE
<222> LOCATION: (22)..(22)
<223> OTHER INFORMATION: X is X1X1 or X1X3 or X3X1 or X1X2 or X2X1
<220> FEATURE:
<221> NAME/KEY: MISC_FEATURE
<222> LOCATION: (23)..(23)
<223> OTHER INFORMATION: X is N or Q for amidated amino acids
<220> FEATURE:
<221> NAME/KEY: MISC_FEATURE
<222> LOCATION: (24)..(24)
<223> OTHER INFORMATION: X is A and G
<220> FEATURE:
<221> NAME/KEY: MISC_FEATURE
<222> LOCATION: (25)..(25)
<223> OTHER INFORMATION: X is F or P
<220> FEATURE:
<221> NAME/KEY: MISC_FEATURE
<222> LOCATION: (26)..(26)
<223> OTHER INFORMATION: X is K, R or H for basic amino acids
<220> FEATURE:
<221> NAME/KEY: MISC_FEATURE
<222> LOCATION: (27)..(27)
<223> OTHER INFORMATION: X is X1X1 or X1X3 or X3X1 or X1X2 or X2X1
<220> FEATURE:
<221> NAME/KEY: MISC_FEATURE
<222> LOCATION: (28)..(28)
<223> OTHER INFORMATION: X is F or P

<400> SEQUENCE: 106

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa
            20                  25

<210> SEQ ID NO 107
<211> LENGTH: 28
<212> TYPE: PRT
<213> ORGANISM: artificial
<220> FEATURE:
<223> OTHER INFORMATION: Completely synthesized peptide construct
<220> FEATURE:
<221> NAME/KEY: MISC_FEATURE
<222> LOCATION: (1)..(1)
<223> OTHER INFORMATION: X is Acetyl or propionyl group, D glycine or D
      alanine, Cyclohexylalanine at amino terminus
<220> FEATURE:
<221> NAME/KEY: MISC_FEATURE
<222> LOCATION: (2)..(2)
<223> OTHER INFORMATION: X is 5-aminopentanoic acid for replacement of 3
      or 4 amino acids of X2 and  X3
<220> FEATURE:
<221> NAME/KEY: MISC_FEATURE
<222> LOCATION: (3)..(3)
<223> OTHER INFORMATION: X is K, R or H for basic amino acids
<220> FEATURE:
<221> NAME/KEY: MISC_FEATURE
<222> LOCATION: (4)..(4)
<223> OTHER INFORMATION: X is N or Q for amidated amino acids
<220> FEATURE:
<221> NAME/KEY: MISC_FEATURE
<222> LOCATION: (5)..(5)
<223> OTHER INFORMATION: X is A and G
<220> FEATURE:
<221> NAME/KEY: MISC_FEATURE
<222> LOCATION: (6)..(6)
<223> OTHER INFORMATION: X is D and E for acidic amino acids
<220> FEATURE:
<221> NAME/KEY: MISC_FEATURE
<222> LOCATION: (7)..(7)
<223> OTHER INFORMATION: X is K, R or H for basic amino acids
<220> FEATURE:
```

```
<221> NAME/KEY: MISC_FEATURE
<222> LOCATION: (8)..(8)
<223> OTHER INFORMATION: X is Gaba for X2X3 or X3X2 or X2X3 or X3X2 or
      X3X3 or X2X2
<220> FEATURE:
<221> NAME/KEY: MISC_FEATURE
<222> LOCATION: (9)..(9)
<223> OTHER INFORMATION: X is K, R or H for basic amino acids
<220> FEATURE:
<221> NAME/KEY: MISC_FEATURE
<222> LOCATION: (10)..(10)
<223> OTHER INFORMATION: X is Gaba for X2X3 or X3X2 or X2X3 or X3X2 or
      X3X3 or X2X2
<220> FEATURE:
<221> NAME/KEY: MISC_FEATURE
<222> LOCATION: (11)..(11)
<223> OTHER INFORMATION: X is A and G
<220> FEATURE:
<221> NAME/KEY: MISC_FEATURE
<222> LOCATION: (12)..(12)
<223> OTHER INFORMATION: X is A and G
<220> FEATURE:
<221> NAME/KEY: MISC_FEATURE
<222> LOCATION: (13)..(13)
<223> OTHER INFORMATION: X is A and G
<220> FEATURE:
<221> NAME/KEY: MISC_FEATURE
<222> LOCATION: (14)..(14)
<223> OTHER INFORMATION: X is T or S
<220> FEATURE:
<221> NAME/KEY: MISC_FEATURE
<222> LOCATION: (15)..(15)
<223> OTHER INFORMATION: X is X1X1 or X1X3 or X3X1 or X1X2 or X2X1
<220> FEATURE:
<221> NAME/KEY: MISC_FEATURE
<222> LOCATION: (16)..(16)
<223> OTHER INFORMATION: X is K, R or H for basic amino acids
<220> FEATURE:
<221> NAME/KEY: MISC_FEATURE
<222> LOCATION: (17)..(17)
<223> OTHER INFORMATION: X is F or P
<220> FEATURE:
<221> NAME/KEY: MISC_FEATURE
<222> LOCATION: (18)..(18)
<223> OTHER INFORMATION: X is Gaba for X2X3 or X3X2 or X2X3 or X3X2 or
      X3X3 or X2X2
<220> FEATURE:
<221> NAME/KEY: MISC_FEATURE
<222> LOCATION: (19)..(19)
<223> OTHER INFORMATION: X is X1X1 or X1X3 or X3X1 or X1X2 or X2X1
<220> FEATURE:
<221> NAME/KEY: MISC_FEATURE
<222> LOCATION: (20)..(20)
<223> OTHER INFORMATION: X is F, W or Y for aromatic amino acids
<220> FEATURE:
<221> NAME/KEY: MISC_FEATURE
<222> LOCATION: (21)..(21)
<223> OTHER INFORMATION: X is K, R or H for basic amino acids
<220> FEATURE:
<221> NAME/KEY: MISC_FEATURE
<222> LOCATION: (22)..(22)
<223> OTHER INFORMATION: X is X1X1 or X1X3 or X3X1 or X1X2 or X2X1
<220> FEATURE:
<221> NAME/KEY: MISC_FEATURE
<222> LOCATION: (23)..(23)
<223> OTHER INFORMATION: X is N or Q for amidated amino acids
<220> FEATURE:
<221> NAME/KEY: MISC_FEATURE
<222> LOCATION: (24)..(24)
<223> OTHER INFORMATION: X is A and G
<220> FEATURE:
<221> NAME/KEY: MISC_FEATURE
<222> LOCATION: (25)..(25)
<223> OTHER INFORMATION: X is F or P
<220> FEATURE:
<221> NAME/KEY: MISC_FEATURE
<222> LOCATION: (26)..(26)
<223> OTHER INFORMATION: X is K, R or H for basic amino acids
<220> FEATURE:
```

```
<221> NAME/KEY: MISC_FEATURE
<222> LOCATION: (27)..(27)
<223> OTHER INFORMATION: X is X1X1 or X1X3 or X3X1 or X1X2 or X2X1
<220> FEATURE:
<221> NAME/KEY: MISC_FEATURE
<222> LOCATION: (28)..(28)
<223> OTHER INFORMATION: X is F or P

<400> SEQUENCE: 107

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa
            20                  25

<210> SEQ ID NO 108
<211> LENGTH: 38
<212> TYPE: PRT
<213> ORGANISM: artificial
<220> FEATURE:
<223> OTHER INFORMATION: Completely synthesized peptide construct

<400> SEQUENCE: 108

Thr Gly Gly Lys Pro Gly Ile Ala Gly Phe Lys Gly Glu Gln Gly Pro
1               5                   10                  15

Lys Gly Glu Pro Gly Gly Gly Asp Gly Gln Glu Glu Lys Ala Gly Val
            20                  25                  30

Val Ser Thr Gly Leu Ile
        35

<210> SEQ ID NO 109
<211> LENGTH: 38
<212> TYPE: PRT
<213> ORGANISM: artificial
<220> FEATURE:
<223> OTHER INFORMATION: Completely synthesized peptide construct
<220> FEATURE:
<221> NAME/KEY: MISC_FEATURE
<222> LOCATION: (1)..(1)
<223> OTHER INFORMATION: X is T or S
<220> FEATURE:
<221> NAME/KEY: MISC_FEATURE
<222> LOCATION: (2)..(2)
<223> OTHER INFORMATION: X is A and G
<220> FEATURE:
<221> NAME/KEY: MISC_FEATURE
<222> LOCATION: (3)..(3)
<223> OTHER INFORMATION: X is A and G
<220> FEATURE:
<221> NAME/KEY: MISC_FEATURE
<222> LOCATION: (4)..(4)
<223> OTHER INFORMATION: X is K, R or H for basic amino acids
<220> FEATURE:
<221> NAME/KEY: MISC_FEATURE
<222> LOCATION: (5)..(5)
<223> OTHER INFORMATION: X is F or P
<220> FEATURE:
<221> NAME/KEY: MISC_FEATURE
<222> LOCATION: (6)..(6)
<223> OTHER INFORMATION: X is A and G
<220> FEATURE:
<221> NAME/KEY: MISC_FEATURE
<222> LOCATION: (7)..(7)
<223> OTHER INFORMATION: X is I, L or V
<220> FEATURE:
<221> NAME/KEY: MISC_FEATURE
<222> LOCATION: (8)..(8)
<223> OTHER INFORMATION: X is A and G
<220> FEATURE:
<221> NAME/KEY: MISC_FEATURE
<222> LOCATION: (9)..(9)
<223> OTHER INFORMATION: X is A and G
<220> FEATURE:
```

```
<221> NAME/KEY: MISC_FEATURE
<222> LOCATION: (10)..(10)
<223> OTHER INFORMATION: X is F, W or Y for aromatic amino acids
<220> FEATURE:
<221> NAME/KEY: MISC_FEATURE
<222> LOCATION: (11)..(11)
<223> OTHER INFORMATION: X is K, R or H for basic amino acids
<220> FEATURE:
<221> NAME/KEY: MISC_FEATURE
<222> LOCATION: (12)..(12)
<223> OTHER INFORMATION: X is A and G
<220> FEATURE:
<221> NAME/KEY: MISC_FEATURE
<222> LOCATION: (13)..(13)
<223> OTHER INFORMATION: X is D and E for acidic amino acids
<220> FEATURE:
<221> NAME/KEY: MISC_FEATURE
<222> LOCATION: (14)..(14)
<223> OTHER INFORMATION: X is N or Q for amidated amino acids
<220> FEATURE:
<221> NAME/KEY: MISC_FEATURE
<222> LOCATION: (15)..(15)
<223> OTHER INFORMATION: X is A and G
<220> FEATURE:
<221> NAME/KEY: MISC_FEATURE
<222> LOCATION: (16)..(16)
<223> OTHER INFORMATION: X is F or P
<220> FEATURE:
<221> NAME/KEY: MISC_FEATURE
<222> LOCATION: (17)..(17)
<223> OTHER INFORMATION: X is K, R or H for basic amino acids
<220> FEATURE:
<221> NAME/KEY: MISC_FEATURE
<222> LOCATION: (18)..(18)
<223> OTHER INFORMATION: X is A and G
<220> FEATURE:
<221> NAME/KEY: MISC_FEATURE
<222> LOCATION: (19)..(19)
<223> OTHER INFORMATION: X is D and E for acidic amino acids
<220> FEATURE:
<221> NAME/KEY: MISC_FEATURE
<222> LOCATION: (20)..(20)
<223> OTHER INFORMATION: X is F or P
<220> FEATURE:
<221> NAME/KEY: MISC_FEATURE
<222> LOCATION: (21)..(21)
<223> OTHER INFORMATION: X is A and G
<220> FEATURE:
<221> NAME/KEY: MISC_FEATURE
<222> LOCATION: (22)..(22)
<223> OTHER INFORMATION: X is A and G
<220> FEATURE:
<221> NAME/KEY: MISC_FEATURE
<222> LOCATION: (23)..(23)
<223> OTHER INFORMATION: X is A and G
<220> FEATURE:
<221> NAME/KEY: MISC_FEATURE
<222> LOCATION: (24)..(24)
<223> OTHER INFORMATION: X is D and E for acidic amino acids
<220> FEATURE:
<221> NAME/KEY: MISC_FEATURE
<222> LOCATION: (25)..(25)
<223> OTHER INFORMATION: X is A and G
<220> FEATURE:
<221> NAME/KEY: MISC_FEATURE
<222> LOCATION: (26)..(26)
<223> OTHER INFORMATION: X is N or Q for amidated amino acids
<220> FEATURE:
<221> NAME/KEY: MISC_FEATURE
<222> LOCATION: (27)..(27)
<223> OTHER INFORMATION: X is D and E for acidic amino acids
<220> FEATURE:
<221> NAME/KEY: MISC_FEATURE
<222> LOCATION: (28)..(28)
<223> OTHER INFORMATION: X is D and E for acidic amino acids
<220> FEATURE:
<221> NAME/KEY: MISC_FEATURE
<222> LOCATION: (29)..(29)
<223> OTHER INFORMATION: X is K, R or H for basic amino acids
```

```
<220> FEATURE:
<221> NAME/KEY: MISC_FEATURE
<222> LOCATION: (30)..(30)
<223> OTHER INFORMATION: X is A and G
<220> FEATURE:
<221> NAME/KEY: MISC_FEATURE
<222> LOCATION: (31)..(31)
<223> OTHER INFORMATION: X is A and G
<220> FEATURE:
<221> NAME/KEY: MISC_FEATURE
<222> LOCATION: (32)..(32)
<223> OTHER INFORMATION: X is I, L or V
<220> FEATURE:
<221> NAME/KEY: MISC_FEATURE
<222> LOCATION: (33)..(33)
<223> OTHER INFORMATION: X is I, L or V
<220> FEATURE:
<221> NAME/KEY: MISC_FEATURE
<222> LOCATION: (34)..(34)
<223> OTHER INFORMATION: X is C or S
<220> FEATURE:
<221> NAME/KEY: MISC_FEATURE
<222> LOCATION: (35)..(35)
<223> OTHER INFORMATION: X is T or S
<220> FEATURE:
<221> NAME/KEY: MISC_FEATURE
<222> LOCATION: (36)..(36)
<223> OTHER INFORMATION: X is A and G
<220> FEATURE:
<221> NAME/KEY: MISC_FEATURE
<222> LOCATION: (37)..(37)
<223> OTHER INFORMATION: X is I, L or V
<220> FEATURE:
<221> NAME/KEY: MISC_FEATURE
<222> LOCATION: (38)..(38)
<223> OTHER INFORMATION: X is I, L or V

<400> SEQUENCE: 109

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa
        35

<210> SEQ ID NO 110
<211> LENGTH: 39
<212> TYPE: PRT
<213> ORGANISM: artificial
<220> FEATURE:
<223> OTHER INFORMATION: Completely synthesized peptide construct
<220> FEATURE:
<221> NAME/KEY: MISC_FEATURE
<222> LOCATION: (1)..(1)
<223> OTHER INFORMATION: X is T or S
<220> FEATURE:
<221> NAME/KEY: MISC_FEATURE
<222> LOCATION: (2)..(2)
<223> OTHER INFORMATION: X is A and G
<220> FEATURE:
<221> NAME/KEY: MISC_FEATURE
<222> LOCATION: (3)..(3)
<223> OTHER INFORMATION: X is A and G
<220> FEATURE:
<221> NAME/KEY: MISC_FEATURE
<222> LOCATION: (4)..(4)
<223> OTHER INFORMATION: X is K, R or H for basic amino acids
<220> FEATURE:
<221> NAME/KEY: MISC_FEATURE
<222> LOCATION: (5)..(5)
<223> OTHER INFORMATION: X is F or P
<220> FEATURE:
<221> NAME/KEY: MISC_FEATURE
<222> LOCATION: (6)..(6)
<223> OTHER INFORMATION: X is A and G
```

-continued

```
<220> FEATURE:
<221> NAME/KEY: MISC_FEATURE
<222> LOCATION: (7)..(7)
<223> OTHER INFORMATION: X is I, L or V
<220> FEATURE:
<221> NAME/KEY: MISC_FEATURE
<222> LOCATION: (8)..(8)
<223> OTHER INFORMATION: X is A and G
<220> FEATURE:
<221> NAME/KEY: MISC_FEATURE
<222> LOCATION: (9)..(9)
<223> OTHER INFORMATION: X is A and G
<220> FEATURE:
<221> NAME/KEY: MISC_FEATURE
<222> LOCATION: (10)..(10)
<223> OTHER INFORMATION: X is F, W or Y for aromatic amino acids
<220> FEATURE:
<221> NAME/KEY: MISC_FEATURE
<222> LOCATION: (11)..(11)
<223> OTHER INFORMATION: X is K, R or H for basic amino acids
<220> FEATURE:
<221> NAME/KEY: MISC_FEATURE
<222> LOCATION: (12)..(12)
<223> OTHER INFORMATION: X is A and G
<220> FEATURE:
<221> NAME/KEY: MISC_FEATURE
<222> LOCATION: (13)..(13)
<223> OTHER INFORMATION: X is D and E for acidic amino acids
<220> FEATURE:
<221> NAME/KEY: MISC_FEATURE
<222> LOCATION: (14)..(14)
<223> OTHER INFORMATION: X is N or Q for amidated amino acids
<220> FEATURE:
<221> NAME/KEY: MISC_FEATURE
<222> LOCATION: (15)..(15)
<223> OTHER INFORMATION: X is A and G
<220> FEATURE:
<221> NAME/KEY: MISC_FEATURE
<222> LOCATION: (16)..(16)
<223> OTHER INFORMATION: X is F or P
<220> FEATURE:
<221> NAME/KEY: MISC_FEATURE
<222> LOCATION: (17)..(17)
<223> OTHER INFORMATION: X is K, R or H for basic amino acids
<220> FEATURE:
<221> NAME/KEY: MISC_FEATURE
<222> LOCATION: (18)..(18)
<223> OTHER INFORMATION: X is A and G
<220> FEATURE:
<221> NAME/KEY: MISC_FEATURE
<222> LOCATION: (19)..(19)
<223> OTHER INFORMATION: X is D and E for acidic amino acids
<220> FEATURE:
<221> NAME/KEY: MISC_FEATURE
<222> LOCATION: (20)..(20)
<223> OTHER INFORMATION: X is F or P
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: MISC_FEATURE
<222> LOCATION: (22)..(22)
<223> OTHER INFORMATION: X is A and G
<220> FEATURE:
<221> NAME/KEY: MISC_FEATURE
<222> LOCATION: (23)..(23)
<223> OTHER INFORMATION: X is A and G
<220> FEATURE:
<221> NAME/KEY: MISC_FEATURE
<222> LOCATION: (24)..(24)
<223> OTHER INFORMATION: X is Acetyl or propionyl group, D glycine or D
      alanine, Cyclohexylalanine at amino terminus
<220> FEATURE:
<221> NAME/KEY: MISC_FEATURE
<222> LOCATION: (25)..(25)
<223> OTHER INFORMATION: X is D and E for acidic amino acids
<220> FEATURE:
<221> NAME/KEY: MISC_FEATURE
```

```
<222> LOCATION: (26)..(26)
<223> OTHER INFORMATION: X is A and G
<220> FEATURE:
<221> NAME/KEY: MISC_FEATURE
<222> LOCATION: (27)..(27)
<223> OTHER INFORMATION: X is N or Q for amidated amino acids
<220> FEATURE:
<221> NAME/KEY: MISC_FEATURE
<222> LOCATION: (28)..(28)
<223> OTHER INFORMATION: X is D and E for acidic amino acids
<220> FEATURE:
<221> NAME/KEY: MISC_FEATURE
<222> LOCATION: (29)..(29)
<223> OTHER INFORMATION: X is D and E for acidic amino acids
<220> FEATURE:
<221> NAME/KEY: MISC_FEATURE
<222> LOCATION: (30)..(30)
<223> OTHER INFORMATION: X is K, R or H for basic amino acids
<220> FEATURE:
<221> NAME/KEY: MISC_FEATURE
<222> LOCATION: (31)..(31)
<223> OTHER INFORMATION: X is A and G
<220> FEATURE:
<221> NAME/KEY: MISC_FEATURE
<222> LOCATION: (32)..(32)
<223> OTHER INFORMATION: X is A and G
<220> FEATURE:
<221> NAME/KEY: MISC_FEATURE
<222> LOCATION: (33)..(33)
<223> OTHER INFORMATION: X is I, L or V
<220> FEATURE:
<221> NAME/KEY: MISC_FEATURE
<222> LOCATION: (34)..(34)
<223> OTHER INFORMATION: X is I, L or V
<220> FEATURE:
<221> NAME/KEY: MISC_FEATURE
<222> LOCATION: (35)..(35)
<223> OTHER INFORMATION: X is C or S
<220> FEATURE:
<221> NAME/KEY: MISC_FEATURE
<222> LOCATION: (36)..(36)
<223> OTHER INFORMATION: X is T or S
<220> FEATURE:
<221> NAME/KEY: MISC_FEATURE
<222> LOCATION: (37)..(37)
<223> OTHER INFORMATION: X is A and G
<220> FEATURE:
<221> NAME/KEY: MISC_FEATURE
<222> LOCATION: (38)..(38)
<223> OTHER INFORMATION: X is I, L or V
<220> FEATURE:
<221> NAME/KEY: MISC_FEATURE
<222> LOCATION: (39)..(39)
<223> OTHER INFORMATION: X is I, L or V

<400> SEQUENCE: 110

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa
        35

<210> SEQ ID NO 111
<211> LENGTH: 39
<212> TYPE: PRT
<213> ORGANISM: artificial
<220> FEATURE:
<223> OTHER INFORMATION: Completely synthesized peptide construct
<220> FEATURE:
<221> NAME/KEY: MISC_FEATURE
<222> LOCATION: (1)..(1)
<223> OTHER INFORMATION: X is T or S
<220> FEATURE:
<221> NAME/KEY: MISC_FEATURE
```

```
<222> LOCATION: (2)..(2)
<223> OTHER INFORMATION: X is A and G
<220> FEATURE:
<221> NAME/KEY: MISC_FEATURE
<222> LOCATION: (3)..(3)
<223> OTHER INFORMATION: X is A and G
<220> FEATURE:
<221> NAME/KEY: MISC_FEATURE
<222> LOCATION: (4)..(4)
<223> OTHER INFORMATION: X is K, R or H for basic amino acids
<220> FEATURE:
<221> NAME/KEY: MISC_FEATURE
<222> LOCATION: (5)..(5)
<223> OTHER INFORMATION: X is F or P
<220> FEATURE:
<221> NAME/KEY: MISC_FEATURE
<222> LOCATION: (6)..(6)
<223> OTHER INFORMATION: X is A and G
<220> FEATURE:
<221> NAME/KEY: MISC_FEATURE
<222> LOCATION: (7)..(7)
<223> OTHER INFORMATION: X is I, L or V
<220> FEATURE:
<221> NAME/KEY: MISC_FEATURE
<222> LOCATION: (8)..(8)
<223> OTHER INFORMATION: X is A and G
<220> FEATURE:
<221> NAME/KEY: MISC_FEATURE
<222> LOCATION: (9)..(9)
<223> OTHER INFORMATION: X is A and G
<220> FEATURE:
<221> NAME/KEY: MISC_FEATURE
<222> LOCATION: (10)..(10)
<223> OTHER INFORMATION: X is F, W or Y for aromatic amino acids
<220> FEATURE:
<221> NAME/KEY: MISC_FEATURE
<222> LOCATION: (11)..(11)
<223> OTHER INFORMATION: X is K, R or H for basic amino acids
<220> FEATURE:
<221> NAME/KEY: MISC_FEATURE
<222> LOCATION: (12)..(12)
<223> OTHER INFORMATION: X is A and G
<220> FEATURE:
<221> NAME/KEY: MISC_FEATURE
<222> LOCATION: (13)..(13)
<223> OTHER INFORMATION: X is D and E for acidic amino acids
<220> FEATURE:
<221> NAME/KEY: MISC_FEATURE
<222> LOCATION: (14)..(14)
<223> OTHER INFORMATION: X is N or Q for amidated amino acids
<220> FEATURE:
<221> NAME/KEY: MISC_FEATURE
<222> LOCATION: (15)..(15)
<223> OTHER INFORMATION: X is A and G
<220> FEATURE:
<221> NAME/KEY: MISC_FEATURE
<222> LOCATION: (16)..(16)
<223> OTHER INFORMATION: X is F or P
<220> FEATURE:
<221> NAME/KEY: MISC_FEATURE
<222> LOCATION: (17)..(17)
<223> OTHER INFORMATION: X is K, R or H for basic amino acids
<220> FEATURE:
<221> NAME/KEY: MISC_FEATURE
<222> LOCATION: (18)..(18)
<223> OTHER INFORMATION: X is A and G
<220> FEATURE:
<221> NAME/KEY: MISC_FEATURE
<222> LOCATION: (19)..(19)
<223> OTHER INFORMATION: X is D and E for acidic amino acids
<220> FEATURE:
<221> NAME/KEY: MISC_FEATURE
<222> LOCATION: (20)..(20)
<223> OTHER INFORMATION: X is F or P
<220> FEATURE:
<221> NAME/KEY: MISC_FEATURE
<222> LOCATION: (21)..(21)
<223> OTHER INFORMATION: X is A and G
<220> FEATURE:
```

```
<221> NAME/KEY: MISC_FEATURE
<222> LOCATION: (22)..(22)
<223> OTHER INFORMATION: X is A and G
<220> FEATURE:
<221> NAME/KEY: MISC_FEATURE
<222> LOCATION: (23)..(23)
<223> OTHER INFORMATION: X is A and G
<220> FEATURE:
<221> NAME/KEY: MISC_FEATURE
<222> LOCATION: (24)..(24)
<223> OTHER INFORMATION: X is 5-aminopentanoic acid for replacement of 3
      or 4 amino acids of X2 and  X3
<220> FEATURE:
<221> NAME/KEY: MISC_FEATURE
<222> LOCATION: (25)..(25)
<223> OTHER INFORMATION: X is D and E for acidic amino acids
<220> FEATURE:
<221> NAME/KEY: MISC_FEATURE
<222> LOCATION: (26)..(26)
<223> OTHER INFORMATION: X is A and G
<220> FEATURE:
<221> NAME/KEY: MISC_FEATURE
<222> LOCATION: (27)..(27)
<223> OTHER INFORMATION: X is N or Q for amidated amino acids
<220> FEATURE:
<221> NAME/KEY: MISC_FEATURE
<222> LOCATION: (28)..(28)
<223> OTHER INFORMATION: X is D and E for acidic amino acids
<220> FEATURE:
<221> NAME/KEY: MISC_FEATURE
<222> LOCATION: (29)..(29)
<223> OTHER INFORMATION: X is D and E for acidic amino acids
<220> FEATURE:
<221> NAME/KEY: MISC_FEATURE
<222> LOCATION: (30)..(30)
<223> OTHER INFORMATION: X is K, R or H for basic amino acids
<220> FEATURE:
<221> NAME/KEY: MISC_FEATURE
<222> LOCATION: (31)..(31)
<223> OTHER INFORMATION: X is A and G
<220> FEATURE:
<221> NAME/KEY: MISC_FEATURE
<222> LOCATION: (32)..(32)
<223> OTHER INFORMATION: X is A and G
<220> FEATURE:
<221> NAME/KEY: MISC_FEATURE
<222> LOCATION: (33)..(33)
<223> OTHER INFORMATION: X is I, L or V
<220> FEATURE:
<221> NAME/KEY: MISC_FEATURE
<222> LOCATION: (34)..(34)
<223> OTHER INFORMATION: X is I, L or V
<220> FEATURE:
<221> NAME/KEY: MISC_FEATURE
<222> LOCATION: (35)..(35)
<223> OTHER INFORMATION: X is C or S
<220> FEATURE:
<221> NAME/KEY: MISC_FEATURE
<222> LOCATION: (36)..(36)
<223> OTHER INFORMATION: X is T or S
<220> FEATURE:
<221> NAME/KEY: MISC_FEATURE
<222> LOCATION: (37)..(37)
<223> OTHER INFORMATION: X is A and G
<220> FEATURE:
<221> NAME/KEY: misc_feature
<222> LOCATION: (38)..(38)
<223> OTHER INFORMATION: Xaa can be any naturally occurring amino acid
<220> FEATURE:
<221> NAME/KEY: MISC_FEATURE
<222> LOCATION: (39)..(39)
<223> OTHER INFORMATION: X is I, L or V

<400> SEQUENCE: 111

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
```

20                  25                  30
Xaa Xaa Xaa Xaa Xaa Xaa Xaa
           35

<210> SEQ ID NO 112
<211> LENGTH: 36
<212> TYPE: PRT
<213> ORGANISM: artificial
<220> FEATURE:
<223> OTHER INFORMATION: Completely synthesized peptide construct
<220> FEATURE:
<221> NAME/KEY: MISC_FEATURE
<222> LOCATION: (1)..(1)
<223> OTHER INFORMATION: X is T or S
<220> FEATURE:
<221> NAME/KEY: MISC_FEATURE
<222> LOCATION: (2)..(2)
<223> OTHER INFORMATION: X is A and G
<220> FEATURE:
<221> NAME/KEY: MISC_FEATURE
<222> LOCATION: (3)..(3)
<223> OTHER INFORMATION: X is A and G
<220> FEATURE:
<221> NAME/KEY: MISC_FEATURE
<222> LOCATION: (4)..(4)
<223> OTHER INFORMATION: X is K, R or H for basic amino acids
<220> FEATURE:
<221> NAME/KEY: MISC_FEATURE
<222> LOCATION: (5)..(5)
<223> OTHER INFORMATION: X is F or P
<220> FEATURE:
<221> NAME/KEY: MISC_FEATURE
<222> LOCATION: (6)..(6)
<223> OTHER INFORMATION: X is A and G
<220> FEATURE:
<221> NAME/KEY: MISC_FEATURE
<222> LOCATION: (7)..(7)
<223> OTHER INFORMATION: X is I, L or V
<220> FEATURE:
<221> NAME/KEY: MISC_FEATURE
<222> LOCATION: (8)..(8)
<223> OTHER INFORMATION: X is A and G
<220> FEATURE:
<221> NAME/KEY: MISC_FEATURE
<222> LOCATION: (9)..(9)
<223> OTHER INFORMATION: X is A and G
<220> FEATURE:
<221> NAME/KEY: MISC_FEATURE
<222> LOCATION: (10)..(10)
<223> OTHER INFORMATION: X is F, W or Y for aromatic amino acids
<220> FEATURE:
<221> NAME/KEY: MISC_FEATURE
<222> LOCATION: (11)..(11)
<223> OTHER INFORMATION: X is K, R or H for basic amino acids
<220> FEATURE:
<221> NAME/KEY: MISC_FEATURE
<222> LOCATION: (12)..(12)
<223> OTHER INFORMATION: X is A and G
<220> FEATURE:
<221> NAME/KEY: MISC_FEATURE
<222> LOCATION: (13)..(13)
<223> OTHER INFORMATION: X is D and E for acidic amino acids
<220> FEATURE:
<221> NAME/KEY: MISC_FEATURE
<222> LOCATION: (14)..(14)
<223> OTHER INFORMATION: X is N or Q for amidated amino acids
<220> FEATURE:
<221> NAME/KEY: MISC_FEATURE
<222> LOCATION: (15)..(15)
<223> OTHER INFORMATION: X is A and G
<220> FEATURE:
<221> NAME/KEY: MISC_FEATURE
<222> LOCATION: (16)..(16)
<223> OTHER INFORMATION: X is F or P
<220> FEATURE:
<221> NAME/KEY: MISC_FEATURE
<222> LOCATION: (17)..(17)

```
<223> OTHER INFORMATION: X is K, R or H for basic amino acids
<220> FEATURE:
<221> NAME/KEY: MISC_FEATURE
<222> LOCATION: (18)..(18)
<223> OTHER INFORMATION: X is A and G
<220> FEATURE:
<221> NAME/KEY: MISC_FEATURE
<222> LOCATION: (19)..(19)
<223> OTHER INFORMATION: X is D and E for acidic amino acids
<220> FEATURE:
<221> NAME/KEY: MISC_FEATURE
<222> LOCATION: (20)..(20)
<223> OTHER INFORMATION: X is F or P
<220> FEATURE:
<221> NAME/KEY: MISC_FEATURE
<222> LOCATION: (21)..(21)
<223> OTHER INFORMATION: X is A and G
<220> FEATURE:
<221> NAME/KEY: MISC_FEATURE
<222> LOCATION: (22)..(22)
<223> OTHER INFORMATION: X is A and G
<220> FEATURE:
<221> NAME/KEY: MISC_FEATURE
<222> LOCATION: (23)..(23)
<223> OTHER INFORMATION: X is A and G
<220> FEATURE:
<221> NAME/KEY: MISC_FEATURE
<222> LOCATION: (24)..(24)
<223> OTHER INFORMATION: X is Acetyl or propionyl group, D glycine or D
      alanine, Cyclohexylalanine at amino terminus
<220> FEATURE:
<221> NAME/KEY: MISC_FEATURE
<222> LOCATION: (25)..(25)
<223> OTHER INFORMATION: X is D and E for acidic amino acids
<220> FEATURE:
<221> NAME/KEY: MISC_FEATURE
<222> LOCATION: (26)..(26)
<223> OTHER INFORMATION: X is A and G
<220> FEATURE:
<221> NAME/KEY: MISC_FEATURE
<222> LOCATION: (27)..(27)
<223> OTHER INFORMATION: X is N or Q for amidated amino acids
<220> FEATURE:
<221> NAME/KEY: MISC_FEATURE
<222> LOCATION: (28)..(28)
<223> OTHER INFORMATION: X is Gaba for X2X3 or X3X2 or X2X3 or X3X2 or
      X3X3 or X2X2
<220> FEATURE:
<221> NAME/KEY: MISC_FEATURE
<222> LOCATION: (29)..(29)
<223> OTHER INFORMATION: X is K, R or H for basic amino acids
<220> FEATURE:
<221> NAME/KEY: MISC_FEATURE
<222> LOCATION: (30)..(30)
<223> OTHER INFORMATION: X is A and G
<220> FEATURE:
<221> NAME/KEY: MISC_FEATURE
<222> LOCATION: (31)..(31)
<223> OTHER INFORMATION: X is A and G
<220> FEATURE:
<221> NAME/KEY: MISC_FEATURE
<222> LOCATION: (32)..(32)
<223> OTHER INFORMATION: X is Gaba for X2X3 or X3X2 or X2X3 or X3X2 or
      X3X3 or X2X2
<220> FEATURE:
<221> NAME/KEY: MISC_FEATURE
<222> LOCATION: (33)..(33)
<223> OTHER INFORMATION: X is C or S
<220> FEATURE:
<221> NAME/KEY: MISC_FEATURE
<222> LOCATION: (34)..(34)
<223> OTHER INFORMATION: X is T or S
<220> FEATURE:
<221> NAME/KEY: MISC_FEATURE
<222> LOCATION: (35)..(35)
<223> OTHER INFORMATION: X is A and G
<220> FEATURE:
<221> NAME/KEY: MISC_FEATURE
<222> LOCATION: (36)..(36)
```

<223> OTHER INFORMATION: X is Gaba for X2X3 or X3X2 or X2X3 or X3X2 or
      X3X3 or X2X2

<400> SEQUENCE: 112

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
                20                  25                  30

Xaa Xaa Xaa Xaa
        35

<210> SEQ ID NO 113
<211> LENGTH: 33
<212> TYPE: PRT
<213> ORGANISM: artificial
<220> FEATURE:
<223> OTHER INFORMATION: Completely synthesized peptide construct
<220> FEATURE:
<221> NAME/KEY: MISC_FEATURE
<222> LOCATION: (1)..(1)
<223> OTHER INFORMATION: X is T or S
<220> FEATURE:
<221> NAME/KEY: MISC_FEATURE
<222> LOCATION: (2)..(2)
<223> OTHER INFORMATION: X is X1X1 or X1X3 or X3X1 or X1X2 or X2X1
<220> FEATURE:
<221> NAME/KEY: MISC_FEATURE
<222> LOCATION: (3)..(3)
<223> OTHER INFORMATION: X is K, R or H for basic amino acids
<220> FEATURE:
<221> NAME/KEY: MISC_FEATURE
<222> LOCATION: (4)..(4)
<223> OTHER INFORMATION: X is F or P
<220> FEATURE:
<221> NAME/KEY: MISC_FEATURE
<222> LOCATION: (5)..(5)
<223> OTHER INFORMATION: X is Gaba for X2X3 or X3X2 or X2X3 or X3X2 or
      X3X3 or X2X2
<220> FEATURE:
<221> NAME/KEY: MISC_FEATURE
<222> LOCATION: (6)..(6)
<223> OTHER INFORMATION: X is X1X1 or X1X3 or X3X1 or X1X2 or X2X1
<220> FEATURE:
<221> NAME/KEY: MISC_FEATURE
<222> LOCATION: (7)..(7)
<223> OTHER INFORMATION: X is F, W or Y for aromatic amino acids
<220> FEATURE:
<221> NAME/KEY: MISC_FEATURE
<222> LOCATION: (8)..(8)
<223> OTHER INFORMATION: X is K, R or H for basic amino acids
<220> FEATURE:
<221> NAME/KEY: MISC_FEATURE
<222> LOCATION: (9)..(9)
<223> OTHER INFORMATION: X is X1X1 or X1X3 or X3X1 or X1X2 or X2X1
<220> FEATURE:
<221> NAME/KEY: MISC_FEATURE
<222> LOCATION: (10)..(10)
<223> OTHER INFORMATION: X is N or Q for amidated amino acids
<220> FEATURE:
<221> NAME/KEY: MISC_FEATURE
<222> LOCATION: (11)..(11)
<223> OTHER INFORMATION: X is A and G
<220> FEATURE:
<221> NAME/KEY: MISC_FEATURE
<222> LOCATION: (12)..(12)
<223> OTHER INFORMATION: X is F or P
<220> FEATURE:
<221> NAME/KEY: MISC_FEATURE
<222> LOCATION: (13)..(13)
<223> OTHER INFORMATION: X is K, R or H for basic amino acids
<220> FEATURE:
<221> NAME/KEY: MISC_FEATURE
<222> LOCATION: (14)..(14)
<223> OTHER INFORMATION: X is X1X1 or X1X3 or X3X1 or X1X2 or X2X1
<220> FEATURE:

```
<221> NAME/KEY: MISC_FEATURE
<222> LOCATION: (15)..(15)
<223> OTHER INFORMATION: X is F or P
<220> FEATURE:
<221> NAME/KEY: MISC_FEATURE
<222> LOCATION: (16)..(16)
<223> OTHER INFORMATION: X is A and G
<220> FEATURE:
<221> NAME/KEY: MISC_FEATURE
<222> LOCATION: (17)..(17)
<223> OTHER INFORMATION: X is A and G
<220> FEATURE:
<221> NAME/KEY: MISC_FEATURE
<222> LOCATION: (18)..(18)
<223> OTHER INFORMATION: X is A and G
<220> FEATURE:
<221> NAME/KEY: MISC_FEATURE
<222> LOCATION: (19)..(19)
<223> OTHER INFORMATION: X is D and E for acidic amino acids
<220> FEATURE:
<221> NAME/KEY: MISC_FEATURE
<222> LOCATION: (20)..(20)
<223> OTHER INFORMATION: X is A and g
<220> FEATURE:
<221> NAME/KEY: MISC_FEATURE
<222> LOCATION: (21)..(21)
<223> OTHER INFORMATION: X is N or Q for amidated amino acids
<220> FEATURE:
<221> NAME/KEY: MISC_FEATURE
<222> LOCATION: (22)..(22)
<223> OTHER INFORMATION: X is D and E for acidic amino acids
<220> FEATURE:
<221> NAME/KEY: MISC_FEATURE
<222> LOCATION: (23)..(23)
<223> OTHER INFORMATION: X is D and E for acidic amino acids
<220> FEATURE:
<221> NAME/KEY: MISC_FEATURE
<222> LOCATION: (24)..(24)
<223> OTHER INFORMATION: X is K, R or H for basic amino acids
<220> FEATURE:
<221> NAME/KEY: MISC_FEATURE
<222> LOCATION: (25)..(25)
<223> OTHER INFORMATION: X is A and G
<220> FEATURE:
<221> NAME/KEY: MISC_FEATURE
<222> LOCATION: (26)..(26)
<223> OTHER INFORMATION: X is A and G
<220> FEATURE:
<221> NAME/KEY: MISC_FEATURE
<222> LOCATION: (27)..(27)
<223> OTHER INFORMATION: X is I, L or V
<220> FEATURE:
<221> NAME/KEY: MISC_FEATURE
<222> LOCATION: (28)..(28)
<223> OTHER INFORMATION: X is I, L or V
<220> FEATURE:
<221> NAME/KEY: MISC_FEATURE
<222> LOCATION: (29)..(29)
<223> OTHER INFORMATION: X is C or S
<220> FEATURE:
<221> NAME/KEY: MISC_FEATURE
<222> LOCATION: (30)..(30)
<223> OTHER INFORMATION: X is T or S
<220> FEATURE:
<221> NAME/KEY: MISC_FEATURE
<222> LOCATION: (31)..(31)
<223> OTHER INFORMATION: X is A and G
<220> FEATURE:
<221> NAME/KEY: MISC_FEATURE
<222> LOCATION: (32)..(32)
<223> OTHER INFORMATION: X is I, L or V
<220> FEATURE:
<221> NAME/KEY: MISC_FEATURE
<222> LOCATION: (33)..(33)
<223> OTHER INFORMATION: X is I, L or V

<400> SEQUENCE: 113

Xaa Xaa Xaa Xaa Xaa Xaa Xaa Xaa Xaa Xaa Xaa Xaa Xaa Xaa Xaa Xaa
```

```
1               5                   10                  15
Xaa Xaa Xaa Xaa Xaa Xaa Xaa Xaa Xaa Xaa Xaa Xaa Xaa Xaa Xaa
            20                  25                  30
Xaa
```

<210> SEQ ID NO 114
<211> LENGTH: 34
<212> TYPE: PRT
<213> ORGANISM: artificial
<220> FEATURE:
<223> OTHER INFORMATION: Completely synthesized peptide construct
<220> FEATURE:
<221> NAME/KEY: MISC_FEATURE
<222> LOCATION: (1)..(1)
<223> OTHER INFORMATION: X is T or S
<220> FEATURE:
<221> NAME/KEY: MISC_FEATURE
<222> LOCATION: (2)..(2)
<223> OTHER INFORMATION: X is X1X1 or X1X3 or X3X1 or X1X2 or X2X1
<220> FEATURE:
<221> NAME/KEY: MISC_FEATURE
<222> LOCATION: (3)..(3)
<223> OTHER INFORMATION: X is K, R or H for basic amino acids
<220> FEATURE:
<221> NAME/KEY: MISC_FEATURE
<222> LOCATION: (4)..(4)
<223> OTHER INFORMATION: X is F or P
<220> FEATURE:
<221> NAME/KEY: MISC_FEATURE
<222> LOCATION: (5)..(5)
<223> OTHER INFORMATION: X is Gaba for X2X3 or X3X2 or X2X3 or X3X2 or
      X3X3 or X2X2
<220> FEATURE:
<221> NAME/KEY: MISC_FEATURE
<222> LOCATION: (6)..(6)
<223> OTHER INFORMATION: X is X1X1 or X1X3 or X3X1 or X1X2 or X2X1
<220> FEATURE:
<221> NAME/KEY: MISC_FEATURE
<222> LOCATION: (7)..(7)
<223> OTHER INFORMATION: X is F, W or Y for aromatic amino acids
<220> FEATURE:
<221> NAME/KEY: MISC_FEATURE
<222> LOCATION: (8)..(8)
<223> OTHER INFORMATION: X is K, R or H for basic amino acids
<220> FEATURE:
<221> NAME/KEY: MISC_FEATURE
<222> LOCATION: (9)..(9)
<223> OTHER INFORMATION: X is X1X1 or X1X3 or X3X1 or X1X2 or X2X1
<220> FEATURE:
<221> NAME/KEY: MISC_FEATURE
<222> LOCATION: (10)..(10)
<223> OTHER INFORMATION: X is N or Q for amidated amino acids
<220> FEATURE:
<221> NAME/KEY: MISC_FEATURE
<222> LOCATION: (11)..(11)
<223> OTHER INFORMATION: X is A and G
<220> FEATURE:
<221> NAME/KEY: MISC_FEATURE
<222> LOCATION: (12)..(12)
<223> OTHER INFORMATION: X is F or P
<220> FEATURE:
<221> NAME/KEY: MISC_FEATURE
<222> LOCATION: (13)..(13)
<223> OTHER INFORMATION: X is K, R or H for basic amino acids
<220> FEATURE:
<221> NAME/KEY: MISC_FEATURE
<222> LOCATION: (14)..(14)
<223> OTHER INFORMATION: X is X1X1 or X1X3 or X3X1 or X1X2 or X2X1
<220> FEATURE:
<221> NAME/KEY: MISC_FEATURE
<222> LOCATION: (15)..(15)
<223> OTHER INFORMATION: X is F or P
<220> FEATURE:
<221> NAME/KEY: MISC_FEATURE
<222> LOCATION: (16)..(16)
<223> OTHER INFORMATION: X is A and G

```
<220> FEATURE:
<221> NAME/KEY: MISC_FEATURE
<222> LOCATION: (17)..(17)
<223> OTHER INFORMATION: X is A and G
<220> FEATURE:
<221> NAME/KEY: MISC_FEATURE
<222> LOCATION: (18)..(18)
<223> OTHER INFORMATION: X is A and G
<220> FEATURE:
<221> NAME/KEY: MISC_FEATURE
<222> LOCATION: (19)..(19)
<223> OTHER INFORMATION: X is Acetyl or propionyl group, D glycine or D
     alanine, Cyclohexylalanine at amino terminus
<220> FEATURE:
<221> NAME/KEY: MISC_FEATURE
<222> LOCATION: (20)..(20)
<223> OTHER INFORMATION: X is D and E for acidic amino acids
<220> FEATURE:
<221> NAME/KEY: MISC_FEATURE
<222> LOCATION: (21)..(21)
<223> OTHER INFORMATION: X is A and G
<220> FEATURE:
<221> NAME/KEY: MISC_FEATURE
<222> LOCATION: (22)..(22)
<223> OTHER INFORMATION: X is N or Q for amidated amino acids
<220> FEATURE:
<221> NAME/KEY: MISC_FEATURE
<222> LOCATION: (23)..(23)
<223> OTHER INFORMATION: X is D and E for acidic amino acids
<220> FEATURE:
<221> NAME/KEY: MISC_FEATURE
<222> LOCATION: (24)..(24)
<223> OTHER INFORMATION: X is D and E for acidic amino acids
<220> FEATURE:
<221> NAME/KEY: MISC_FEATURE
<222> LOCATION: (25)..(25)
<223> OTHER INFORMATION: X is K, R or H for basic amino acids
<220> FEATURE:
<221> NAME/KEY: MISC_FEATURE
<222> LOCATION: (26)..(26)
<223> OTHER INFORMATION: X is A and G
<220> FEATURE:
<221> NAME/KEY: MISC_FEATURE
<222> LOCATION: (27)..(27)
<223> OTHER INFORMATION: X is A and G
<220> FEATURE:
<221> NAME/KEY: MISC_FEATURE
<222> LOCATION: (28)..(28)
<223> OTHER INFORMATION: X is I, L or V
<220> FEATURE:
<221> NAME/KEY: MISC_FEATURE
<222> LOCATION: (29)..(29)
<223> OTHER INFORMATION: X is I, L or V
<220> FEATURE:
<221> NAME/KEY: MISC_FEATURE
<222> LOCATION: (30)..(30)
<223> OTHER INFORMATION: X is C or S
<220> FEATURE:
<221> NAME/KEY: MISC_FEATURE
<222> LOCATION: (31)..(31)
<223> OTHER INFORMATION: X is T or S
<220> FEATURE:
<221> NAME/KEY: MISC_FEATURE
<222> LOCATION: (32)..(32)
<223> OTHER INFORMATION: X is A and G
<220> FEATURE:
<221> NAME/KEY: MISC_FEATURE
<222> LOCATION: (33)..(33)
<223> OTHER INFORMATION: X is I, L or V
<220> FEATURE:
<221> NAME/KEY: MISC_FEATURE
<222> LOCATION: (34)..(34)
<223> OTHER INFORMATION: X is I, L or V

<400> SEQUENCE: 114

Xaa Xaa Xaa Xaa Xaa Xaa Xaa Xaa Xaa Xaa Xaa Xaa Xaa Xaa Xaa Xaa
1               5                   10                  15
```

Xaa Xaa Xaa Xaa Xaa Xaa Xaa Xaa Xaa Xaa Xaa Xaa Xaa Xaa
            20                  25                  30

Xaa Xaa

<210> SEQ ID NO 115
<211> LENGTH: 33
<212> TYPE: PRT
<213> ORGANISM: artificial
<220> FEATURE:
<223> OTHER INFORMATION: Completely synthesized peptide construct
<220> FEATURE:
<221> NAME/KEY: MISC_FEATURE
<222> LOCATION: (1)..(1)
<223> OTHER INFORMATION: X is T or S
<220> FEATURE:
<221> NAME/KEY: MISC_FEATURE
<222> LOCATION: (2)..(2)
<223> OTHER INFORMATION: X is X1X1 or X1X3 or X3X1 or X1X2 or X2X1
<220> FEATURE:
<221> NAME/KEY: MISC_FEATURE
<222> LOCATION: (3)..(3)
<223> OTHER INFORMATION: X is K, R or H for basic amino acids
<220> FEATURE:
<221> NAME/KEY: MISC_FEATURE
<222> LOCATION: (4)..(4)
<223> OTHER INFORMATION: X is F or P
<220> FEATURE:
<221> NAME/KEY: MISC_FEATURE
<222> LOCATION: (5)..(5)
<223> OTHER INFORMATION: X is Gaba for X2X3 or X3X2 or X2X3 or X3X2 or
      X3X3 or X2X2
<220> FEATURE:
<221> NAME/KEY: MISC_FEATURE
<222> LOCATION: (6)..(6)
<223> OTHER INFORMATION: X is X1X1 or X1X3 or X3X1 or X1X2 or X2X1
<220> FEATURE:
<221> NAME/KEY: MISC_FEATURE
<222> LOCATION: (7)..(7)
<223> OTHER INFORMATION: X is F, W or Y for aromatic amino acids
<220> FEATURE:
<221> NAME/KEY: MISC_FEATURE
<222> LOCATION: (8)..(8)
<223> OTHER INFORMATION: X is K, R or H for basic amino acids
<220> FEATURE:
<221> NAME/KEY: MISC_FEATURE
<222> LOCATION: (9)..(9)
<223> OTHER INFORMATION: X is X1X1 or X1X3 or X3X1 or X1X2 or X2X1
<220> FEATURE:
<221> NAME/KEY: MISC_FEATURE
<222> LOCATION: (10)..(10)
<223> OTHER INFORMATION: X is N or Q for amidated amino acids
<220> FEATURE:
<221> NAME/KEY: MISC_FEATURE
<222> LOCATION: (11)..(11)
<223> OTHER INFORMATION: X is A and G
<220> FEATURE:
<221> NAME/KEY: MISC_FEATURE
<222> LOCATION: (12)..(12)
<223> OTHER INFORMATION: X is F or P
<220> FEATURE:
<221> NAME/KEY: MISC_FEATURE
<222> LOCATION: (13)..(13)
<223> OTHER INFORMATION: X is K, R or H for basic amino acids
<220> FEATURE:
<221> NAME/KEY: MISC_FEATURE
<222> LOCATION: (14)..(14)
<223> OTHER INFORMATION: X is X1X1 or X1X3 or X3X1 or X1X2 or X2X1
<220> FEATURE:
<221> NAME/KEY: MISC_FEATURE
<222> LOCATION: (15)..(15)
<223> OTHER INFORMATION: X is F or P
<220> FEATURE:
<221> NAME/KEY: MISC_FEATURE
<222> LOCATION: (16)..(16)
<223> OTHER INFORMATION: X is A and G
<220> FEATURE:
<221> NAME/KEY: MISC_FEATURE

```
<222> LOCATION: (17)..(17)
<223> OTHER INFORMATION: X is A and G
<220> FEATURE:
<221> NAME/KEY: MISC_FEATURE
<222> LOCATION: (18)..(18)
<223> OTHER INFORMATION: X is A and G
<220> FEATURE:
<221> NAME/KEY: MISC_FEATURE
<222> LOCATION: (19)..(19)
<223> OTHER INFORMATION: X is 5-aminopentanoic acid for replacement of 3
     or 4 amino acids of X2 and  X3
<220> FEATURE:
<221> NAME/KEY: MISC_FEATURE
<222> LOCATION: (20)..(20)
<223> OTHER INFORMATION: X is D and E for acidic amino acids
<220> FEATURE:
<221> NAME/KEY: MISC_FEATURE
<222> LOCATION: (21)..(21)
<223> OTHER INFORMATION: X is A and G
<220> FEATURE:
<221> NAME/KEY: MISC_FEATURE
<222> LOCATION: (22)..(22)
<223> OTHER INFORMATION: X is N or Q for amidated amino acids
<220> FEATURE:
<221> NAME/KEY: MISC_FEATURE
<222> LOCATION: (23)..(23)
<223> OTHER INFORMATION: X is D and E for acidic amino acids
<220> FEATURE:
<221> NAME/KEY: MISC_FEATURE
<222> LOCATION: (24)..(24)
<223> OTHER INFORMATION: X is D and E for acidic amino acids
<220> FEATURE:
<221> NAME/KEY: MISC_FEATURE
<222> LOCATION: (25)..(25)
<223> OTHER INFORMATION: X is K, R or H for basic amino acids
<220> FEATURE:
<221> NAME/KEY: MISC_FEATURE
<222> LOCATION: (26)..(26)
<223> OTHER INFORMATION: X is A and G
<220> FEATURE:
<221> NAME/KEY: MISC_FEATURE
<222> LOCATION: (27)..(27)
<223> OTHER INFORMATION: X is A and G
<220> FEATURE:
<221> NAME/KEY: MISC_FEATURE
<222> LOCATION: (28)..(28)
<223> OTHER INFORMATION: X is I, L or V
<220> FEATURE:
<221> NAME/KEY: MISC_FEATURE
<222> LOCATION: (29)..(29)
<223> OTHER INFORMATION: X is I, L or V
<220> FEATURE:
<221> NAME/KEY: MISC_FEATURE
<222> LOCATION: (30)..(30)
<223> OTHER INFORMATION: X is C or S
<220> FEATURE:
<221> NAME/KEY: MISC_FEATURE
<222> LOCATION: (31)..(31)
<223> OTHER INFORMATION: X is T or S
<220> FEATURE:
<221> NAME/KEY: MISC_FEATURE
<222> LOCATION: (32)..(32)
<223> OTHER INFORMATION: X is A and G
<220> FEATURE:
<221> NAME/KEY: MISC_FEATURE
<222> LOCATION: (33)..(33)
<223> OTHER INFORMATION: X is I, L or V
<220> FEATURE:
<221> NAME/KEY: MISC_FEATURE
<222> LOCATION: (34)..(34)
<223> OTHER INFORMATION: X is I, L or V

<400> SEQUENCE: 115

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30
```

Xaa

```
<210> SEQ ID NO 116
<211> LENGTH: 31
<212> TYPE: PRT
<213> ORGANISM: artificial
<220> FEATURE:
<223> OTHER INFORMATION: Completely synthesized peptide construct
<220> FEATURE:
<221> NAME/KEY: MISC_FEATURE
<222> LOCATION: (1)..(1)
<223> OTHER INFORMATION: X is T or S
<220> FEATURE:
<221> NAME/KEY: MISC_FEATURE
<222> LOCATION: (2)..(2)
<223> OTHER INFORMATION: X is X1X1 or X1X3 or X3X1 or X1X2 or X2X1
<220> FEATURE:
<221> NAME/KEY: MISC_FEATURE
<222> LOCATION: (3)..(3)
<223> OTHER INFORMATION: X is K, R or H for basic amino acids
<220> FEATURE:
<221> NAME/KEY: MISC_FEATURE
<222> LOCATION: (4)..(4)
<223> OTHER INFORMATION: X is F or P
<220> FEATURE:
<221> NAME/KEY: MISC_FEATURE
<222> LOCATION: (5)..(5)
<223> OTHER INFORMATION: X is Gaba for X2X3 or X3X2 or X2X3 or X3X2 or
      X3X3 or X2X2
<220> FEATURE:
<221> NAME/KEY: MISC_FEATURE
<222> LOCATION: (6)..(6)
<223> OTHER INFORMATION: X is X1X1 or X1X3 or X3X1 or X1X2 or X2X1
<220> FEATURE:
<221> NAME/KEY: MISC_FEATURE
<222> LOCATION: (7)..(7)
<223> OTHER INFORMATION: X is F, W or Y for aromatic amino acids
<220> FEATURE:
<221> NAME/KEY: MISC_FEATURE
<222> LOCATION: (8)..(8)
<223> OTHER INFORMATION: X is K, R or H for basic amino acids
<220> FEATURE:
<221> NAME/KEY: MISC_FEATURE
<222> LOCATION: (9)..(9)
<223> OTHER INFORMATION: X is X1X1 or X1X3 or X3X1 or X1X2 or X2X1
<220> FEATURE:
<221> NAME/KEY: MISC_FEATURE
<222> LOCATION: (10)..(10)
<223> OTHER INFORMATION: X is N or Q for amidated amino acids
<220> FEATURE:
<221> NAME/KEY: MISC_FEATURE
<222> LOCATION: (11)..(11)
<223> OTHER INFORMATION: X is A and G
<220> FEATURE:
<221> NAME/KEY: MISC_FEATURE
<222> LOCATION: (12)..(12)
<223> OTHER INFORMATION: X is F or P
<220> FEATURE:
<221> NAME/KEY: MISC_FEATURE
<222> LOCATION: (13)..(13)
<223> OTHER INFORMATION: X is K, R or H for basic amino acids
<220> FEATURE:
<221> NAME/KEY: MISC_FEATURE
<222> LOCATION: (14)..(14)
<223> OTHER INFORMATION: X is X1X1 or X1X3 or X3X1 or X1X2 or X2X1
<220> FEATURE:
<221> NAME/KEY: MISC_FEATURE
<222> LOCATION: (15)..(15)
<223> OTHER INFORMATION: X is F or P
<220> FEATURE:
<221> NAME/KEY: MISC_FEATURE
<222> LOCATION: (16)..(16)
<223> OTHER INFORMATION: X is Acetyl or propionyl group, D glycine or D
      alanine, Cyclohexylalanine at amino terminus
<220> FEATURE:
<221> NAME/KEY: MISC_FEATURE
<222> LOCATION: (17)..(17)
```

```
<223> OTHER INFORMATION: X is A and G
<220> FEATURE:
<221> NAME/KEY: MISC_FEATURE
<222> LOCATION: (18)..(18)
<223> OTHER INFORMATION: X is A and G
<220> FEATURE:
<221> NAME/KEY: MISC_FEATURE
<222> LOCATION: (19)..(19)
<223> OTHER INFORMATION: X is A and G
<220> FEATURE:
<221> NAME/KEY: MISC_FEATURE
<222> LOCATION: (20)..(20)
<223> OTHER INFORMATION: X is D and E for acidic amino acids
<220> FEATURE:
<221> NAME/KEY: MISC_FEATURE
<222> LOCATION: (21)..(21)
<223> OTHER INFORMATION: X is A and G
<220> FEATURE:
<221> NAME/KEY: MISC_FEATURE
<222> LOCATION: (22)..(22)
<223> OTHER INFORMATION: X is N or Q for amidated amino acids
<220> FEATURE:
<221> NAME/KEY: MISC_FEATURE
<222> LOCATION: (23)..(23)
<223> OTHER INFORMATION: X is Gaba for X2X3 or X3X2 or X2X3 or X3X2 or
      X3X3 or X2X2
<220> FEATURE:
<221> NAME/KEY: MISC_FEATURE
<222> LOCATION: (24)..(24)
<223> OTHER INFORMATION: X is K, R or H for basic amino acids
<220> FEATURE:
<221> NAME/KEY: MISC_FEATURE
<222> LOCATION: (25)..(25)
<223> OTHER INFORMATION: X is A and G
<220> FEATURE:
<221> NAME/KEY: MISC_FEATURE
<222> LOCATION: (26)..(26)
<223> OTHER INFORMATION: X is A and G
<220> FEATURE:
<221> NAME/KEY: MISC_FEATURE
<222> LOCATION: (27)..(27)
<223> OTHER INFORMATION: X is Gaba for X2X3 or X3X2 or X2X3 or X3X2 or
      X3X3 or X2X2
<220> FEATURE:
<221> NAME/KEY: MISC_FEATURE
<222> LOCATION: (28)..(28)
<223> OTHER INFORMATION: X is C or S
<220> FEATURE:
<221> NAME/KEY: MISC_FEATURE
<222> LOCATION: (29)..(29)
<223> OTHER INFORMATION: X is T or S
<220> FEATURE:
<221> NAME/KEY: MISC_FEATURE
<222> LOCATION: (30)..(30)
<223> OTHER INFORMATION: X is A and G
<220> FEATURE:
<221> NAME/KEY: MISC_FEATURE
<222> LOCATION: (31)..(31)
<223> OTHER INFORMATION: X is Gaba for X2X3 or X3X2 or X2X3 or X3X2 or
      X3X3 or X2X2

<400> SEQUENCE: 116

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa
            20                  25                  30

<210> SEQ ID NO 117
<211> LENGTH: 36
<212> TYPE: PRT
<213> ORGANISM: artificial
<220> FEATURE:
<223> OTHER INFORMATION: Completely synthesized peptide construct

<400> SEQUENCE: 117
```

```
Thr Gly Gly Lys Pro Gly Ile Ala Gly Phe Lys Gly Glu Gln Gly Pro
1               5                   10                  15

Lys Gly Glu Pro Gly Gly Gly Asp Leu Leu Lys Asn Gly Glu Arg Ile
            20                  25                  30

Glu Lys Val Glu
        35

<210> SEQ ID NO 118
<211> LENGTH: 36
<212> TYPE: PRT
<213> ORGANISM: artificial
<220> FEATURE:
<223> OTHER INFORMATION: Completely synthesized peptide construct
<220> FEATURE:
<221> NAME/KEY: MISC_FEATURE
<222> LOCATION: (1)..(1)
<223> OTHER INFORMATION: X is T or S
<220> FEATURE:
<221> NAME/KEY: MISC_FEATURE
<222> LOCATION: (2)..(2)
<223> OTHER INFORMATION: X is A and G
<220> FEATURE:
<221> NAME/KEY: MISC_FEATURE
<222> LOCATION: (3)..(3)
<223> OTHER INFORMATION: X is A and G
<220> FEATURE:
<221> NAME/KEY: MISC_FEATURE
<222> LOCATION: (4)..(4)
<223> OTHER INFORMATION: X is K, R or H for basic amino acids
<220> FEATURE:
<221> NAME/KEY: MISC_FEATURE
<222> LOCATION: (5)..(5)
<223> OTHER INFORMATION: X is F or P
<220> FEATURE:
<221> NAME/KEY: MISC_FEATURE
<222> LOCATION: (6)..(6)
<223> OTHER INFORMATION: X is A and G
<220> FEATURE:
<221> NAME/KEY: MISC_FEATURE
<222> LOCATION: (7)..(7)
<223> OTHER INFORMATION: X is I, L or V
<220> FEATURE:
<221> NAME/KEY: MISC_FEATURE
<222> LOCATION: (8)..(8)
<223> OTHER INFORMATION: X is A and G
<220> FEATURE:
<221> NAME/KEY: MISC_FEATURE
<222> LOCATION: (9)..(9)
<223> OTHER INFORMATION: X is A and G
<220> FEATURE:
<221> NAME/KEY: MISC_FEATURE
<222> LOCATION: (10)..(10)
<223> OTHER INFORMATION: X is F, W or Y for aromatic amino acids
<220> FEATURE:
<221> NAME/KEY: MISC_FEATURE
<222> LOCATION: (11)..(11)
<223> OTHER INFORMATION: X is K, R or H for basic amino acids
<220> FEATURE:
<221> NAME/KEY: MISC_FEATURE
<222> LOCATION: (12)..(12)
<223> OTHER INFORMATION: X is A and G
<220> FEATURE:
<221> NAME/KEY: MISC_FEATURE
<222> LOCATION: (13)..(13)
<223> OTHER INFORMATION: X is D and E for acidic amino acids
<220> FEATURE:
<221> NAME/KEY: MISC_FEATURE
<222> LOCATION: (14)..(14)
<223> OTHER INFORMATION: X is N or Q for amidated amino acids
<220> FEATURE:
<221> NAME/KEY: MISC_FEATURE
<222> LOCATION: (15)..(15)
<223> OTHER INFORMATION: X is A and G
<220> FEATURE:
<221> NAME/KEY: MISC_FEATURE
<222> LOCATION: (16)..(16)
```

```
<223> OTHER INFORMATION: X is F or P
<220> FEATURE:
<221> NAME/KEY: MISC_FEATURE
<222> LOCATION: (17)..(17)
<223> OTHER INFORMATION: X is K, R or H for basic amino acids
<220> FEATURE:
<221> NAME/KEY: MISC_FEATURE
<222> LOCATION: (18)..(18)
<223> OTHER INFORMATION: X is A and G
<220> FEATURE:
<221> NAME/KEY: MISC_FEATURE
<222> LOCATION: (19)..(19)
<223> OTHER INFORMATION: X is D and E for acidic amino acids
<220> FEATURE:
<221> NAME/KEY: MISC_FEATURE
<222> LOCATION: (20)..(20)
<223> OTHER INFORMATION: X is F or P
<220> FEATURE:
<221> NAME/KEY: MISC_FEATURE
<222> LOCATION: (21)..(21)
<223> OTHER INFORMATION: X is A and G
<220> FEATURE:
<221> NAME/KEY: MISC_FEATURE
<222> LOCATION: (22)..(22)
<223> OTHER INFORMATION: X is A and G
<220> FEATURE:
<221> NAME/KEY: MISC_FEATURE
<222> LOCATION: (23)..(23)
<223> OTHER INFORMATION: X is A and G
<220> FEATURE:
<221> NAME/KEY: MISC_FEATURE
<222> LOCATION: (24)..(24)
<223> OTHER INFORMATION: X is D and E for acidic amino acids
<220> FEATURE:
<221> NAME/KEY: MISC_FEATURE
<222> LOCATION: (25)..(25)
<223> OTHER INFORMATION: X is I, L or V
<220> FEATURE:
<221> NAME/KEY: MISC_FEATURE
<222> LOCATION: (26)..(26)
<223> OTHER INFORMATION: X is I, L or V
<220> FEATURE:
<221> NAME/KEY: MISC_FEATURE
<222> LOCATION: (27)..(27)
<223> OTHER INFORMATION: X is K, R or H for basic amino acids
<220> FEATURE:
<221> NAME/KEY: MISC_FEATURE
<222> LOCATION: (28)..(28)
<223> OTHER INFORMATION: X is N or Q for amidated amino acids
<220> FEATURE:
<221> NAME/KEY: MISC_FEATURE
<222> LOCATION: (29)..(29)
<223> OTHER INFORMATION: X is A and G
<220> FEATURE:
<221> NAME/KEY: MISC_FEATURE
<222> LOCATION: (30)..(30)
<223> OTHER INFORMATION: X is D and E for acidic amino acids
<220> FEATURE:
<221> NAME/KEY: MISC_FEATURE
<222> LOCATION: (31)..(31)
<223> OTHER INFORMATION: X is K, R or H for basic amino acids
<220> FEATURE:
<221> NAME/KEY: MISC_FEATURE
<222> LOCATION: (32)..(32)
<223> OTHER INFORMATION: X is I, L or V
<220> FEATURE:
<221> NAME/KEY: MISC_FEATURE
<222> LOCATION: (33)..(33)
<223> OTHER INFORMATION: X is D and E for acidic amino acids
<220> FEATURE:
<221> NAME/KEY: MISC_FEATURE
<222> LOCATION: (34)..(34)
<223> OTHER INFORMATION: X is K, R or H for basic amino acids
<220> FEATURE:
<221> NAME/KEY: MISC_FEATURE
<222> LOCATION: (35)..(35)
<223> OTHER INFORMATION: X is I, L or V
<220> FEATURE:
<221> NAME/KEY: MISC_FEATURE
```

<222> LOCATION: (36)..(36)
<223> OTHER INFORMATION: X is D and E for acidic amino acids

<400> SEQUENCE: 118

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa
        35

<210> SEQ ID NO 119
<211> LENGTH: 37
<212> TYPE: PRT
<213> ORGANISM: artificial
<220> FEATURE:
<223> OTHER INFORMATION: Completely synthesized peptide construct
<220> FEATURE:
<221> NAME/KEY: MISC_FEATURE
<222> LOCATION: (1)..(1)
<223> OTHER INFORMATION: X is T or S
<220> FEATURE:
<221> NAME/KEY: MISC_FEATURE
<222> LOCATION: (2)..(2)
<223> OTHER INFORMATION: X is A and G
<220> FEATURE:
<221> NAME/KEY: MISC_FEATURE
<222> LOCATION: (3)..(3)
<223> OTHER INFORMATION: X is A and G
<220> FEATURE:
<221> NAME/KEY: MISC_FEATURE
<222> LOCATION: (4)..(4)
<223> OTHER INFORMATION: X is K, R or H for basic amino acids
<220> FEATURE:
<221> NAME/KEY: MISC_FEATURE
<222> LOCATION: (5)..(5)
<223> OTHER INFORMATION: X is F or P
<220> FEATURE:
<221> NAME/KEY: MISC_FEATURE
<222> LOCATION: (6)..(6)
<223> OTHER INFORMATION: X is A and G
<220> FEATURE:
<221> NAME/KEY: MISC_FEATURE
<222> LOCATION: (7)..(7)
<223> OTHER INFORMATION: X is I, L or V
<220> FEATURE:
<221> NAME/KEY: MISC_FEATURE
<222> LOCATION: (8)..(8)
<223> OTHER INFORMATION: X is A and G
<220> FEATURE:
<221> NAME/KEY: MISC_FEATURE
<222> LOCATION: (9)..(9)
<223> OTHER INFORMATION: X is A and G
<220> FEATURE:
<221> NAME/KEY: MISC_FEATURE
<222> LOCATION: (10)..(10)
<223> OTHER INFORMATION: X is F, W or Y for aromatic amino acids
<220> FEATURE:
<221> NAME/KEY: MISC_FEATURE
<222> LOCATION: (11)..(11)
<223> OTHER INFORMATION: X is K, R or H for basic amino acids
<220> FEATURE:
<221> NAME/KEY: MISC_FEATURE
<222> LOCATION: (12)..(12)
<223> OTHER INFORMATION: X is A and G
<220> FEATURE:
<221> NAME/KEY: MISC_FEATURE
<222> LOCATION: (13)..(13)
<223> OTHER INFORMATION: X is D and E for acidic amino acids
<220> FEATURE:
<221> NAME/KEY: MISC_FEATURE
<222> LOCATION: (14)..(14)
<223> OTHER INFORMATION: X is N or Q for amidated amino acids
<220> FEATURE:
<221> NAME/KEY: MISC_FEATURE

```
<222> LOCATION: (15)..(15)
<223> OTHER INFORMATION: X is A and G
<220> FEATURE:
<221> NAME/KEY: MISC_FEATURE
<222> LOCATION: (16)..(16)
<223> OTHER INFORMATION: X is F or P
<220> FEATURE:
<221> NAME/KEY: MISC_FEATURE
<222> LOCATION: (17)..(17)
<223> OTHER INFORMATION: X is K, R or H for basic amino acids
<220> FEATURE:
<221> NAME/KEY: MISC_FEATURE
<222> LOCATION: (18)..(18)
<223> OTHER INFORMATION: X is A and G
<220> FEATURE:
<221> NAME/KEY: MISC_FEATURE
<222> LOCATION: (19)..(19)
<223> OTHER INFORMATION: X is D and E for acidic amino acids
<220> FEATURE:
<221> NAME/KEY: MISC_FEATURE
<222> LOCATION: (20)..(20)
<223> OTHER INFORMATION: X is F or P
<220> FEATURE:
<221> NAME/KEY: MISC_FEATURE
<222> LOCATION: (21)..(21)
<223> OTHER INFORMATION: X is A and G
<220> FEATURE:
<221> NAME/KEY: MISC_FEATURE
<222> LOCATION: (22)..(22)
<223> OTHER INFORMATION: X is A and G
<220> FEATURE:
<221> NAME/KEY: MISC_FEATURE
<222> LOCATION: (23)..(23)
<223> OTHER INFORMATION: X is A and G
<220> FEATURE:
<221> NAME/KEY: MISC_FEATURE
<222> LOCATION: (24)..(24)
<223> OTHER INFORMATION: X is Acetyl or propionyl group, D glycine or D
      alanine, Cyclohexylalanine at amino terminus
<220> FEATURE:
<221> NAME/KEY: MISC_FEATURE
<222> LOCATION: (25)..(25)
<223> OTHER INFORMATION: X is D and E for acidic amino acids
<220> FEATURE:
<221> NAME/KEY: MISC_FEATURE
<222> LOCATION: (26)..(26)
<223> OTHER INFORMATION: X is I, L or V
<220> FEATURE:
<221> NAME/KEY: MISC_FEATURE
<222> LOCATION: (27)..(27)
<223> OTHER INFORMATION: X is I, L or V
<220> FEATURE:
<221> NAME/KEY: MISC_FEATURE
<222> LOCATION: (28)..(28)
<223> OTHER INFORMATION: X is K, R or H for basic amino acids
<220> FEATURE:
<221> NAME/KEY: MISC_FEATURE
<222> LOCATION: (29)..(29)
<223> OTHER INFORMATION: X is N or Q for amidated amino acids
<220> FEATURE:
<221> NAME/KEY: MISC_FEATURE
<222> LOCATION: (30)..(30)
<223> OTHER INFORMATION: X is A and G
<220> FEATURE:
<221> NAME/KEY: MISC_FEATURE
<222> LOCATION: (31)..(31)
<223> OTHER INFORMATION: X is D and E for acidic amino acids
<220> FEATURE:
<221> NAME/KEY: MISC_FEATURE
<222> LOCATION: (32)..(32)
<223> OTHER INFORMATION: X is K, R or H for basic amino acids
<220> FEATURE:
<221> NAME/KEY: MISC_FEATURE
<222> LOCATION: (33)..(33)
<223> OTHER INFORMATION: X is I, L or V
<220> FEATURE:
<221> NAME/KEY: MISC_FEATURE
<222> LOCATION: (34)..(34)
<223> OTHER INFORMATION: X is D and E for acidic amino acids
```

```
<220> FEATURE:
<221> NAME/KEY: MISC_FEATURE
<222> LOCATION: (35)..(35)
<223> OTHER INFORMATION: X is K, R or H for basic amino acids
<220> FEATURE:
<221> NAME/KEY: MISC_FEATURE
<222> LOCATION: (36)..(36)
<223> OTHER INFORMATION: X is I, L or V
<220> FEATURE:
<221> NAME/KEY: MISC_FEATURE
<222> LOCATION: (37)..(37)
<223> OTHER INFORMATION: X is D and E for acidic amino acids

<400> SEQUENCE: 119

Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa
            35

<210> SEQ ID NO 120
<211> LENGTH: 33
<212> TYPE: PRT
<213> ORGANISM: artificial
<220> FEATURE:
<223> OTHER INFORMATION: Completely synthesized peptide construct
<220> FEATURE:
<221> NAME/KEY: MISC_FEATURE
<222> LOCATION: (1)..(1)
<223> OTHER INFORMATION: X is T or S
<220> FEATURE:
<221> NAME/KEY: MISC_FEATURE
<222> LOCATION: (2)..(2)
<223> OTHER INFORMATION: X is A and G
<220> FEATURE:
<221> NAME/KEY: MISC_FEATURE
<222> LOCATION: (3)..(3)
<223> OTHER INFORMATION: X is A and G
<220> FEATURE:
<221> NAME/KEY: MISC_FEATURE
<222> LOCATION: (4)..(4)
<223> OTHER INFORMATION: X is K, R or H for basic amino acids
<220> FEATURE:
<221> NAME/KEY: MISC_FEATURE
<222> LOCATION: (5)..(5)
<223> OTHER INFORMATION: X is F or P
<220> FEATURE:
<221> NAME/KEY: MISC_FEATURE
<222> LOCATION: (6)..(6)
<223> OTHER INFORMATION: X is A and G
<220> FEATURE:
<221> NAME/KEY: MISC_FEATURE
<222> LOCATION: (7)..(7)
<223> OTHER INFORMATION: X is I, L or V
<220> FEATURE:
<221> NAME/KEY: MISC_FEATURE
<222> LOCATION: (8)..(8)
<223> OTHER INFORMATION: X is A and G
<220> FEATURE:
<221> NAME/KEY: MISC_FEATURE
<222> LOCATION: (9)..(9)
<223> OTHER INFORMATION: X is A and G
<220> FEATURE:
<221> NAME/KEY: MISC_FEATURE
<222> LOCATION: (10)..(10)
<223> OTHER INFORMATION: X is F, W or Y for aromatic amino acids
<220> FEATURE:
<221> NAME/KEY: MISC_FEATURE
<222> LOCATION: (11)..(11)
<223> OTHER INFORMATION: X is K, R or H for basic amino acids
<220> FEATURE:
<221> NAME/KEY: MISC_FEATURE
<222> LOCATION: (12)..(12)
<223> OTHER INFORMATION: X is A and G
```

```
<220> FEATURE:
<221> NAME/KEY: MISC_FEATURE
<222> LOCATION: (13)..(13)
<223> OTHER INFORMATION: X is D and E for acidic amino acids
<220> FEATURE:
<221> NAME/KEY: MISC_FEATURE
<222> LOCATION: (14)..(14)
<223> OTHER INFORMATION: X is N or Q for amidated amino acids
<220> FEATURE:
<221> NAME/KEY: MISC_FEATURE
<222> LOCATION: (15)..(15)
<223> OTHER INFORMATION: X is A and G
<220> FEATURE:
<221> NAME/KEY: MISC_FEATURE
<222> LOCATION: (16)..(16)
<223> OTHER INFORMATION: X is F or P
<220> FEATURE:
<221> NAME/KEY: MISC_FEATURE
<222> LOCATION: (17)..(17)
<223> OTHER INFORMATION: X is K, R or H for basic amino acids
<220> FEATURE:
<221> NAME/KEY: MISC_FEATURE
<222> LOCATION: (18)..(18)
<223> OTHER INFORMATION: X is A and G
<220> FEATURE:
<221> NAME/KEY: MISC_FEATURE
<222> LOCATION: (19)..(19)
<223> OTHER INFORMATION: X is D and E for acidic amino acids
<220> FEATURE:
<221> NAME/KEY: MISC_FEATURE
<222> LOCATION: (20)..(20)
<223> OTHER INFORMATION: X is F or P
<220> FEATURE:
<221> NAME/KEY: MISC_FEATURE
<222> LOCATION: (21)..(21)
<223> OTHER INFORMATION: X is A and G
<220> FEATURE:
<221> NAME/KEY: MISC_FEATURE
<222> LOCATION: (22)..(22)
<223> OTHER INFORMATION: X is A and G
<220> FEATURE:
<221> NAME/KEY: MISC_FEATURE
<222> LOCATION: (23)..(23)
<223> OTHER INFORMATION: X is A and G
<220> FEATURE:
<221> NAME/KEY: MISC_FEATURE
<222> LOCATION: (24)..(24)
<223> OTHER INFORMATION: X is Acetyl or propionyl group, D glycine or D
     alanine, Cyclohexylalanine at amino terminus
<220> FEATURE:
<221> NAME/KEY: MISC_FEATURE
<222> LOCATION: (25)..(25)
<223> OTHER INFORMATION: X is Gaba for X2X3 or X3X2 or X2X3 or X3X2 or
     X3X3 or X2X2
<220> FEATURE:
<221> NAME/KEY: MISC_FEATURE
<222> LOCATION: (26)..(26)
<223> OTHER INFORMATION: X is K, R or H for basic amino acids
<220> FEATURE:
<221> NAME/KEY: MISC_FEATURE
<222> LOCATION: (27)..(27)
<223> OTHER INFORMATION: X is N or Q for amidated amino acids
<220> FEATURE:
<221> NAME/KEY: MISC_FEATURE
<222> LOCATION: (28)..(28)
<223> OTHER INFORMATION: X is A and G
<220> FEATURE:
<221> NAME/KEY: MISC_FEATURE
<222> LOCATION: (29)..(29)
<223> OTHER INFORMATION: X is D and E for acidic amino acids
<220> FEATURE:
<221> NAME/KEY: MISC_FEATURE
<222> LOCATION: (30)..(30)
<223> OTHER INFORMATION: X is K, R or H for basic amino acids
<220> FEATURE:
<221> NAME/KEY: MISC_FEATURE
<222> LOCATION: (31)..(31)
<223> OTHER INFORMATION: X is Gaba for X2X3 or X3X2 or X2X3 or X3X2 or
     X3X3 or X2X2
```

```
<220> FEATURE:
<221> NAME/KEY: MISC_FEATURE
<222> LOCATION: (32)..(32)
<223> OTHER INFORMATION: X is K, R or H for basic amino acids
<220> FEATURE:
<221> NAME/KEY: MISC_FEATURE
<222> LOCATION: (33)..(33)
<223> OTHER INFORMATION: X is Gaba for X2X3 or X3X2 or X2X3 or X3X2 or
      X3X3 or X2X2

<400> SEQUENCE: 120

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa

<210> SEQ ID NO 121
<211> LENGTH: 33
<212> TYPE: PRT
<213> ORGANISM: artificial
<220> FEATURE:
<223> OTHER INFORMATION: Completely synthesized peptide construct
<220> FEATURE:
<221> NAME/KEY: MISC_FEATURE
<222> LOCATION: (1)..(1)
<223> OTHER INFORMATION: X is T or S
<220> FEATURE:
<221> NAME/KEY: MISC_FEATURE
<222> LOCATION: (2)..(2)
<223> OTHER INFORMATION: X is A and G
<220> FEATURE:
<221> NAME/KEY: MISC_FEATURE
<222> LOCATION: (3)..(3)
<223> OTHER INFORMATION: X is A and G
<220> FEATURE:
<221> NAME/KEY: MISC_FEATURE
<222> LOCATION: (4)..(4)
<223> OTHER INFORMATION: X is K, R or H for basic amino acids
<220> FEATURE:
<221> NAME/KEY: MISC_FEATURE
<222> LOCATION: (5)..(5)
<223> OTHER INFORMATION: X is F or P
<220> FEATURE:
<221> NAME/KEY: MISC_FEATURE
<222> LOCATION: (6)..(6)
<223> OTHER INFORMATION: X is A and G
<220> FEATURE:
<221> NAME/KEY: MISC_FEATURE
<222> LOCATION: (7)..(7)
<223> OTHER INFORMATION: X is I, L or V
<220> FEATURE:
<221> NAME/KEY: MISC_FEATURE
<222> LOCATION: (8)..(8)
<223> OTHER INFORMATION: X is A and G
<220> FEATURE:
<221> NAME/KEY: MISC_FEATURE
<222> LOCATION: (9)..(9)
<223> OTHER INFORMATION: X is A and G
<220> FEATURE:
<221> NAME/KEY: MISC_FEATURE
<222> LOCATION: (10)..(10)
<223> OTHER INFORMATION: X is F, W or Y for aromatic amino acids
<220> FEATURE:
<221> NAME/KEY: MISC_FEATURE
<222> LOCATION: (11)..(11)
<223> OTHER INFORMATION: X is K, R or H for basic amino acids
<220> FEATURE:
<221> NAME/KEY: MISC_FEATURE
<222> LOCATION: (12)..(12)
<223> OTHER INFORMATION: X is A and G
<220> FEATURE:
<221> NAME/KEY: MISC_FEATURE
<222> LOCATION: (13)..(13)
<223> OTHER INFORMATION: X is D and E for acidic amino acids
```

```
-continued

<220> FEATURE:
<221> NAME/KEY: MISC_FEATURE
<222> LOCATION: (14)..(14)
<223> OTHER INFORMATION: X is N or Q for amidated amino acids
<220> FEATURE:
<221> NAME/KEY: MISC_FEATURE
<222> LOCATION: (15)..(15)
<223> OTHER INFORMATION: X is A and G
<220> FEATURE:
<221> NAME/KEY: MISC_FEATURE
<222> LOCATION: (16)..(16)
<223> OTHER INFORMATION: X is F or P
<220> FEATURE:
<221> NAME/KEY: MISC_FEATURE
<222> LOCATION: (17)..(17)
<223> OTHER INFORMATION: X is K, R or H for basic amino acids
<220> FEATURE:
<221> NAME/KEY: MISC_FEATURE
<222> LOCATION: (18)..(18)
<223> OTHER INFORMATION: X is A and G
<220> FEATURE:
<221> NAME/KEY: MISC_FEATURE
<222> LOCATION: (19)..(19)
<223> OTHER INFORMATION: X is D and E for acidic amino acids
<220> FEATURE:
<221> NAME/KEY: MISC_FEATURE
<222> LOCATION: (20)..(20)
<223> OTHER INFORMATION: X is F or P
<220> FEATURE:
<221> NAME/KEY: MISC_FEATURE
<222> LOCATION: (21)..(21)
<223> OTHER INFORMATION: X is A and G
<220> FEATURE:
<221> NAME/KEY: MISC_FEATURE
<222> LOCATION: (22)..(22)
<223> OTHER INFORMATION: X is A and G
<220> FEATURE:
<221> NAME/KEY: MISC_FEATURE
<222> LOCATION: (23)..(23)
<223> OTHER INFORMATION: X is A and G
<220> FEATURE:
<221> NAME/KEY: MISC_FEATURE
<222> LOCATION: (24)..(24)
<223> OTHER INFORMATION: X is Acetyl or propionyl group, D glycine or D
      alanine, Cyclohexylalanine at amino terminus
<220> FEATURE:
<221> NAME/KEY: MISC_FEATURE
<222> LOCATION: (25)..(25)
<223> OTHER INFORMATION: X is 5-aminopentanoic acid for replacement of 3
      or 4 amino acids of X2 and  X3
<220> FEATURE:
<221> NAME/KEY: MISC_FEATURE
<222> LOCATION: (26)..(26)
<223> OTHER INFORMATION: X is K, R or H for basic amino acids
<220> FEATURE:
<221> NAME/KEY: MISC_FEATURE
<222> LOCATION: (27)..(27)
<223> OTHER INFORMATION: X is N or Q for amidated amino acids
<220> FEATURE:
<221> NAME/KEY: MISC_FEATURE
<222> LOCATION: (28)..(28)
<223> OTHER INFORMATION: X is A and G
<220> FEATURE:
<221> NAME/KEY: MISC_FEATURE
<222> LOCATION: (29)..(29)
<223> OTHER INFORMATION: X is D and E for acidic amino acids
<220> FEATURE:
<221> NAME/KEY: MISC_FEATURE
<222> LOCATION: (30)..(30)
<223> OTHER INFORMATION: X is K, R or H for basic amino acids
<220> FEATURE:
<221> NAME/KEY: MISC_FEATURE
<222> LOCATION: (31)..(31)
<223> OTHER INFORMATION: X is Gaba for X2X3 or X3X2 or X2X3 or X3X2 or
      X3X3 or X2X2
<220> FEATURE:
<221> NAME/KEY: MISC_FEATURE
<222> LOCATION: (32)..(32)
<223> OTHER INFORMATION: X is K, R or H for basic amino acids
```

```
<220> FEATURE:
<221> NAME/KEY: MISC_FEATURE
<222> LOCATION: (33)..(33)
<223> OTHER INFORMATION: X is Gaba for X2X3 or X3X2 or X2X3 or X3X2 or
      X3X3 or X2X2

<400> SEQUENCE: 121

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa

<210> SEQ ID NO 122
<211> LENGTH: 33
<212> TYPE: PRT
<213> ORGANISM: artificial
<220> FEATURE:
<223> OTHER INFORMATION: Completely synthesized peptide construct
<220> FEATURE:
<221> NAME/KEY: MISC_FEATURE
<222> LOCATION: (1)..(1)
<223> OTHER INFORMATION: X is T or S
<220> FEATURE:
<221> NAME/KEY: MISC_FEATURE
<222> LOCATION: (2)..(2)
<223> OTHER INFORMATION: X is X1X1 or X1X3 or X3X1 or X1X2 or X2X1
<220> FEATURE:
<221> NAME/KEY: MISC_FEATURE
<222> LOCATION: (3)..(3)
<223> OTHER INFORMATION: X is K, R or H for basic amino acids
<220> FEATURE:
<221> NAME/KEY: MISC_FEATURE
<222> LOCATION: (4)..(4)
<223> OTHER INFORMATION: X is F or P
<220> FEATURE:
<221> NAME/KEY: MISC_FEATURE
<222> LOCATION: (5)..(5)
<223> OTHER INFORMATION: X is Gaba for X2X3 or X3X2 or X2X3 or X3X2 or
      X3X3 or X2X2
<220> FEATURE:
<221> NAME/KEY: MISC_FEATURE
<222> LOCATION: (6)..(6)
<223> OTHER INFORMATION: X is X1X1 or X1X3 or X3X1 or X1X2 or X2X1
<220> FEATURE:
<221> NAME/KEY: MISC_FEATURE
<222> LOCATION: (7)..(7)
<223> OTHER INFORMATION: X is F, W or Y for aromatic amino acids
<220> FEATURE:
<221> NAME/KEY: MISC_FEATURE
<222> LOCATION: (8)..(8)
<223> OTHER INFORMATION: X is K, R or H for basic amino acids
<220> FEATURE:
<221> NAME/KEY: MISC_FEATURE
<222> LOCATION: (9)..(9)
<223> OTHER INFORMATION: X is X1X1 or X1X3 or X3X1 or X1X2 or X2X1
<220> FEATURE:
<221> NAME/KEY: MISC_FEATURE
<222> LOCATION: (10)..(10)
<223> OTHER INFORMATION: X is N or Q for amidated amino acids
<220> FEATURE:
<221> NAME/KEY: MISC_FEATURE
<222> LOCATION: (11)..(11)
<223> OTHER INFORMATION: X is A and G
<220> FEATURE:
<221> NAME/KEY: MISC_FEATURE
<222> LOCATION: (12)..(12)
<223> OTHER INFORMATION: X is F or P
<220> FEATURE:
<221> NAME/KEY: MISC_FEATURE
<222> LOCATION: (13)..(13)
<223> OTHER INFORMATION: X is K, R or H for basic amino acids
<220> FEATURE:
<221> NAME/KEY: MISC_FEATURE
<222> LOCATION: (14)..(14)
```

-continued

```
<223> OTHER INFORMATION: X is X1X1 or X1X3 or X3X1 or X1X2 or X2X1
<220> FEATURE:
<221> NAME/KEY: MISC_FEATURE
<222> LOCATION: (15)..(15)
<223> OTHER INFORMATION: X is F or P
<220> FEATURE:
<221> NAME/KEY: MISC_FEATURE
<222> LOCATION: (16)..(16)
<223> OTHER INFORMATION: X is A and G
<220> FEATURE:
<221> NAME/KEY: MISC_FEATURE
<222> LOCATION: (17)..(17)
<223> OTHER INFORMATION: X is A and G
<220> FEATURE:
<221> NAME/KEY: MISC_FEATURE
<222> LOCATION: (18)..(18)
<223> OTHER INFORMATION: X is A and G
<220> FEATURE:
<221> NAME/KEY: MISC_FEATURE
<222> LOCATION: (19)..(19)
<223> OTHER INFORMATION: X is D and E for acidic amino acids
<220> FEATURE:
<221> NAME/KEY: MISC_FEATURE
<222> LOCATION: (20)..(20)
<223> OTHER INFORMATION: X is A and G
<220> FEATURE:
<221> NAME/KEY: MISC_FEATURE
<222> LOCATION: (21)..(21)
<223> OTHER INFORMATION: X is N or Q for amidated amino acids
<220> FEATURE:
<221> NAME/KEY: MISC_FEATURE
<222> LOCATION: (22)..(22)
<223> OTHER INFORMATION: X is D and E for acidic amino acids
<220> FEATURE:
<221> NAME/KEY: MISC_FEATURE
<222> LOCATION: (23)..(23)
<223> OTHER INFORMATION: X is D and E for acidic amino acids
<220> FEATURE:
<221> NAME/KEY: MISC_FEATURE
<222> LOCATION: (24)..(24)
<223> OTHER INFORMATION: X is K, R or H for basic amino acids
<220> FEATURE:
<221> NAME/KEY: MISC_FEATURE
<222> LOCATION: (25)..(25)
<223> OTHER INFORMATION: X is A and G
<220> FEATURE:
<221> NAME/KEY: MISC_FEATURE
<222> LOCATION: (26)..(26)
<223> OTHER INFORMATION: X is A and G
<220> FEATURE:
<221> NAME/KEY: MISC_FEATURE
<222> LOCATION: (27)..(27)
<223> OTHER INFORMATION: X is I, L or V
<220> FEATURE:
<221> NAME/KEY: MISC_FEATURE
<222> LOCATION: (28)..(28)
<223> OTHER INFORMATION: X is I, L or V
<220> FEATURE:
<221> NAME/KEY: MISC_FEATURE
<222> LOCATION: (29)..(29)
<223> OTHER INFORMATION: X is C or S
<220> FEATURE:
<221> NAME/KEY: MISC_FEATURE
<222> LOCATION: (30)..(30)
<223> OTHER INFORMATION: X is T or S
<220> FEATURE:
<221> NAME/KEY: MISC_FEATURE
<222> LOCATION: (31)..(31)
<223> OTHER INFORMATION: X is A and G
<220> FEATURE:
<221> NAME/KEY: MISC_FEATURE
<222> LOCATION: (32)..(32)
<223> OTHER INFORMATION: X is I, L or V
<220> FEATURE:
<221> NAME/KEY: MISC_FEATURE
<222> LOCATION: (33)..(33)
<223> OTHER INFORMATION: X is I, L or V

<400> SEQUENCE: 122
```

```
Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa

<210> SEQ ID NO 123
<211> LENGTH: 34
<212> TYPE: PRT
<213> ORGANISM: artificial
<220> FEATURE:
<223> OTHER INFORMATION: Completely synthesized peptide construct
<220> FEATURE:
<221> NAME/KEY: MISC_FEATURE
<222> LOCATION: (1)..(1)
<223> OTHER INFORMATION: X isT or S
<220> FEATURE:
<221> NAME/KEY: MISC_FEATURE
<222> LOCATION: (2)..(2)
<223> OTHER INFORMATION: X is X1X1 or X1X3 or X3X1 or X1X2 or X2X1
<220> FEATURE:
<221> NAME/KEY: MISC_FEATURE
<222> LOCATION: (3)..(3)
<223> OTHER INFORMATION: X is K, R or H for basic amino acids
<220> FEATURE:
<221> NAME/KEY: MISC_FEATURE
<222> LOCATION: (4)..(4)
<223> OTHER INFORMATION: X is F or P
<220> FEATURE:
<221> NAME/KEY: MISC_FEATURE
<222> LOCATION: (5)..(5)
<223> OTHER INFORMATION: X is Gaba for X2X3 or X3X2 or X2X3 or X3X2 or
      X3X3 or X2X2
<220> FEATURE:
<221> NAME/KEY: MISC_FEATURE
<222> LOCATION: (6)..(6)
<223> OTHER INFORMATION: X is X1X1 or X1X3 or X3X1 or X1X2 or X2X1
<220> FEATURE:
<221> NAME/KEY: MISC_FEATURE
<222> LOCATION: (7)..(7)
<223> OTHER INFORMATION: X is F, W or Y for aromatic amino acids
<220> FEATURE:
<221> NAME/KEY: MISC_FEATURE
<222> LOCATION: (8)..(8)
<223> OTHER INFORMATION: X is K, R or H for basic amino acids
<220> FEATURE:
<221> NAME/KEY: MISC_FEATURE
<222> LOCATION: (9)..(9)
<223> OTHER INFORMATION: X is X1X1 or X1X3 or X3X1 or X1X2 or X2X1
<220> FEATURE:
<221> NAME/KEY: MISC_FEATURE
<222> LOCATION: (10)..(10)
<223> OTHER INFORMATION: X is N or Q for amidated amino acids
<220> FEATURE:
<221> NAME/KEY: MISC_FEATURE
<222> LOCATION: (11)..(11)
<223> OTHER INFORMATION: X is A and G
<220> FEATURE:
<221> NAME/KEY: MISC_FEATURE
<222> LOCATION: (12)..(12)
<223> OTHER INFORMATION: X is F or P
<220> FEATURE:
<221> NAME/KEY: MISC_FEATURE
<222> LOCATION: (13)..(13)
<223> OTHER INFORMATION: X is K, R or H for basic amino acids
<220> FEATURE:
<221> NAME/KEY: MISC_FEATURE
<222> LOCATION: (14)..(14)
<223> OTHER INFORMATION: X is X1X1 or X1X3 or X3X1 or X1X2 or X2X1
<220> FEATURE:
<221> NAME/KEY: MISC_FEATURE
<222> LOCATION: (15)..(15)
<223> OTHER INFORMATION: X is F or P
<220> FEATURE:
<221> NAME/KEY: MISC_FEATURE
```

```
<222> LOCATION: (16)..(16)
<223> OTHER INFORMATION: X is A and G
<220> FEATURE:
<221> NAME/KEY: MISC_FEATURE
<222> LOCATION: (17)..(17)
<223> OTHER INFORMATION: X is A and G
<220> FEATURE:
<221> NAME/KEY: MISC_FEATURE
<222> LOCATION: (18)..(18)
<223> OTHER INFORMATION: X is A and G
<220> FEATURE:
<221> NAME/KEY: MISC_FEATURE
<222> LOCATION: (19)..(19)
<223> OTHER INFORMATION: X is Acetyl or propionyl group, D glycine or D
      alanine, Cyclohexylalanine at amino terminus
<220> FEATURE:
<221> NAME/KEY: MISC_FEATURE
<222> LOCATION: (20)..(20)
<223> OTHER INFORMATION: X is D and E for acidic amino acids
<220> FEATURE:
<221> NAME/KEY: MISC_FEATURE
<222> LOCATION: (21)..(21)
<223> OTHER INFORMATION: X is A and G
<220> FEATURE:
<221> NAME/KEY: MISC_FEATURE
<222> LOCATION: (22)..(22)
<223> OTHER INFORMATION: X is N or Q for amidated amino acids
<220> FEATURE:
<221> NAME/KEY: MISC_FEATURE
<222> LOCATION: (23)..(23)
<223> OTHER INFORMATION: X is D and E for acidic amino acids
<220> FEATURE:
<221> NAME/KEY: MISC_FEATURE
<222> LOCATION: (24)..(24)
<223> OTHER INFORMATION: X is D and E for acidic amino acids
<220> FEATURE:
<221> NAME/KEY: MISC_FEATURE
<222> LOCATION: (25)..(25)
<223> OTHER INFORMATION: X is K, R or H for basic amino acids
<220> FEATURE:
<221> NAME/KEY: MISC_FEATURE
<222> LOCATION: (26)..(26)
<223> OTHER INFORMATION: X is A and G
<220> FEATURE:
<221> NAME/KEY: MISC_FEATURE
<222> LOCATION: (27)..(27)
<223> OTHER INFORMATION: X is A and G
<220> FEATURE:
<221> NAME/KEY: MISC_FEATURE
<222> LOCATION: (28)..(28)
<223> OTHER INFORMATION: X is I, L or V
<220> FEATURE:
<221> NAME/KEY: MISC_FEATURE
<222> LOCATION: (29)..(29)
<223> OTHER INFORMATION: X is I, L or V
<220> FEATURE:
<221> NAME/KEY: MISC_FEATURE
<222> LOCATION: (30)..(30)
<223> OTHER INFORMATION: X is C or S
<220> FEATURE:
<221> NAME/KEY: MISC_FEATURE
<222> LOCATION: (31)..(31)
<223> OTHER INFORMATION: X is T or S
<220> FEATURE:
<221> NAME/KEY: MISC_FEATURE
<222> LOCATION: (32)..(32)
<223> OTHER INFORMATION: X is A and G
<220> FEATURE:
<221> NAME/KEY: MISC_FEATURE
<222> LOCATION: (33)..(33)
<223> OTHER INFORMATION: X is I, L or V
<220> FEATURE:
<221> NAME/KEY: MISC_FEATURE
<222> LOCATION: (34)..(34)
<223> OTHER INFORMATION: X is I, L or V

<400> SEQUENCE: 123

Xaa Xaa Xaa Xaa Xaa Xaa Xaa Xaa Xaa Xaa Xaa Xaa Xaa Xaa Xaa Xaa
```

```
  1               5                   10                  15
Xaa Xaa Xaa Xaa Xaa Xaa Xaa Xaa Xaa Xaa Xaa Xaa Xaa Xaa Xaa
            20                  25                  30
Xaa Xaa
```

<210> SEQ ID NO 124
<211> LENGTH: 34
<212> TYPE: PRT
<213> ORGANISM: artificial
<220> FEATURE:
<223> OTHER INFORMATION: Completely synthesized peptide construct
<220> FEATURE:
<221> NAME/KEY: MISC_FEATURE
<222> LOCATION: (1)..(1)
<223> OTHER INFORMATION: X is T or S
<220> FEATURE:
<221> NAME/KEY: MISC_FEATURE
<222> LOCATION: (2)..(2)
<223> OTHER INFORMATION: X is X1X1 or X1X3 or X3X1 or X1X2 or X2X1
<220> FEATURE:
<221> NAME/KEY: MISC_FEATURE
<222> LOCATION: (3)..(3)
<223> OTHER INFORMATION: X is K, R or H for basic amino acids
<220> FEATURE:
<221> NAME/KEY: MISC_FEATURE
<222> LOCATION: (4)..(4)
<223> OTHER INFORMATION: X is F or P
<220> FEATURE:
<221> NAME/KEY: MISC_FEATURE
<222> LOCATION: (5)..(5)
<223> OTHER INFORMATION: X is Gaba for X2X3 or X3X2 or X2X3 or X3X2 or
    X3X3 or X2X2
<220> FEATURE:
<221> NAME/KEY: MISC_FEATURE
<222> LOCATION: (6)..(6)
<223> OTHER INFORMATION: X is X1X1 or X1X3 or X3X1 or X1X2 or X2X1
<220> FEATURE:
<221> NAME/KEY: MISC_FEATURE
<222> LOCATION: (7)..(7)
<223> OTHER INFORMATION: X is F, W or Y for aromatic amino acids
<220> FEATURE:
<221> NAME/KEY: MISC_FEATURE
<222> LOCATION: (8)..(8)
<223> OTHER INFORMATION: X is K, R or H for basic amino acids
<220> FEATURE:
<221> NAME/KEY: MISC_FEATURE
<222> LOCATION: (9)..(9)
<223> OTHER INFORMATION: X is X1X1 or X1X3 or X3X1 or X1X2 or X2X1
<220> FEATURE:
<221> NAME/KEY: MISC_FEATURE
<222> LOCATION: (10)..(10)
<223> OTHER INFORMATION: X is N or Q for amidated amino acids
<220> FEATURE:
<221> NAME/KEY: MISC_FEATURE
<222> LOCATION: (11)..(11)
<223> OTHER INFORMATION: X is A and G
<220> FEATURE:
<221> NAME/KEY: MISC_FEATURE
<222> LOCATION: (12)..(12)
<223> OTHER INFORMATION: X is F or P
<220> FEATURE:
<221> NAME/KEY: MISC_FEATURE
<222> LOCATION: (13)..(13)
<223> OTHER INFORMATION: X is K, R or H for basic amino acids
<220> FEATURE:
<221> NAME/KEY: MISC_FEATURE
<222> LOCATION: (14)..(14)
<223> OTHER INFORMATION: X is X1X1 or X1X3 or X3X1 or X1X2 or X2X1
<220> FEATURE:
<221> NAME/KEY: MISC_FEATURE
<222> LOCATION: (15)..(15)
<223> OTHER INFORMATION: X is F or P
<220> FEATURE:
<221> NAME/KEY: MISC_FEATURE
<222> LOCATION: (16)..(16)
<223> OTHER INFORMATION: X is A and G

```
<220> FEATURE:
<221> NAME/KEY: MISC_FEATURE
<222> LOCATION: (17)..(17)
<223> OTHER INFORMATION: X is A and G
<220> FEATURE:
<221> NAME/KEY: MISC_FEATURE
<222> LOCATION: (18)..(18)
<223> OTHER INFORMATION: X is A and G
<220> FEATURE:
<221> NAME/KEY: MISC_FEATURE
<222> LOCATION: (19)..(19)
<223> OTHER INFORMATION: X is 5-aminopentanoic acid for replacement of 3
      or 4 amino acids of X2 and  X3
<220> FEATURE:
<221> NAME/KEY: MISC_FEATURE
<222> LOCATION: (20)..(20)
<223> OTHER INFORMATION: X is D and E for acidic amino acids
<220> FEATURE:
<221> NAME/KEY: MISC_FEATURE
<222> LOCATION: (21)..(21)
<223> OTHER INFORMATION: X is A and G
<220> FEATURE:
<221> NAME/KEY: MISC_FEATURE
<222> LOCATION: (22)..(22)
<223> OTHER INFORMATION: X is N or Q for amidated amino acids
<220> FEATURE:
<221> NAME/KEY: MISC_FEATURE
<222> LOCATION: (23)..(23)
<223> OTHER INFORMATION: X is D and E for acidic amino acids
<220> FEATURE:
<221> NAME/KEY: MISC_FEATURE
<222> LOCATION: (24)..(24)
<223> OTHER INFORMATION: X is D and E for acidic amino acids
<220> FEATURE:
<221> NAME/KEY: MISC_FEATURE
<222> LOCATION: (25)..(25)
<223> OTHER INFORMATION: X is K, R or H for basic amino acids
<220> FEATURE:
<221> NAME/KEY: MISC_FEATURE
<222> LOCATION: (26)..(26)
<223> OTHER INFORMATION: X is A and G
<220> FEATURE:
<221> NAME/KEY: MISC_FEATURE
<222> LOCATION: (27)..(27)
<223> OTHER INFORMATION: X is A and G
<220> FEATURE:
<221> NAME/KEY: MISC_FEATURE
<222> LOCATION: (28)..(28)
<223> OTHER INFORMATION: X is I, L or V
<220> FEATURE:
<221> NAME/KEY: MISC_FEATURE
<222> LOCATION: (29)..(29)
<223> OTHER INFORMATION: X is I, L or V
<220> FEATURE:
<221> NAME/KEY: MISC_FEATURE
<222> LOCATION: (30)..(30)
<223> OTHER INFORMATION: X is C or S
<220> FEATURE:
<221> NAME/KEY: MISC_FEATURE
<222> LOCATION: (31)..(31)
<223> OTHER INFORMATION: X is T or S
<220> FEATURE:
<221> NAME/KEY: MISC_FEATURE
<222> LOCATION: (32)..(32)
<223> OTHER INFORMATION: X is A an G
<220> FEATURE:
<221> NAME/KEY: MISC_FEATURE
<222> LOCATION: (33)..(33)
<223> OTHER INFORMATION: X is I, L or V
<220> FEATURE:
<221> NAME/KEY: MISC_FEATURE
<222> LOCATION: (34)..(34)
<223> OTHER INFORMATION: X is I, L or V

<400> SEQUENCE: 124

Xaa Xaa Xaa Xaa Xaa Xaa Xaa Xaa Xaa Xaa Xaa Xaa Xaa Xaa Xaa Xaa
1               5                   10                  15
```

```
Xaa Xaa Xaa Xaa Xaa Xaa Xaa Xaa Xaa Xaa Xaa Xaa Xaa Xaa
            20                  25                  30

Xaa Xaa

<210> SEQ ID NO 125
<211> LENGTH: 31
<212> TYPE: PRT
<213> ORGANISM: artificial
<220> FEATURE:
<223> OTHER INFORMATION: Completely synthesized peptide construct
<220> FEATURE:
<221> NAME/KEY: MISC_FEATURE
<222> LOCATION: (1)..(1)
<223> OTHER INFORMATION: X is T or S
<220> FEATURE:
<221> NAME/KEY: MISC_FEATURE
<222> LOCATION: (2)..(2)
<223> OTHER INFORMATION: X is X1X1 or X1X3 or X3X1 or X1X2 or X2X1
<220> FEATURE:
<221> NAME/KEY: MISC_FEATURE
<222> LOCATION: (3)..(3)
<223> OTHER INFORMATION: X is K, R or H for basic amino acids
<220> FEATURE:
<221> NAME/KEY: MISC_FEATURE
<222> LOCATION: (4)..(4)
<223> OTHER INFORMATION: X is F or P
<220> FEATURE:
<221> NAME/KEY: MISC_FEATURE
<222> LOCATION: (5)..(5)
<223> OTHER INFORMATION: X is Gaba for X2X3 or X3X2 or X2X3 or X3X2 or
      X3X3 or X2X2
<220> FEATURE:
<221> NAME/KEY: MISC_FEATURE
<222> LOCATION: (6)..(6)
<223> OTHER INFORMATION: X is X1X1 or X1X3 or X3X1 or X1X2 or X2X1
<220> FEATURE:
<221> NAME/KEY: MISC_FEATURE
<222> LOCATION: (7)..(7)
<223> OTHER INFORMATION: X is F, W or Y for aromatic amino acids
<220> FEATURE:
<221> NAME/KEY: MISC_FEATURE
<222> LOCATION: (8)..(8)
<223> OTHER INFORMATION: X is K, R or H for basic amino acids
<220> FEATURE:
<221> NAME/KEY: MISC_FEATURE
<222> LOCATION: (9)..(9)
<223> OTHER INFORMATION: X is X1X1 or X1X3 or X3X1 or X1X2 or X2X1
<220> FEATURE:
<221> NAME/KEY: MISC_FEATURE
<222> LOCATION: (10)..(10)
<223> OTHER INFORMATION: X is N or Q for amidated amino acids
<220> FEATURE:
<221> NAME/KEY: MISC_FEATURE
<222> LOCATION: (11)..(11)
<223> OTHER INFORMATION: X is A and G
<220> FEATURE:
<221> NAME/KEY: MISC_FEATURE
<222> LOCATION: (12)..(12)
<223> OTHER INFORMATION: X is F or P
<220> FEATURE:
<221> NAME/KEY: MISC_FEATURE
<222> LOCATION: (13)..(13)
<223> OTHER INFORMATION: X is K, R or H for basic amino acids
<220> FEATURE:
<221> NAME/KEY: MISC_FEATURE
<222> LOCATION: (14)..(14)
<223> OTHER INFORMATION: X is X1X1 or X1X3 or X3X1 or X1X2 or X2X1
<220> FEATURE:
<221> NAME/KEY: MISC_FEATURE
<222> LOCATION: (15)..(15)
<223> OTHER INFORMATION: X is F or P
<220> FEATURE:
<221> NAME/KEY: MISC_FEATURE
<222> LOCATION: (16)..(16)
<223> OTHER INFORMATION: X is Acetyl or propionyl group, D glycine or D
      alanine, Cyclohexylalanine at amino terminus
<220> FEATURE:
```

```
<221> NAME/KEY: MISC_FEATURE
<222> LOCATION: (17)..(17)
<223> OTHER INFORMATION: X is A and G
<220> FEATURE:
<221> NAME/KEY: MISC_FEATURE
<222> LOCATION: (18)..(18)
<223> OTHER INFORMATION: X is A and G
<220> FEATURE:
<221> NAME/KEY: MISC_FEATURE
<222> LOCATION: (19)..(19)
<223> OTHER INFORMATION: X is A and G
<220> FEATURE:
<221> NAME/KEY: MISC_FEATURE
<222> LOCATION: (20)..(20)
<223> OTHER INFORMATION: X is D and E for acidic amino acids
<220> FEATURE:
<221> NAME/KEY: MISC_FEATURE
<222> LOCATION: (21)..(21)
<223> OTHER INFORMATION: X is A and G
<220> FEATURE:
<221> NAME/KEY: MISC_FEATURE
<222> LOCATION: (22)..(22)
<223> OTHER INFORMATION: X is N or Q for amidated amino acids
<220> FEATURE:
<221> NAME/KEY: MISC_FEATURE
<222> LOCATION: (23)..(23)
<223> OTHER INFORMATION: X is Gaba for X2X3 or X3X2 or X2X3 or X3X2 or
      X3X3 or X2X2
<220> FEATURE:
<221> NAME/KEY: MISC_FEATURE
<222> LOCATION: (24)..(24)
<223> OTHER INFORMATION: X is K, R or H for basic amino acids
<220> FEATURE:
<221> NAME/KEY: MISC_FEATURE
<222> LOCATION: (25)..(25)
<223> OTHER INFORMATION: X is A and G
<220> FEATURE:
<221> NAME/KEY: MISC_FEATURE
<222> LOCATION: (26)..(26)
<223> OTHER INFORMATION: X is A and G
<220> FEATURE:
<221> NAME/KEY: MISC_FEATURE
<222> LOCATION: (27)..(27)
<223> OTHER INFORMATION: X is Gaba for X2X3 or X3X2 or X2X3 or X3X2 or
      X3X3 or X2X2
<220> FEATURE:
<221> NAME/KEY: MISC_FEATURE
<222> LOCATION: (28)..(28)
<223> OTHER INFORMATION: X is C or S
<220> FEATURE:
<221> NAME/KEY: MISC_FEATURE
<222> LOCATION: (29)..(29)
<223> OTHER INFORMATION: X is T or S
<220> FEATURE:
<221> NAME/KEY: MISC_FEATURE
<222> LOCATION: (30)..(30)
<223> OTHER INFORMATION: X is A and G
<220> FEATURE:
<221> NAME/KEY: MISC_FEATURE
<222> LOCATION: (31)..(31)
<223> OTHER INFORMATION: X is Gaba for X2X3 or X3X2 or X2X3 or X3X2 or
      X3X3 or X2X2

<400> SEQUENCE: 125

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

<210> SEQ ID NO 126
<211> LENGTH: 20
<212> TYPE: PRT
<213> ORGANISM: Homo sapiens
<220> FEATURE:
<221> NAME/KEY: MISC_FEATURE
<222> LOCATION: (352)..(371)
```

```
<223> OTHER INFORMATION: Type II Collagen

<400> SEQUENCE: 126

Asp Ala Gly Glu Pro Gly Ile Ala Gly Phe Lys Gly Asp Gln Gly Pro
1               5                   10                  15

Lys Gly Glu Thr
            20
```

METHODS OF PREPARATION AND COMPOSITION OF PEPTIDE CONSTRUCTS USEFUL FOR TREATMENT OF RHEUMATOID ARTHRITIS

This invention incorporates by reference the subject matter of U.S. patent application Ser. No. 11/443,314 filed May 31, 2006. The subject matter of the attached "Sequence Listing" is incorporated herein by reference.

INTRODUCTION

The invention is related to peptide constructs, i.e., polypeptides obtained by linking together two or more peptides based on or derived from different molecules, which are useful in the treatment or prevention of autoimmune diseases, particularly rheumatoid arthritis, asthma, allergies, and host versus graft (or graft versus host) rejection, as well as to compositions containing same, methods for producing same and methods for using same.

BACKGROUND

Autoimmune conditions are characterized by the body attacking itself by mounting an immune response against itself. The goal of these treatments is to turn off, dampen or redirect this inappropriate immune response. The goal of a vaccination approach is to eliminate, reduce or redirect an immune response against self-antigens. As noted by a recent Institutes of Medicine report, autoimmune diseases are a major target area proposed for vaccines and are the third major area for expenditure of healthcare in the US behind cancer and cardiovascular diseases.

Various antigens often with defined epitopes recognized for some human leukocyte antigens (HLA) genotypes, have been identified, including those associated with insulin dependent diabetes mellitus (IDDM), rheumatoid arthritis (RA) (e.g. collagen type II 390-402 IAGFKGEQGPKGE (SEQ ID NO. 1), systemic lupus erythematosus (SLE), ankylosing spondylitis (AS), pemphigus vulgaris (PV) (epidermal cell adhesion molecule desmoglein 190-204), multiple sclerosis (MS), myelin proteolipid (MPL) (peptide sequence KNIVTPRT (SEQ ID NO. 2), certain types of psoriasis, and uveoretintis (Hammer et al., HLA class I peptide binding specificity and autoimmunity. 1997, Adv. Immunol, 66:67 Tisch et al., Induction of Glutamic Acid Decarboxylase 65-Specific Th2 Cells and Suppression of Autoimmune Diabetes at Late Stages of Disease Is Epitope Dependent 1999, J. Immunol. 163:1178; Yoon et al., Control of Autoimmune Diabetes in NOD Mice by GAD Expression or Suppression in .beta. Cells 1999, Science 284:1183; Ruiz et al., Suppressive Immunization with DNA Encoding a Self-Peptide Prevents Autoimmune Disease: Modulation of T Cell Costimulation 1999, J. Immunol., 162:3336; Krco et al., Identification of T Cell Determinants on Human Type II Collagen Recognized by HLA-DQ8 and HLA-DQ6 Transgenic Mice 1999, J. Immunol., 163:1661). In other cases, peptides are known that induce in animals, a condition similar to ones found in humans, such as GDKVSFFCKNKEKKC (SEQ ID NO. 3) for antiphospholipid antibodies associated with thrombosis (Gharavi et al., GDKV-Induced Antiphospholipid Antibodies Enhance Thrombosis and Activate Endothelial Cells In Vivo and In Vitro 1999, J. Immunol., 163:2922) or myelin peptides for experimental autoimmune encephalitis (EAE) as a model for MS (Ruiz et al., supra, Araga et al., A Complementary Peptide Vaccine That Induces T Cell Anergy and Prevents Experimental Allergic Neuritis in Lewis Rats 1999, J. Immunol., 163:476-482; Karin et al., Short Peptide-Based Tolerogens Without Self-Antigenic or Pathogenic Activity Reverse Autoimmune Disease 1999, J. Immunol., 160:5188; Howard et al., Mechanisms of immunotherapeutic intervention by anti-CD40L (CD154) antibody in an animal model of multiple sclerosis 1999, J. Clin. Invest., 103:281).

Moreover, glutamic acid decarboxylase (GAD) and specific peptides have been identified associated with IDDM (Tisch et al., supra; Yoon et al., supra). Many of these conditions are also characterized by elevated levels of one or more different cytokines and other effectors such as tumor necrosis factor (TNF) (Kleinau et al., Importance of CD23 for Collagen-Induced Arthritis: Delayed Onset and Reduced Severity in CD23-Deficient Mice 1999, J. Immunol. 162: 4266; Preckel et al., Partial agonism and independent modulation of T cell receptor and CD8 in hapten-specific cytotoxic T cells 1998, Eur. J. Immunol., 28:3706; Wooley et al., Influence of a recombinant human soluble tumor necrosis factor receptor FC fusion protein on type II collagen-induced arthritis in mice 1993, J. Immunol., 151:6602) as well as autoantibodies, including in some cases, anti-costimulator molecules, in particular, those for Cytotoxic T-lymphocyte-Associated protein 4 ((CTLA-4) (CD152)) on CD4+ cells (Matsui et al., Autoantibodies to T Cell Costimulatory Molecules in Systemic Autoimmune Diseases 1999, J. Immunol., 162:4328).

Efforts are underway to attack cells or cellular products of the immune system and thereby treat autoimmune conditions, allergies, asthma and transplantation rejection using as reagents presumptive antigenic peptides or proteins, peptides representing certain T cells, monoclonal antibodies (Mabs) or recombinant proteins binding various effector cells or molecules such as tumor necrosis factor alpha (TNFα) and IgE.

The following immunomodulatory approaches are contrasted with the mode of action for antigen specific products. For example, a fusion protein LFA-3TIP (Amevive™ from Biogen), purportedly a molecule composed of the first extracellular domain of LFA-3 fused to the hinge (CH2 and CH3 domains of human IgG1=TIP) which targets the CD2 receptor on T cells is being evaluated for psoriasis and for xeno and allograft rejection. LFA-3TIP is bi-functional (i.e., two identical LFA-3 regions and TIP) and therefore is a complex conjugate molecule. According to Biogen, LFA-3TIP is a recombinant fusion protein designed to modulate the immune response by blocking the cellular pathway that activates T cells. Presumably, the compound is acting on a subset of memory effector cells with a down modulation or re-direction of modulation activity.

Other antigen non-specific approaches also utilize monoclonal antibodies that act on activated T cells and down regulate them such as using anti-CD3 (Protein Design Laboratories) or blocking antigen presenting cells (APC) and T cell interaction by anti-intercellular adhesion molecule 3 ((ICAM-3) (ICOS)). Another such example is MEDI-507 (Medimmune) which is believed to be a humanized monoclonal antibody for psoriasis that also targets CD2 presumably for removing or inactivating those cell types. Other diseases such as tissue transplantation rejection and allergies are also being tested by this approach.

In contrast to acting on cell surface markers such as ICAM-3, peptide rhuMab-E25 (Genentech) binds to circulating IgE with the goal of preventing activation of mast cells. rhuMab-E25 is believed to be a humanized monoclonal antibody against IgE. Other researchers are developing monoclonal antibodies to act directly on agents causing disease symptoms. Remicade Infliximab (Centocor) is purported to be a monoclonal antibody to TNFα while anti CD40 ligand has been used for treatment in animal model of MS (Howard et al., supra). A recombinant generated designed protein Enbrel (Immunex) is purported to comprise two molecules of r-DNA derived TNFα soluble receptor, and is intended to block TNFα's action.

It should be noted, however, that many of these agents are not disease specific and often recognize and could disadvantageously affect normal cellular and body constituents that have a defined and necessary role in needed normal immune defenses.

One example of an antigen disease specific approach is to treat MS patients by oral administration of myelin proteins. Collagen type II for treatment of patients with rheumatoid arthritis can also be used. These treatments are designed to target the gut-associated lymphoid tissues (GALT) to induce tolerance by antigen specific suppression of the immune system. It is not known if these treatments would use the intact protein or a hydrolyzate containing smaller peptides; Wucherpfennig et al., Shared human T cell receptor V beta usage to immunodominant regions of myelin basic protein. 1990, Science, 248:1016; Ota et al., T-cell recognition of an immunodominant myelin basic protein epitope in multiple sclerosis 1990, Nature, 346; 183).

A related approach to treat autoimmune conditions is the use of an oral formulation of peptide(s) as immunogen given in large quantities. The peptide represents a sequence that is thought to be the autoimmune epitope itself or a modified form which may have altered binding or improved stability properties. By use of the peptide it is believed that either the normal peptide or an altered peptide ligand (APL) will bind to the T cell receptor (TCR) and induce a state of anergy with an antigen presenting cell (APC) (Faith et al., An Altered Peptide Ligand Specifically Inhibits Th2 Cytokine Synthesis by Abrogating TCR Signaling 1999, J. Immunol., 162:1836; Soares et al., Differential Activation of T Cells by Natural Antigen Peptide Analogues: Influence on Autoimmune and Alloimmune In Vivo T Cell Responses 1998, J. Immunol., 160:4768; Croft et al., Partial activation of naive CD4 T cells and tolerance induction in response to peptide presented by resting B cells 1997, J. Immunol., 159:3257, Ding et al., Differential Effects of CD28 Engagement and IL-12 on T Cell Activation by Altered Peptide Ligands 1998, J. Immunol., 161:6614; Hin et al., Cutting Edge: N-Hydroxy Peptides: A New Class of TCR Antagonists 1999, J. Immunol., 163:2363). Some of the approaches with APL include using related amino acids such a D amino acids (Koch et al., A Synthetic CD4-CDR3 Peptide Analog Enhances Skin Allograft Survival Across a MHC Class II Barrier 1998, J. Immunol., 161:421), amino acids with substituted side chains (Palma et al., Use of Antagonist Peptides to Inhibit In Vitro T Cell Responses to Par j1, the Major Allergen of *Parietaria judaica* Pollen 1999, J. Immunol., 162:1982), methylene groups to replace peptide bonds in the peptide backbone (Meda et al., Betaamyloid (25-35) peptide and IFN-gamma synergistically induce the production of the chemotactic cytokine MCP-1/JE in monocytes and microglial cells 1996, J. Immunol., 157:1213) and N-hydroxyl peptides (Hin et al., supra).

Various substitutions of side chains of the major histocompatability complex (MHC) and T cell receptor (TCR) molecules have also been contemplated by the prior art (Clay et al., Changes in the Fine Specificity of gp100(209-217)-Reactive T Cells in Patients Following Vaccination with a Peptide Modified at an HLA-A2.1 Anchor Residue 1999, J. Immunol., 162:1749). For example, with insulin activity it has been shown that a one amino acid change on the α-chain can abolish its oral immune tolerance activity in two (2) mechanistically different IDDM murine models (Homann et al., Insulin in Oral Immune "Tolerance": A One-Amino Acid Change in the B Chain Makes the Difference 1999, J. Immunol., 163:1833). Although not an autoimmune epitope, a single change from threonine to alanine can abolish biological activity (Sutherland et al., An 11-Amino Acid Sequence in the Cytoplasmic Domain of CD40 Is Sufficient for Activation of c-Jun N-Terminal Kinase, Activation of MAPKAP Kinase-2, Phosphorylation of I B, and Protection of WEHI-231 Cells from Anti-IgM-Induced Growth Arrest 1999, J. Immunol., 162:4720) while a switch from phenylalanine to alanine converts the bee venom phospholipase to an inactive form (Faith et al., supra) as does a switch from tyrosine to alanine convert from active to inactive for another system (Hausman et al., Peptide Recognition by Two HLA-A2/Tax11-19-Specific T Cell Clones in Relationship to Their MHC/Peptide/TCR Crystal Structures 1999, J. Immunol., 162:5389).

In yet another approach based on peptide materials, truncated peptides of autoimmune inducing epitope are used as an antagonist in an animal model to treat a particular condition (Karin et al. supra). Synthetic amino acid polymers that are thought to represent epitopes which contain Tyrosine tyrosine (Y), Glutamic glutamic acid (E), alanine (A) and lysine (K) to target T cells such as Copolymer 1 have been contemplated. For example, Copaxone has been used as an oral tolerance delivery approach to treat MS patients where Copaxone is believed to be a synthetic copolymer of four amino acids (Hafler et al., supra 1988, J. Immunol., 141:131). Modified peptides of peptide epitopes are also being studied for treatment of various autoimmune conditions including MS and PV (desmoglein-3) (Hammer, et al., supra 1997, Adv. Immunol., 66:67; Wucherpfennig et al., Structural Basis for Major Histocompatibility Complex (MHC)-Linked Susceptibility to Autoimmunity: Charged Residues of a Single MHC Binding Pocket Confer Selective Presentation of Self-Peptides in Pemphigus Vulgaris 1995, PNAS, 92:11935). The use of myelin proteolipid associated peptide epitope, a polymer or derivative of this epitope for MS has been further contemplated (Hammer et al., supra 1997, Adv. Immunol., 66:67).

In other approaches, peptides that are unique to the T cell antigen receptor molecule have been contemplated for a psoriasis vaccine such as IR 502 while others have been contemplated for rheumatoid arthritis. These peptides are found in a particular part of the variable region usually the third hyper-variable region of the beta chain of the T cell antigen receptor (TCRaVX) (Kotzin et al., Preferential T-Cell Receptor β-Chain Variable Gene Use in Myelin Basic Protein-Reactive T-Cell Clones from Patients with Multiple Sclerosis 1991, Proc Nat Acad Ssi US, 88:9161; Oksenberg, et al., Limited heterogeneity of rearranged T-cell receptor V alpha transcripts in brains of multiple sclerosis patients. 1990, Nature, 345:344). For example, in an immune response to TCR.alpha.V3 (Sutherland et al., supra 1999, J. Immunol., 162:4720) a peptide is generated whose objective is to eliminate particular T cells, and by removing the T cells responsible for the condition, treat the underlying condition. However, this approach has the disadvantageous potential of eliminating other T cells that contain the same αV3 peptide sequence besides the one responsible for the autoimmune condition.

Still another peptide approach uses complimentary peptide vaccine that induces T cell anergy and prevents EAE in rats by induction of anti-TCR antibodies (a la antiidiotype) and thereby elimination of these cells (Araga et al., supra 1999, J. Immunol., 163:476).

For some diseases the appearance of such modified self antigens is part of the disease process, the approach may be completely different. For example in Alzheimer's disease (AD), the normally cleared amyloid beta (Aβ) protein fragments are deposited in AD plaques wherein the desired response is to slow down, arrest or even reverse deposition and the subsequent pathological effects.

To accomplish this therapeutic approach, two basic immunological approaches have been evaluated requiring the use of so called "active" and/or "passive" agents.

Generally, "passive agents" as known in the art are composed of Mabs targeting cytokines, or cell surface marker, or soluble receptor with similar binding specificity. However, a problem encountered with "passive agents" is that they must be frequently administered parenterally for the life of the patient. Moreover, the Mabs or soluble receptor must be "humanized" (huMab) to allow long term administration and to avoid potential long term adverse effects. Hence, the production and sale of Mabs comprises one of the largest markets for treating chronic long-term conditions in the developed world.

For autoimmune uses, the use of agents for treatment ranges from insulin for type 1 diabetes to modern biotechnology treatments related to monoclonal antibodies and soluble receptors to complement cytokines and/or cell surface markers. Well known examples of modern biotechnology treatments include Remicade®, Enbrel® Humira® for rheumatoid arthritis, Amieve® and several interferon-β products for MS. Other examples of Mabs include materials used in clinical trials for psoriasis and MS. However, these products only act upon the major abnormal amounts of molecule such as TNF-α, complement, or cells with a particular surface marker and fail to treat the underlying condition.

For the treatment of AD, Aβ Mabs are being investigated as potential products by a number of private corporations. Notably, one known Aβ Mab investigated by Lilly is effective in decreasing Aβ burden in the cerebral cortex of "AD" mice. This finding confirms previous reports of beneficial effects of plaque reduction in "AD" transgenic mice by other known Ab both Mab and Pab investigated by Elan (Bard et al., Epitope and isotype specificities of antibodies to beta-amyloid peptide for protection against Alzheimer's disease-like neuropathology, Proc Natl Acad Sci U.S.A. 2003 Feb. 18; 100(4):2023-8; DeMattos et al. Peripheral anti-A beta antibody alters CNS and plasma A beta clearance and decreases brain A beta burden in a mouse model of Alzheimer's disease, Proc Natl Acad Sci U.S.A. 2001 Jul. 17; 98(15):8850-5).

However, it should be noted that not all of the known Mab anti-A13 being tested were shown to be effective (Bard et al. supra). Differences have been found in the ability of the respective antibodies to pass the blood brain barrier (BBB). Clearly, the mechanism by which A13 plaques are reduced is not understood.

For example, the necessity for inclusion of the Fc region was shown to be required in one compound entitled 3D3 which was found in the central nervous system (CNS) (Bard et al.). The Mab 3D3 was mediated by binding to phagocytes. It was shown by the art that 3D3 (IgG2b) and 10D5 (IgG1) were effective in reducing A13 plaques but not 16C11 (IgG1) and 21F12 (IgG2a). Both IgG2a and IgG2b subclasses are considered as complement fixing antibodies that bind to Fc receptors. Furthermore, an association between A13 plaque reduction and affinity of the Mabs was not validated. Further, Mab m266, is believed to act on CNS A13 levels by serving as a sequestering agent acting from its plasma location given that it is not found in the CNS (DeMattos et al). It appears from the art that m266, 3D3 and 10D5 act by different mechanisms in plaque clearance wherein all three Mabs act as A13 sinks in dialysis assays.

With regard to "active agents" in the treatment of Aβ, the objective is to induce the body to produce molecules to counteract or neutralize the agent. Hence, "active agents" can be considered vaccines that induce a long lived adaptative immune response in patients through induction of antibodies and/or by Cytotoxic Lymphocytes (CTL) or other cellular mechanisms to clear or impede the deposition of Aβ. Several reports have shown induction of immune responses having effects on plaque formation in murine AD models (Schenk et al. 1999 Immunization with amyloid-beta attenuates Alzheimer-disease-like pathology in the PDAPP mouse Nature 400: 173, Sigurdsson et al. 2001 Immunization with a nontoxic/nonfibrillar amyloid-beta homologous peptide reduces Alzheimer's disease-associated pathology in transgenic mice Am J Pathol 159:439).

The role of antibodies has been implicated in both the "passive" and the "active" immunization approach. However, the role of CTL or other cellular responses is less certain. For example, antibody alone may be sufficient for plaque clearance (Schenk et al., supra).

In spite of the state of the art with respect to recombinant proteins and their use as therapeutics, only a very few recombinant proteins based vaccine are available as an approved successful vaccine, for hepatitis B surface antigen (HBsAg). Recombinant protein vaccines for HSV, several other viruses, *Chlamydia*, Lyme disease have all either not been commercially successful or failed to meet approvable criteria and scientists using them are now looking for enhancers such as cytokines, new adjuvants etc.

Major problems are also associated with viral vector vaccines. The primary problem is the immune response induced against the vector itself. This induced immune response severely limits the number and frequency of subsequent injections/boosters that can be administered. Moreover, some adenoviruses have the potential for causing allergic conditions such as celiac disease. It is also known that many viral proteins, including some from HIV and HSV contain immunosuppressive epitopes. Viral proteins are also suspected as causative agents for other autoimmune conditions such as type 1 diabetes, multiple sclerosis (MS), myocarditis, and Graves disease.

Similarly, virus like particles (VLP) also suffer from the same disadvantages noted for viral vector vaccines whereby the particles incorporate antigenic epitope(s) of the plant, animal or bacterial virus (plasmid) where it is expressed in the VLP containing the foreign antigen of interest perhaps in a fusion protein along with the epitopes of the host virus or plasmid.

Another disadvantage in using a DNA-based vaccine including for autoimmune conditions is the possibility of the vaccine DNA being integrated into the host's genome. One alternative is to conjugate a particular epitope to a carrier protein to avoid such incorporation into the genome. It is known within the art to use large carrier proteins such as keyhole limpet hemocyanin (KLH), bovine serum albumin (BSA), or Antigenics' heat shock proteins (HSP) coupled/conjugated or incorporated with a virus protein.

Other options for peptide delivery of peptide epitopes include the use of synthetic biodegradable microparticles like poly(lactide-co-glycolide) PLG with aggregated antigen. Still other delivery technologies for peptide antigens include AutoVac™ of Pharmexa. Other small molecule delivery technologies for peptides are Antigen Express's 'Ii-Key' delivery, phage display and multiple antigen presentation (MAPS) technologies (Rosenthal 2005 Immune peptide enhancement of peptide based vaccines Frontiers in Bioscience 1:478-482).

But again, many of the known approaches have the major disadvantage of using large, very immunogenic carriers. Moreover, patient populations requiring such therapeutics have usually been exposed to many of these same antigens during their lifetimes. Hence, and similar to vaccine vector delivery of antigens, clearance of the antigen can be so vigorous in the previously exposed host that no response will occur to the new antigen. On the other hand, a strong immune response may occur upon reintroduction of the vector. For example, in the case of the conjugate VP22 containing HSV-1 protein, the response may be undesirable given that a majority of adults have had one or more exposures to HSV-1 (Muran-yiova et al. 1991 Immunoprecipitation of herpes simplex virus polypeptides with human sera is related to their ELISA titre. Acta Virol. 35:252-9).

Hence, it is critical that the therapeutic be a small peptide used as a potential antigen as in Epimmune's Padre™ or CEL-SCI's Ligand Epitope Antigen Presenting System (L.E.A.P.S.™) technology as described in U.S. Pat. No. 5,652,342, the contents of which are incorporated herein by reference.

L.E.A.P.S. uses small peptides referred to as T cell binding ligands (TCBL's) as a peptide antigen delivery technology wherein the TCBL's are peptide sequences derived from the human immune system molecules known or suspected to bind to human T cells. Although L.E.A.P.S. includes a first peptide which is an antigenic peptide associated with disease or the causative organism of disease covalently bonded to a second peptide which is a T cell binding ligand, the heterofunctional cellular immunological reagents taught by U.S. Pat. No. 5,652,342 are not antigen (disease) specific in certain cases. Instead, U.S. Pat. No. 5,652,342 teaches T cell binding ligands including portions of MHC Classes I and II or accessory molecules such as β-2-microglobulin, portions of LFA-3, portions of the Fc region of the heavy chain of immunoglobulins, and Ia$^+$ molecules and generally teaches for the antigens associated with auto-immunity such as IDDM, RA and thyroiditis, further the patent fails to provide more antigen (disease) specific treatment.

Hence, there is a need for approaches to treating autoimmune diseases with immunotherapeutics requiring more specific and lower doses of active substance and less frequent dosing. The therapeutics should also allow for the option of subcutaneous, oral intradermal, intranasal or transdermal administration wherein the active portion of the therapeutics should be comprised of substantially smaller molecules (3-5000 Da) that are more likely to be able to cross the blood brain barrier.

Moreover, the need extends to treatments that do not require monoclonal antibodies or receptor agonists to molecules that are critical to maintaining normal body function such as TNF-α soluble receptor or those that require "humanization".

There is further a need for therapeutics that does not eliminate essential or necessary T cells other than those responsible for the underlying disease. The therapeutics should only act upon the major abnormal molecule or cell while preventing or inducing a high response against the vector or delivery molecule.

There is further a need for a therapeutic that is not integrated into the host's genome wherein it may alter other normal or onco genes, their expression or activation.

There is still further a need for providing specific antigenic peptides associated with disease or the causative organism that can be linked with a T cell binding ligand such as L.E.A.P.S. Moreover, the therapeutics should be manufactured and be cost effective in its production and stable during storage before use.

BRIEF SUMMARY OF THE INVENTION

The present invention provides peptide constructs useful for treatment of autoimmune disease, particularly for rheumatoid arthritis, asthma, allergy, and tissue transplantation rejection (including both host-versus-graft and graft-versus-host rejection), which differ from the above approaches used with antigenic peptide alone. The novel constructs bind in an antigen specific manner and redirect the T cell in the direction of a non-deleterious autoimmune response, primarily from a Th1 to a Th2 immune response, but where advantageous, primarily from a Th2 to a Th1 immune response. Alternatively, the novel constructs include one peptide component which will bind to T cells associated with autoimmune disease, asthma, allergies or host versus graft or graft versus host rejection while a second peptide component will bind to sites on the T cells which will preclude the normal sequence of events required for cell activation thereby initiating an abortative T cell modulation resulting in cell anergy and apoptosis.

Specifically, the novel peptides of this invention include peptide constructs of the following formula (I):

P1-x-P2 (I)

where P1 is a peptide associated with autoimmune disease, allergy or asthma, or tissue transplantation rejection and which will bind to an antigen receptor on a set or subset of T cells; P2 is an immune response modifying peptide which will (i) cause a directed immune response by said set or subset of T cells to which the peptide P1 is attached or (ii) bind to a T cell receptor which will cause said set or subset of T cells to which the peptide P1 is attached to initiate, but not complete, an immune response causing said set or subset of T cells to undergo anergy and apoptosis; and x is a direct bond or linker for covalently bonding P1 and P2.

The present invention also provides a first method for treating or preventing inappropriate autoimmune response in individuals at risk for autoimmune disease, allergic reactions, asthma or host-graft or graft-host rejection, wherein a pharmacologically effective amount of a peptide construct of formula (I) is administered to the individual to effectively eliminate the set or subset of T cells involved in the autoimmune response.

The present invention also provides a second method for modulating an inappropriate autoimmune response in individuals at risk for autoimmune disease, allergic reactions, asthma or host-graft or graft-host rejection, wherein a pharmacologically effective amount of a peptide construct of formula (I) is administered to the individual to redirect the autoimmune response from a Th1 to a Th2 immune response, or from a Th2 to a Th1 immune response, whereby the inappropriate autoimmune response is modulated to decrease or eliminate the adverse effects associated with the inappropriate autoimmune response.

BRIEF DESCRIPTION OF THE DRAWINGS

The invention will now be explained in greater detail by the following description and specific embodiments and with the aid of the accompanying drawings.

DETAILED DESCRIPTION OF THE INVENTION

Figure 1:
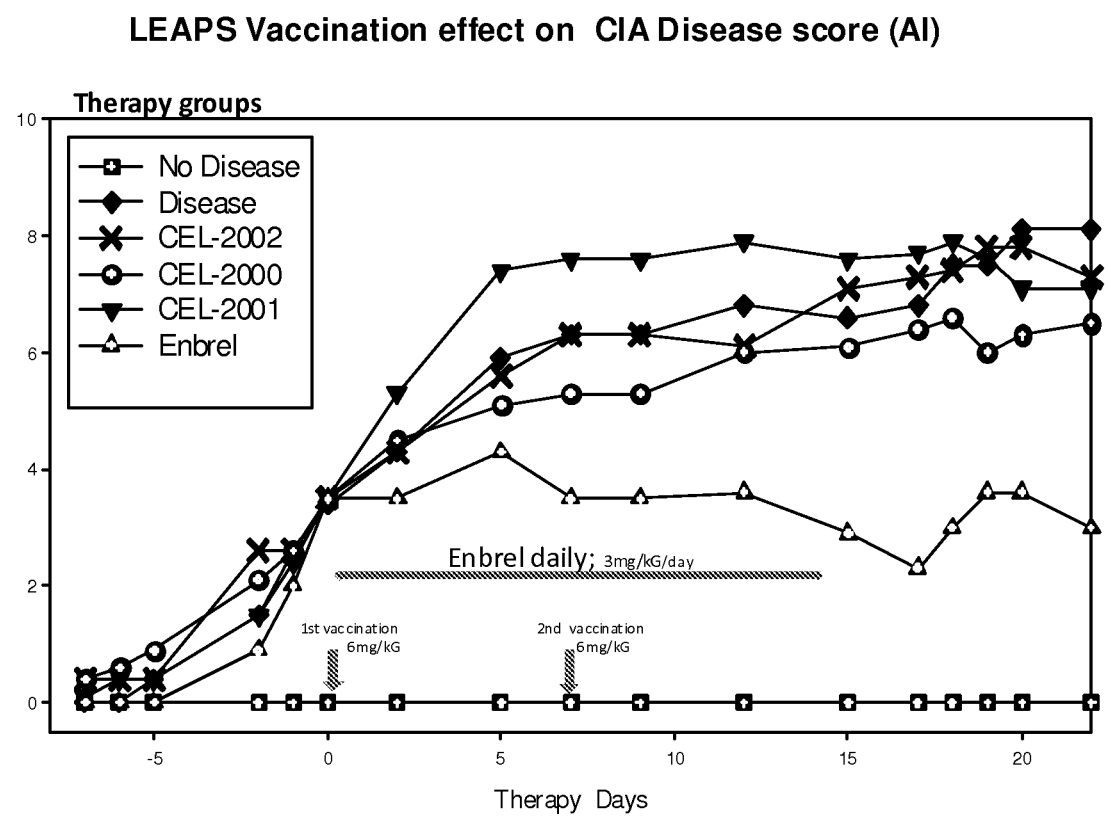
FIG. 1 represents data from mice received two treatments of 33 nmoles (for CEL2000 equivalent to 4.8 mg/kG) of CEL-2000, (the same dose as used for the L.E.A.P.S. HSV vaccines), or other conjugates of the same collagen peptide used in CEL-2000 (SEQ ID NO. 99) using the same ICBLs as in the HSV or EAM systems for comparison using a GMP grade ICFA adjuvant. Shown is group average AI score +/−sd for controls (No Disease) induced squares bottom flat line curve, (Disease induced no Treatment [Upper diamond]), disease induced Enbrel given every day [open right side up triangle] and 3 vaccine groups (CEL-2000 [big X], CEL-2001 (CII (SEQ ID NO 83) conjugated to CEL-1000 (SEQ ID NO. 20) [open circles] (=SEQ ID NO. 89) and CEL-2002 (CII peptide alone (SEQ ID NO 83) [upside triangle]) treatment groups.

It has been reported that the, failure of mature CD8 cells to simultaneously engage their TCR and CD8 co-receptor, triggers an activation process that begins with inhibition of CD8 gene expression through methylation and concludes with up-regulation of surface Fas and Fas ligand and cellular apoptosis (Pestano et al., Inactivation of Misselected CD8 T Cells by CD8 Gene Methylation and Cell Death 1999, Science, 284:1187). This is consistent with the results of others where if full engagement of certain very major coreceptors are not effected then an activation process, but abortative in nature, leading to apoptosis occurs (see also Gogolak et al., Collaboration of TCR-, CD4- and CD28 mediated signaling in antigen-specific MHC class II-restricted T-cells 1996, Immunol. Let. 54:135; Grakoui et al., The Immunological Synapse: A Molecular Machine Controlling T Cell Activation 1999, Science, 285:221; Malissen, Dancing the Immunological Two-Step 1999, Science, 285: 207; Redpath et al., Cutting Edge: Trimolecular Interaction of TCR with MHC Class II and Bacterial Superantigen Shows a Similar Affinity to MHC:Peptide Ligands 1999, J. Immunol., 163:6; Preckel et al., supra 1998, Eur. J. Immunol., 28:3706; Sambhara et al., Programmed cell death of T cells signaled by the T cell receptor and the alpha 3 domain of class I MHC 1991, Science, 252:1424; Kishimoto et al., Strong TCR Ligation Without Costimulation Causes Rapid Onset of Fas-Dependent Apoptosis of Naive Murine CD4 T Cells 1999, J. Immunol., 163:1817; Kubo et al., CD28 Costimulation Accelerates IL-4 Receptor Sensitivity and IL-4-Mediated Th2 Differentiation 1999, J. Immunol., 163: 2432).

Therefore, a different approach would be to have a modulation but not with a full sequence of events that cause diseases, the construct binding in an antigen specific manner with the antigenic epitope but the TCBL ligand binding to a site on another molecule associated with certain early events that are early intermediates in the full expression pathway thereby occupying the space and causing an early event in the process of activation (such as $Ca^{++}$ flux, activation of various phosphatases, membrane migration events, such as "patching" or "capping", changes in RNA metabolism) but not supporting the complete activation process which can be thought of as culminating in antigen specific antibody or non-antibody mediated specific cytotoxic T lymphocyte activity such as killing of infected or tumor cells, by acting on DNA synthesis, cell division, or cytokine secretion, namely, without allowing the ultimate tertiary complex of binding events (MHC, antigen TCR and CD4 (or CD8)) necessary for full activation by being out of the normal temporal sequence of events. Perhaps this early binding would be of such strength that it does not disassociate and allow the cell surface rearrangement necessary for the full and normal sequence of modulatory events, such as, proliferation or secretion of late cytokines such as Fas, TNF-α or IFN-γ and thereby prohibiting events found in an autoimmune disease associated pathway with complete T cell activation. For example, initially after antigen binding to the TCR ICAM-1 (also known as CD54) on APC binding to a T cell's LFA-1 (also known as CD11a/CD18) there is a shifting away and a rearrangement with clustering of the MHC and antigenic peptides on APC binding eventually by migration on T cell membrane to a clustering of TC and CD4 (or CD8) (Malissen supra 1999, Science, 285:207; Grakoui et al., supra 1999, Science, 285:221).

According to one embodiment of this invention, such rearrangement is prevented by the close association in a peptide construct using a TCBL from ICAM-1, LFA-3 (aa2642), VLWKKQKDKVAELENSE (SEQ ID NO.4) (Osborn et al., Amino acid residues required for binding of lymphocyte function-associated antigen 3 (CD58) to its counter-receptor CD2 1995, JEM, 181:429), by either the disparity in the temporal binding or higher strength of binding activity, thereby preventing the rearrangements and other more intimate interactions necessary for activation. Initially these sites are close together but normally rearrangements on the T cell surface occur during the activation process so by preventing this shift activation should not occur. Likewise, a TCBL from CD4 that binds to the TCR and CD3 may be used as the TCBL in the peptide construct of this invention. Its binding to the T cell recognition site will inhibit subsequent events from occurring (MHC II with CD4 or β-2 with CD8).

Still another approach is a construct which redirects the immune response initiated by the natural autoimmune inducing event from a Th1 to a Th2 response (e.g., Lowrie et al., Therapy of tuberculosis in mice by DNA vaccination 1999, Nature, 400:269; Tisch et al., supra 1999, J. Immunol., 163:1178). As used herein, a Th2 directed response is one which directs the immune response toward the Th2 direction, thus favoring production of Th2 associated cytokines IL-5, IL-4, IL-10, IL-13, TNF-α and antibody isotypes IgG1 and IgG3 in mice (or comparables in man) as opposed to Th1, where the immune response favors production of cytokines IFN-γ, IL-2, IL-6, IL-12 cytokines and antibody isotypes IgG2a and IgG2b in mice and cytotoxic T cell activity. It is understood, of course, that a "Th2 directed response" is not intended to imply an exclusively Th2 response, but rather a mixed immune response which is weighted to favor a Th2 profile.

According to this embodiment a TCBL associated with Th2 responses; e.g., peptide G from MHC class II (Zimmerman et al., A new approach to T cell activation: natural and synthetic conjugates capable of activating T cells 1996, Vacc. Res., 5:91, 5:102; Rosenthal et al., 1999, Vaccine), IL-4 or IL-5 or peptides known to stimulate IL-4 or IL-5 synthesis are used as the TCBL along with the autoimmune inducing peptide (e.g., Hammer et al., supra, Krco et al., supra, Araga et al., supra, Ota et al., supra, Ruiz et al., supra, Yoon et al., supra, Dittel et al., Presentation of the Self Antigen Myelin Basic Protein by Dendritic Cells Leads to Experimental Autoimmune Encephalomyelitis 1999, J. Immunol., 163:32; Gautam et al., A Viral Peptide with Limited Homology to a Self Peptide Can Induce Clinical Signs of Experimental Autoimmune Encephalomyelitis 1998, J. Immunol., 161:60, the disclosures of which are incorporated herein by reference thereto) in the peptide conjugate. These peptide constructs may be used, for example, to treat type I diabetes. In an animal model the mechanism of diabetes prevention in the RIP-NP model was shown to be mediated by insulin β-chain, and IL-4 producing regulatory cells acting as bystander suppressors (Homann et al., supra 1999, J. Immunol., 163:1833). Such redirection of immune responses have been previously reported by a DNA vaccine for TB which redirected the immune response from an inefficient response Th2 to a response that was a very effective Th1 (Lowrie et al., supra 1999, Nature, 400:269). Thus, redirecting an already existing immune response from a Th1 to a Th2 would be effective for treating autoimmune related diseases. A TCBL involved in CD28 costimulation (Kubo et al., supra) could also be effective for this purpose. If, on the other hand, the need was to redirect from a Th1 to a Th2, much less likely to be needed since many autoimmune conditions are thought to be the manifestation of deleterious Th1 effects, then a TCBL such as peptide derG, DGQEEKAGVVSTGLI (SEQ ID NO. 2) (Zimmerman et al., supra; Rosenthal et al., supra) or ones known to stimulate IL-4, IL-10, or TGFβ synthesis would be used along with the autoimmune inducing peptide.

Yet another approach is to use the peptide construct to not activate the normal immune process but to activate the process leading to apoptosis of the T cell by using as the TCBL a ligand that binds to a site on the T cell whose normal binding and activation leads to apoptosis of the T cell; such as the TNF-receptor of the T cell, in which the TCBL would be the TNF-α ligand portion. Examples of such TNF peptides known to activate macrophages are amino acids 70-80 PSTHVLITHTI (SEQ ID NO. 5) (Britton et al., 1998, I & I, 66:2122) and perhaps the antagonist peptide represented by DFLPHYKNTSLGHRP (SEQ ID NO. 6) of another region (Chirinos-Rojas et al., A Peptidomimetic Antagonist of TNF-α-Mediated Cytotoxicity Identified from a Phage-Displayed Random Peptide Library 1998, J. Immunol., 161: 5621). It has been suggested in WO 99/36903A1 that the H4-1-BB ligand is useful as a treatment for autoimmune-disease similar to uses for flt3-L and CD40L; therefore, H4-1BB may also be used asTCBL for inclusion with autoimmune antigens to form the inventive peptide construct. Other such TCBL examples are available from application with Fas and Fas-ligand including the noncleavable Fas-ligand (WO 99/36079A1).

Since autoimmune reactive cells in disease are most likely already activated and may be expressing Fas (Tomita et al., Tetrapeptide DEVD-aldehyde or YVADchloromethylketone inhibits Fas/Apo-1(CD95)-mediated apoptosis in renal-cell-cancer cells 1996, Int. J. Can., 68:132; Lie et al., Synthesis and biological activity of four kinds of reversed peptides 1996, Biol. Pharma. Bul. 19:1602) the Fas-ligand or the sequence obtained by reverse engineering technique to determine amino acid (aa) sequence acting as receptor for DEVD-aldehyde or YVAD (SEQ ID NO. 17) chloromethylketone, may also be used as the TCBL. Representatives from another pair, IFN-γ and the IFN-γ ligand can also be used as TCBL's in the invention peptide constructs.

In this invention the antigenic peptide and the peptide for T cell binding (TCBL) may be directly linked together in any order (i.e., N-terminal of one to C-terminal of other or vice versa) or the peptide may be covalently bonded by a spacer or linker molecule. With regard to linkers between the two domains, suitable examples include a thioether bond between an amino terminus bromoacetylated peptide and a carboxyl terminus cysteine, often preceded by a diglycine sequence (Zimmerman et al., supra), carbodiimide linkages, a multiple glycine, e.g., from 3 to 6 glycines, such as triglycine, with or without one or two serines, separation between the two entities, e.g., GGGS (SEQ ID NO.7), GGGSS (SEQ ID NO. 8), GGGGS (SEQ ID NO.9), GGGGSS (SEQ ID NO. 10), GGGSGGGS (SEQ ID NO.11), etc., and other conventional linkages, such as, for example, the direct linkages such as, EDS, SPDP, and MBS, as disclosed in the aforementioned U.S. Pat. No. 5,652,342.

Thus, the peptide constructs of this invention may be conveniently represented by the following formula (I):

P1-x-P2     (I)

where P1 is a peptide associated with autoimmune disease, allergy or asthma, or transplantation rejection and which will bind to an antigen receptor on a set or subset of T cells;

P2 is an immune response modifying peptide which will bind to T cells to cause a directed immune response by said set or subset of T cells to which the peptide P1 is attached or which will bind to a T cell receptor which will cause said set or subset of T cells to which the peptide P1 is attached to initiate, but not complete, an immune response causing said set or subset of T cells to undergo anergy and apoptosis; and x is a direct bond or linker for covalently bonding P1 and P2.

The TCBL portion of the immunomodulatory peptide construct of this invention, i.e., $P_2$, may comprise a discontinuous epitope composed of two small regions separated by a loop or by a single chain short peptide in place of the loop (Shan et al., Characterization of scFv-Ig Constructs Generated from the Anti-CD20 mAb 1F5 Using Linker Peptides of Varying Lengths 1999, J. Immunol., 162:6589). For example, an eight amino acid group, LRGGGGSS (SEQ ID NO. 12), of 11.2 angstroms in length (Reineke et al., A synthetic mimic of a discontinuous binding site on interleukin-10 1999, Nature Biotechnology, 17:271) has been used to form a single peptide from two smaller discontinuous peptides of IL-10, thereby forming a TCBL which could be used for redirection from a Th1 to a Th2, in combination with, for example, the IDDM, PV or MS inducing epitopes (Hammer et al., supra Tisch et al., supra).

Linkers (X) of varying lengths to form a single chain may be used, for example, GGGS (SEQ ID NO. 7), GGGGS (SEQ ID NO. 9), including, from among 1 or more repeats of this tetrapeptide or pentapeptide, e.g., GGGSGGGS (SEQ ID NO. 11), GGGSGTGSGSGS (SEQ ID NO. 22). Such linkers may result in a tertiary structure which might be of use to form a more avid TCBL (Shan et al., supra).

Although not strictly limited, the peptide constructs of this invention may have as many as about 200 amino acids in its sequence, preferably up to about 150 amino acids, and especially, up to about 100 amino acids. The minimum number of amino acids is also not strictly limited but usually each of the peptide components P1 and P2 will have at least about 4, preferably at least about 6, and more preferably at least about 8 or 9 amino acids in order to provide the appropriate epitope configuration for effectively binding to the appropriate site on the T cells of interest. Thus, the peptide constructs of this invention will usually contain from about 20 to about 100 or more amino acids.

The peptide constructs may be prepared using conventional solid state peptide synthesis, provided however, that for constructs having more than about 40 amino acids, especially more than about 50 amino acids, it is usually convenient and preferred to prepare shorter segments and then link the shorter segments using well known techniques in solid phase peptide synthesis.

The peptide constructs may be prepared using conventional solution phase condensation chemistry of smaller peptides prepared by solid phase peptide synthesis, provided however, that for constructs having more than about 40 amino acids, especially more than about 50 amino acids, it is usually convenient and preferred to prepare shorter segments and then link the shorter segments using well known techniques in solid phase peptide synthesis.

Alternatively, the peptide constructs of this invention may be prepared using well known genetic engineering methods. Further details on methods for producing the instant peptide constructs can be found in the aforementioned U.S. Pat. No. 5,652,342.

Improved versions of the peptide constructs are comprised of variables X1 to X12 substitutions where each of X1 to X12 describe a group of particular types of amino acids based on their features. For example, it is known that amino acids can be nonpolar, hydrophobic while another group of amino acids are polar, uncharged amino acids that are hydrophilic. Still further, it is known that amino acids can be grouped as those that are polar, charged, hydrophilic amino acids further subdivided between acidic and basic amino acids. Table 1 describes the chemical and structural features along with the corresponding amino acids.

TABLE 1

| Chemical or Structural Feature | Amino Acid |
|---|---|
| Polar/hydrophilic | N, Q, S, T, K, R, H, D, E, (C, Y)* |
| Non-polar/hydrophobic | (G), A, V, L, I, P, Y, F, W, M, C |
| H-bonding | C, W, N, Q, S, T, Y, K, R, H, D, E |
| Sulfur containing | C, M |
| Charged at Neutral pH Negative/acidic | D, E, (C) |
| Charged at Neutral pH Positive/basic | K, R, (H) |
| Ionizable | D, E, H, C, Y, K, R |
| Aromatic | F, W, Y, (H, no UV absorption) |
| Aliphatic | G, A, V, L, I, P |
| Forms covalent cross-link (disulfide bond) | C |
| Cyclic | P |

*Note: Amino acids in parentheses have the indicated character to a limited extent.

Table 2 describes the amino acids for $X_1$ to $X_{10}$ wherein the amino acids for $X_1$ to $X_{10}$ have been selected on their common chemical and structural features as shown in Table 1 for inclusion in the improved variants of the invention. Instances of $X_2X_3$ or $X_3X_2$ or $X_2X_3$ or $X_3X_2$ or $X_3X_3$ or $X_2X_2$ can be replaced by $X_{11}$ or by gamma amino butyric acid (GABA) wherein the common feature is that the amino function is on the γcarbon and not the α-carbon. Instances of $X_1X_1$ or $X_1X_3$ or $X_3X_1$ or $X_1X_2$ or $X_2X_1$ can be replaced by $X_{15}$. Modifications for increased stability at the amino terminus by use of an acetyl or propionyl group, D glycine or D alanine or use of cyclohexylalanine at the amino terminus to reduce proteolysis are contemplated by the substitution of $X_{12}$. As shown in the improved variants of the sequence, $X_{12}$ can be present or not present on the sequence. It is noted that the sequences in computer readable form do not include $X_{12}$. However, the presence of the modification is present for all sequences where disclosed in the instant specification. Similarly, modifications by use of 5-aminopentanoic acid for replacement of lengths of 3 or 4 amino acids of $X_2$ and $X_3$ are also contemplated by the invention and represented as $X_{13}$ wherein the lengths of 3 or 4 amino acids of $X_2$ and $X_3$ can be replaced by 5-aminopentanoic acid. Although $X_{13}$ is not properly an amino acid, it is used as a place holder in some SEQ ID NO.'s to indicate 5-aminopentanoic acid bonded to the adjacent or underlying amino acid for improved stability. $X_{14}$ is a variable selected from any of $X_1$, $X_2$, $X_3$, $X_4$, $X_5$, $X_6$, $X_7$, $X_8$, $X_9$, or $X_{10}$.

TABLE 2

| Variable | Amino Acid | Chemical or Structural Feature |
|---|---|---|
| $X_1$ | A and G | Aliphatic, non polar |
| $X_2$ | D and E for acidic amino acids | Polar acidic, H-bonding, Charged at Neutral pH Negative, Ionizable |
| $X_3$ | I, L or V | Non-polar, branched, non-cyclic alkyl hydrocarbon |
| $X_4$ | K, R or H for basic amino acids | Polar basic/hydrophilic, H-bonding, Ionizable |
| $X_5$ | C or S | Polar charged with similar features as described in U.S. Pat. No. 5,019,384 |

TABLE 2-continued

| Variable | Amino Acid | Chemical or Structural Feature |
|---|---|---|
| $X_6$ | F, W or Y for aromatic amino acids | Non-polar/hydrophobic, Aromatic |
| $X_7$ | F or P | Non-polar/hydrophobic, Ring Structure* |
| $X_8$ | M or Nle (Norleucine)$^\Psi$ | Natural and non-natural branched chain |
| $X_9$ | N or Q for amidated amino acids | Polar/hydrophilic, H-bonding, Equivalent sized, acid carboxylic acid group |
| $X_{10}$ | T or S | Polar/hydrophilic, H-bonding, Capable of binding non-amino acid molecules to protein |
| $X_{11}$ | Gaba$^\chi$ for $X_2 X_3$ or $X_3 X_2$ or $X_2 X_3$ or $X_3 X_2$ or $X_3 X_3$ or $X_2 X_2$ | Amino function is on $\gamma$ carbon and not $\alpha$ carbon |
| $X_{12}$ | Acetyl or propionyl group, D glycine or D alanine, Cyclohexylalanine at amino terminus | Improved stability |
| $X_{13}$ | 5-aminopentanoic acid for replacement of 3 or 4 amino acids of $X_2$ and $X_3$ | Improved Stability |
| $X_{14}$ | $X_1, X_2, X_3, X_4, X_5, X_6, X_7, X_8, X_9,$ or $X_{10}$ | |
| $X_{15}$ | $X_1 X_1$ or $X_1 X_3$ or $X_3 X_1$ or $X_1 X_2$ or $X_2 X_1$ | |

*W is not added because W is less stable than F or P as described in U.S. Pat. No. 5,109,384
$^\Psi$isomeric to leucine and isoleucine but not found in proteins and formed in the deamination of lysine. Also called caprine.
$^\chi$Gamma amino butyric acid The novel peptide constructs of this invention can also be used to treat autoimmune disease such as rheumatoid arthritis (RA). In this case, the peptide antigen(s) used to make the construct would be antigens with defined epitopes recognized for human leukocyte antigens (HLA) genotypes associated with for example, RA, combined with a TCBL as described above to either suppress or redirect the immune response. As one of the major sources of antigenic materials causing autoimmune disease is thought to be the M literature references cited herein, the disclosures of which are incorporated herein, in their entirety, by reference thereto. Additional examples, may also be found in the following literature (de Lalla et al., Cutting Edge: Identification of Novel T Cell Epitopes in Lol p5a by Computational Prediction 1999, J. Immunol., 163:1725 (Lol p5a allergen from rye grass); Gautam et al., supra 1998, J. Immunol., 161:60); as well as many others available to one of ordinary skill in the art.

INTRODUCTION

The collagen induced arthritis (CIA) mouse model effectively mimics human disease to allow testing and development of rheumatoid arthritis (RA) therapies. A Ligand Epitope Antigen Presentation System (L.E.A.P.S.) peptide hetero-conjugate vaccine has been developed and evaluated that contains as one component an epitope of human collagen type II, and it has been determined in the CIA model that this vaccine is capable of limiting disease progression, as demonstrated by pathology, histopathology and arthritis index score. L.E.A.P.S. technology converts a small peptide containing a disease specific epitope into an immunogen by attaching it a T cell binding peptide (TCBL) and presenting it to an immune cell. In this case, a peptide from human $\beta 2$ microglobulin (J) is used as a TCBL. The antigen is also called an immunogen and it is able to induce an immune response wherein antigen can be used inter-changeably with immunogen. However, small antigens sometimes referred and better described as epitopes are unable to induce an immune response without being made larger, or having other properties changed to make them into immunogens e.g., by adding a TCBL.

The L.E.A.P.S. technology elicits a defined immune response to a specific immunogen directing in the desired targeted direction and for the appropriate immunomodulation. Based on the data collected, to date, it is postulated that CEL-2000, which is peptide J combined with the human type II collagen peptide 254-273 and not gB, ICP27 of gD (all from HSV 1), is a successful candidate as a therapeutic vaccine for RA.

BACKGROUND

The need for new treatments for rheumatoid arthritis (RA) using therapeutic vaccines is highlighted by its inclusion in the Institute of Medicine (TOM) "Vaccines for the 21st Century". The TOM lists RA in the top category of the 28 potentially new vaccines evaluated. Seven (7) vaccines were in this top category, "Level I Most Favorable Saves most Money & Quality Adjusted Life Year's (QALY)" including besides RA, vaccines for multiple sclerosis, insulin dependent diabetes, cytomegalo and influenza viruses, Group B *Streptococcus* and *Streptococcus pneumomniae*.

Efforts to develop vaccines for RA and evaluate them in animal models of human disease have shown promise, but to date these efforts have met with only limited success. Obstacles that have stood in the way of development of a successful RA vaccine include: 1) identification of the epitope or epitopes to elicit a protective therapeutic response, 2) selection of an appropriate delivery technology and 3) demonstration of an appropriate therapeutic response in different models of the same disease. A specific targeted antigen, preferably a peptide that acts the same in humans and an appropriate animal model with disease symptoms and pathology similar, if not identical to those seen in humans, are both important issues to consider when developing a vaccine for an autoimmune condition. The antigen issue is achieved, in part, based on findings that collagen Type II from at least 2 species (chicken and bovine) can induce arthritis in mice and rats, and in the case of human collagen Type II, or peptides thereof, can be recognized by cells or antibodies from RA patients, CIA induced rodents or both. The choice of the appropriate immunogen to specifically modulate an autoimmune response is critical to the success of a therapeutic vaccine. Several protein epitopes from collagen type II have been identified as relevant for consideration as the appropriate immunogen for an RA vaccine. In addition, antibodies to citrullated peptides have been identified in RA and RA is known to be associated with a PAD gene defect, the enzyme responsible for citrullation (i.e. post-translational conversion of an adrgine residue in a protein into a citrulline residue). Another prime feature has been to identify a peptide(s) for use with the L.E.A.P.S. that has generated positive interest for human, mouse, and rat systems and is evaluable by cellular and serological studies. Human collagen type II, within residues 235-280 and more specifically between 254 to 273, is the peptide which best fits overall these criteria and is close in sequence to the peptides from bovine and chicken collagen Type II which is used to induce disease in mice. Incorporation of this collagen Type II peptide agrees with Sette et al.'s recent findings of using peptides that contained overlapping CD4 and B cell epitopes in his system for optimal activity. Sette, A., M. Moutaftsi, J. Moyron-Quiroz, M. M. McCausland, D. H. Davies, R. J. Johnston, B. Peters, B. M. Rafii-El-Idrissi, J. Hoffmann, H. P. Su, K. Singh, D. N. Garboczi, S. Head, H. Grey, P. L. Felgner, and S. Crotty. 2008. Selective CD4+ T cell help for antibody responses to a large viral pathogen: deterministic linkage of specificities. Immunity Vol. 28:847-858. Known work has used peptides that contained overlapping B cell, CD4 as well as CD8 epitopes.

Preliminary studies indicate that the L.E.A.P.S. technology is an appropriate technology to deliver a human collagen type II epitope as a therapeutic vaccine in a murine CIA model of RA. The L.E.A.P.S. technology has been used successfully to elicit beneficial immune responses in actual disease-challenge models and in several different strains of mice differing in their MHC backgrounds. These include: A) Th1 and DTH responses to an HIV epitope, HGP30, in BALB/c mice, B) protective immune responses against herpes simplex virus (HSV-1) challenge of Balb/C, C3H, A/J and C57BL6 mice as a prophylactic vaccine and C) immune response modulation resulting in useful therapeutic effects when used as a vaccine for experimental autoimmune myocarditis (EAM) model in A/J mice and in the CIA model of RA in DBA/1J mice. Although the L.E.A.P.S. technology has not been evaluated with human cells or as yet in clinical studies, there have been more animal protection efficacy studies with the L.E.A.P.S. than the Padre™ and Ii-Key™ technologies. The demonstrated efficacy of L.E.A.P.S. vaccines in mice with different MHC backgrounds suggest that CEL-2000, will most likely also be effective in man.

Several rodent and rabbit models of RA which are currently used to test RA therapies, are also suitable for testing RA vaccines and are readily available for evaluation. Arthritis can be induced in mice as well as in rats by immunization with chicken or bovine collagen Type II in combination with appropriate adjuvants or by adjuvant alone, in which case the condition is referred to as adjuvant induced arthritis (AIA) instead of CIA, to closely mimic acute or chronic rheumatoid arthritis in joint pathology, inflammation, bone erosion and remodeling, cartilage alterations and pannus changes. A type of arthritis can also be induced in the rabbit with ovalbumin.

A therapeutic vaccine has several advantages over the current immunosuppressive therapies used to treat RA. Unlike anti-cytokine therapies, the vaccine develops a targeted, specific modulation of the pathogenic immune response. The targeted nature of the immunization should minimize the side effects and risks of infection that can occur from current cytokine antagonist therapy. Current therapies are passive in nature, involve larger amounts of materials must be given frequently often in a clinic or hospital setting and are prone to be immunogenic after prolonged use and generate immune responses to the therapeutic agent especially if not of human origin or humanized which can neutralize the therapeutic agent. In contrast, a limited number of immunizations with a vaccine should be required to halt and prevent or possibly reverse the progression of RA.

A therapeutic vaccine for RA will be different from the classical anti-infection vaccines since it will be administered during the course of the disease, after disease signs can be diagnosed. The challenge will be to provide therapy as late as possible after initiation of the disease process and appearance of clinical symptoms.

Prior studies on L.E.A.P.S. vaccines for infectious diseases L.E.A.P.S. prophylactic vaccinations are mentioned. In theses studies, the vaccine as with CEL-2000 utilizes the "J" T or immune cell binding ligand (T/ICBL), a peptide derived from human β2 microglobulin, to convert a peptide from a pathogen into a therapeutic vaccine. Rosenthal, K. S., H. Mao, W. T. Home and D. H. Zimmerman (1999), "Immunization with a L.E.A.P.S. Heteroconjugate Vaccine Containing a CTL epitope and a Peptide from Beta-2-Microglobulin Elicits a Protective and DTH Response to Herpes Simplex Virus Type 1", Vaccine 17: 535-542; N. Goel, D. H. Zimmerman and K. S. Rosenthal 2003, "A L.E.A.P.S.™ Heteroconjugate Vaccine Containing a T Cell Epitope From HSV-1 Glycoprotein D Elicits Th1 Responses and Protection", Vaccine 21:4410-4420; Zimmerman, D and Rosenthal, K 2005, "The L.E.A.P.S. Approach to Vaccine Development", Frontiers in Bioscience 10:790-798; Goel, N, Zimmerman, D and Rosenthal, K 2005, "Ligand Epitope Antigen Presentation System Vaccines Against Herpes Simplex Virus", Frontiers in Bioscience 10:966-974. It has been demonstrated in several different systems that vaccines with the J-ICBL promote Th1 responses. Such responses are sufficient for protection from herpes simplex virus type 1 (HSV-1) disease. Protection was elicited by incorporation of 3 different HSV1 peptides from either gB, gD or ICP 27 proteins into J-L.E.A.P.S. vaccines. Ablation of CD4 and CD8 cells and IFN-γ prevented establishment of the immune response during the inductive phase but, only CD4 cells and IFN-γ were essential for delivery of the protection if ablation was done after immunization but just prior to challenge. Similar findings were seen for a DTH challenge in the Balb/C mice with a different conjugate. The protection in all cases were immunogen specific and required covalent linkage of the immunogenic peptide to the J peptide, since free HSV peptide or the HSV-1 peptide coupled with another peptide were not protective. Furthermore, immunization with the J peptide or J-linked vaccines did not elicit antibody responses unless the vaccines were followed by a boost challenge with the specific antigen or HSV-1.

Another prior study on L.E.A.P.S. vaccines is for EAM model L.E.A.P.S. therapeutic vaccination. Cihakova D, J G Barin, M Kimura, G C Baldeviano, M V Talor, D H Zimmerman, E Talor, N R Rose, 2008, "Conjugated Peptide Ligand is Able to Prevent and Treat Experimental Autoimmune Myocarditis, is a Strong Stimulator of Cell and Humoral Immunity", Int J Immunopharmacol 8:624-633. Similar to CEL-2000, immunization of A/J mice with a L.E.A.P.S. heteroconjugate having the pathogenic My-1 peptide from murine cardiac myosin linked to "J" conferred both protection and treatment against experimental autoimmune myocarditis (EAM). These findings were for a L.E.A.P.S. vaccine protecting against EAM, a condition induced in A/J mice with the My-1 peptide from murine cardiac myosin. While the J-My-1 vaccine was not evaluated with other models this condition can be induced by coxsackie virus B3 infection as well as immunization with murine cardiac myosin (MCM) 1. Therapies for EAM induced by My-1 such as monoclonal antibodies (for TNF-α or IL-1β), anti-complement receptor, cobra venom or recombinant proteins such as IFN-γ are effective only if given in the first week, during the induction phase but are ineffective when given by day 10 or later.

One possible conclusion is that the L.E.A.P.S. vaccine J-My1 was antigen specific (for My-1), did not induce a general anergy as for the anti PPD response, had little effect on antibody to My-1, reduced proliferative responses to My-1 and did this without acting as a general mitogen or polyclonal activator. Expanded numbers of activated CD69+ and CD44+CD4+ and CD8+ cells, as well as increased CD11c+ DCs were observed in the spleens. No differences in CD4+CD25+ FoxP3+ Treg cell numbers were detected in the spleen or the target heart organ. Examination of the chemokine and cytokine response with the Quantikine ELISA kits for IFN-γ, TGF-β, TNF-α, IL-1α, IL4, IL10, IL2, Histamine, IP-10, MIP-1a of sera and spleens were unremarkable, however cardiac tissue showed a significant decrease in MIP-1α and IP10. This is in contrast to the elevated levels of these molecules in another EAM model and the ability of monoclonal antibody ablation to MIP-1α or MCP-1 to reduce disease severity. Although IL-17 may be involved, it was not studied as reagents were not available.

Unfortunately, fewer doses or less vaccine than the 100 nmol per dose used every 7 days were not tested in this EAM study (3 times more in amount and frequency was used than in our previous HSV vaccine studies which used only 2 doses of 33 nmol peptide). Individual, unrepresentative mice exhibited anaphylaxis to the vaccine regimen. Based on studies, it is believed these adverse events will not be observed in older animals as in the CIA model or can be circumvented by using altered dosing (amounts and timing), drug prophylaxis or altered peptide ligands (APLs).

The following five studies are of CEL-2000 therapeutic vaccine for collagen induced arthritis (CIA) where the first step was to identify a good animal model for testing the vaccine, which is the collagen induced arthritis (CIA) model in young (6-7) week old male DBA/1J mice. These mice received 2 injections of bovine collagen the first in complete Freund's adjuvant (CFA) on day 0 and then 3 weeks later on day 21, in Incomplete CFA. After the second collagen injection, the mice were evaluated daily for any joint swelling or redness. Each of the paws was scored on a 4 point scale (arthritis index Arthritis Index (AI)) with respect to the number of digits with symptoms and the thickness of the paw measured, at least 3-4 times a week. Each mouse was weighed weekly.

The first study is the CIA model CEL-2000 therapeutic vaccination conjugate specificity effect on AI scores (study 4.1 see FIG. 1 and legend). When significant disease is noted, usually about day 28, the mice are grouped (n=8) with a range of scores between 1 and 6 and group mean of 2.5 to 3. At this point the therapy begins according to protocol. Controls include groups with induced disease but no therapy and groups of healthy mice without induced disease. A therapy control of Enbrel (3 mg/kG daily) was included. In this study (FIG. 1), mice received two treatments of 33 nmoles (for CEL-2000 equivalent to 4.8 mg/kG) of CEL-2000, (the same dose as used for the L.E.A.P.S. HSV vaccines), or other conjugates of the same collagen peptide used in CEL-2000 using the same ICBLs as in the HSV or EAM systems for comparison using a GMP grade ICFA adjuvant.

Shown is group average AI score +/−sd for controls (No Disease) induced squares bottom flat line curve, (Disease induced no Treatment [Upper diamond]), disease induced Enbrel given every day [open right side up triangle] and 3 vaccine groups (CEL-2000 [big X], CEL-2001, where CEL-2001 is the core collagen type II peptide huCII354-373, and CEL-2002 is the huCII354-373 conjugated to CEL-1000 derG see CS112 114 or 118 [open circles] (CII peptide alone [upside triangle]) treatment groups.

CEL-2000 treatment limited the progression of disease, as indicated by AI scores, which were reduced to a greater extent than was seen with other conjugates, CEL-2001 or CEL-2002, in the same rank order as seen for similar L.E.A.P.S. conjugates in the EAM or HSV systems. AI scores are evaluations on a scale of 0=normal to 4=maximal effect of joint thickening, redness, immobilization of joints in a digit or total paw for each of the 4 paws in the CIA mouse model of rheumatoid arthritis. Enbrel treatment given on a daily basis for the first 14 days was slightly more effective than the vaccine as this dose and timing. This suggests a larger dose of CEL-2000 might be more effective.

Figure 2:
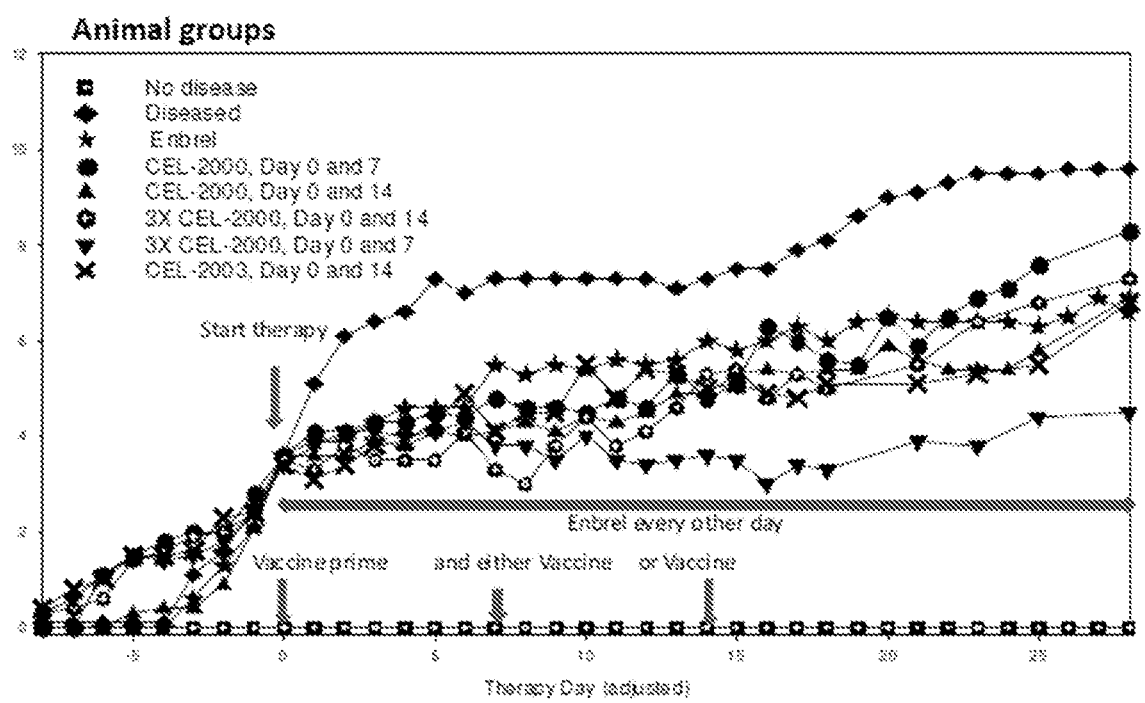
FIG. 2 represents a study where CEL-2000 treatment with 2 doses of 33 or 100 nmol (the dose used in the EAM study) was given subcutaneously on days 0 and 7 as in the EAM study or 0 and 14 as for the HSV. Most regimes reduced the progression of arthritis disease to levels that were at least as good as those of mice treated with Enbrel (every other day for the 28 days of the study). Immunization of mice with the 100 nmol dose (3× treatment) on days 0 and 7 appeared to limit the progression of disease throughout the experimental period. The CEL-2003 links the murine $CH_{254-273}$ sequence to the J ICBL. This trial suggests that the dosage and schedule of administration (time between initial and second immunization) are important parameters for CEL-2000 treatment. Use of a student "t" test analysis of treatment groups at day 7 days 14 and 21 to calculate the p value showed the 3× dose of CEL-2000 on day 0 and 14 followed by 3× on day 0 and 7 or 1× on day 0 and 7 is equivalent to 0 and 14 and slightly better than Enbrel every other day for all 28 days.
Figure 3:
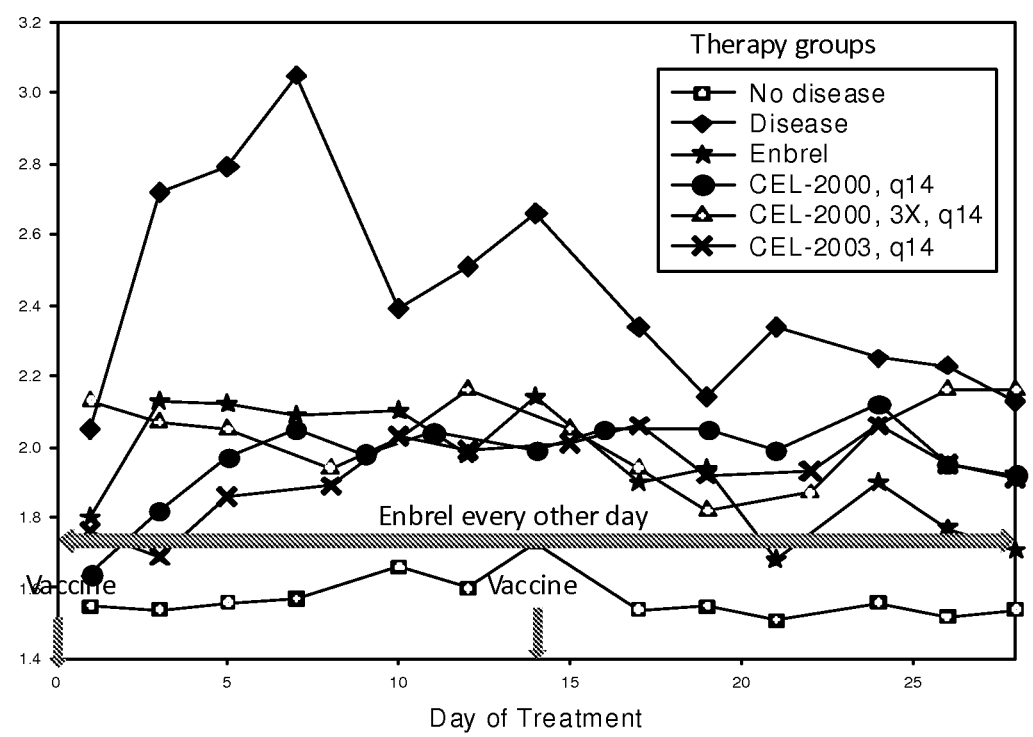
FIG. 3 represents CIA Model analysis of foot pad thickness as evidence of CEL2000 therapeutic vaccine efficacy. The animal groups and vaccines used are described in FIGS. 1 and 2. Measurement of the footpad thickness of the mice for the first two weeks of vaccine therapy was compared to Enbrel therapy as a more independent and completely objective measurement.

The second study is for the CIA model CEL-2000 therapeutic vaccination conjugate dose amount and timing effect on AI scores (study 4.2 see FIG. 2 and legend).

The ability of the CEL-2000 also referred to as J-huICBL (SEQ ID NO 852) and HuC-II$_{254\text{-}273}$ to modulate immune response to promote protective, preventative and therapeutic immune responses prompted its further evaluation in the application to therapy for CIA.

We next investigated the amount as used in study 1 (see study 4.1) or in the EAM study (see study 3.2) and on a 7 or 14 day immunization schedule.

Treatment started when group score was 3.5. This was done to have all groups starting with same score, as opposed to the range between 2.5 and 3.5 seen in the first study. The same dose of Enbrel as was used in the first study but was given every other day for the entire study period of 28 days.

CEL-2000 treatment limited the progression of disease, as indicated by reduced AI scores. Joint thickening, redness, immobilization of joints in a digit or total paw as measured for each of the 4 paws in the CIA mouse model of rheumatoid arthritis was reduced.

The outcomes of different CEL-2000 treatment schedules were compared with Enbrel. In this study, CEL-2000 treatment with 2 doses of 33 or 100 nmol (the dose used in the EAM study) given subcutaneously on days 0 and 7 as in the EAM study or 0 and 14 as for the HSV. Most regimes reduced the progression of arthritis disease to levels that were at least as good as those of mice treated with Enbrel (every other day for the 28 days of the study). Immunization of mice with the 100 nmol dose (3× treatment) on days 0 and 7 appeared to limit the progression of disease throughout the experimental period as shown in FIG. 2. The CEL-2003 links the corresponding murine CII254-273 sequence DAGEPGIAGFKGDQGPKGET (SEQ ID NO. 126) to the J ICBL. This trial suggests that the dosage and schedule of administration (time between initial and second immunization) are important parameters for CEL-2000 treatment. Use of a student "t" test analysis of treatment groups at day 7 days 14 and 21 to calculate the p value showed the 3× dose of CEL-2000 on day 0 and 14 followed by 3× on day 0 and 7 or 1× on day 0 and 7 is equivalent to 0 and 14 and slightly better than Enbrel every other day for all 28 days.

They do not restore the thickness to the no disease condition, but offer substantial benefit in reducing swelling.

Figure 4:
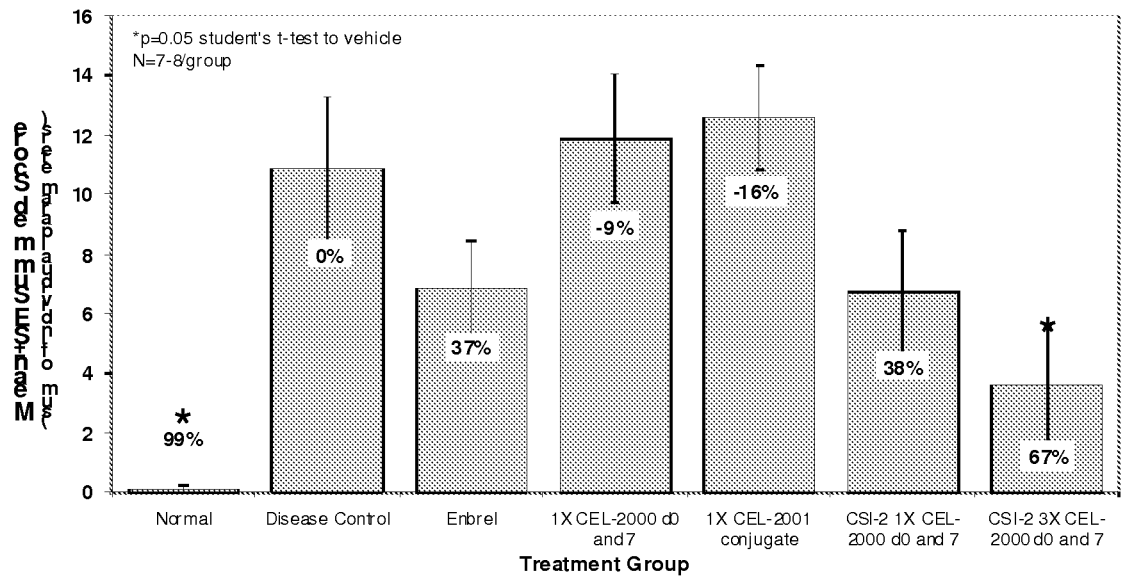
FIG. 4 represents a summary plot of the analysis performed cores of the 4 tissue areas, pannus membrane, inflammation, bone and cartilage from the following groups: Control no disease; CIA disease: CIA Disease Enbrel daily for 14 days continued for 2 more weeks before termination: CEL-2000 and CEL-2001 groups (vaccinated on day 0 and 7) from study 1 (FIG. 1) and from study 2 (FIG. 2) 1× and 3×CEL-2000 vaccinated groups on day 0 and 7.

The fourth study is for the CIA model CEL-2000 therapeutic vaccination; histopathology (study 4.4 see FIG. 4 and legend). At the termination of the experiments the animals were euthanized, the right rear feet were collected and stored individually in buffered formalin to be fixed in preparation for paraffin embedding, sectioning, staining and analysis. The feet in buffered formalin were sent for processing, reading and plotting of the data (representative sections from mid group specimens were photographed).

The pathologists scored the feet for disease pathology in 4 areas: inflammation, pannus, cartilage and bone. FIG. 4 is a summary plot of the analysis performed cores of the 4 areas from the following groups: Control no disease; CIA disease: CIA Disease Enbrel daily for 14 days continued for 2 more weeks before termination: CEL-2000 and CEL-2001 groups (vaccinated on day 0 and 7) from study 1 (FIG. 1) and from study 2 (FIG. 2) 1× and 3×CEL-2000 vaccinated groups on day 0 and 7.

Findings: Normal mouse hind paw and ankle from normal control animal are normal. CIA Disease mouse-hind paw and ankle from disease control animal have marked inflammation and moderate cartilage damage with mild pannus and bone resorption in the ankle and most digit joints. For CIA treated with Enbrel for 14 days hind paw and ankle from arthritic animal have mild inflammation and cartilage damage with minimal pannus and bone resorption in some digit joints. CIA plus CEL-2000 100 nmol on days 0 and 7—hind paw and ankle from arthritic animal treated with 3×CEL-2000 on days 0 and 7 have mild inflammation and minimal cartilage damage with minimal pannus and less bone resorption in fewer digit joints.

As is seen in FIG. 4, clearly the best protected group (least diseased) by all 4 criteria was the 3×CEL-2000 vaccinated mice on days 0 and 7. Clearly, 14 days after cessation of therapy with Enbrel, the mice had developed significant disease to levels that were not statistically different from untreated CIA mice, while the 3×CEL-2000 group even 3 weeks after immunization statistically had less disease pathology.

Hence, 2 vaccinations with CEL-2000 at 100 nmol provided more lasting effect than the multiple Enbrel treatments during the 28 day period. Still to be determined is the dose amount, frequency and timing of CEL-2000 beyond 28 days.

The fifth study is for the CIA-model CEL-2000 vaccination serum antibodies (study 4.5). Antibody production to the vaccine peptides, collagen or citrulline or components used to make vaccines were evaluated in mouse sera from the previous two sets of studies. As expected, all sera recognized the bovine collagen molecule used to induce the disease. Neither the dose, amount of vaccine, nor timing of vaccination seemed to affect the titer or isotype. These results are not surprising. No antibodies were detected with reactivity to the citrulline using a citrulline fibrin peptide substrate in the ELISA. Although some antibodies bound to the vaccine peptides, it did not seem as if specific antibodies were generated against the "J" T/ICBL but only to the collagen peptide portion. The CIA control and CIA plus Enbrel sera did not have any antibodies to the CEL-2000 vaccine components, although by 14 days after start of Enbrel therapy antibodies could be detected to Enbrel. (data not shown) L.E.A.P.S. conjugates serum cytokine studies As shown EAM and FIGS. 1-4 for CIA, L.E.A.P.S. vaccines are effective therapeutic vaccines and based on other data the action does not appear to involve antibodies. Examination of sera of other mice that received vaccines with the same "J" immune cell binding ligand (ICBL) as for CEL-2000, elicit a spectrum of cytokines including most notably IL12 within 3 days (well before any circulating antibodies) which progresses to include notably IFN-γ within 10 days.

The outcome of the immune response to vaccines is likely at least in part determined by the cytokines elicited by the immunization. Cytokines elicited by immunization of A/J mice with either the J, JgD or JH peptides emulsified in Seppic ISA51 were evaluated from serum obtained on days 3, 10 and 24 after immunization using Ray Biotech protein microarrays. Interestingly, the cytokine profiles of serum obtained from mice immunized with either the JgD or the JH vaccines contained very similar results which were different from the adjuvant alone or the unmodified J ICBL vaccinated control mice. By the third day after immunization, there were increases in IL12p70, RANTES, GMCSF, MCP5, MCP1, IL9, and IL17 but not TNF-α levels. The response progressed towards expression of IFN-γ by day 10 and 24 with continued IL12, RANTES, MCP5, IL9 production and increases in IL2, and IFN-γ production with a spike of IL17 on day 10. IL12 is produced by DCs and macrophages and promotes the development of Th1 responses which are characterized by production of IL2 and IFN-γ. These results indicate a progression from a DC1 (DC mediated response) to a Th1 type of response but the progression lacks the induction of the acute phase cytokines IL1, TNF-α and IL6 that would accompany a TLR activation of DC1 cells. The most remarkable change in cytokine levels upon immunization with the unmodified J ICBL was a reduction in IL10 levels, an effect that would also support a Th1 response. L.E.A.P.S. conjugates ex vivo studies A major goal of the L.E.A.P.S. vaccines has been to establish an ex vivo tissue culture system to study the effects and optimize the structure of the vaccines. It has been realized after many attempts with murine spleen cells, that these spleen cells are down regulated and or respond poorly to J-L.E.A.P.S. vaccines in tissue culture. Recent ex vivo studies with bone marrow cells indicate that two different J-L.E.A.P.S. vaccines (JH and JgD) can initiate and direct the nature of the subsequent immune response by production of IL12 but not TNF-α. It is the type of response that would counteract an antibody initiated hypersensitivity such as RA without exacerbating the condition by also stimulation production of TNF-α. Examples for CEL-2000:

Studies can determine whether the vaccine can stop arrest and or reverse the RA disease process once initiated whether bystander or epitope spreading is a key element or process behind the mechanism of action, the role of CD4CD25 Treg & IL17 in the vaccine's action, if CEL-2000 is also effective as a therapeutic vaccine in other species and models of arthritis, such as the CIA and AIA models in rats and mice. Develop adequate manufacturing source for having a sufficient reproducible supply of High Quality CEL-2000 peptide and standards for analytical assay development, formulation, stability studies and material available for animal safety/toxicity studies and phase I clinical studies. Conducting animal safety/toxicology studies necessary for IND filing and conducting phase I studies for CEL-2000 as a therapeutic peptide vaccine for rheumatoid arthritis. As a prelude to Phase 1 clinical trials, the effects of CEL-2000 should be evaluated on purified human dendritic cells (DCs). Differences in the nature of the mouse and human immune responses, especially DCs, can influence the outcomes of vaccine administration. The ability of CEL-2000 to elicit a response and cause the secretion of relevant cytokines in ex vivo studies of murine and human cells would provide the means to standardize treatment, evaluate some parameters of toxicity and help to define the mechanism of action of CEL-2000. $P_1$ for rheumatoid arthritis One antigen with defined epitopes recognized for rheumatoid arthritis (RA) is collagen type II including the peptide from position 254-273, (Krco et al., "Characterization of the antigenic structure of human type II collagen", J Immunol, 1996 Apr. 15; 156(8):2761-8; Myers et al., "Characterization of a tolerogenic T cell epitope of type II collagen and its relevance to collagen-induced arthritis", J Immunol., 1992 Aug. 15; 149(4):1439-43; Baldwin et al., "Structure of cDNA clones coding for human type II procollagen. The alpha 1(II) chain is more similar to the alpha 1(I) chain than two other alpha chains of fibrillar collagens", Biochem J. 1989 Sep. 1; 262(2):521-8).

For example, the collagen type II 254-273 is shown below.

```
TGGKPGIAGFKGEQGPKGEP       (SEQ ID NO. 83)
```

The improved variants of collagen type II 254-273 are as follows.

$$(\text{SEQ ID NO. 84})$$
$$X_{10}X_1X_1X_4X_7X_1X_3X_1X_1X_6X_4X_1X_2X_9X_1X_7X_4X_1X_2X_7$$
or
$$(\text{SEQ ID NO. 85})$$
$$X_{10}X_{15}X_4X_7X_{11}X_{15}X_6X_4X_{15}X_9X_1X_7X_4X_{15}X_7$$

Other various antigens often with defined epitopes recognized for rheumatoid arthritis (RA) are collagen type II 390-402.

For example, the collagen type II 390-402 as previously described as SEQ ID NO. 1 is shown below.

```
IAGFKGEQGPKGE          (SEQ ID NO. 1)
```

The improved variants of collagen type II 390-402 are as follows.

$$(\text{SEQ ID NO. 23})$$
$$X_3X_1X_1X_6X_4X_1X_2X_9X_1X_7X_4X_1X_2$$
or
$$X_{12}X_3X_1X_1X_6X_4X_1X_2X_9X_1X_7X_4X_1X_2$$

Peptides from type II human collagen (Krco et al. (1999 Identification of T cell determinants on human type II collagen recognized by HLA-DQ8 and HLA-DQ6 transgenic mice. J Immunol. 163 (3):1661-5) referred therein as Peptide G 54-73 is shown by the SEQ ID NO. 54.

The improved variants from type II human collagen are as follows.

$$X_2X_1X_2X_1X_1X_4X_7X_1X_4X_1X_1X_2X_4X_1X_7X_7X_1X_7X_9X_1 \quad \text{(SEQ ID NO. 55)}$$

or $$X_{12}X_2X_1X_2X_1X_1X_4X_7X_1X_4X_1X_1X_2X_4X_1X_7X_7X_1X_7X_9X_1 \quad \text{(SEQ ID NO. 56)}$$

Peptide K at positions 94-113 is shown by SEQ ID NO. 57 (Krco et al., id.).

GLDGAKGEAGAPGVKGESGS (SEQ ID NO. 57)

The improved variants of Peptide K at positions 94-113 SEQ ID NO. 57 are shown as follows.

$$X_1X_3X_2X_1X_1X_4X_1X_2X_1X_1X_1X_7X_1X_3X_4X_1X_2X_{10}X_1X_{10} \quad \text{(SEQ ID NO. 58)}$$

or $$X_{12}X_1X_3X_2X_1X_1X_4X_1X_2X_1X_1X_1X_7X_1X_3X_4X_1X_2X_{10}X_1X_{10} \quad \text{(SEQ ID NO. 59)}$$

or $$X_1X_{11}X_1X_1X_4X_1X_2X_1X_1X_1X_7X_1X_3X_4X_1X_2X_{10}X_1X_{10} \quad \text{(SEQ ID NO. 60)}$$

or $$X_{12}X_1X_{11}X_1X_1X_4X_1X_2X_1X_1X_1X_7X_1X_3X_4X_1X_2X_{10}X_1X_{10} \quad \text{(SEQ ID NO. 61)}$$

Peptide 44 at positions 554-573 is shown by SEQ ID NO. 62 (Krco et al., id.).

FERGAAGIAGDKGDRGDVGEK (SEQ ID NO. 62)

The improved variants of Peptide 44 at positions 554-573 of SEQ ID NO. 62 are shown as follows.

$$X_2X_4X_1X_1X_1X_1X_3X_1X_1X_2X_4X_1X_2X_4X_1X_2X_3X_1X_2 \ X_4 \quad \text{(SEQ ID NO. 63)}$$

or $$X_{12}X_2X_4X_1X_1X_1X_1X_3X_1X_1X_2X_4X_1X_2X_4X_1X_2X_3X_1X_2 \ X_4 \quad \text{(SEQ ID NO. 64)}$$

or $$X_2X_4X_1X_1X_1X_1X_3X_1X_1X_2X_4X_1X_2X_4X_1X_{11}X_1X_2 \ X_4 \quad \text{(SEQ ID NO. 65)}$$

or $$X_{12}X_2X_4X_1X_1X_1X_1X_3X_1X_1X_2X_4X_1X_2X_4X_1X_{11}X_1X_2 \ X_4 \quad \text{(SEQ ID NO. 66)}$$

The protein osteopontin (OPN) contains a peptide referred shown by the SEQ ID NO. 500 (Yamamoto et al., (2003) Essential role of the cryptic epitope SLAYGLR within osteopontin in a murine model of rheumatoid arthritis. J. Clin. Invest. 112:181-188).

SLAYGLR (SEQ ID NO. 67)

The improved variants osteopontin (OPN) are shown as follows.

$$X_{10}X_3X_1X_6X_1X_3X_4 \quad \text{(SEQ ID NO. 68)}$$

or $$X_{12}X_{10}X_3X_1X_6X_1X_3X_4 \quad \text{(SEQ ID NO. 69)}$$

A peptide naJP1 is indicated by SEQ ID NO. 70 (Prakken et al. (2004), Epitope-specific immunotherapy induces immune deviation of proinflammatory T cells in rheumatoid arthritis, Proc Nat Acad Sci USA 101:4228-4233).

QKRAAYKQYGHAAFE (SEQ ID NO. 70)

The improved variants of naJP1 are indicated by the following.

$$X_9X_4X_4X_1X_1X_6X_4X_9X_6X_1X_4X_1X_1X_7X_2 \quad \text{(SEQ ID NO. 71)}$$

or $$X_{12}X_9X_4X_4X_1X_1X_6X_4X_9X_6X_1X_4X_1X_1X_7X_2 \quad \text{(SEQ ID NO. 72)}$$

A peptide dnaJPv is indicated by SEQ ID NO. 73 (Prakken et al., id.).

ERAAYDQYGHAAFE (SEQ ID NO. 73)

The improved variants of dnaJPv are indicated by the following.

$$X_2X_4X_1X_1X_6X_2X_9X_6X_1X_4X_1X_1X_7X_2 \quad \text{(SEQ ID NO. 74)}$$

or $$X_{12}X_2X_4X_1X_1X_6X_2X_9X_6X_1X_4X_1X_1X_7X_2 \quad \text{(SEQ ID NO. 75)}$$

P$_2$ or TCBL EPITOPES

Type I diabetes is an autoimmune condition that most likely involves the Th1 pathway or if CTL is contemplated then the T1 pathway. Redirection of an antigen specific immune response from the Th1 to Th2 pathway may result in a non-diabetic condition.

One TCBL that is known to re-direct the Th1 to Th2 pathway is peptide "derG". The peptide "derG" can be conjugated to a specific antigen wherein the conjugated construct can direct the immune response to the peptide antigen toward the Th2 pathway. One example of such a construct is the L.E.A.P.S. construct.

Similarly, the TCBL peptide "G" or the improved version "derG" can direct the immune response down the Th2 pathway. The directed response is based upon data from several systems using peptide antigens from HSV, HIV, malaria, TB and murine myosin for antigen specific induction of antibody isotypes, DTH, and cytokine secretion (IL2, IL4 and IFN-γ). The basis for the directed response is also founded on observed protection upon pathogen challenge as well as immune cell types evaluated to demonstrate effects of treatment with L.E.A.P.S. constructs.

As shown previously, one TCBL sequence contemplated in the L.E.A.P.S. construct of the present invention is the peptide "G" shown by SEQ ID NO. 14.

```
NGQEEKAGVVSTGLIGGG        (SEQ ID NO. 14)
```

The improved variants of peptide "G" are shown by SEQ ID NO. 24.

```
                                  (SEQ ID NO. 24)
X9X1X9X2X2X4X1X1X3X3X5X10X1X3X3X1X1X1
or

X12X9X1X9X2X2X4X1X1X3X3X5X10X1X3X3X1X1X1
or

X12X9X1X9X11X4X1X1X11X5X10X1X11X1X1X1
```

One variant of the peptide "G" is the compound known as "derG" with a triglycine spacer linked to the N terminus of the antigens having the sequence shown by SEQ ID NO. 50.

```
DGQEEKAGVVSTGLIGGG        (SEQ ID NO. 20)
```

The improved variants of the peptide "G" are shown by the following.

```
                                  (SEQ ID NO. 78)
X2X1X9X2X2X4X1X1X3X3X5X10X1X3X3X1X1X1
or

X12X2X1X9X2X2X4X1X1X3X3X5X10X1X3X3X1X1X1
or (SEQ ID NO. 79)
X13X2X1X9X2X2X4X1X1X3X3X5X10X1X3X3X1X1X1

(SEQ ID NO. 25 or 80)
X12X2X1X9X11X4X1X1X11X5X10X1X11X1X1X1
```

Other TCBL's and spacers are also contemplated by the invention such as ICAM1, LFA-3 (aa26-42) as shown by SEQ ID NO. 4 (Osborn et al., supra).

```
VLWKKQKDKVAELENSE        (SEQ ID NO. 4)
```

The improved variants of ICAM-1, LFA-3 (aa26-42) are shown by SEQ ID NO. 26.

```
                                  (SEQ ID NO. 26)
X3X3X6X4X4X9X4X2X4X3X1X2X3X2X9X5X2
or

X12X3X3X6X4X4X9X4X2X4X3X1X2X3X2X9X5X2
or

X12X11X6X4X4X9X4X2X4X3X1X11X9X5X2
or

X12X11X6X4X4X9X4X2X4X3X1X13X9X5X2
```

The peptide J is shown by the SEQ ID NO. 21.

```
DLLKNGERIEKVEGGG        (SEQ ID NO. 21)
```

The improved variants of above peptide are shown by SEQ ID NO. 27.

```
                                  (SEQ ID NO. 27)
X2X3X3X4X9X1X2X4X3X2X4X3X2
or

X12X2X3X3X4X9X1X2X4X3X2X4X3X2
or

X12X11X4X9X1X2X4X11X4X11
or

X12X13X4X9X1X2X4X11X4X11
```

The extended version of the peptide J is shown by the SEQ ID NO. 52.

```
DLLKNGERIEKVEGGG        (SEQ ID NO. 52)
```

The improved variants of above peptide are shown by SEQ ID NO. 53.

```
                                  (SEQ ID NO. 53)
X2X3X3X4X9X1X2X4X3X2X4X3X2X1X1X1
or

X12X2X3X3X4X9X1X2X4X3X2X4X3X2X1X1X1
or

X12X11X4X9X1X2X4X11X4X11X1X1X1
or

X12X13X4X9X1X2X4X11X4X11X1X1X1
```

Examples of TNF peptides known to activate macrophages are amino acids 70-80 as shown in SEQ ID NO. 5 (Britton et al., A Tumor Necrosis Factor Mimetic Peptide Activates a Murine Macrophage Cell Line To Inhibit Mycobacterial Growth in a Nitric Oxide-Dependent Fashion 1998, I & I, 66:2122).

```
PSTHVLITHTI        (SEQ ID NO. 5)
```

The improved variants of the above TNF peptides are shown by SEQ ID NO. 28.

```
                                  (SEQ ID NO. 28)
X7X5X10X4X3X3X3X10X4X10X3
or

X12X7X5X10X4X3X3X3X10X4X10X3
or

X12X7X5X10X4X11X10X4X10X3
or

X12X7X5X10X4X13X10X4X10X3
```

The antagonist peptide of another region of TNF peptides is shown by SEQ ID NO. 29 (Chirinos-Rojas et al., supra).

```
DFLPHYKNTSLGHRP        (SEQ ID NO. 29)
```

The improved variants of above TNF peptides are shown by SEQ ID NO. 30.

$$X_2X_6X_3X_7X_4X_6X_4X_9X_{10}X_5X_3X_1X_4X_4X_7 \quad \text{(SEQ ID NO. 30)}$$

or $$X_{12}X_2X_6X_3X_7X_4X_6X_4X_9X_{10}X_5X_3X_1X_4X_4X_7$$

Still further, the TCBLs contemplated by the invention can be selected from any of the sequence above but are not restricted to just the LFA-3 or FasL sequences described above (Lie et al. or Tomita et al., supra).

For example, another TCBL can be the Hu IL-10 aa152-160 shown by SEQ ID NO. 15 as previously described.

AYMTMKIRN        (SEQ ID NO. 15)

The improved variants of Hu IL-10 aa152-160 are shown by SEQ ID NO. 31.

$$X_1X_6X_8X_{10}X_8X_4X_3X_4X_9 \quad \text{(SEQ ID NO. 31)}$$

or $$X_{12}X_1X_6X_8X_{10}X_8X_4X_3X_4X_9$$

Two discontinuous epitopes of IL-10 as shown by SEQ ID NO. 32 are also contemplated by the invention for redirection of immune responses (Gesser et al., supra; Lie et al. supra and Tomita et al. supra).

DNQLLETCKQDRLRNRRGNGSSTHFEGNLPC        (SEQ ID NO. 32)

The improved variants of above peptide IL-10 as shown by SEQ ID NO. 32 are shown by SEQ ID NO. 33.

$$\text{(SEQ ID NO. 33)}$$
$$X_2X_9X_9X_3X_3X_2X_{10}X_5X_4X_9X_2X_4X_3X_4X_9X_4X_4X_1X_9X_1X_5X_5X_{10}X_4$$
$$X_6X_2X_1X_9X_3X_7X_5$$

or $$X_{12}X_2X_9X_9X_3X_3X_2X_{10}X_5X_4X_9X_2X_4X_3X_4X_9X_4X_4X_1X_9X_1X_5X_5$$
$$X_{10}X_4X_6X_2X_1X_9X_3X_7X_5$$

or $$X_{12}X_2X_9X_9X_{11}X_{10}X_5X_4X_9X_2X_4X_3X_4X_9X_4X_4X_1X_9X_1X_5X_5X_{10}X_4$$
$$X_6X_2X_1X_9X_3X_7X_5$$

or $$X_{12}X_2X_9X_9X_{13}X_{10}X_5X_4X_9X_2X_4X_3X_4X_9X_4X_4X_1X_9X_1X_5X_5X_{10}X_4$$
$$X_6X_2X_1X_9X_3X_7X_5$$

Another TCBL sequence contemplated by the invention is the α3 domain amino acids 223-229 of the human MHC I TCBL peptide E with a spacer. The sequence is shown by SEQ ID NO. 16.

DQTQDTEGGC        (SEQ ID NO. 16)

The improved variants of α3 domain amino acids 223-229 are shown by SEQ ID NO. 34.

$$X_2X_9X_{10}X_9X_2X_{10}X_2X_1X_1X_5 \quad \text{(SEQ ID NO. 34)}$$

or $$X_{12}X_2X_9X_{10}X_9X_2X_{10}X_2X_1X_1X_5$$

The IL-1β at positions 163-171 shown by SEQ ID NO. 13 can also be used to form a peptide construct according to another embodiment of this invention (Bajpai et al., supra; Beckers et al., supra; Fresca et al., supra; Antoni et al., supra).

VQGEESNDK        (SEQ ID NO. 13)

The improved variants of IL-1β at positions 163-171 are shown by SEQ ID NO. 35.

$$X_3X_9X_1X_2X_2X_5X_9X_2X_4 \quad \text{(SEQ ID NO. 35)}$$

or $$X_{12}X_3X_9X_1X_2X_2X_5X_9X_2X_4$$

or $$X_{12}X_3X_9X_1X_{11}X_5X_9X_2X_4$$

However, constructs containing spacers are also contemplated in additional embodiments. For example, peptide "J" with a triglycine spacer shown by SEQ ID NO. 21 can be formed.

DLLKNGERIEKVEGGG        (SEQ ID NO. 21)

The improved variants of peptide "J" with the triglycine spacer are shown by SEQ ID NO. 36.

$$\text{(SEQ ID NO. 36)}$$
$$X_2X_3X_3X_4X_9X_1X_2X_4X_3X_2X_4X_3X_2X_1X_1X_1$$

or $$X_{12}X_2X_3X_3X_4X_9X_1X_2X_4X_3X_2X_4X_3X_2X_1X_1X_1$$

or $$X_{12}X_{11}X_4X_9X_1X_2X_4X_{11}X_4X_{11}X_1X_1X_1$$

or $$X_{12}X_{13}X_4X_9X_1X_2X_4X_{11}X_4X_{11}X_1X_1X_1$$

A TCBL for the homologue of the C-terminal of human IL-10 (AYMTMKIRN), which is equivalent to SEQ ID NO. 15, is shown by SEQ ID NO. 15 (Kurte et al., "A Synthetic Peptide Homologous to Functional Domain of Human IL-10 Down-Regulates Expression of MHC Class I and Transporter Associated with Antigen Processing 1/2 in Human Melanoma Cells", J of Immunol 2004, 173:1731-1737).

The improved variants of the TCBL for the homologue of the C-terminal of human pf IL-10 are as follows.

(SEQ ID NO. 76)

$X_1X_6X_8X_{10}X_8X_4X_3X_4X_9$ (SEQ ID NO. 77)

$X_{12}X_1X_6X_8X_{10}X_8X_4X_3X_4X_9$

Variable Linker Sequences

The improved versions of many of the sequence of the invention can contain multiple glycines 3 to 6 glycines in length. In particular, carbodiimides are commonly used to modify proteins on their carboxylate groups. They react with proteins at about pH of 5 to 6 and can be used either alone or in combination with amines to create new amide bonds off the carboxyl. The reaction producing various new adducts are well known within the art.

For example, a triglycine with or without one or two serines to separate two portions of the conjugate can be made by carbidiimide modification. The triglycine with a single serine is shown by the SEQ ID NO. 7.

GGGS  (SEQ ID NO. 7)

The improved variants of the triglycine with a single serine are shown by SEQ ID NO. 37.

(SEQ ID NO. 37)
$X_1X_1X_1X_5$
or
$X_{12}X_1X_1X_1X_5$

For a trigylcine with two serines, the spacer is shown by SEQ ID NO. 8.

GGGSS  (SEQ ID NO. 8)

The improved variants of trigylcine with two serines are shown by SEQ ID NO. 38.

(SEQ ID NO. 38)
$X_1X_1X_1X_5X_5$
or
$X_{12}X_1X_1X_1X_5X_5$

For four glycines with a single serine, the spacer is shown by SEQ ID NO. 9.

GGGGS  (SEQ ID NO. 9)

The improved variants of four glycines with a single serine are shown by SEQ ID NO. 39.

(SEQ ID NO. 39)
$X_1X_1X_1X_1X_5$
or
$X_{12}X_1X_1X_1X_1X_5$

An example of four glycines with a two serines is shown by the SEQ ID NO. 10.

GGGGSS  (SEQ ID NO. 10)

The improved variants of four glycines with a two serines are shown by SEQ ID NO. 40.

(SEQ ID NO. 40)
$X_1X_1X_1X_1X_5$
or
$X_{12}X_1X_1X_1X_1X_5$

An example of a spacer having three glycines interspaced with a single serine followed by three glycines and a serine is shown by the SEQ ID NO. 11.

GGGSGGGS  (SEQ ID NO. 11)

The improved variants of a spacer having three glycines interspaced with a single serine followed by three glycines and a serine are shown by SEQ ID NO. 41.

(SEQ ID NO. 41)
$X_1X_1X_1X_5X_1X_1X_1X_5$
or
$X_{12}X_1X_1X_1X_5X_1X_1X_1X_5$

Other conventional linkages contemplated by the invention are direct linkages taught by the aforementioned U.S. Pat. No. 5,652,342. Examples of bifunctional linkers which can be employed in the present invention to covalently link the T cell specific binding ligand and antigen associated with disease or a causative agent of disease, or epitope thereof include N-succinimidyl-3-(2-pyridyldthio)propinate (hereinafter "SPDP") (Pharmacia, Piscataway, N.J.), which activates and allows formation of a bridge between two sulfhydryl groups of cysteines or a bridge between a derivatized (propinatedthiolyated) primary amino group and a cysteine; m-maleimidobenzoyl-N-hydroxysuccimide ester (hereinafter "MBS") (Pierce Chemical, Rockford, Ill.), which activates an amino group and then couples by a sulfhydryl group to a cysteine sulfydryl so as to form a disulfide bond between the two polypeptides; and 1-ethyl-3-(3dimethylaminopropyl)carbodiimide (hereinafter "EDC") (Pierce Chemical, Rockford, Ill.), which can cross-link two polypeptides by sequentially activating the carboxyl group of one polypeptide and then adding such to an amino group of another polypeptide. N-isocyano-ethylmorphlin, bis-diazotized-benzidine, benzoquone and glutaraldehyde, which are other reagents commonly employed to link polypeptides, can be employed in the present invention and are available from Pierce Chemical, Rockford, Ill.; Eastman Kodak Chemicals, Rochester, N.Y.; Serva, Westbury, N.Y.; Sigma Chemical Co., St. Louis, Mo.; and E. Merck, Darnstadt, West Germany (Briand et al., Synthetic peptides as antigens: pitfalls of conjugation methods, 1985, J. Immunol. Meth., 78: 59; Kitagawa et al., Enzyme coupled immunoassay of insulin using a novel coupling reagent J. Biochem., 79: 233 (1976); Liu et al., Biochem., 18: 690 (1979); Ternynck et al., Immunochem., 14: 767 (1977); and Drevin et al., Covalent coupling of proteins to erythrocytes by isocyanide. A new, sensitive and mild technique for identification and estimation of antibodies by passive hemagglutination J. Immunol. Meth., 77: 9 (1985)). One example of a conventional heterofunctional linker is shown by an eight amino acid group is shown by SEQ ID NO. 12.

LRGGGGSS  (SEQ ID NO. 12)

The improved variants of above peptide are shown by SEQ ID NO. 42.

$$X_3X_4X_1X_1X_1X_1X_5X_5 \quad \text{(SEQ ID NO. 42)}$$

or $$X_{12}X_3X_4X_1X_1X_1X_1X_5X_5$$

The invention also contemplates formation of a single peptide from two smaller discontinuous peptides of IL-10 that are 11.2 angstroms in length to form a TCBL to redirect from a Th1 to a Th2 in combination with, for example, the IDDM, PV or MS inducing epitopes (Reineke et al., supra).

Linkers of varying lengths to form a single chain may also be used. For example, GGGS (SEQ ID NO. 7), GGGGS (SEQ ID NO. 9) including 1 or more repeats of the tetrapeptide or pentapeptide can be formed into the sequence shown by the following SEQ ID NO. 22 (Uger et al., supra).

GGGSGTGSGSGS (SEQ ID NO. 22)

The improved variants of SEQ ID NO. 22 are shown by SEQ ID NO. 43.

(SEQ ID NO. 43)

$X_1X_1X_1X_5X_1X_{10}X_1X_5X_1X_5X_1X_5$ or $X_{12}X_1X_1X_1X_5X_1X_{10}X_1X_5X_1X_5X_1X_5$

It is also noted that any of the linkers provided herein may result in a tertiary structure which might be of use to form a more avid TCBL.

The invention will now be described in further detail by way of representative examples; however, the present invention is not limited to the examples and should be construed to cover the subject matter as defined in appended claims and equivalents thereto.

As part of the understanding of the Examples, it is understood that any of the Examples may contain alternatively the above mentioned variable sequence listings SEQ ID NO.'s 7, 37, 8, 38, 10, 40, 11, 41, 12, 42, 22, and 43. However, for purposes of exemplifying the Examples a spacer GGG is shown.

Example 1

Rheumatoid arthritis (RA), is a condition where excess tumor necrosis factor-α (TNF-α) production is a problem and a major point of attack for new treatments. The following peptide construct is prepared for use in the treatment of RA:

(SEQ ID NO. 86)

PSTHVLITHTI-<u>GGG</u>-TGGKPGIAGFKGEQGPKGEP

TNF-$\alpha_{70-80}$ linker C-$II_{254-273}$ where the peptide TNF-$\alpha_{70-80}$ is known to activate macrophages (10) and the collagen type II peptide C-$II_{254-273}$ (TGGKPGIAGFKGEQGPKGEP (SEQ ID NO. 83)) is an epitope associated with RA. Thus, this peptide construct will be useful to achieve abortative T cell modulation since the improper sequence of events occurs with a binding that precludes the normal activation process.

Similar effects will be achieved using a peptide construct similar to the above but obtained by using, in place of TNF-α peptide α70-80, the following: TNF-α antagonist: DFLPHYKNTSLGHRP (SEQ ID NO.18) (Chirinos-Rojas et al., supra) as follows.

(SEQ ID NO. 87)

DFLPHYKNTSLGHRP-GGG-TGGKPGMFKGEQGPKGEP

TNF-αantagonist peptide spacer CII254-273

Example 2

As a different approach for treating RA, the following peptide construct is prepared utilizing peptide G or a derivative thereof (derG) (DGQEEKAGVVSTGLI (SEQ ID NO. 20)) from MHC-IIβ2 (135-149) to redirect the immune response from a Th1 to a Th2:

(SEQ ID NO. 88)

NGQEEKAGVVSTGLI-<u>GGGGS</u>-TGGKPGIAGFKGEQGPKGEP (MHC-IIβ2) linker C-$II_{254-273}$ or (SEQ ID NO. 89)

DGQEEKAGVVSTGLI-<u>GGGGS</u>-TGGKPGIAGFKGEQGPKGEP derG(MHC-IIβ2) linker C-$II_{254-273}$ or (SEQ ID NO. 90)

DGQEEKAGVVSTGLI-<u>GGG</u>-TGGKPGIAGFKGEQGPKGEP derG(MHC-IIβ2) linker C-$II_{254-273}$

Example 3

The following peptide constructs are improved versions of SEQ ID NO. 90 in Example 2 prepared by utilizing the improved SEQ ID NO. 78-80, and its associated variants, as the TCBL, and the improved SEQ ID NO. 84 as the antigenic epitope.

(SEQ ID NO. 91)

$X_2X_1X_9X_2X_2X_4X_1X_1X_3X_3X_5X_{10}X_1X_3X_3X_1X_1X_1X_{10}X_1X_1X_4X_7X_1$ $X_3X_1X_1X_6X_4X_1X_2X_9X_1X_7X_4X_1X_2X_7$ (SEQ ID NO. 92)

$X_{12}X_2X_1X_9X_2X_2X_4X_1X_1X_3X_3X_5X_{10}X_1X_3X_3X_1X_1X_1X_{10}X_1X_1X_4$ $X_7X_1X_3X_1X_1X_6X_4X_1X_2X_9X_1X_7X_4X_1X_2X_7$ (SEQ ID NO. 93)

$X_{13}X_2X_1X_9X_2X_2X_4X_1X_1X_3X_3X_5X_{10}X_1X_3X_3X_1X_1X_1X_{10}X_1X_1X_4$ $X_7X_1X_3X_1X_1X_6X_4X_1X_2X_9X_1X_7X_4X_1X_2X_7$ (SEQ ID NO. 94)

$X_{12}X_2X_1X_9X_{11}X_4X_1X_1X_{11}X_5X_{10}X_1X_{11}X_1X_1X_1X_{10}X_1X_1X_4X_7X_1$ $X_3X_1X_1X_6X_4X_1X_2X_9X_1X_7X_4X_1X_2X_7$

Example 4

The following peptide constructs are improved versions of SEQ ID NO. 90 in Example 2 prepared by utilizing the improved SEQ ID NO. 78-80, and its variants as the TCBL, and the improved SEQ ID NO. 85 as the antigenic epitope.

(SEQ ID NO. 95)
$X_2X_1X_9X_2X_2X_4X_1X_1X_3X_3X_5X_{10}X_1X_3X_3X_1X_1X_1X_{10}X_{15}X_4X_7X_{11}$
$X_{15}X_6X_4X_{15}X_9X_1X_7X_4X_{15}X_7$ (SEQ ID NO. 96)
$X_{12}X_2X_1X_9X_2X_2X_4X_1X_1X_3X_3X_5X_{10}X_1X_3X_3X_1X_1X_1X_{10}X_{15}X_4X_7$
$X_{11}X_{15}X_6X_4X_{15}X_9X_1X_7X_4X_{15}X_7$ (SEQ ID NO. 97)
$X_{13}X_2X_1X_9X_2X_2X_4X_1X_1X_3X_3X_5X_{10}X_1X_3X_3X_1X_1X_1X_{10}X_{15}X_4X_7$
$X_{11}X_{15}X_6X_4X_{15}X_9X_1X_7X_4X_{15}X_7$ (SEQ ID NO. 98)
$X_{12}X_2X_1X_9X_{11}X_4X_1X_1X_{11}X_5X_{10}X_1X_1X_1X_1X_{10}X_{15}X_4X_7X_{11}$
$X_{15}X_6X_4X_{15}X_9X_1X_7X_4X_{15}X_7$

Example 5

The following peptide construct is an example of a variant of SEQ ID NO. 21 (peptide J) as the TCBL and SEQ ID NO. 83 as the antigenic epitope.

(SEQ ID NO. 99)
DLLKNGERIEKVEGGGTGGKPGIAGFKGEQGPKGEP

Data showing the activity of this SEQ ID NO. 99 and of SEQ ID NO. 89 and SEQ ID NO 83 which are less effective in the murine CIA model of RA are shown in studies 1-5 and FIGS. 1-4.

Example 6

The following peptide constructs are improved versions of SEQ ID NO. 99 prepared by utilizing the improved SEQ ID NO. 27 (peptide J), and its variants as the TCBL, and the improved SEQ ID NO. 84 as the antigenic epitope.

(SEQ ID NO. 100)
$X_2X_3X_3X_4X_9X_1X_2X_4X_3X_2X_4X_3X_2X_1X_1X_{10}X_1X_1X_4X_7X_1X_3X_1$
$X_1X_6X_4X_1X_2X_9X_1X_7X_4X_1X_2X_7$ (SEQ ID NO. 101)
$X_{12}X_2X_3X_3X_4X_9X_1X_2X_4X_3X_2X_4X_3X_2X_1X_1X_1X_{10}X_1X_1X_4X_7X_1X_3$
$X_1X_1X_6X_4X_1X_2X_9X_1X_7X_4X_1X_2X_7$ (SEQ ID NO. 102)
$X_{12}X_{11}X_4X_9X_1X_2X_4X_{11}X_4X_{11}X_1X_1X_1X_{10}X_1X_1X_4X_7X_1X_3X_1X_1$
$X_6X_4X_1X_2X_9X_1X_7X_4X_1X_2X_7$ (SEQ ID NO. 103)
$X_{12}X_{13}X_4X_9X_1X_2X_4X_{11}X_4X_{11}X_1X_1X_1X_{10}X_1X_1X_4X_7X_1X_3X_1X_1$
$X_6X_4X_1X_2X_9X_1X_7X_4X_1X_2X_7$

Example 7

The following peptide constructs are improved versions of SEQ ID NO. 99 prepared by utilizing the improved SEQ ID NO. 27, and its variants as the TCBL and the improved SEQ ID NO. 85 as the antigenic epitope.

(SEQ ID NO. 104)
$X_2X_3X_3X_4X_9X_1X_2X_4X_3X_2X_4X_3X_2X_1X_1X_1X_{10}X_{15}X_4X_7X_{11}X_{15}X_6$
$X_4X_{15}X_9X_1X_7X_4X_{15}X_7$ (SEQ ID NO. 105)
$X_{12}X_2X_3X_3X_4X_9X_1X_2X_4X_3X_2X_4X_3X_2X_1X_1X_1X_{10}X_{15}X_4X_7X_{11}$
$X_{15}X_6X_4X_{15}X_9X_1X_7X_4X_{15}X_7$ (SEQ ID NO. 106)
$X_{12}X_{11}X_4X_9X_1X_2X_4X_{11}X_4X_{11}X_1X_1X_1X_{10}X_{15}X_4X_7X_{11}X_{15}X_6X_4$
$X_{15}X_9X_1X_7X_4X_{15}X_7$ (SEQ ID NO. 107)
$X_{12}X_{13}X_4X_9X_1X_2X_4X_{11}X_4X_{11}X_1X_1X_1X_{10}X_{15}X_4X_7X_{11}X_{15}X_6X_4$
$X_{15}X_9X_1X_7X_4X_{15}X_7$

Reverso Forms

Example 8

The following peptide construct is an example of a variant of SEQ ID NO. 83 as the antigenic epitope and SEQ ID NO. 20 as the TCBL in a reverso form.

(SEQ ID NO. 108)
TGGKPGIAGFKGEQGPKGEPGGGDGQEEKAGVVSTGLI

Example 9

The following peptide constructs are improved versions of SEQ ID NO. 108 in Example 8 prepared by utilizing the improved SEQ ID NO. 78-80, and its associated variants, as the TCBL, and the improved SEQ ID NO. 84 as the antigenic epitope, in a reverso form.

(SEQ ID NO. 109)
$X_{10}X_1X_1X_4X_7X_1X_3X_1X_1X_6X_4X_1X_2X_9X_1X_7X_4X_1X_2X_7X_1X_1X_2$
$X_1X_9X_2X_2X_4X_1X_1X_3X_3X_5X_{10}X_1X_3X_3$ (SEQ ID NO. 110)
$X_{10}X_1X_1X_4X_7X_1X_3X_1X_1X_6X_4X_1X_2X_9X_1X_7X_4X_1X_2X_7X_1X_1X_{12}$
$X_2X_1X_9X_2X_2X_4X_1X_1X_3X_3X_5X_{10}X_1X_3X_3$ (SEQ ID NO. 111)
$X_{10}X_1X_1X_4X_7X_1X_3X_1X_1X_6X_4X_1X_2X_9X_1X_7X_4X_1X_2X_7X_1X_1X_{13}$
$X_2X_1X_9X_2X_2X_4X_1X_1X_3X_3X_5X_{10}X_1X_3X_3$ (SEQ ID NO. 112)
$X_{10}X_1X_1X_4X_7X_1X_3X_1X_1X_6X_4X_1X_2X_9X_1X_7X_4X_1X_2X_7X_1X_1X_{12}$
$X_2X_1X_9X_{11}X_4X_1X_1X_{11}X_5X_{10}X_1X_{11}$

Example 10

The following peptide constructs are improved versions of SEQ ID NO. 108 in Example 8 prepared by utilizing the improved SEQ ID NO. 78, and its variants as the TCBL, and the improved SEQ ID NO. 85 as the antigenic epitope, in a reverso form.

(SEQ ID NO. 113)
$X_{10}X_{15}X_4X_7X_{11}X_{15}X_6X_4X_{15}X_9X_1X_7X_4X_{15}X_7X_1X_1X_1X_2X_1X_9X_2$
$X_2X_4X_1X_1X_3X_3X_5X_{10}X_1X_3X_3$ (SEQ ID NO. 114)
$X_{10}X_{15}X_4X_7X_{11}X_{15}X_6X_4X_{15}X_9X_1X_7X_4X_{15}X_7X_1X_1X_1X_{12}X_2X_1$
$X_9X_2X_2X_4X_1X_1X_3X_3X_5X_{10}X_1X_3X_3$ (SEQ ID NO. 115)
$X_{10}X_{15}X_4X_7X_{11}X_{15}X_6X_4X_{15}X_9X_1X_7X_4X_{15}X_7X_1X_1X_1X_{13}X_2X_1$
$X_9X_2X_2X_4X_1X_1X_3X_3X_5X_{10}X_1X_3X_3$ (SEQ ID NO. 116)
$X_{10}X_{15}X_4X_7X_{11}X_{15}X_6X_4X_{15}X_9X_1X_7X_4X_{15}X_7X_{12}X_1X_1X_1X_2X_1$
$X_9X_{11}X_4X_1X_1X_{11}X_5X_{10}X_1X_{11}$

Example 11

The following peptide construct is an example of a variant of SEQ ID NO. 83 as the antigenic epitope and SEQ ID NO. 21 as the TCBL.

```
TGGKPGIAGFKGEQGPKGEPGGGDLLKNGERIEKVE    (SEQ ID NO. 117)
```

Example 12

The following peptide constructs are improved versions of SEQ ID NO. 116 in Example 11 prepared by utilizing the improved SEQ ID NO. 27, and its associated variants, as the TCBL, and the improved SEQ ID NO. 84 as the antigenic epitope, in a reverso form.

(SEQ ID NO. 118)
$X_{10}X_1X_1X_4X_7X_1X_3X_1X_1X_6X_4X_1X_2X_9X_1X_7X_4X_1X_2X_7X_1X_1X_1X_2$
$X_3X_3X_4X_9X_1X_2X_4X_3X_2X_4X_3X_2$ (SEQ ID NO. 119)
$X_{10}X_1X_1X_4X_7X_1X_3X_1X_1X_6X_4X_1X_2X_9X_1X_7X_4X_1X_2X_7X_1X_1X_1X_{12}$
$X_2X_3X_3X_4X_9X_1X_2X_4X_3X_2X_4X_3X_2$ (SEQ ID NO. 120)
$X_{10}X_1X_1X_4X_7X_1X_3X_1X_1X_6X_4X_1X_2X_9X_1X_7X_4X_1X_2X_7X_1X_1X_1X_{12}$
$X_{11}X_4X_9X_1X_2X_4X_{11}X_4X_{11}$ (SEQ ID NO. 121)
$X_{10}X_1X_1X_4X_7X_1X_3X_1X_1X_6X_4X_1X_2X_9X_1X_7X_4X_1X_2X_7X_1X_1X_1X_{12}$
$X_{13}X_4X_9X_1X_2X_4X_{11}X_4X_{11}$

Example 13

The following peptide constructs are improved versions of SEQ ID NO. 116 in Example 11 prepared by utilizing the improved SEQ ID NO. 27, and its variants as the TCBL, and the improved SEQ ID NO. 85 as the antigenic epitope, in a reverso form.

(SEQ ID NO. 122)
$X_{10}X_{15}X_4X_7X_{11}X_{15}X_6X_4X_{15}X_9X_1X_7X_4X_{15}X_7X_1X_1X_1X_2X_1X_9X_2$
$X_2X_4X_1X_1X_3X_3X_5X_{10}X_1X_3X_3$ (SEQ ID NO. 123)
$X_{10}X_{15}X_4X_7X_{11}X_{15}X_6X_4X_{15}X_9X_1X_7X_4X_{15}X_7X_1X_1X_1X_{12}X_2X_1$
$X_9X_2X_2X_4X_1X_1X_3X_3X_5X_{10}X_1X_3X_3$ (SEQ ID NO. 124)
$X_{10}X_{15}X_4X_7X_{11}X_{15}X_6X_4X_{15}X_9X_1X_7X_4X_{15}X_7X_1X_1X_1X_{13}X_2X_1$
$X_9X_2X_2X_4X_1X_1X_3X_3X_5X_{10}X_1X_3X_3$ (SEQ ID NO. 125)
$X_{10}X_{15}X_4X_7X_{11}X_{15}X_6X_4X_{15}X_9X_1X_7X_4X_{15}X_7X_{12}X_1X_1X_1X_2X_1$
$X_9X_{11}X_4X_1X_1X_{11}X_5X_{10}X_1X_{11}$

Example 14

The following peptide construct is an example of a variant of SEQ ID NO. 20 as the TCBL and SEQ ID NO. 1 as the antigenic epitope as shown in SEQ ID NO. 44.

```
DGQEEKAGVVSTGLIGGGIAGFKGEQGPKGE    (SEQ ID NO. 44)
```

Example 15

The following reverse peptide construct is an example of a variant of SEQ ID NO. 1 as the antigenic epitope and SEQ ID NO. 20 as the TCBL as shown in SEQ ID NO. 46.

```
IAGFKGEQGPKGEGGGDGQEEKAGVVSTGLI    (SEQ ID NO. 46)
```

Example 16

The following peptide construct is an example of a variant of SEQ ID NO. 21 as the TCBL and SEQ ID NO. 1 as the antigenic epitope as shown in SEQ ID NO. 48.

```
DLLKNGERIEKVEGGGIAGFKGEQGPKGE    (SEQ ID NO. 48)
```

Example 17

The following reverse peptide construct is an example of a variant of SEQ ID NO. 1 as the antigenic epitope and SEQ ID NO. 21 as the TCBL as shown in SEQ ID NO. 50.

```
IAGFKGEQGPKGEGGGDLLKNGERIEKVE    (SEQ ID NO. 50)
```

Example 18

The following peptide construct is an example of a variant of SEQ ID NO. 20 as the TCBL and SEQ ID NO. 54 as the antigenic epitope as shown in SEQ ID NO. 81.

```
DGQEEKAGVVSTGLIGGGDGEAGKPGKAGERGPPGPQG    (SEQ ID NO. 81)
```

The invention being thus described, it will be obvious that the same may be varied in many ways such that each of SEQ ID NO. 57, SEQ ID NO. 62, SEQ ID NO. 67, SEQ ID NO. 70, and SEQ ID NO. 73 or any of the antigenic peptides contained herein can be constructed so as outlined including a reversed form as shown by Examples 8-13, 15 and 17. Such variations are not to be regarded as a departure from the spirit scope of the invention and all such modifications are intended to be included within the scope of the following claims.

What is claimed is:

1. An immunomodulatory peptide construct having the formula $P_1$-x-$P_2$ where $P_1$ is a derivative of SEQ ID NO. 1;

$P_2$ is selected from the group consisting of SEQ ID NO. 14, SEQ ID NO. 20, SEQ ID NO. 4, SEQ ID NO. 21, SEQ ID NO. 52, SEQ ID NO. 5, SEQ ID NO. 15, SEQ ID NO. 32, SEQ ID NO. 16, SEQ ID NO. 13 and SEQ ID NO. 29;

x is a direct bond or linker for covalently bonding $P_1$ and $P_2$; wherein x is bound to a C terminus of peptide $P_2$ and an N terminus of peptide $P_1$; and wherein the derivative of SEQ ID NO. 1 has a change to SEQ ID NO. 1 selected from the group consisting of:
i) a replacement of an alanine residue at position 2 with a glycine residue;
ii) a replacement of a glycine residue at position 3 with an alanine residue;
iii) a replacement of a glycine residue at position 6 with an alanine residue;
iv) a replacement of a glutamic acid residue at position 7 with an aspartic acid residue;
v) a replacement of a glutamine residue at position 8 with an asparagine residue;
vi) a replacement of a glycine residue at position 9 with an alanine residue;
vii) a replacement of a glycine residue at position 12 with an alanine residue; or
viii) a replacement of a glutamic acid residue at position 13 with an aspartic acid residue.

2. A peptide construct having the formula $P_1$-x-$P_2$ where $P_1$ is a derivative of SEQ ID NO. 1;

$P_2$ is selected from the group consisting of SEQ ID NO. 14, SEQ ID NO. 20, SEQ ID NO. 4, SEQ ID NO. 21, SEQ ID NO. 52, SEQ ID NO. 5, SEQ ID NO. 15, SEQ ID NO. 32, SEQ ID NO. 16, SEQ ID NO. 13 and SEQ ID NO. 29; and x links $P_1$ and $P_2$; and wherein the derivative of SEQ ID NO. 1 has a change to SEQ ID NO. 1 selected from the group consisting of:
i) a replacement of an alanine residue at position 2 with a glycine residue;
ii) a replacement of a glycine residue at position 3 with an alanine residue;
iii) a replacement of a glycine residue at position 6 with an alanine residue;
iv) a replacement of a glutamic acid residue at position 7 with an aspartic acid residue;
v) a replacement of a glutamine residue at position 8 with an asparagine residue;
vi) a replacement of a glycine residue at position 9 with an alanine residue;
vii) a replacement of a glycine residue at position 12 with an alanine residue; or
viii) a replacement of a glutamic acid residue at position 13 with an aspartic acid residue.

3. The peptide construct of claim 2, wherein $P_2$ is SEQ ID NO. 21.

* * * * *